(12) United States Patent
Tanimoto et al.

(10) Patent No.: US 7,534,897 B2
(45) Date of Patent: May 19, 2009

(54) INDOLE ARYLSULFONAIMIDE COMPOUNDS EXHIBITING PGD 2 RECEPTOR ANTAGONISM

(75) Inventors: Norihiko Tanimoto, Koka (JP);
Yoshiharu Hiramatsu, Osaka (JP);
Susumu Mitsumori, Osaka (JP);
Masanao Inagaki, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 586 days.

(21) Appl. No.: 10/514,317

(22) PCT Filed: May 15, 2003

(86) PCT No.: PCT/JP03/06076

§ 371 (c)(1),
(2), (4) Date: Nov. 15, 2004

(87) PCT Pub. No.: WO03/097598

PCT Pub. Date: Nov. 27, 2003

(65) Prior Publication Data

US 2005/0171143 A1    Aug. 4, 2005

(30) Foreign Application Priority Data

May 16, 2002    (JP) .............................. 2002-142126

(51) Int. Cl.
*C07D 209/04* (2006.01)
*C07D 209/42* (2006.01)
*A61K 31/405* (2006.01)
*A61K 31/40* (2006.01)

(52) U.S. Cl. ........................ 548/469; 548/492; 548/503; 514/415; 514/419

(58) Field of Classification Search ................ 548/469, 548/503, 492; 514/415, 419
See application file for complete search history.

(56) References Cited

U.S. PATENT DOCUMENTS 4,774,240 A * 9/1988 Boshagen et al. ......... 514/228.2
5,204,121 A   4/1993 Bucheler et al.

FOREIGN PATENT DOCUMENTS

| DE | 39 09 600 | 9/1990 |
| EP | 0 425 906 A2 | 5/1991 |
| EP | 0 451 634 A2 | 10/1991 |
| EP | 0 473 024 A1 | 3/1992 |
| EP | 1 170 594 A2 | 1/2002 |
| JP | 61-249960 | 11/1986 |
| JP | 62-198659 | 9/1987 |
| JP | 62-249969 | 10/1987 |
| JP | 02-193965 | 7/1990 |
| JP | 03-151360 | 6/1991 |
| JP | 04-230363 | 8/1992 |
| JP | 04-234846 | 8/1992 |
| JP | 04-257578 | 9/1992 |
| JP | 08-157471 | 6/1996 |

(Continued)

OTHER PUBLICATIONS

F. Z. Dorwald "Side Reactions in Organic Synthesis: A Guide to Successful Synthesis Design" 2005, Wiley-VCH Verlag GmbH and Co. KGaA Weinheim.*
Chemical Abstracts, vol. 117, Abstract No. 19896.

(Continued)

*Primary Examiner*—Rita J Desai
*Assistant Examiner*—John Mabry
(74) *Attorney, Agent, or Firm*—Finnegan, Henderson, Farabow, Garrett & Dunner, LLP.

(57) ABSTRACT

A compound having CRTH2 receptor antagonism, represented by the following formula (I). The compound is useful for the treatment of allergic diseases having a relation to eosinophils and the like.

A compound of the formula (I):

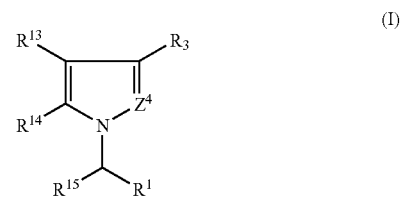

wherein
a group represented by the formula:

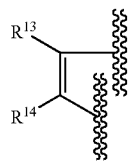

is a group represented by the formula:

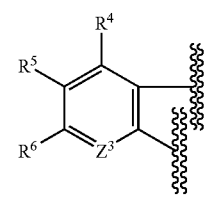

and the like, $R^1$ is carboxy and the like, $R^3$ is —$(CH_2)_n$—N(—Y)—$SO_2$—Ar and the like, the other symbols are as defined in claim 1.

3 Claims, No Drawings

FOREIGN PATENT DOCUMENTS

| | | |
|---|---|---|
| JP | 08-175991 A | 7/1996 |
| JP | 08-245587 | 9/1996 |
| JP | 11-106337 | 4/1999 |
| JP | 11-116477 A | 4/1999 |
| JP | 11-322600 A | 11/1999 |
| JP | 11-343279 A | 12/1999 |
| WO | WO 97/44031 | 11/1997 |
| WO | WO 98/25915 | 6/1998 |
| WO | WO 01/14882 A | 3/2001 |
| WO | WO 01/66520 | 9/2001 |
| WO | WO 01/79169 | 10/2001 |
| WO | WO 02/051837 A2 * | 7/2002 |

OTHER PUBLICATIONS

Arimura, A., et al., "Antiasthmatic Activity of a Novel Thromboxane $A_2$ Antagonist, S-1452, in Guinea Pigs," Int. Arch. Allergy Immunol., 1992, pp. 239-246, vol. 98.

Coleman, R. A., et al., "VIII. International Union of Pharmacology Classification of Prostanoid Receptors: Properties, Distribution, and Structure of the Receptors and Their Subtypes," Pharmacological Reviews, The American Society for Pharmacology and Experimental Therapeutics, 1994, pp. 205-229, vol. 46, No. 2.

Giles, H., et al., "The classification of prostaglandin DP-receptors in platelets and vasculative using BW A868C, a novel, selective and potent competitive antagonist," Br. J. Pharmacol, 1989, pp. 291-300, vol. 96.

Hirai, H. et al., "Prostaglandin D2 Selectively Induces Chemotaxis in T Helper Type 2 Cells, Eosinophils, and Basophils via Seven-Transmembrane Receptor CRTH2," J. Exp. Med., 2001, pp. 255-261, vol. 193, No. 2.

Jochen, G.W., et al., "pH dependency of the binding of [$^3$H]BAY U 3405 and various non-labelled ligands to the thromboxane $A_2$/prostaglandin $H_2$ receptor of human platelet membranes," European Journal of Pharmacology—Molecular Pharmacology Section, 1992, pp. 149-156, vol. 226.

Kishino, J., et al., "Kinetic studies on stereospecific recognition by the thromboxane $A_2$/prostaglandin $H_2$ receptor of the antagonist, S-145," Br. J. Pharmacol., 1991, pp. 1883-1888, vol. 103.

Magnussen, H. et al., "Effects of a thromboxane-receptor antagonist, BAY u 3405, on prostaglandin $D_2$- and exercise-induced bronchoconstriction," J. Allergy Clin. Immunol., 1992, pp. 1119-1126, vol. 89, No. 6.

Mais, De, et al., Thromboxane $A_2$ receptor antagonists. Synthesis and activities of phenylsulfonamido derivatives, Eur. J. Med. Chem., 1991, pp. 821-827, vol. 26.

Narumiya, S. et al., "Different responsiveness of prostaglandin $D_2$-sensitive systems to prostaglandin $D_2$ and its analogues," Br. J. Pharmacol., 1985, pp. 367-375, vol. 85.

Raible, D.G., et al., "Mast Cell Mediators Prostaglandin -$D_2$ And Histamine Activate Human Eosinophils," The Journal of Immunology, 1992, pp. 3536-3542, vol. 148, No. 11.

Rangachari, P.K., et al., "Effects of a Selective DP Receptor Agonist (BW 245C) and Antagonist (BW A868C) on the Canine Colonic Epithelium: An Argument for a Different DP Receptor?" The Journal of Pharmacology and Experimental Therapeutics, 1995, pp. 611-617, vol. 275, No. 2.

Woodward, D.F., et al., "Studies on the Ocular Pharmacology of Prostaglandin $D_2$," Investigative Ophthalmology & Visual Science, 1990, pp. 138-146, vol. 31, No. 1.

Supplementary European search Report mailed Jul. 19, 2007 for Application No. 03725791.2-2101.

Mais De et al. "Thromboxane A2 receptor antagonists. Synthesis and activities of phenylsulfonamido derivatives", European Journal of Medicinal Chemistry, vol. 26, No. 8, 1991, pp. 821-827, XP002441477, Paris.

* cited by examiner

INDOLE ARYLSULFONAIMIDE COMPOUNDS EXHIBITING PGD 2 RECEPTOR ANTAGONISM

TECHNICAL FIELD

This invention relates to a new compound having CRTH2 receptor antagonistic activity.

BACKGROUND ART

Prostaglandin $D_2$ ($PGD_2$), a metabolite derived from arachidonic acid through $PGG_2$ and $PGH_2$, is known to have a variety of potent biological activities. For example, $PGD_2$ is involved in biological actions such as sleep induction and hormone secretion in the central nervous system, inhibition of platelet aggregation, contraction of airway smooth muscle, and relaxation or constriction of vascular smooth muscle in the peripheral tissue (Pharmacol. Rev. (1994) 46, 205-229). In addition, $PGD_2$ is the major metabolite of arachidonic acid produced by mast cells and can cause strong bronchoconstriction, increased vascular permeability, and migration of inflammatory cells such as eosinophils. From these findings, $PGD_2$ is considered to be deeply involved in the pathogenesis in allergic diseases such as asthma.

Formerly, only DP receptor is known as a $PGD_2$ receptor and antagonists against its receptor are described in WO 98/25915, WO 01/66520, WO 01/79169 and the like.

However, it was suggested that there would be other $PGD_2$ receptors different from DP receptor because BW-245C which is a selective agonist against DP receptor did not have activity for eosinphil infiltration (J. Immunol. (1992) 148, 3536-3542; Invest. Ophthalmol. Vis. Sci. (1990) 31, 138-146; Br. J. Pharmacol. (1985) 85, 367-375; J. Pharmacol. Exp. Ther. (1995) 275, 611-617 etc.). Recently, it was reported that CRTH2 receptor is the other $PGD_2$ receptor and $PGD_2$ causes wandering of eosinophils and basophils vir this receptor (J. Exp. Med. (2001) 193, 255-261).

An antagonist against thromboxane $A_2$ ($TXA_2$) receptor and a platelet aggregation inhibitor having similar structure to a compound of the present invention are described in JP-A-61-249960, JP-A-62-198659, JP-A-62-249969, JP-A-2-193965, JP-A-3-151360, JP-A-4-230363, JP-A-4-234846, JP-A-4-257578, JP-A-8-157471, JP-A-8-245587, DE 3909600, Eur. J. Med. Chem., (1991) 26(8), 821-827. However, PGD2 antagonistic activity of the above compounds has not been described in them.

It is described in JP-A-3-151360 that 3-(4-chlorophenylsulfonylamino)-9-(2-carboxymethyl)-1,2,3,4-tetrahydrocarbazole and its ethyl ester have $TXA_2$ antagonistic activity and $TXA_2$ synthetase inhibitory activity. However, concrete value of the activities is not described in the document.

It is described in Eur. J. Med. Chem., 1991, 26(8), 821-827 that 3-(4-chlorophenylsulfonylaminoehtyl)indole-1-acetic acid and 3-(4-chlorophenylsulfonylaminopropyl)indole-1-acetic acid have antagonistic activity against $TXA_2/PGH_2$ receptor.

It is described that 3-(4-fluorophenylsulfonamide)-1,2,3,4-tetrahydro-9-carbazole propionic acid is useful for therapeutic agent for allergic dermatitis, allergic dermatitis vir delayed type allergy reaction, and psoriasis in JP-A-7-175991, WO 97/44031, JP-A-11-106337 and JP-A-11-116477. It is described in JP-A-11-322600 that the above compound has depression activity for Chemokine production. Further, it is described in J. Allergy Clin. Immunol. (1992) 89, 1119-1126 that there is possibility that the above compound will have $PGD_2$ antagonistic activity via DP receptor because it shows a depression effect against bronchus constriction caused $PGD_2$. However, according to 1) $PGD_2$ also binds $TXA_2$ receptor in high concentration range (more than 1 μM) (Eur. J. Pharmacol. (1992) 226, 149-156; Br. J. Pharmacol. (1991) 103, 1883-1888 etc., 2) antagonists against $TXA_2$ receptor which have weak receptor affinity for DP receptor show the same depression effect (Int. Arch. Allergy Immunol. 1992, 98, 239-246, and 3) selective DP receptor antagonists does not show a depression effect against bronchus constriction caused $PGD_2$ (Br. J. Pharmacol. (1989) 96, 291-300), it is known time that the above depression effect is caused by depressing the reaction via thromboxane receptor and the above compound does not have direct DP receptor antagonistic activity at the present.

It is described in EP 1170594 that 4 compounds selectively binds CRTH2 receptor in comparison with DP receptor. However, the structures of the compounds are not similar to the compound of the present invention and details such as binding activities are not described.

DISCLOSURE OF INVENTION

The inventors of the present invention find out new compounds having a selective CRTH2 receptor antagonistic activity but not having a $TXA_2$ receptor antagonistic activity.

The present invention relates to

I) a compound of the formula (I):

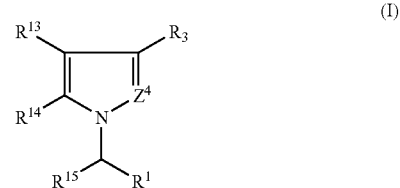

wherein
a group represented by the formula:

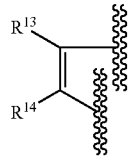

is a group represented by the formula:

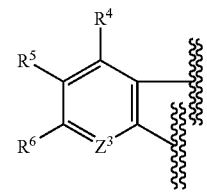

wherein $Z^3$ is =N— or =C(—$R^7$)—;
$R^4$, $R^5$, $R^6$ and $R^7$ are each independently hydrogen, halogen, haloalkyl, carboxy, alkyloxycarbonyl, optionally substituted alkyl, optionally substituted alkenyl, optionally substituted cycloalkyl, optionally substituted aryl, optionally substituted aralkyl, a group represented by the formula:

—S(O)pR$^8$ wherein p is an integer from 0 to 2 and R$^8$ is alkyl or optionally substituted aryl, a group represented by the formula: —NR$^9$R$^{10}$ wherein R$^9$ and R$^{10}$ are each independently hydrogen, alkyl, optionally substituted aryl, optionally substituted aralkyl or acyl, or a group represented by the formula: —OR$^{11}$ wherein R$^{11}$ is hydrogen, alkyl, optionally substituted aryl, optionally substituted aralkyl, alkanesulfonyl, optionally substituted arylsulfonyl, optionally substituted aralkylsulfonyl, or haloalkyl;

R$^1$ is carboxy, alkyloxycarbonyl, optionally substituted aminocarbonyl or tetrazolyl;

Z$^4$ is —N= or —C(—R$^2$)=; R$^2$ is hydrogen, alkyl or halogen;

R$^{15}$ is hydrogen or alkyl;

R$^3$ is a group represented by the formula: —(CH$_2$)n-N(—Y)—SO$_2$—Ar wherein n is an integer from 1 to 3; Y is hydrogen, alkyl, alkenyl, alkynyl, optionally substituted aryl, optionally substituted aralkyl, optionally substituted heteroarylalkyl or optionally substituted arylalkenyl; and Ar is optionally substituted aryl or optionally substituted heteroaryl, a group represented by the formula:

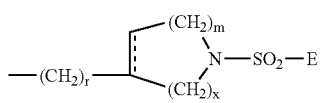

wherein r is an integer from 0 to 2; x is an integer from 0 to 3; m is an integer from 1 to 3; a broken line represents the presence or absence of a bond; E is optionally substituted aryl, optionally substituted heteroaryl, alkyl, optionally substituted aralkyl or optionally substituted arylalkenyl, a group represented by the formula:

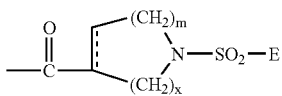

wherein x is an integer from 0 to 3; m is an integer from 1 to 3; a broken line represents the presence or absence of a bond; E is optionally substituted aryl, optionally substituted heteroaryl, alkyl, optionally substituted aralkyl or optionally substituted arylalkenyl, a group represented by the formula: —CR$^{23}$R$^{24}$—CR$^{25}$R$^{26}$—(CH$_2$)y-N(—Y)—SO$_2$—Ar wherein Ar and Y are as defined above; y is 0 or 1; one of R$^{23}$ or R$^{24}$ is alkyl, the other is hydrogen, alkyl, or aryl; or R$^{23}$ and R$^{24}$ are taken together to form a group represented by the formula: —(CH$_2$)t- wherein t is an integer from 2 to 5; R$^{25}$ and R$^{26}$ are each independently hydrogen or alkyloxyalkyl, a group represented by the formula:

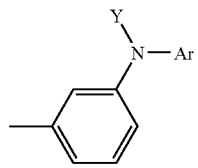

wherein Y and Ar are as defined above, or a group represented by the formula:

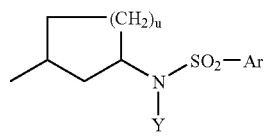

wherein Y and Ar are as defined above and u is 1 or 2; or a group represented by the formula:

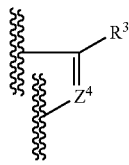

is a group represented by the formula:

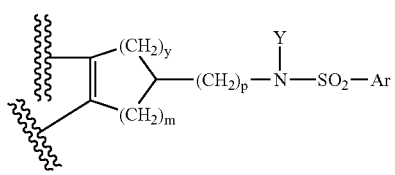

wherein y is an integer from 1 to 3, and m, p, Y and Ar are as defined above, a group represented by the formula:

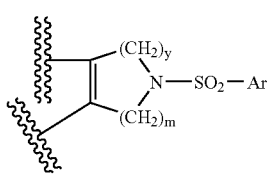

wherein m, y and Ar are as defined above, or a group represented by the formula:

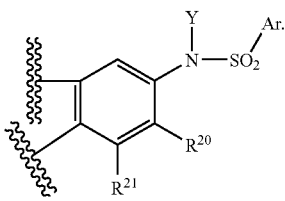

wherein Y and Ar are as defined above; R$^{20}$ is hydrogen or alkyl; and R$^{21}$ is hydrogen or halogen; but excluding compounds 3-(4-chlorophenylsulfonylamino)-9-(2-carboxymethyl)-1,2,3,4-tetrahydrocarbazole, its ethyl ester, 3-(4-chlorophenylsulfonylaminoethyl)indole1-acetic acid, and 3-(4-chlorophenylsulfonylaminopropyl)indole acetic acid; or R$^{13}$ is hydrogen, alkyl, aralkyl, acyl or a group represented by the formula: —OR$^{16}$ wherein R$^{16}$ is hydrogen or alkyl, and R$^{14}$ is hydrogen or alkyl: or a group represented by the formula:

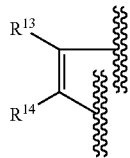

is a group represented by the formula:

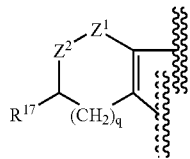

wherein q is an integer from 0 to 3; $R^{17}$ is hydrogen or alkyl; $Z^1$ is —$CH_2$—, —C(=O)—, —C(=NOH)—, or —C(=NOMe)-; $Z^2$ is a group represented by the formula: —S(=O)s- wherein s is an integer from 0 to 2, a group represented by the formula: —N(—$R^{22}$)— wherein $R^{22}$ is hydrogen, alkyl, alkyloxycarbonyl or acyl, or a group represented by the formula: —$CR^{18}R^{19}$— wherein $R^{18}$ and $R^{19}$ are each independently hydrogen, alkyl or aryl; or $R^{18}$ and $R^{19}$ are taken together to form a group represented by the formula: —$(CH_2)$t- wherein t is an integer from 2 to 5; $R^1$ and $R^{15}$ are as defined above; and a group represented by the formula:

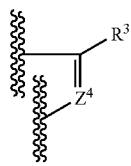

is a group represented by the formula:

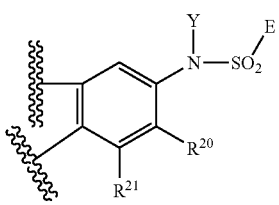

wherein Y, E, $R^{20}$ and $R^{21}$ are as defined above;
a prodrug, a pharmaceutically acceptable salt, or a solvate thereof.

Further, this invention relates to the following II) to XV).
II) A compound as described in I), wherein a group represented by the formula:

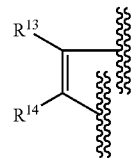

is a group represented by the formula:

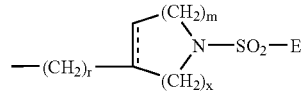

wherein $Z^3$ is =C(—$R^7$)—; $R^4$, $R^5$, $R^6$ and $R^7$ are as defined in I);
$Z^4$ is —C(—$R^2$)=; $R^2$ is as defined in I);
$R^{15}$ is hydrogen; and
$R^3$ is a group represented by the formula: —$(CH_2)$n-N(—Y)—$SO_2$—Ar wherein n is an integer from 1 to 3; Y is hydrogen, alkyl, alkenyl, optionally substituted aryl, optionally substituted aralkyl, or optionally substituted heteroarylalkyl; and Ar is optionally substituted aryl or optionally substituted heteroaryl,
a group represented by the formula:

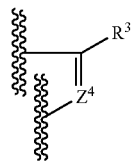

wherein r is an integer from 0 to 2; x is an integer from 0 to 3; m is an integer from 1 to 3; a broken line represents the presence or absence of a bond; E is optionally substituted aryl or optionally substituted heteroaryl; or
a group represented by the formula:

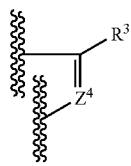

is a group represented by the formula:

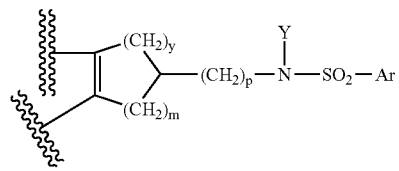

wherein y is an integer from 1 to 3, and m, p, Y and Ar are as defined above, a group represented by the formula:

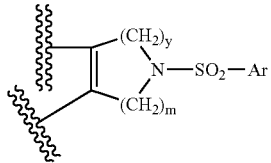

wherein m, y and Ar are as defined above, or
a group represented by the formula:

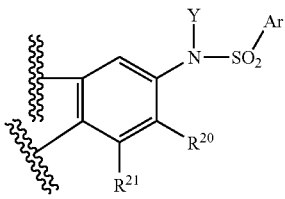

wherein Y and Ar are as defined in I), and $R^{20}$ and $R^2$ are hydrogen,
a prodrug, a pharmaceutically acceptable salt, or a solvate thereof.

III) A compound as described in I) or II), wherein Y is alkyl, alkenyl, optionally substituted aryl or optionally substituted aralkyl, a prodrug, a pharmaceutically acceptable salt, or a solvate thereof.

IV) A compound as described in II), wherein $R^3$ is a group represented by the formula: $-(CH_2)n-N(-Y)-SO_2-Ar$ wherein n is 2 or 3; Y is hydrogen, alkyl, alkenyl, or aralkyl; and Ar is as defined in I), a prodrug, a pharmaceutically acceptable salt, or a solvate thereof.

V) A compound as described in II), wherein $R^3$ is a group represented by the formula:

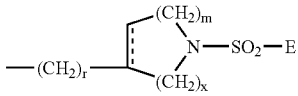

wherein m is 1; r is 0; x is 2; a broken line represents the presence or absence of a bond; and E is as defined in II), a prodrug, a pharmaceutically acceptable salt, or a solvate thereof.

VI) A compound as described in II), wherein a group represented by the formula:

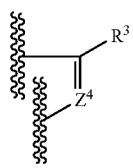

is a group represented by the formula:

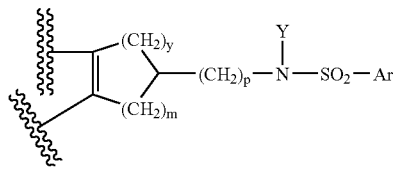

wherein m is 2; p is 0; y is 1; Y is hydrogen, alkyl, alkenyl or aralkyl; and Ar is as defined in I), a prodrug, a pharmaceutically acceptable salt, or a solvate thereof.

VII) A compound as described in II), wherein a group represented by the formula:

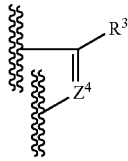

is a group represented by the formula:

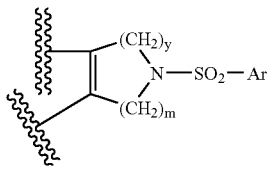

wherein m is 1 or 2; y is 1 or 2; and Ar is as defined in II), a prodrug, a pharmaceutically acceptable salt, or a solvate thereof.

VIII) A compound as described in II), wherein a group represented by the formula:

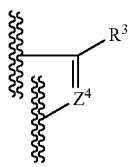

is a group represented by the formula:

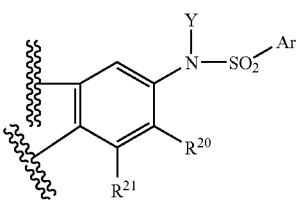

wherein Y is hydrogen, alkyl, alkenyl or aralkyl; and $R^{20}$, $R^{21}$ and Ar are as defined in I), a prodrug, a pharmaceutically acceptable salt, or a solvate thereof.

IX) A compound as described in any one of I) to VIII), wherein $R^1$ is carboxy, a prodrug, a pharmaceutically acceptable salt, or a solvate thereof.

X) A compound as described in any one of I) to IX), wherein $R^4$, $R^5$, $R^6$ and $R^7$ are each independently hydrogen, halogen, alkyl, alkenyl, optionally substituted aryl or optionally substituted aralkyl, a prodrug, a pharmaceutically acceptable salt, or a solvate thereof.

XI) A compound as described in any one of I) to X), wherein $R^2$ is hydrogen or alkyl, a prodrug, a pharmaceutically acceptable salt, or a solvate thereof.

XII) A pharmaceutical composition containing a compound, a prodrug, a pharmaceutically acceptable salt, or a solvate thereof as described in any one of I) to XI).

XIII) A pharmaceutical composition as described in XII), which is used for an antagonist against the CRTH2 receptor.

XIV) A method for treating a disease relating to the CRTH2 receptor, which comprises administrating a compound as described in I).

XV) Use of the compound as described in I) for the preparation of a pharmaceutical composition for treating a disease relating to the CRTH2 receptor.

The following compounds are included in the compounds represented by the formula (I).

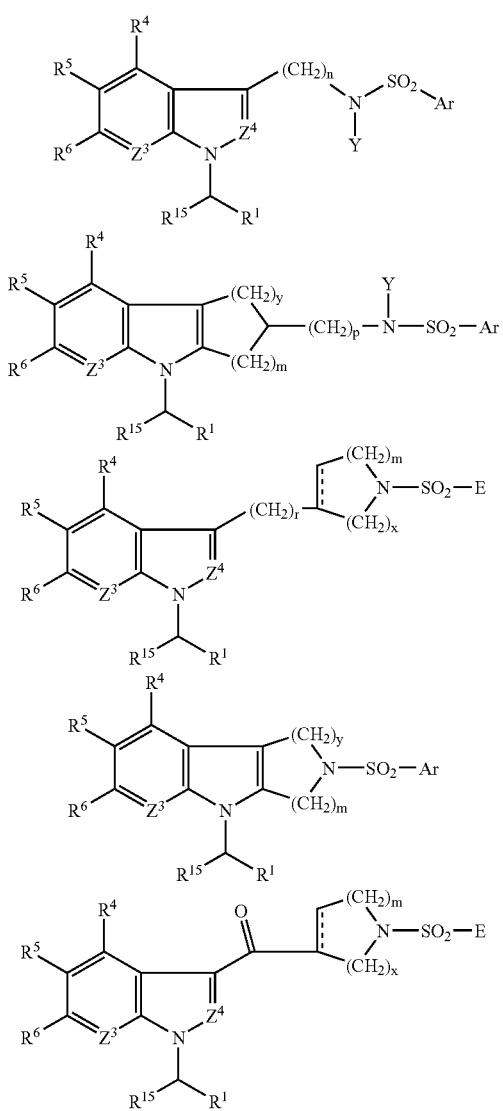

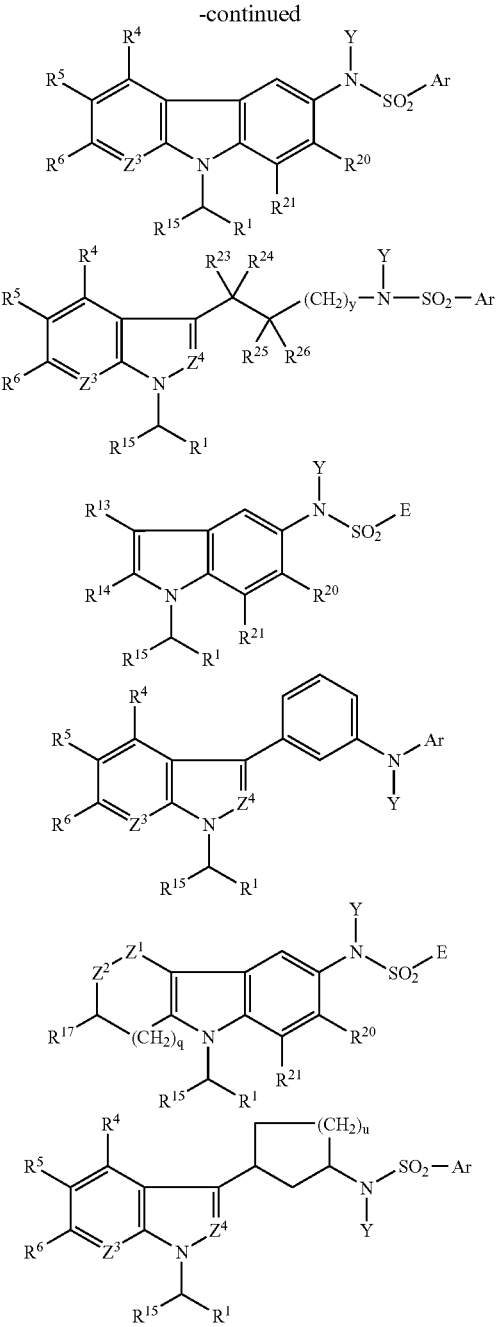

wherein each symbol in the above structures is as defined in I).

The details of the present invention are as follows.

In the present specification, the term "halogen" means fluoro, chloro, bromo, and iodo. Fluoro, chloro, and bromo are preferred as halogen.

In the present specification, the term "alkyl" employed alone or in combination with other terms includes a straight- or branched chain monovalent hydrocarbon group having 1 to 8 carbon atom(s). Examples of alkyl are methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. C1 to C6 alkyl is preferred. C1 to C3 alkyl is more preferred.

In the present specification, the term "cycloalkyl" employed alone or in combination with other terms includes a mono cycloalkyl having 3 to 8 carbon atom. Examples of cycloalkyl are cyclopropyl, cyclobutyl, cyclopentyl, cyclohexyl, cycloheptyl, cyclooctyl, and the like. C3 to C6 cycloalkyl is preferred.

In the specification, the term "alkenyl" employed alone or in combination with other terms includes a straight- or branched chain monovalent hydrocarbon group having 2 to 8 carbon atoms and one or more double bond(s). Examples of the alkenyl are vinyl, allyl, 1-propenyl, 2-propenyl, crotonyl, isopentenyl, a variety of butenyl isomers and the like. C2 to C6 alkenyl is preferred. C2 to C4 alkenyl is more preferred.

In the specification, the term "alkynyl" employed alone or in combination with other terms includes a straight or branched chain monovalent hydrocarbon group having 2 to 8 carbon atoms and one or more triple bond(s). Examples of the alkynyl are ethynyl, 1-propynyl, 2-propynyl and the like. C2 to C6 alkynyl is preferred. C2 to C4 alkynyl is more preferred.

In the present specification, the term "aryl" employed alone or in combination with other terms includes monocyclic or condensed ring aromatic hydrocarbons. Examples of aryl are phenyl, 1-naphtyl, 2-naphtyl, anthryl, and the like. Phenyl, 1-naphtyl, and 2-naphtyl are preferred. Phenyl is more preferred.

The term "aralkyl" employed alone or in combination with other terms includes the above mentioned "alkyl" substituted with the above mentioned one or more "aryl" at any possible position. Examples of the aralkyl are benzyl, phenylethyl (e.g., 2-phenylethyl), phenylpropyl (e.g., 3-phenylpropyl), naphthylmethyl (e.g., 1-naphthylmethyl and 2-naphthylmethyl), anthrylmethyl (e.g., 9-anthrylmethyl), and the like. Benzyl, 2-phenylethyl, 1-naphthylmethyl and 2-naphthylmethyl are preferred. Benzyl and 2-phenylethyl are more preferred.

The term "aralkyl" herein used includes the above mentioned "alkyl" substituted with the above mentioned one or more "aryl" at any possible position. Examples of the aralkyl are benzyl, phenylethyl (e.g., 2-phenylethyl), phenylpropyl (e.g., 3-phenylpropyl), naphthylmethyl (e.g., 1-naphthylmethyl and 2-naphthylmethyl), anthrylmethyl (e.g., 9-anthrylmethyl), and the like. Benzyl, 2-phenylethyl, 1-naphthylmethyl and 2-naphthylmethyl are preferred. Benzyl and 2-phenylethyl are more preferred.

The term "arylalkenyl" herein used includes the above mentioned "alkenyl" substituted with the above mentioned one or more "aryl" at any possible position. Examples of the arylalkenyl are phenylallyl, naphthylallyl, and the like.

In the present specification, the term "non-aromatic heterocyclic group" includes a 5 to 7 membered non-aromatic ring which contains one or more hetero atoms selected from the group consisting of oxygen, sulfur, and nitrogen atoms in the ring, and the 5 to 7 membered non-aromatic ring may be condensed with two or more rings. Examples of the non-aromatic heterocyclic group are pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidyl (e.g., piperidino, 2-piperidyl), piperazinyl (e.g., 1-piperazinyl), indolynyl (e.g., 1-indolynyl), isoindolinyl (e.g., isoindolinyl), morpholinyl (e.g., morpholino, 3-morpholinyl), and the like.

In the present specification, the term "heteroaryl" employed alone or in combination with other terms includes a 5 to 6 membered aromatic heterocyclic group which contains one or more hetero atoms selected from the group consisting of oxygen, sulfur, and nitrogen atoms in the ring. The aromatic heterocyclic group may be fused with the above mentioned cycloalkyl, above mentioned aryl, above mentioned non-aromatic heterocyclic group, and other heteroaryl at any possible position. The heteroaryl which is a monocyclic or fused ring may be bonded at any possible position. Examples of the heteroaryl are pyrrolyl (e.g., 1-pyrrolyl, 2-pyrrolyl, 3-pyrrolyl), furyl (e.g., 2-furyl, 3-furyl), thienyl (e.g., 2-thienyl 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl(e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolyl (2-isoindolyl), indolyl (e.g., 1-indolyl, 2-indolyl, 3-indolyl), indazolyl (e.g., 3-indazolyl), purinyl (e.g., 8-purinyl), quinolizinyl (e.g., 2-quinolizinyl), isoquinolyl (e.g., 3-isoquinolyl), quinolyl (e.g., 2-quinolyl, 5-quinolyl), phthalazinyl (e.g., 1-phthalazinyl), naphthyridinyl (e.g., 2-naphthyridinyl), quinolanyl (2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl), benzodioxolyl (e.g., 1,3-benzodioxolyl) and the like.

Thienyl, benzothienyl, dibenzothienyl, benzodioxolyl, oxazolyl, and the like are preferred as heteroaryl of Ar.

The term "heteroarylalkyl" herein used includes the above-mentioned "alkyl" substituted with the above-mentioned one or more "heteroaryl" at any possible position. Examples of the heteroarylalkyl are thienylalkyl, furylalkyl, pyrrolylalkyl, imidazolylalkyl, pyrazolylalkyl, thiazolylalkyl, isothiazolylalkyl, isoxazolylalkyl, oxazolylalkyl, pyridylalkyl, and the like. Thienylmethyl (e.g., 2-thienylmethyl), thienylethyl (e.g., 2-(thiophen-2-yl)ethyl), furylmethyl (e.g., 2-furylmethyl), furylethyl (e.g., 2-(furan-2-yl)ethyl), pyrrolylmethyl (e.g., 2-pyrrolylmethyl), pyrrolylethyl (e.g., 2-(pyrrol-2-yl)ethyl), imidazolylmethyl (e.g., 2-imidazolylmethyl, 4-imidazolylmethyl), imidazolylethyl (e.g., 2-(imidazol-2-yl)ethyl), pyrazolylmethyl (e.g., 3-pyrazolylmethyl), pyrazolylethyl (e.g., 2-(pyrazol-3-yl)ethyl), thiazolylmethyl (e.g., 2-thiazolylmethyl), thiazolylethyl (e.g., 2-(thiazol-2-yl)ethyl), isothiazolylmethyl (e.g., 3-isothiazolylmethyl), isoxazolylmethyl (e.g., 3-isoxazolylmethyl), oxazolylmethyl (e.g., 2-oxazolylmethyl), oxazolylethyl (e.g., 2-(oxazol-2-yl)ethyl), pyridylmethyl (e.g., 2-pyridylmethyl, 3-pyridylmethyl, 4-pyridylmethyl), pyridylethyl (e.g., 2-pyridylethyl) and the like are exemplified.

Thienylmethyl is preferred as heteroaryl of Y.

The term "alkyloxy" herein used are methyloxy, ethyloxy, n-propyloxy, isopropyloxy, n-butyloxy, isobutyloxy, sec-butyloxy, tert-butyloxy, and the like. Methyloxy, ethyloxy, n-propyloxy, isopropyloxy and n-butyloxy are preferred. C1 to C3 alkyloxy is more preferred.

The term "alkylthio" herein used are methylthio, ethylthio, n-propylthio, isopropylthio, n-butylthio, isobutylthio, sec-butylthio, tert-butylthio, and the like. Methylthio, ethylthio, n-propylthio, isopropylthio and n-butylthio are preferred. C1 to C3 alkylthio is more preferred.

In the present specification, phenyloxy, naphthyloxy, and the like are exemplified as "aryloxy."

In the present specification, phenylthio, naphthylthio, and the like are exemplified as "arylthio."

In the present specification, phenylazo, naphthylazo, and the like are exemplified as "arylazo."

The term "alkyloxycarbonyl" herein used are methyloxycarbonyl, ethyloxycarbonyl, n-propyloxycarbonyl, isopropyloxycarbonyl, n-butyloxycarbonyl, tert-butyloxycarbonyl, n-pentyloxycarbonyl and the like. Methyloxycarbonyl and ethyloxycarbonyl are preferred. C1 to C3 alkyloxycarbonyl are more preferred.

In the present specification, the term "acyl" employed alone or in combination with other terms includes alkylcarbonyl in which alkyl group is the above-mentioned "alkyl" and arylcarbonyl in which aryl group is the above-mentioned "aryl". "Alkyl" and "aryl" may be substituted respectively with substituents exemplified in the following "optionally substituted alkyl" and "optionally substituted aryl". Examples of the acyl are acetyl, propyonyl, butyloyl, benzoyl, and the like.

In the present specification, the term "haloalkyl" employed alone or in combination with other terms includes the above-mentioned "alkyl" which is substituted with the above-mentioned "halogen" at 1 to 8 positions, preferably, at 1 to 5. Examples of the haloalkyl are trifluoromethyl, trichloromethyl, difluoroethyl, trifluoroethyl, dichloroethyl, trichloroethyl, chloromethyl, and the like. Preferable is trifluoromethyl.

Examples of the term "acyloxy" herein used are acetyloxy, propionyloxy, benzoyloxy and the like.

Examples of the term "alkanesulfonyl" herein used are methanesulfonyl, ethanesulfonyl, n-propanesulfonyl, isopropanesulfonyl, n-butanesulfonyl, isobutanesulfonyl, sec-butanesulfonyl, tert-butanesulfonyl, and the like. Methanesulfonyl and ethanesulfonyl are preferred.

Examples of the term "arylsulfonyl" herein used are phenylsulfonyl, naphthylsulfonyl, and the like.

Examples of the term "aralkylsulfonyl" herein used are benzylsulfonyl, phenylethylsulfonyl, and the like.

Example of the term "heteroarylsulfonyl" herein used is pyrrolylsulfonyl or the like.

In the present specification, the term "optionally substituted amino" employed alone or in combination with other terms includes amino which may be substituted with one or two of the above-mentioned "alkyl", above-mentioned "aryl", above-mentioned "aralkyl", above-mentioned "heteroaryl", above-mentioned "heteroarylalkyl", above-mentioned "acyl", above-mentioned "alkyloxycarbonyl" and/or "alkanesulfonyl". Examples of the optionally substituted amino are amino, methylamino, dimethylamino, ethylmethylamino, diethylamino, benzylamino, acetylamino, benzoylamino, methyloxycarbonylamino, methanesulfonylamino, and the like. Preferable are amino, methylamino, dimethylamino, ethylmethylamino, diethylamino, acetylamino, methanesulfonylamino.

Examples of the term "optionally substituted aminocarbonyl" herein used are aminocarbonyl, methylaminocarbonyl, dimethylaminocarbonyl, ethylmethylaminocarbonyl, diethylaminocarbonyl, benzylamino, acetylamino, methanesulfonylaminocarbonyl and the like. Preferable are aminocarbonyl, methylaminocarbonyl, dimethylaminocarbonyl, and methanesulfonylaminocarbonyl.

In the present specification, the term "optionally substituted ureide" includes ureide substituted with one or more of the above-mentioned "alkyl", above-mentioned "aryl", above-mentioned "aralkyl", above-mentioned "heteroaryl", above-mentioned "heteroarylalkyl" or above-mentioned "acyl".

The substituents of "optionally substituted alkyl" are cycloalkyl, alkenyl, alkyliden, hydroxy, alkyloxy, mercapto, alkylthio, halogen, nitro, cyano, carboxy, alkyloxycarbonyl, haloalkyl, haloalkyloxy, optionally substituted amino, optionally substituted aminocarbonyl, acyl, acyloxy, optionally substituted non-aromatic heterocyclic group, aryloxy (e.g., phenyloxy), aralkyloxy (e.g., benzyloxy), alkanesulfonyl, guanidino, an azo group, and the like. These substituents are able to locate at one or more of any possible positions.

Preferable are alkyloxy, hydroxy, optionally substituted amino, aryloxy, and the like as substituents of "optionally substituted alkyl" for $R^4$, $R^5$, $R^6$, and $R^7$.

The substituents of "optionally substituted cycloalkyl" are alkyl, cycloalkyl, alkenyl, alkyliden, hydroxy, alkyloxy, mercapto, alkylthio, halogen, nitro, cyano, carboxy, alkyloxycarbonyl, haloalkyl, haloalkyloxy, optionally substituted amino, optionally substituted aminocarbonyl, acyl, acyloxy, aryloxy (e.g., phenyloxy), aralkyloxy (e.g., benzyloxy), alkanesulfonyl, guanidino, an azo group, and the like. These substituents are able to locate at one or more of any possible positions.

Preferable are alkyl, halogen, and the like as substituents of "optionally substituted cycloalkyl" for $R^4$, $R^5$, $R^6$, and $R^7$.

The substituents of "optionally substituted alkenyl" are alkyl, cycloalkyl, alkyliden, hydroxy, alkyloxy, mercapto, alkylthio, halogen, nitro, cyano, carboxy, alkyloxycarbonyl, haloalkyl, haloalkyloxy, optionally substituted amino, optionally substituted aminocarbonyl, acyl, acyloxy, aryl, aryloxy (e.g., phenyloxy), aralkyl, aralkyloxy (e.g., benzyloxy), alkanesulfonyl, guanidino, an azo group, and the like. These substituents are able to locate at one or more of any possible positions.

Preferable are halogen, aryl, and the like as substituents of "optionally substituted alkenyl" for $R^4$, $R^5$, $R^6$, and $R^7$.

The substituents of "optionally substituted aryl", "optionally substituted aralkyl", "optionally substituted heteroaryl", "optionally substituted arylsulfonyl", "optionally substituted aralkylsulfonyl", and "optionally substituted non-aromatic heterocyclic group" herein used are alkyl, haloalkyl, cycloalkyl, alkenyl, alkynyl, hydroxy, alkyloxy, haloalkyloxy, aryloxy, aralkyloxy, mercapto, alkylthio, halogen, nitro, cyano, carboxy, alkyloxycarbonyl, acyl, acyloxy, alkanesulfonyl, guanidino, an azo group, optionally substituted amino, optionally substituted aminocarbonyl, aryl which may be substituted with one or more of the substituents selected from Substituents group C, heteroaryl which may be substituted with one or more of the substituents selected from Substituents group C, non-aromatic heterocyclic group which may be substituted with one or more of the substituents selected from Substituents group C, aralkyl which may be substituted with one or more of the substituents selected from Substituents group C, optionally substituted ureide, and the like. These substituents are able to locate at one or more of any possible positions (Substituents group C: alkyl, haloalkyl, cycloalkyl, alkenyl, alkynyl, hydroxy, alkyloxy, haloalkyloxy, aryloxy, aralkyloxy, mercapto, alkylthio, halogen, nitro, cyano, carboxy, alkyloxycarbonyl, acyl, acyloxy, alkanesulfonyl, guanidino, an azo group, optionally substituted amino, and optionally substituted aminocarbonyl).

Preferable are alkyl, alkyloxy, halogen, and the like as substituents of "optionally substituted aryl" for $R^4$, $R^5$, $R^6$, and $R^7$.

Preferable are alkyl, alkyloxy, halogen, and the like as substituents of "optionally substituted aryl" for $R^8$.

Preferable are alkyl, alkyloxy, halogen, and the like as substituents of "optionally substituted aryl" for $R^9$ and $R^{10}$.

Preferable are alkyl, alkyloxy, halogen, and the like as substituents of "optionally substituted aryl" for $R^{11}$.

Preferable are alkyl, alkyloxy, halogen, and the like as substituents of "optionally substituted aryl" for Y.

Preferable are alkyl, alkyloxy, aryloxy, halogen, benzyl, phenyl which may be substituted with substituents selected from Substituents group B, and the like as substituents of "optionally substituted aryl" for Ar (Substituents group B: alkyl, alkyloxy, aryloxy, halogen, and benzyl).

Preferable are alkyl, halogen, and the like as substituents of "optionally substituted aralkyl" for $R^4$, $R^5$, $R^6$, and $R^7$.

Preferable are alkyl, halogen, and the like as substituents of "optionally substituted aralkyl" for $R^9$ and $R^{10}$.

Preferable are alkyl, halogen, and the like as substituents of "optionally substituted aralkyl" for $R^{11}$.

Preferable are alkyl, alkyloxy, nitro, halogen, and the like as substituents of "optionally substituted aralkyl" for Y.

Preferable are alkyl, alkyloxy, aryloxy, halogen, benzyl, phenyl which may be substituted with substituents selected from Substituents group B, and the like as substituents of "optionally substituted heteroaryl" for Ar (Substituents group B: alkyl, alkyloxy, aryloxy, halogen, and benzyl).

Preferable are alkyl and the like as substituents of "optionally substituted arylsulfonyl" for $R^{11}$.

Preferable are alkyl and the like as substituents of "optionally substituted aralkylsulfonyl" for $R^{11}$.

BEST MODE FOR CARRYING OUT THE INVENTION

The compounds represented by the formula (I) of the present invention can be synthesized by reacting the compounds represented by the following formula (IIa) to (IIk):

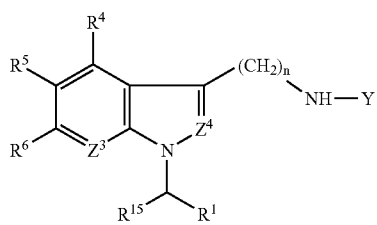
(IIa)

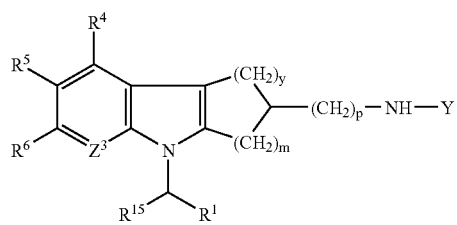
(IIb)

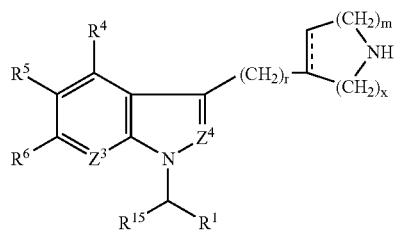
(IIc)

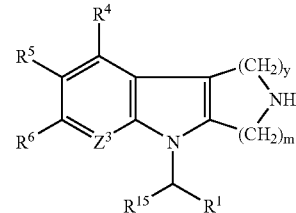
(IId)

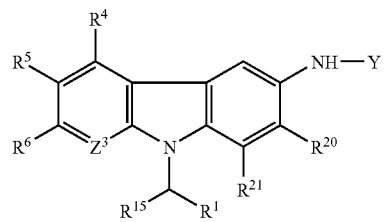
(IIe)

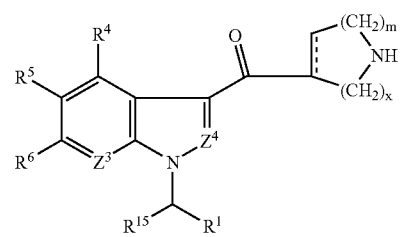
(IIf)

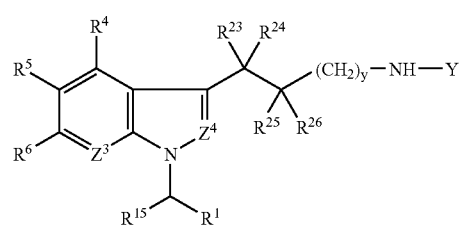
(IIg)

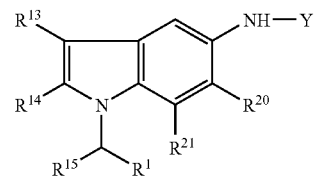
(IIh)

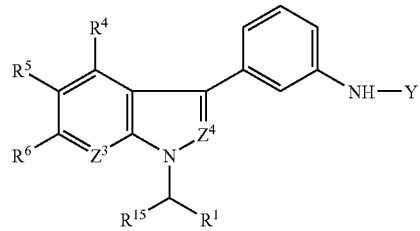
(IIi)

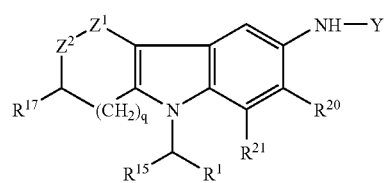
(IIj)

-continued

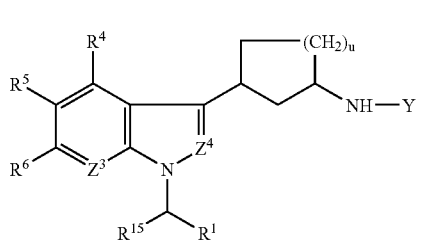
(IIk)

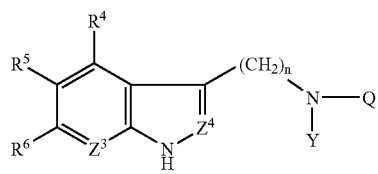
(IIIa)

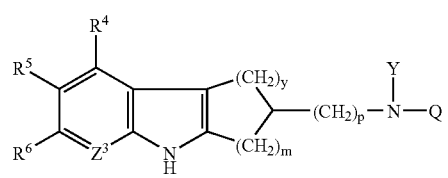
(IIIb)

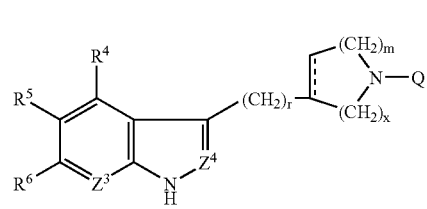
(IIIc)

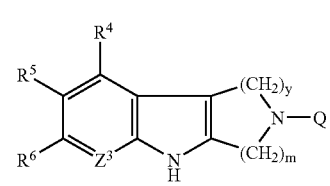
(IIId)

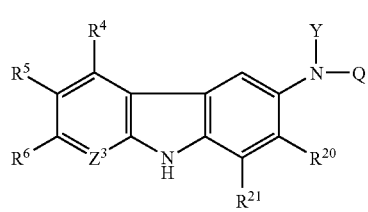
(IIIe)

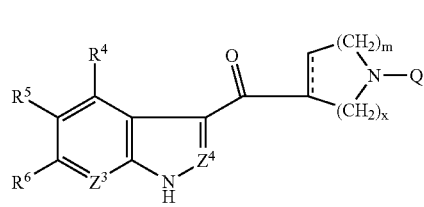
(IIIf)

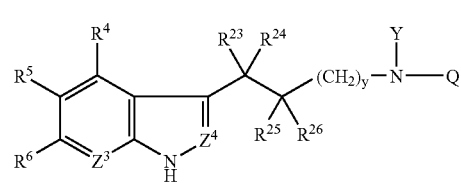
(IIIg)

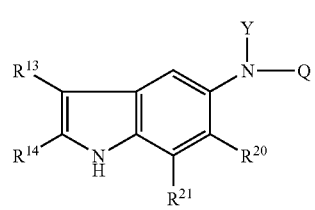
(IIIh)

wherein $R^1$ is alkyloxycarbonyl and the other symbols are as defined in I) or their salts with 1 to 5 eq. of a compound represented by the formula Ar—SO$_2$—X$^1$ or E-SO$_2$—X$^1$ wherein Ar and E are as defined in I), and $X^1$ is halogen in an inactive solvent at 0° C. to room temperature for 5 min. to several hours. This reaction can be carried out in the presence of 1 to 5 eq. of a base. Triethylamine, pyridine, potassium carbonate, sodium carbonate, potassium hydrogen carbonate, sodium hydrogen carbonate, potassium hydroxide, sodium hydroxide and the like are preferred as a base. Pyridine, acetonitrile, dichloromethane, tetrahydrofuran (THF) and the like are preferred as an inactive solvent, and they can be used themselves or mixed solvents with water.

When Y is hydrogen in the above synthesized compound, the compound wherein Y is alkyl, alkenyl, optionally substituted aryl or optionally substituted aralkyl can be synthesized by reacting with Y—X$^2$ wherein $X^2$ is halogen, optionally substituted alkanesulfonyloxy or optionally substituted arylsulfonyloxy in an inactive solvent such as THF, diethylether, N,N-dimethylformamide (DMF), dimethylsulfoxide (DMSO), acetonitrile, acetone, toluene and the like in the presence of a base such as sodium hydroxide, potassium hydroxide, potassium t-butoxide, potassium carbonate and the like at 0° C. to 80° C. for 30 min. to several hours. Further, the compound wherein Y is alkyl, alkenyl, optionally substituted aralkyl and the like can be synthesized by reactive amination. For example, the above compound can be synthesized by reacting the compound represented by the formula (IIa), (IIb), or (IIe) wherein Y is hydrogen with corresponding aldehyde or ketone in a solvent such as THF, dichloromethane and the like in the presence of 1 to 5 eq. of sodium borohydride, sodium cyanotrihydroborate or triacetoxyborohydride at 0° C. to 80° C. for 30 min. to several hours. This reaction can be carried out in the presence of 0.1 to 5 eq. of an acidic catalyst such as hydrochloric acid, acetic acid, p-toluenesulfonic acid and the like. After the reaction, the compound represented by the formula (I) can be synthesized by the above-mentioned sulfonylation.

The compound represented by the formula (I) wherein $R^1$ is carboxy can be synthesized by acidic hydrolysis or alkali hydrolysis of ester in accordance with the usual hydrolysis condition after the above mentioned reaction.

The compound represented by the formula (IIe) can be synthesized by the method described in JP-A-8-169879 and the like.

The compounds represented by the formula (IIa) to (IIk) can be synthesized using the compounds represented by the following formula (IIIa) to (IIIk) as a starting material.

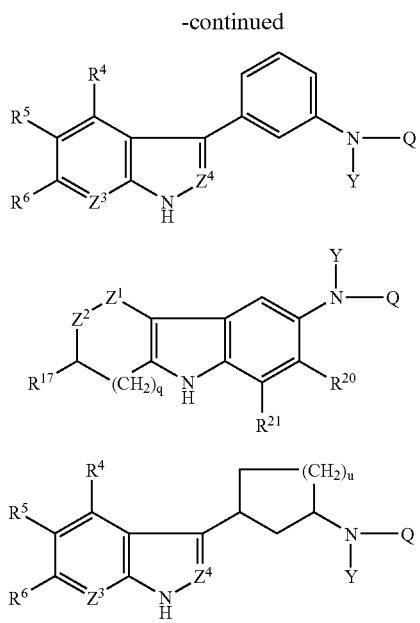

(IIIi)

(IIIj)

(IIIk)

wherein each symbol is as defined in I) and Q is hydrogen.

The compounds represented by the formula (IIa) to (IIk), their salts of inorganic acid such as hydrochloric acid, sulfuric acid and the like or organic acid such as acetic acid, trifluoroacetic acid and the like can be synthesized in accordance with the following processes 1) to 3);

1) An amino group of the compound represented by the formula (IIIa)~(IIIk) wherein Q is hydrogen is protected with amino protecting group such as t-butoxycarbonyl, benzyloxycarbonyl, allyloxycarbonyl and the like in accordance with the method described in PROTECTIVE GROUP IN ORGANIC SYNTHSIS. JOHN WILEY & SONS, INC. and the like.

2) The indole derivatives having an alkyloxycarbonylmethyl group on its nitrogen atom is synthesized by reacting the obtained compound in the above process with 1 to 5 eq. of a compound represented by the formula: $X^1$—$CH_2CO_2R^{12}$ wherein $X^1$ is halogen and $R^{12}$ is alkyl in an inactive solvent such as pyridine, acetonitrile, dichloromethane, THF, DMF, DMSO, acetone, methylethylketone, methylisobutylketone and the like in the presence of 1 to 5 eq. of a base such as sodium hydride, potassium hydride, potassium t-butoxide, potassium carbonate and the like at 0 to 100° C. for 1 h to 20 h. 0.1 to 1 eq. of a phase transfer catalyst such as tetrabutylammonium chloride, tetrabutylammonium bromide, tetrabutylammonium iodide, benzyltriethylammonium chloride, benzyltributylammonium chloride and the like may be added to the above reaction mixture.

3) Q, an amino protective group, is deprotected by the usual deprotecting reaction.

The compounds represented by the formula (IIIc) and (IIId), and the compounds represented by the formula (IIIa), (IIIb), and (IIIe) wherein Y is not hydrogen can be introduced into the compound of the formula (I) by the above mentioned sulfonylation and alkyloxycarbonylmethylation of nitrogen atom on the indole ring without protection of an amino group.

The compound represented by the formula (I) is a compound having a selective antagonistic activity against CRTH2 receptor but not having an antagonistic activity against $TXA_2$ receptor. Especially, the compounds represented by the following formula (Ia) to (Ie) are preferred as such compound.

A compound of the formula (Ia):

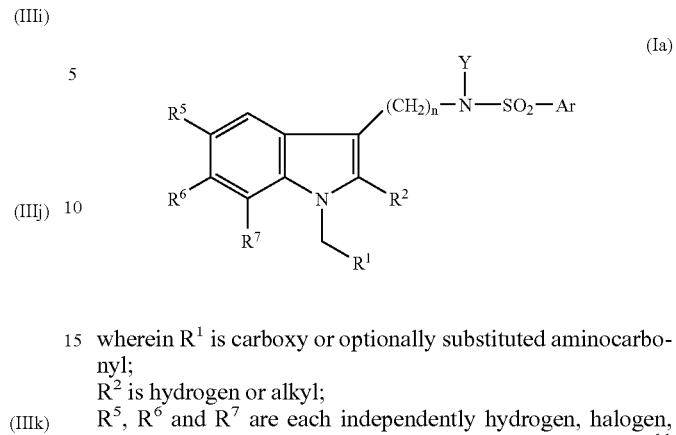

(Ia)

wherein $R^1$ is carboxy or optionally substituted aminocarbonyl;

$R^2$ is hydrogen or alkyl;

$R^5$, $R^6$ and $R^7$ are each independently hydrogen, halogen, alkyl, or a group represented by the formula: —$OR^{11}$ wherein $R^{11}$ is alkyl;

Y is hydrogen, alkyl, alkenyl, phenyl, phenylalkyl which may be substituted with one or more substituents selected from Substituents group A, naphthylalkyl which may be substituted with one or more substituents selected from Substituents group A, or thienylalkyl which may be substituted with one or more substituents selected from Substituents group A (Substituents group A: alkyl, alkyloxy, and nitro);

Ar is phenyl which may be substituted with one or more substituents selected from Substituents group B, biphenyl which may be substituted with one or more substituents selected from Substituents group B, thienyl which may be substituted with one or more substituents selected from Substituents group B or dibenzothienyl which may be substituted with one or more substituents selected from Substituents group B (Substituents group B: alkyl, alkyloxy, aryloxy, halogen, hydroxy, and benzyl); and n is 1, 2, or 3, a prodrug, a pharmaceutically acceptable salt, or a solvate thereof.

A compound represented by the formula (Ib):

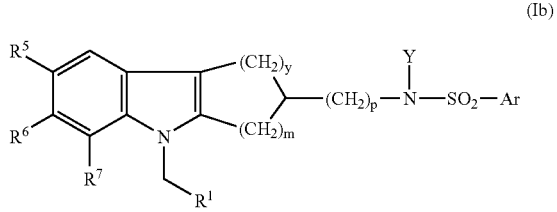

(Ib)

wherein $R^1$ is carboxy or optionally substituted aminocarbonyl;

$R^5$, $R^6$ and $R^7$ are each independently hydrogen, halogen, alkyl, or a group represented by the formula: —$OR^{11}$ wherein $R^{11}$ is alkyl;

Y is hydrogen, alkyl, alkenyl, phenyl, phenylalkyl which may be substituted with one or more substituents selected from Substituents group A, naphthylalkyl which may be substituted with one or more substituents selected from Substituents group A, or thienylalkyl which may be substituted with one or more substituents selected from Substituents group A (Substituents group A: alkyl, alkyloxy and nitro);

Ar is phenyl which may be substituted with one or more substituents selected from Substituents group A, biphenyl which may be substituted with one or more substituents selected from Substituents group A, thienyl which may be substituted with one or more substituents selected from Substituents group A, or dibenzothienyl which may be substituted with one or more substituents selected from Substituents group A (Substituents group A: halogen, alkyl, alkyloxy, aryloxy, hydroxy, and benzyl);

m is 1 or 2;
p is 0 or 1; and
y is 0, 1, or 2,
a prodrug, a pharmaceutically acceptable salt, or a solvate thereof.

A compound represented by the formula (Ic):

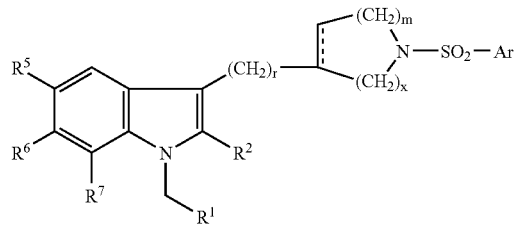

wherein $R^1$ is carboxy or optionally substituted aminocarbonyl;
$R^2$ is hydrogen or alkyl;
$R^5$, $R^6$ and $R^7$ are each independently hydrogen, halogen, alkyl, or a group represented by the formula: —$OR^{11}$ wherein $R^{11}$ is alkyl;
Ar is phenyl which may be substituted with one or more substituents selected from Substituents group B, biphenyl which may be substituted with one or more substituents selected from Substituents group B, thienyl which may be substituted with one or more substituents selected from Substituents group B, or dibenzothienyl which may be substituted with one or more substituents selected from Substituents group B (Substituents group B: alkyl, alkyloxy, aryloxy, halogen, hydroxy, and benzyl;
m is 1, 2, or 3;
r is 0 or 1; and
x is 0, 1, or 2,
a prodrug, a pharmaceutically acceptable salt, or a solvate thereof.

A compound represented by the formula (Id):

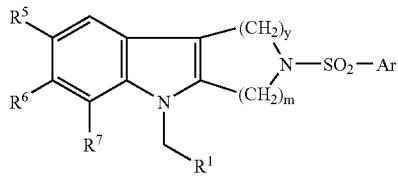

wherein $R^1$ is carboxy or optionally substituted aminocarbonyl;
$R^5$, $R^6$ and $R^7$ are each independently hydrogen, halogen, alkyl, or a group represented by the formula: —$OR^{11}$ wherein $R^{11}$ is alkyl;
Ar is phenyl which may be substituted with one or more substituents selected from Substituents group B, biphenyl which may be substituted with one or more substituents selected from Substituents group B, thienyl which may be substituted with one or more substituents selected from Substituents group B or dibenzothienyl which may be substituted with one or more substituents selected from Substituents group B (Substituents group B: alkyl, alkyloxy, aryloxy, halogen, hydroxy, and benzyl);
m is 1 or 2; and
y is 1 or 2,
a prodrug, a pharmaceutically acceptable salt, or a solvate thereof.

A compound represented by the formula (Ie):

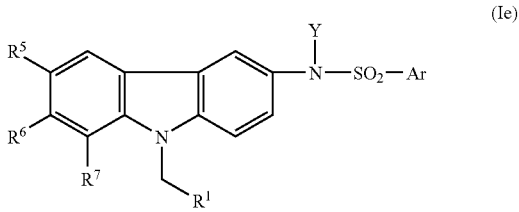

wherein $R^1$ is carboxy or optionally substituted aminocarbonyl;
$R^5$, $R^6$ and $R^7$ are each independently hydrogen, halogen, alkyl, or a group represented by the formula: —$OR^{11}$ wherein $R^{11}$ is alkyl;
Y is hydrogen, alkyl, alkenyl, phenyl, phenylalkyl which may be substituted with one or more substituents selected from Substituents group A, naphthylalkyl which may be substituted with one or more substituents selected from Substituents group A, or thienylalkyl which may be substituted with one or more substituents selected from Substituents group A (Substituents group A: alkyl, alkyloxy and nitro); and
Ar is phenyl which may be substituted with one or more substituents selected from Substituents group B, biphenyl which may be substituted with one or more substituents selected from Substituents group B, thienyl which may be substituted with one or more substituents selected from Substituents group B or dibenzothienyl which may be substituted with one or more substituents selected from Substituents group B (Substituents group B: alkyl, alkyloxy, aryloxy, halogen, hydroxy, and benzyl), a prodrug, a pharmaceutically acceptable salt, or a solvate thereof.

The term "solvate" includes, for example, solvates with organic solvents, hydrates, and the like. A solvate may coordinate with an arbitrary number of organic solvent molecules. A hydrate may coordinate with an arbitrary number of water molecules. A hydrate is preferred.

The term "compound of the present invention" herein used includes a pharmaceutically acceptable salt. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, maleic acid, fumaric acid, benzenesulfonic acid, p-toluenesulfonic acid, and the like). These salts can be formed by the usual method.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. The method of both selection and manufacture of appropriate prodrug derivatives is described in, for example. Design of Prodrugs, Elsevier. Amsterdam, 1985).

For instance, prodrugs such as an ester derivative which is prepared by reacting a basal acid compound with a suitable alcohol, or an amide derivative which is prepared by reacting a basal acid compound with a suitable amine are exemplified when the compounds according to present invention have a carboxylic group. Particularly preferred esters as prodrugs are methyl ester, ethyl ester, n-propyl ester, isopropyl ester, n-butyl ester, isobutyl ester, tert-butyl ester, morpholinoethyl ester, N,N-diethylglycolamido ester, and the like. For instance, prodrugs such as an acyloxy derivative which is prepared by reacting a basal hydroxy compound with a suitable acyl halide or a suitable acid anhydride, or an amide derivative which is prepared by reacting a basal acid compound with a suitable amine are exemplified when the compounds according to present invention have a hydroxy group. Particularly preferred acyloxy derivatives as prodrugs —$OCOC_2H_5$, —$OCO(t-Bu)$, —$OCOC_{15}H_{31}$, —$OCO(m-COONa-Ph)$, —$COCH_2CH_2COONa$, —$OCOCH(NH_2)CH_3$, —$OCOCH_2N(CH_3)_2$, and the like. For instance, prodrugs such as an amide derivative which is prepared by reacting a basal amino compound with a suitable acid halide or a suitable acid anhydride are exemplified when the compounds according to present invention have an amino group. Particularly preferred amide as prodrugs are —$NHCO(CH_2)_{20}CH_3$, —$NHCOCH(NH_2)CH_3$, and the like.

The compound of the present invention is not restricted to any particular isomers but includes all possible isomers and racemic modifications.

The compounds of the present invention show excellent CRTH2 receptor antagonism as described in examples mentioned later. Therefore, the pharmaceutical composition of the prsent invention may be used as a treating and/or preventing agent for allergic diseases having a relation to eosinophils, such as asthma, allergic rhinitis, allergic dermatitis, morbilli papulosi (guinea worm disease and the like), vasculitis, polyarteritis, dermal eosinophilic granuloma, autoimmune disease (e.g., multiple sclerosis, graft rejection, etc.), simple pulmonary eosinophilia, histiocytosis (Histiocytosis), pneumonia, aspergillosis, pleurisy, sarcoidosis, idiopathic pulmonary fibrosis, eosinophilic leucocytosis, filariasis, schistosomiasis, trichiniasis, coccidioidomycosis, tuberculous, bronchogenic cancer, lymphoma, Hodgkin's disease and the like.

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 0.1 to 100 mg/kg/day, and preferably 1 to 20 mg/kg/day for adult.

EXAMPLE

The following examples and experiments are provided to further illustrate the present invention and are not to be construed as limiting the scope.

Abbreviations described below are used in the following examples.

Me: Methyl
Et: Ethyl
iPr: isopropyl
Ph: Phenyl
Boc: t-butoxycarbonyl
THF: tetrahydrofuran
MeOH: Methanol
Naphthyl: naphthyl
Benzyl: benzyl
Thienyl: thienyl
Biphenyl: biphenyl
Dibenzothiophene: dibenzothiophene Example 1

Compound Ia-9 and Compound Ia-51

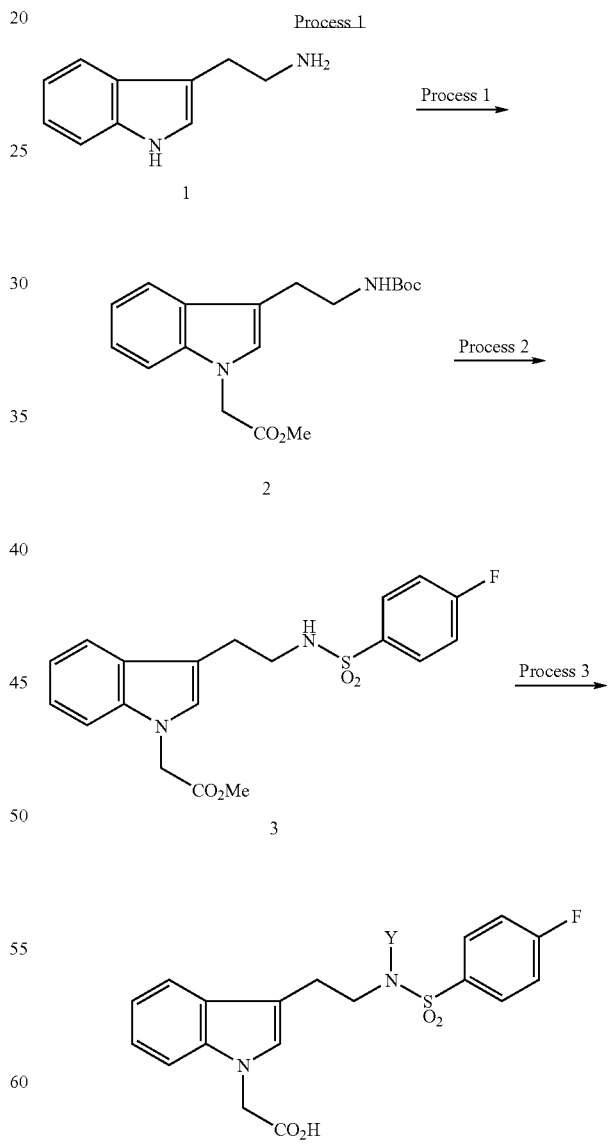

Y = H : Ia-9
Y = $CH_2Ph$ : Ia-51

To a solution of tryptamine (1) (20 g, 0.125 mol) in dioxane (160 mL)-water (80 mL) was added a mixture of sodium carbonate (39.7 g, 0.374 mol) and di-tert-butyl dicarbonate (31.5 mL, 0.137 mol) in dioxane (20 mL) at ice-cooling and the resulting mixture was stirred for 2.5 h. After adding 2 mol/L hydrochloric acid to the reaction mixture, the mixture was extracted with ethyl acetate. The organic layer was washed with brine, dried and concentrated in vacuo to give a residue (42.49 g). 7.0 g of the residue was dissolved in methyl ethyl ketone (150 mL). To the mixture were added potassium carbonate (11.15 g, 80.7 mmol) and methyl bromoacetate (10.2 mL, 0.108 mol), and the resulting mixture was heated for 48 h at reflux. The mixture was diluted with ethyl acetate. The resulting mixture was washed with dilute hydrochloric acid and aqueous sodium hydrogencarbonate respectively, dried and concentrated in vacuo. The residue was subjected to silica gel column chromatography (hexane:ethyl acetate=2:1) to give compound (2) (4.57 g; yield 51%).

Process 2

To a solution of Compound (2) (1.5 g, 4.5 mmol) in dichloromethane (10 mL) was added trifluoroacetic acid (10 mL) and the mixture was stirred for 10 min. at room temperature. The reaction mixture was concentrated in vacuo and neutralized with 2 mol/L aqueous sodium carbonate. The resulting mixture was extracted with ethyl acetate. The organic layer was washed with brine, dried and concentrated in vacuo to give a residue (983 mg). 120 mg of the residue was dissolved in dichloromethane (3 mL). To a solution were added triethylamine (0.108 mL, 0.775 mmol) and 4-fluorobenzenesulfonylchloride (121 mg, 0.622 mmol) and the resulting mixture was stirred for 2 h at room temperature. The mixture was diluted with ethyl acetate, washed with dilute hydrochloric acid and aqueous sodium hydrogencarbonate respectively, dried, and concentrated in vacuo. The residue was subjected to silica gel column chromatography (hexane:ethyl acetate=3:2) to give compound (3) (99 mg; yield 46%).

Process 3

To a solution of compound (3) (99 mg, 0.254 mmol) in MeOH (1.5 mL)-THF (1.5 mL) was added 2 mol/L aqueous sodium hydroxide (0.76 mL, 1.52 mmol) and the resulting mixture was stirred for 5.5 h at room temperature. The mixture was acidified with dilute hydrochloric acid and extracted with ethyl acetate. The organic layer was washed with water and brine, dried, and concentrated in vacuo to give compound (Ia-9) (79 mg; yield 83%). The physical property of the compound is shown in Table 12.

Process 4

To a solution of compound (3) (132 mg, 0.339 mmol) in N,N-dimethylformamide (2 ml) were added benzyl bromide (48 μL, 0.407 mmol) and potassium carbonate (70 mg, 0.509 mmol) and the resulting mixture was stirred for 21.5 h at 50° C. The reaction mixture was poured in water and extracted with ethyl acetate. The organic layer was washed with brine, dried, and concentrated in vacuo. The residue was dissolved in MeOH (2 mL)-THF (2 mL). To the solution was added 2 mol/L aqueous sodium hydroxide (1.1 mL, 2.2 mmol) and the mixture was stirred for 5 h at room temperature. The resulting mixture was diluted with water and washed with diethyl ether. The aqueous layer was acidified with dilute hydrochloric acid and extracted with ethyl acetate. The organic layer was washed with water and brine, dried, and concentrated in vacuo to give compound (Ia-51) (175 mg; yield 99%). The physical property of the compound is shown below.

Example 2

Compound Ib-20 and Compound Ib-29

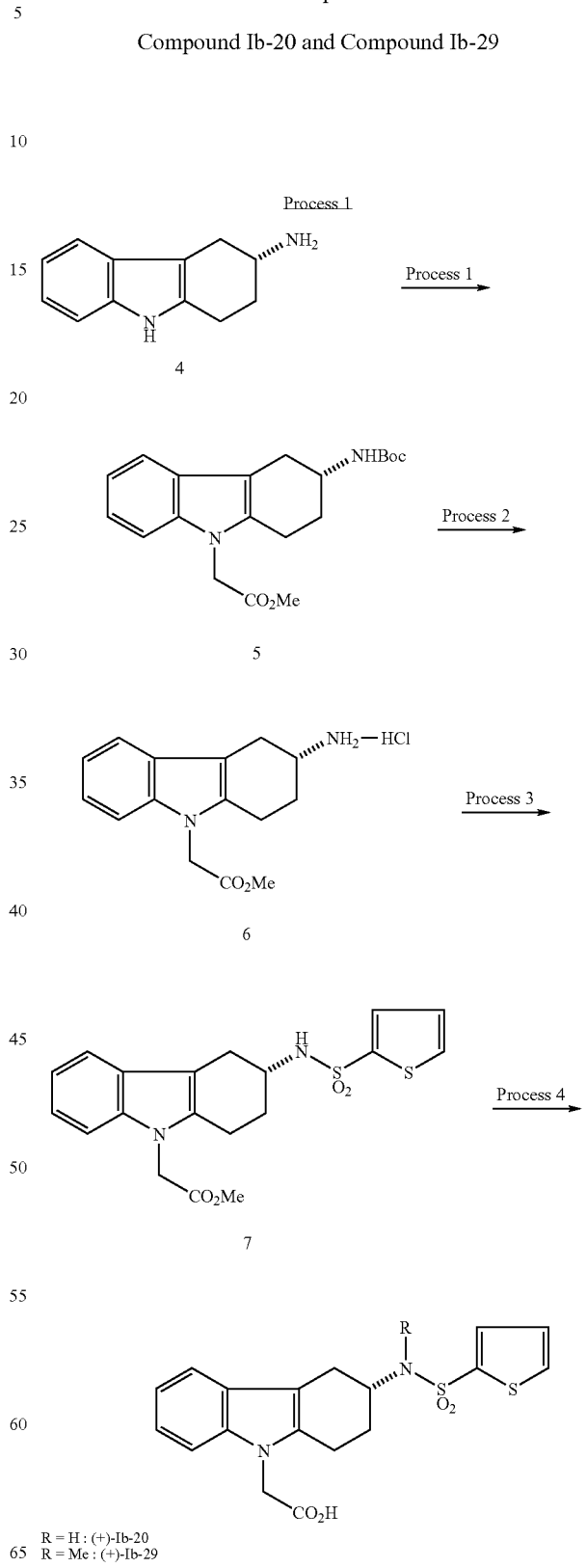

To a solution of (3R)-3-amino-1,2,3,4-tetrahydrocarbozole (4) (3.33 g, 17.9 mmol) described in JP-A-62-198659 in 1,4-dioxane (33 mL) was added di-tert-butyl dicarbonate (4.1 g, 18.8 mmol) and the resulting mixture was stirred for 2 h at room temperature. The residue obtained by vacuum concentration was dissolved in methyl ethyl ketone (52 mL). To the mixture were added potassium carbonate (4.52 g, 32.7 mmol), benzyltriethylammonium chloride (0.74 g, 3.26 mmol), and methyl bromoacetate (5.00 g, 32.7 mmol) and the mixture was heated for 4 h at reflux. The insoluble residue was filtered off and the filtrate was concentrated in vacuo. The residue was diluted with ethyl acetate, washed with water, dried, and concentrated in vacuo. The residue was crystallized from hexane-diethyl ether to give compound (5) (4.36 g; yield 68%, mp. 127-130° C.).

Process 2

To a solution of compound (5) (4.25 g, 11.9 mmol) in ethyl acetate (12 mL) was added 4 mol/L hydrochloric acid-ethyl acetate (12 mL, 48.0 mmol) and the resulting mixture was stirred for 2 h at room temperature. The precipitated crystalline was filtered off and washed with ethyl acetate to give compound (6) (3.44 g; yield 98%).

Process 3

To a solution of compound (6) (295 mg, 1.0 mmol) in THF (6 mL) were added triethylamine (0.30 g, 3.0 mmol) and 2-thiophenesulfonyl chloride (296 mg, 1.62 mmol), and the resulting mixture was stirred for 16 h at room temperature. The reaction mixture was diluted with water and extracted with ethyl acetate. The organic layer was washed with dilute hydrochloric acid and water, dried over magnesium sulphate, and concentrated in vacuo. The residue was subjected to silica gel column chromatography (hexane:ethyl acetate=1:1) to give compound (7) (379 mg; yield 94%).

Process 4

To a solution of compound (7) (371 mg, 0.917 mmol) in MeOH (1.2 mL)-THF (1.2 mL) was added 4 mol/L aqueous sodium hydroxide (0.6 mL, 2.4 mmol) and the resulting mixture was stirred for 2 h at room temperature. The reaction mixture was diluted with water, acidified with dilute hydrochloric acid, and extracted with ethyl acetate. The organic layer was washed with water, dried over magnesium sulphate, and concentrated in vacuo to give compound (+)-Ib-20 (343 mg; yield 91%).

Process 5

To a solution of compound (7) (243 mg, 0.622 mmol) in N,N-dimethylformamide (2 mL) were added potassium carbonate (0.26 g 1.87 mmol) and methyl iodide (0.27 g, 1.90 mmol) and the resulting mixture was stirred for 2.5 h at room temperature. The reaction mixture was diluted with ethyl acetate, washed with water, dried, and concentrated in vacuo. The residue was dissolved in MeOH (1 mL)-THF (1 mL). To the mixture was added 4 mol/L aqueous sodium hydroxide (0.4 mL, 1.6 mmol) and the mixture was stirred for 3 h at room temperature. The reaction mixture was diluted with water, acidified with dilute hydrochloric acid, and extracted with ethyl acetate. The organic layer was washed with water, dried, and concentrated in vacuo. The residue was crystallized form hexane-ethyl acetate to give compound (+)-Ib-29 (217 mg; yield 88%). The physical property of the compound is shown below.

Example 3

Compound Ic-14

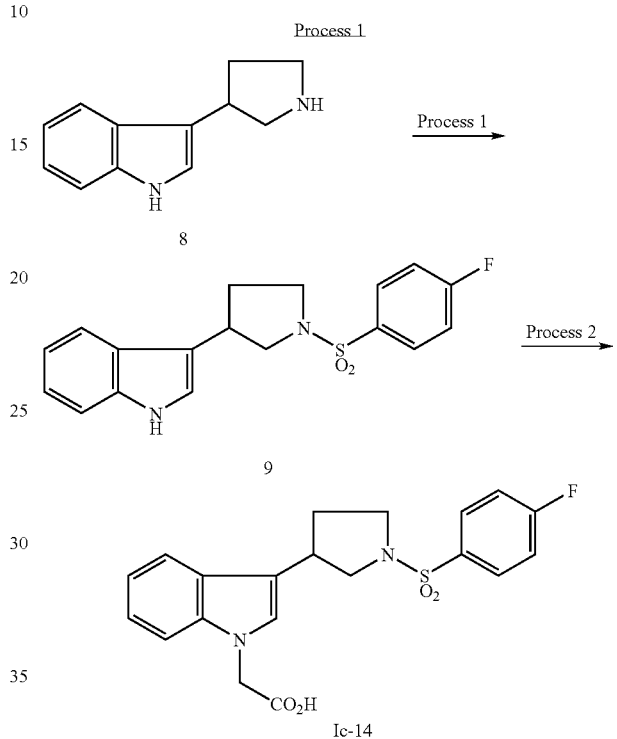

To a solution of compound (8) (610 mg, 3.28 mmol, Synthesis, 443 (1997)) in THF (6 mL) were added triethylamine (0.50 g, 4.92 mmol) and 4-fluorobenzenesulfonyl chloride (0.70 g, 3.60 mmol), and the resulting mixture was stirred for 1.5 h at room temperature. The reaction mixture was diluted with water and extracted with ethyl acetate. The organic layer was washed with dilute hydrochloric acid and water respectively, dried, and concentrated in vacuo. The resulting residue was subjected to silica gel column chromatography (toluene-ethyl acetate=5:1) to give compound (9) (856 mg; yield 76%).

Process 2

To a solution of compound (9) (800 mg, 2.32 mmol) in methyl ethyl ketone (8 mL) were added potassium carbonate (0.96 g, 6.96 mmol), benzyltriethylammonium chloride (106 mg, 0.464 mmol), and methyl bromoacetate (1.06 g, 6.96 mmol), and the resulting mixture was heated for 2.5 h at reflux. The reaction mixture was diluted with water and extracted with toluene. The organic layer was washed with water, dried, and concentrated in vacuo. The resulting residue was subjected to silica gel column chromatography (toluene-ethyl acetate=5:1) and obtained material was dissolved in MeOH (2.8 ml)-THF (1.4 ml). To the solution was added 4 mol/L aqueous sodium hydroxide (1.4 mL, 5.6 mmol) and the mixture was stirred for 2 h at room temperature. The reaction mixture was diluted with water, acidified with dilute hydrochloric acid, and extracted with ethyl acetate. The organic layer was washed with water, dried, and concentrated in vacuo. The resulting residue was crystallized from hexane-ethyl acetate to give compound Ic-14 (717 mg; yield 79%). The physical property of the compound is shown below.

Example 4

Compound Id-2

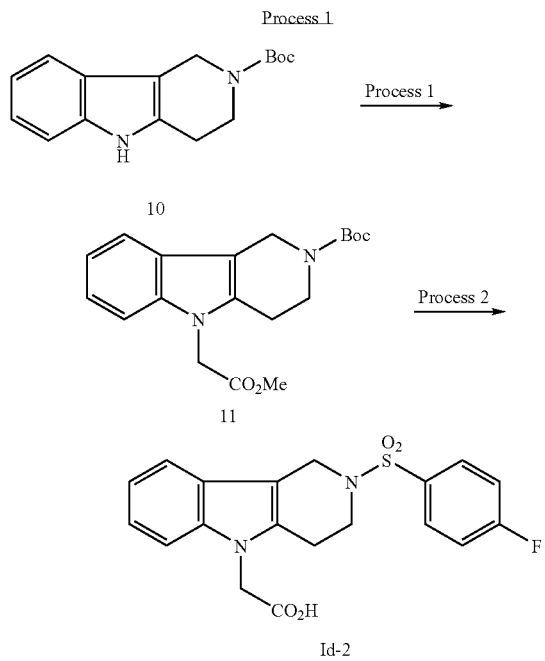

To a solution of compound (10) (1.25 g, 4.59 mmol) in methyl ethyl ketone (20 mL) prepared by the method described in Journal of Organic Chemistry, 62, 2676(1997) were added potassium carbonate (1.9 g, 13.77 mmol), methyl bromoacetate (1.74 mL, 18.36 mmol), and benzyltriethylammonium chloride (209 mg, 0.92 mmol), and the resulting mixture was heated for 20 h at reflux. The mixture was diluted with ethyl acetate, washed with water and brine respectively, dried, and concentrated in vacuo. The residue was subjected to silica gel column chromatography (hexane-ethyl acetate, 3:1) to give compound (11) (1.18 g; yield 75%).

Process 2

To a solution of compound (11) (355 mg, 1.03 mmol) in diethyl ether (0.5 mL) was added 4 mol/L hydrochloric acid-ethyl acetate (2.06 mL, 8.24 mmol), and the resulting mixture was stirred for 3 h at room temperature. The precipitated hydrochloric acid salt was filtered off, washed with diethyl ether, and dissolved in THF (3 mL). To this mixture were added triethylamine (0.37 mL, 2.66 mmol) and 4-fluorobenzenesulfonyl chloride (365 mg, 1.88 mmol). The resulting mixture was stirred for 16 h at room temperature, diluted with ethyl acetate, washed with dilute hydrochloric acid and aqueous sodium hydrogencarbonate respectively, dried, and concentrated in vacuo. The residue was subjected to silica gel column chromatography (hexane:ethyl acetate=2:1). The product material was dissolved in MeOH (8 mL)-THF (4 mL). To the mixture was added 1 mol/L aqueous sodium hydroxide (1.8 mL, 1.8 mmol) and the resulting mixture was stirred for 16 h at room temperature. The reaction mixture was diluted with water and washed with diethyl ether. To the aqueous layer was added dilute hydrochloric acid and the precipitated crystalline was filtered off, washed with water, and dried to give compound Id-2 (192 mg; yield 48%). The physical property of the compound is shown below.

Example 5

Compound Ie-2 and Compound Ie-5

To a solution of compound (12) (509 mg, 2 mmol) prepared by the method described in JP-A-8-169879 in THF (10 mL) were added triethylamine (0.84 mL, 6 mmol) and 4-fluorobenzenesulfonyl chloride (506 mg, 2.6 mmol), and the resulting mixture was stirred for 19 h at room temperature. The mixture was diluted with ethyl acetate, washed with dilute hydrochloric acid and aqueous sodium hydrogencarbonate respectively, dried and concentrated in vacuo. The residue was subjected to silica gel column chromatography (toluene:ethyl acetate=4:1) to give compound (13) (725 mg; yield 88%).

Process 2

To a solution of compound (13) (309 mg, 0.75 mmol) in MeOH (6 mL)-THF (3 mL) was added 1 mol/L aqueous sodium hydroxide (1.9 mL, 1.9 mmol) and the resulting mixture was stirred for 21 h at room temperature. The mixture was acidified with dilute hydrochloric acid and extracted with ethyl acetate. The organic layer was washed with water and brine, dried, and concentrated in vacuo. The residue was crystallized from ethyl acetate-hexane to give compound Ie-2 (287 mg; yield 96%). The physical property of the compound is shown below.

Process 3

To a solution of compound (13) (363 mg, 0.88 mmol) in N,N-dimethylformamide (3.6 ml) were added methyl iodide (250 mg, 1.76 mmol) and potassium carbonate (182 mg, 1.32 mmol), and the resulting mixture was stirred for 19 h at room temperature. The reaction mixture was poured into water, extracted with ethyl acetate-hexane (1:2). The organic layer was washed with brine, dried, concentrated in vacuo. The residue was dissolved in MeOH-THF (2:1). To the mixture was added 1 mol/L aqueous sodium hydroxide (1.8 mL, 1.8 mmol) and the resulting mixture was stirred for 26 h at room temperature. The mixture was diluted with water and washed with diethyl ether. The aqueous layer was acidified with dilute hydrochloric acid and extracted with ethyl acetate. The organic layer was washed with water and brine, dried, and concentrated in vacuo. The residue was crystallized from hexane to give compound Ie-5 (293 mg; yield 84%). The physical property of the compound is shown below.

Example 6

Compound Ih-1

Process 1

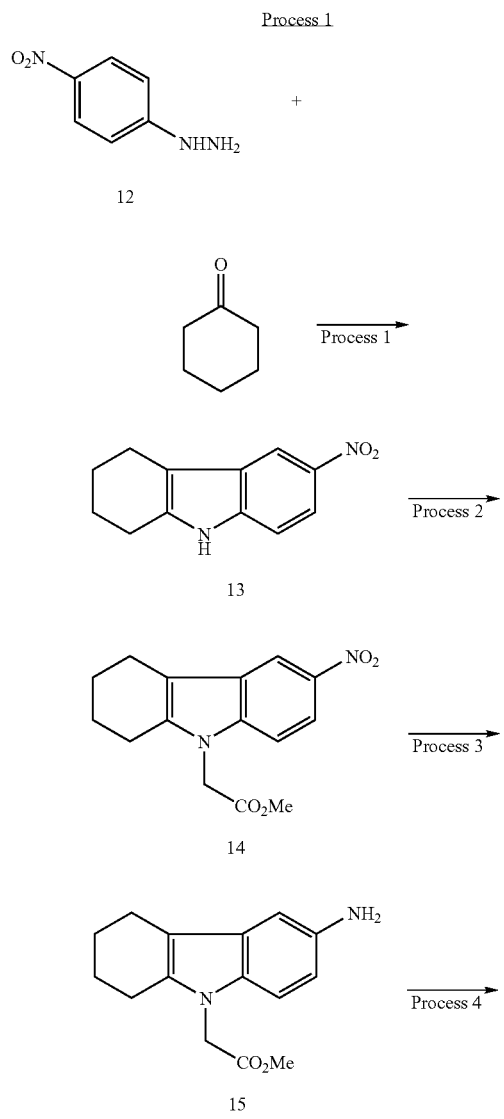

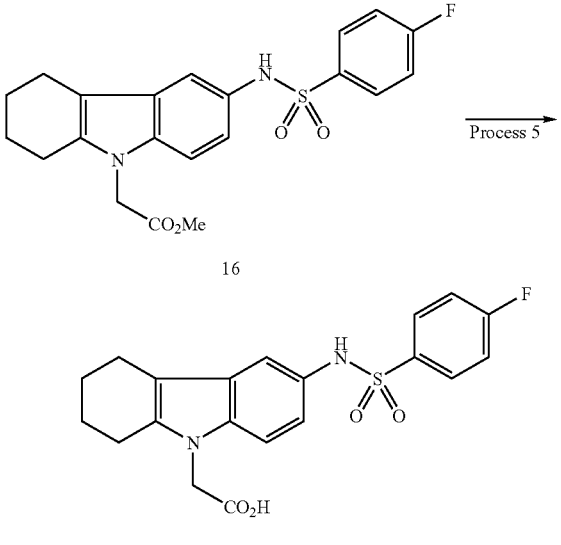

The mixture of p-nitrophenylhydrazine (12) (15.0 g, 97.9 mmol) and cyclohexanone (10.15 ml, 97.9 mmol) in acetic acid (45 ml) was heated and stirred for 20 minutes at 60° C. To the reaction mixture was added conc. hydrochloric acid (15 ml) and the resulting mixture was heated for 1.5 h at reflux. To the reaction mixture was added water (50 ml), heated for 10 minutes at reflux, and allowed to cool to room temperature. The precipitated crystal was filtered off, washed with water, and recrystallized from ethanol-water to give 6-nitrotetrahydrocarbazole (13) (17.0 g; yield 80%).

Process 2

The mixture of compound (13) (6.80 g, 31.44 mmol), methyl bromoacetate (8.93 ml, 94.32 mmol), potassium carbonate (13 g, 94 mmol), benzyltriethylammonium chloride (1.43 g, 6.28 mmol) in methyl ethyl ketone (100 ml) was heated for 1 h at reflux. The reaction mixture was concentrated in vacuo and the resulting residue was diluted with ethyl acetate, washed with water, dried, and concentrated in vacuo. The residue was recrystallized from ethyl acetate-hexane to give compound (14) (7.93 g; yield 87%).

Process 3

The mixture of compound (14) (7.92 g, 27.47 mmol) and palladium hydroxide (20% wt, 1.0 g) in THF (70 ml) and MeOH (14 ml) was stirred for 7 h under hydrogen atmosphere. After removing the catalyst, the reaction mixture was concentrated in vacuo. The residue was subjected to silica gel column chromatography (hexane:ethyl acetate=1:1) to give compound (15) (5.89 g; yield 83%).

Process 4

To a solution of compound (15) (3.89 g, 15.0 mmol) in THF (30 ml) were added triethylamine (4.18 ml, 30 mmol) and 4-fluorobenzenesulfonyl chloride (3.07 g, 15.8 mmol), and the resulting mixture was stirred for 1 h at room temperature. To the reaction mixture was added dilute hydrochloric acid and the mixture was extracted with ethyl acetate. The organic layer was washed with water, dried, and concentrated in vacuo. The residue was crystallized from ethyl acetate-hexane to give compound (16) (5.93 g; yield 95%).

Process 5

To a solution of compound (16) (350 mg, 0.84 mmol) in MeOH (4 ml)-THF (2 ml) was added 2 mol/L aqueous sodium hydroxide (1 mL, 2 mmol) and the resulting mixture was stirred for 15 h at room temperature. To the reaction mixture was added dilute hydrochloric acid and the mixture was extracted with ethyl acetate. The organic layer was washed with water, dried, and concentrated in vacuo. The residue was crystallized from ethyl acetate-hexane to give compound Ih-1 (268 mg; yield 79%). The physical property of the compound is shown below.

The compounds which were shown in the following Tables were synthesized in a manner similar to those described in Examples 1 to 6.

TABLE 1

| No | $R^1$ | $R^2$ | $R^4$ | $R^5$ | $R^6$ | $R^7$ | $R^{15}$ | n | Y | Ar |
|---|---|---|---|---|---|---|---|---|---|---|
| Ia-1 | COOH | H | H | H | H | H | H | 1 | H | $C_6H_5$ |
| Ia-2 | COOH | H | H | H | H | H | H | 1 | H | 4-F—$C_6H_4$ |
| Ia-3 | COOH | H | H | H | H | H | H | 1 | Me | $C_6H_5$ |
| Ia-4 | COOH | H | H | H | H | H | H | 1 | Me | 4-F—$C_6H_4$ |
| Ia-5 | COOH | H | H | H | H | H | H | 1 | $CH_2C_6H_5$ | $C_6H_5$ |
| Ia-6 | COOH | H | H | H | H | H | H | 1 | $CH_2C_6H_5$ | 4-F—$C_6H_4$ |
| Ia-7 | COOH | H | H | H | H | H | H | 2 | H | $C_6H_5$ |
| Ia-8 | COOH | H | H | H | H | H | H | 2 | H | 2-F—$C_6H_4$ |
| Ia-9 | COOH | H | H | H | H | H | H | 2 | H | 4-F—$C_6H_4$ |
| Ia-10 | COOH | H | H | H | H | H | H | 2 | H | 2-Me—$C_6H_4$ |
| Ia-11 | COOH | H | H | H | H | H | H | 2 | H | 4-Me—$C_6H_4$ |
| Ia-12 | COOH | H | H | H | H | H | H | 2 | H | 4-OMe—$C_6H_4$ |
| Ia-13 | COOH | H | H | H | H | H | H | 2 | H | 2-thienyl |
| Ia-14 | COOH | H | H | H | H | H | H | 2 | H | 3-thienyl |
| Ia-15 | COOH | H | H | H | H | H | H | 2 | H | 4-F-biphenyl |
| Ia-16 | COOH | H | H | H | H | H | H | 2 | H | $C_6H_4$-4-$OC_6H_5$ |
| Ia-17 | COOH | H | H | H | H | H | H | 2 | H | dibenzothiophene-3-yl |
| Ia-18 | COOH | Me | H | H | H | H | H | 2 | H | $C_6H_5$ |
| Ia-19 | COOH | Me | H | H | H | H | H | 2 | H | 2-F—$C_6H_4$ |
| Ia-20 | COOH | Me | H | H | H | H | H | 2 | H | 4-F—$C_6H_4$ |
| Ia-21 | COOH | Me | H | H | H | H | H | 2 | H | 2-thienyl |
| Ia-22 | COOH | Me | H | H | H | H | H | 2 | H | 3-thienyl |
| Ia-23 | COOH | H | H | H | H | Me | H | 2 | H | $C_6H_5$ |
| Ia-24 | COOH | H | H | H | H | Me | H | 2 | H | 2-F—$C_6H_4$ |
| Ia-25 | COOH | H | H | H | H | Me | H | 2 | H | 4-F—$C_6H_4$ |

TABLE 2

| No | $R^1$ | $R^2$ | $R^4$ | $R^5$ | $R^6$ | $R^7$ | $R^{15}$ | n | Y | Ar |
|---|---|---|---|---|---|---|---|---|---|---|
| Ia-26 | COOH | H | H | H | H | Me | H | 2 | H | 4-OMe—$C_6H_4$ |
| Ia-27 | COOH | H | H | H | H | Me | H | 2 | H | 3-thienyl |
| Ia-28 | COOH | H | H | OMe | H | H | H | 2 | H | 4-F—$C_6H_4$ |
| Ia-29 | COOH | H | H | OMe | H | H | H | 2 | H | 2-thienyl |
| Ia-30 | COOH | H | H | Cl | H | H | H | 2 | H | $C_6H_5$ |
| Ia-31 | COOH | H | H | Cl | H | H | H | 2 | H | 2-F—$C_6H_4$ |
| Ia-32 | COOH | H | H | Cl | H | H | H | 2 | H | 4-F—$C_6H_4$ |
| Ia-33 | COOH | H | H | Cl | H | H | H | 2 | H | 4-OMe—$C_6H_4$ |
| Ia-34 | COOH | H | H | F | H | H | H | 2 | H | $C_6H_5$ |
| Ia-35 | COOH | H | H | F | H | H | H | 2 | H | 2-F—$C_6H_4$ |
| Ia-36 | COOH | H | H | F | H | H | H | 2 | H | 4-F—$C_6H_5$ |
| Ia-37 | COOH | H | H | H | F | H | H | 2 | H | 4-F—$C_6H_5$ |
| Ia-38 | COOH | H | H | H | H | H | H | 2 | Me | $C_6H_5$ |

TABLE 2-continued

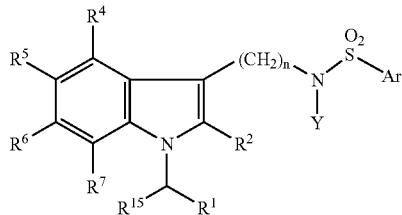

| No | $R^1$ | $R^2$ | $R^4$ | $R^5$ | $R^6$ | $R^7$ | $R^{15}$ | n | Y | Ar |
|---|---|---|---|---|---|---|---|---|---|---|
| Ia-39 | COOH | H | H | H | H | H | H | 2 | Me | 4-F—$C_6H_4$ |
| Ia-40 | COOH | H | H | H | H | H | H | 2 | Me | 3-thienyl |
| Ia-41 | COOH | Me | H | H | H | H | H | 2 | Me | 4-F—$C_6H_4$ |
| Ia-42 | COOH | H | H | H | H | Me | H | 2 | Me | 4-F—$C_6H_4$ |
| Ia-43 | COOH | H | H | OMe | H | H | H | 2 | Me | 4-F—$C_6H_4$ |
| Ia-44 | COOH | H | H | Cl | H | H | H | 2 | Me | 4-F—$C_6H_4$ |
| Ia-45 | COOH | H | H | F | H | H | H | 2 | Me | 4-F—$C_6H_4$ |
| Ia-46 | COOH | H | H | H | F | H | H | 2 | Me | 4-F—$C_6H_5$ |
| Ia-47 | COOH | H | H | H | H | H | H | 2 | $CH_2CH=CH_2$ | 4-F—$C_{64}$ |
| Ia-48 | COOH | H | H | H | H | H | H | 2 | iPr | 4-F—$C_6H_4$ |
| Ia-49 | COOH | H | H | H | H | H | H | 2 | $C_6H_5$ | 4-F—$C_6H_4$ |
| Ia-50 | COOH | H | H | H | H | H | H | 2 | $CH_2C_6H_5$ | $C_6H_5$ |
| Ia-51 | COOH | H | H | H | H | H | H | 2 | $CH_2C_6H_5$ | 4-F—$C_6H_4$ |
| Ia-52 | CONHMs | H | H | H | H | H | H | 2 | $CH_2C_6H_5$ | 4-F—$C_6H_4$ |

TABLE 3

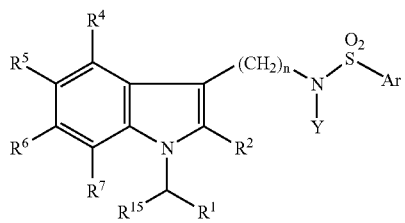

| No | $R^1$ | $R^2$ | $R^4$ | $R^5$ | $R^6$ | $R^7$ | $R^{15}$ | n | Y | Ar |
|---|---|---|---|---|---|---|---|---|---|---|
| Ia-53 | COOH | H | H | H | H | H | H | 2 | $CH_2C_6H_5$ | 4-OMe—$C_6H_4$ |
| Ia-54 | COOH | H | H | H | H | H | H | 2 | $CH_2C_6H_5$ | 3-thienyl |
| Ia-55 | COOH | Me | H | H | H | H | H | 2 | $CH_2C_6H_5$ | 4-F—$C_6H_4$ |
| Ia-56 | COOH | H | H | H | H | Me | H | 2 | $CH_2C_6H_5$ | 4-F—$C_6H_4$ |
| Ia-57 | COOH | H | H | OMe | H | H | H | 2 | $CH_2C_6H_5$ | 4-F—$C_6H_4$ |
| Ia-58 | COOH | H | H | Cl | H | H | H | 2 | $CH_2C_6H_5$ | 4-F—$C_6H_4$ |
| Ia-59 | COOH | H | H | F | H | H | H | 2 | $CH_2C_6H_5$ | 4-F—$C_6H_4$ |
| Ia-60 | COOH | H | H | H | F | H | H | 2 | $CH_2C_6H_5$ | 4-F—$C_6H_5$ |
| Ia-61 | COOH | H | H | H | H | H | H | 2 | $CH_2C_6H_4$2-Me | 4-F—$C_6H_4$ |
| Ia-62 | COOH | H | H | H | H | H | H | 2 | $CH_2C_6H_4$-4-OMe | 4-F—$C_6H_4$ |
| Ia-63 | COOH | H | H | H | H | H | H | 2 | $CH_2C_6H_4$4-$NO_2$ | 4-F—$C_6H_4$ |
| Ia-64 | COOH | H | H | H | H | H | H | 2 | $CH_2$-1-naphthyl | 4-F—$C_6H_4$ |
| Ia-65 | COOH | H | H | H | H | H | H | 2 | $CH_2$-2-thienyl | 4-F—$C_6H_4$ |
| Ia-66 | COOH | H | H | H | H | H | H | 2 | $CH_2CH_2C_6H_5$ | 4-F—$C_6H_4$ |
| Ia-67 | COOH | H | H | H | H | H | H | 3 | H | $C_6H_5$ |
| Ia-68 | COOH | H | H | H | H | H | H | 3 | H | 2-F—$C_6H_4$ |
| Ia-69 | COOH | H | H | H | H | H | H | 3 | H | 4-F—$C_6H_4$ |
| Ia-70 | COOH | H | H | H | H | H | H | 3 | H | 2-Me—$C_6H_4$ |
| Ia-71 | COOH | H | H | H | H | H | H | 3 | H | 4-Me—$C_6H_4$ |
| Ia-72 | COOH | H | H | H | H | H | H | 3 | H | 4-OMe—$C_6H_4$ |
| Ia-73 | COOH | H | H | H | H | H | H | 3 | H | 2-thienyl |
| Ia-74 | COOH | H | H | H | H | H | H | 3 | H | $C_6H_4$-4-$OC_6H_5$ |
| Ia-75 | COOH | Me | H | H | H | H | H | 3 | H | $C_6H_5$ |
| Ia-76 | COOH | Me | H | H | H | H | H | 3 | H | 4-F—$C_6H_4$ |
| Ia-77 | COOH | H | H | Cl | H | H | H | 3 | H | $C_6H_5$ |
| Ia-78 | COOH | H | H | Cl | H | H | H | 3 | H | 2-F—$C_6H_4$ |

TABLE 4

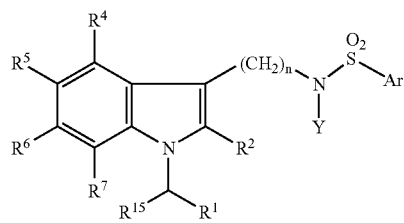

| No | R¹ | R² | R⁴ | R⁵ | R⁶ | R⁷ | R¹⁵ | n | Y | Ar |
|---|---|---|---|---|---|---|---|---|---|---|
| Ia-79  | COOH | H  | H | Cl | H | H | H  | 3 | H | 4-F—$C_6H_4$ |
| Ia-80  | COOH | H  | H | H  | H | H | H  | 3 | Me | $C_6H_5$ |
| Ia-81  | COOH | H  | H | H  | H | H | H  | 3 | Me | 4-F—$C_6H_4$ |
| Ia-82  | COOH | H  | H | H  | H | H | H  | 3 | Me | 3-thienyl |
| Ia-83  | COOH | Me | H | H  | H | H | H  | 3 | Me | 4-F—$C_6H_4$ |
| Ia-84  | COOH | H  | H | H  | H | H | H  | 3 | $CH_2C_6H_5$ | $C_6H_5$ |
| Ia-85  | COOH | H  | H | H  | H | H | H  | 3 | $CH_2C_6H_5$ | 4-F—$C_6H_4$ |
| Ia-86  | COOH | H  | H | H  | H | H | H  | 3 | $CH_2C_6H_5$ | 3-thienyl |
| Ia-87  | COOH | H  | H | H  | H | H | H  | 2 | $CH_2CH_2C_6H_5$ | 4-Me—$C_6H_4$ |
| Ia-88  | COOH | H  | H | H  | H | H | H  | 2 | H | 4-Cl-$C_6H_4$ |
| Ia-89  | COOH | H  | H | F  | H | H | H  | 2 | H | 4-OMe—$C_6H_4$ |
| Ia-90  | COOH | H  | H | F  | H | H | H  | 2 | H | 2-thienyl |
| Ia-91  | COOH | H  | H | H  | H | H | H  | 2 | $CH_2CH_2C_6H_5$ | 2-thienyl |
| Ia-92  | COOH | H  | H | Cl | H | H | H  | 2 | $CH_2CH_2C_6H_5$ | 4-F—$C_6H_4$ |
| Ia-93  | COOH | H  | H | H  | H | H | H  | 2 | $CH_2CH{=}CHC_6H_5$ | 4-F—$C_6H_4$ |
| Ia-94  | COOH | H  | H | H  | H | H | H  | 2 | $CH_2CH_2CH_2C_6H_5$ | 4-F—$C_6H_4$ |
| Ia-95  | COOH | H  | H | F  | H | H | H  | 2 | H | 4-Me—$C_6H_4$ |
| Ia-96  | COOH | H  | H | F  | H | H | H  | 2 | H | 2-naphthyl |
| Ia-97  | COOH | H  | H | F  | H | H | H  | 2 | H | 4-$NO_2$—$C_6H_4$ |
| Ia-98  | COOH | H  | H | F  | H | H | H  | 2 | H | 1-naphthyl |
| Ia-99  | COOH | H  | H | F  | H | H | H  | 2 | H | 4-CN—$C_6H_4$ |
| Ia-100 | COOH | H  | H | OH | H | H | H  | 2 | H | 2-F—$C_6H_4$ |
| Ia-101 | COOH | F  | H | H  | H | H | H  | 2 | H | 4-F—$C_6H_4$ |
| Ia-102 | COOH | F  | H | H  | H | H | H  | 2 | Me | 4-F—$C_6H_4$ |
| Ia-103 | COOH | F  | H | H  | H | H | H  | 2 | $CH_2C_6H_5$ | 4-F—$C_6H_4$ |
| Ia-104 | COOH | H  | H | Cl | H | H | Me | 2 | H | 4-F—$C_6H_4$ |

TABLE 5

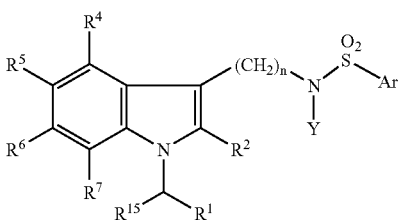

| No | R¹ | R² | R⁴ | R⁵ | R⁶ | R⁷ | R¹⁵ | n | Y | Ar |
|---|---|---|---|---|---|---|---|---|---|---|
| Ia-105 | COOH | H | H | Cl | H | H | Me | 2 | Me | 4-F—$C_6H_4$ |
| Ia-106 | COOH | H | H | Cl | H | H | Me | 2 | $CH_2C_6H_5$ | 4-F—$C_6H_4$ |

TABLE 6

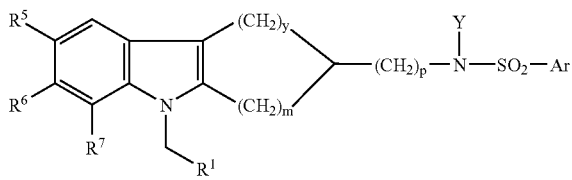

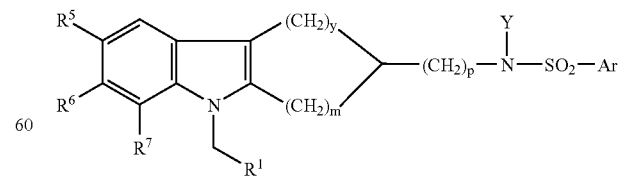

| No | R¹ | R⁵ | R⁶ | R⁷ | y | m | p | Y | Ar |
|---|---|---|---|---|---|---|---|---|---|
| Ib-1 | COOH | H | H | H | 1 | 1 | 0 | H | $C_6H_5$ |
| Ib-2 | COOH | H | H | H | 1 | 1 | 0 | H | 4-F—$C_6H_4$ |
| Ib-3 | COOH | H | H | H | 1 | 1 | 0 | H | 4-Me—$C_6H_4$ |
| Ib-4 | COOH | H | H | H | 1 | 1 | 0 | H | 2-thienyl |

TABLE 6-continued

| No | R¹ | R⁵ | R⁶ | R⁷ | y | m | p | Y | Ar |
|---|---|---|---|---|---|---|---|---|---|
| Ib-5 | COOH | H | H | H | 1 | 1 | 0 | Me | $C_6H_5$ |
| Ib-6 | COOH | H | H | H | 1 | 1 | 0 | Me | 4-F—$C_6H_4$ |
| Ib-7 | COOH | H | H | H | 1 | 1 | 0 | Me | 4-Me—$C_6H_4$ |
| Ib-8 | COOH | H | H | H | 1 | 1 | 0 | Me | 2-thienyl |
| Ib-9 | COOH | H | H | H | 1 | 1 | 0 | Et | $C_6H_5$ |
| Ib-10 | COOH | H | H | H | 1 | 1 | 0 | $CH_2C_6H_5$ | $C_6H_5$ |
| Ib-11 | COOH | H | H | H | 1 | 1 | 0 | $CH_2C_6H_5$ | 4-F—$C_6H_4$ |
| Ib-12 | COOH | H | H | H | 1 | 1 | 0 | $CH_2C_6H_5$ | 4-Me—$C_6H_4$ |
| Ib-13 | COOH | H | H | H | 1 | 1 | 0 | $CH_2C_6H_5$ | 2-thienyl |
| Ib-14 | COOH | H | H | H | 1 | 2 | 0 | H | $C_6H_5$ |
| Ib-15 | COOH | H | H | H | 1 | 2 | 0 | H | 2-F—$C_6H_4$ |
| Ib-16 | COOH | H | H | H | 1 | 2 | 0 | H | 4-F—$C_6H_4$ |
| Ib-17 | COOH | H | H | H | 1 | 2 | 0 | H | 4-Cl—$C_6H_4$ |
| Ib-18 | COOH | H | H | H | 1 | 2 | 0 | H | 4-Me—$C_6H_4$ |
| Ib-19 | COOH | H | H | H | 1 | 2 | 0 | H | 4-OMe—$C_6H_4$ |
| Ib-20 | COOH | H | H | H | 1 | 2 | 0 | H | 2-thienyl |

TABLE 7

| No | R¹ | R⁵ | R⁶ | R⁷ | y | m | p | Y | Ar |
|---|---|---|---|---|---|---|---|---|---|
| Ib-21 | COOH | H | H | H | 1 | 2 | 0 | H | 3-thienyl |
| Ib-22 | COOH | H | H | H | 1 | 2 | 0 | H | 5-benzyl-2-thienyl |
| Ib-23 | COOH | H | H | H | 1 | 2 | 0 | Me | $C_6H_5$ |
| Ib-24 | COOH | H | H | H | 1 | 2 | 0 | Me | 2-F—$C_6H_4$ |
| Ib-25 | COOH | H | H | H | 1 | 2 | 0 | Me | 4-F—$C_6H_4$ |
| Ib-26 | COOH | H | H | H | 1 | 2 | 0 | Me | 4-Cl—$C_6H_4$ |
| Ib-27 | COOH | H | H | H | 1 | 2 | 0 | Me | 4-Me—$C_6H_4$ |
| Ib-28 | COOH | H | H | H | 1 | 2 | 0 | Me | 4-OMe—$C_6H_4$ |
| Ib-29 | COOH | H | H | H | 1 | 2 | 0 | Me | 2-thienyl |
| Ib-30 | COOH | H | H | H | 1 | 2 | 0 | Me | 3-thienyl |
| Ib-31 | COOH | H | H | H | 1 | 2 | 0 | Me | 5-benzyl-2-thienyl |
| Ib-32 | COOH | H | H | H | 1 | 2 | 0 | Et | 4-F—$C_6H_4$ |
| Ib-33 | COOH | H | H | H | 1 | 2 | 0 | Et | 4-OMe—$C_6H_4$ |
| Ib-34 | COOH | H | H | H | 1 | 2 | 0 | $CH_2C_6H_5$ | 4-Me—$C_6H_4$ |
| Ib-35 | COOH | Cl | H | H | 1 | 2 | 0 | H | $C_6H_5$ |
| Ib-36 | COOH | Cl | H | H | 1 | 2 | 0 | H | 4-F—$C_6H_4$ |
| Ib-37 | COOH | Cl | H | H | 1 | 2 | 0 | H | 4-Me—$C_6H_4$ |
| Ib-38 | COOH | Cl | H | H | 1 | 2 | 0 | H | 4-OMe—$C_6H_4$ |
| Ib-39 | COOH | Cl | H | H | 1 | 2 | 0 | H | 3-thienyl |
| Ib-40 | COOH | Cl | H | H | 1 | 2 | 0 | Me | $C_6H_5$ |
| Ib-41 | COOH | Cl | H | H | 1 | 2 | 0 | Me | 4-F—$C_6H_4$ |
| Ib-42 | COOH | Cl | H | H | 1 | 2 | 0 | Me | 4-Me—$C_6H_4$ |
| Ib-43 | COOH | Cl | H | H | 1 | 2 | 0 | Me | 4-OMe—$C_6H_4$ |
| Ib-44 | COOH | Cl | H | H | 1 | 2 | 0 | Me | 3-thienyl |
| Ib-45 | COOH | Cl | H | H | 1 | 2 | 0 | $CH_2C_6H_5$ | 4-F—$C_6H_4$ |
| Ib-46 | COOH | F | H | H | 1 | 2 | 0 | H | 4-F—$C_6H_4$ |
| Ib-47 | COOH | F | H | H | 1 | 2 | 0 | Me | 4-F—$C_6H_4$ |

TABLE 8

| No | R¹ | R⁵ | R⁶ | R⁷ | y | m | p | Y | Ar |
|---|---|---|---|---|---|---|---|---|---|
| Ib-48 | COOH | F | H | H | 1 | 2 | 0 | $CH_2C_6H_5$ | 4-F—$C_6H_4$ |
| Ib-49 | COOH | H | H | H | 2 | 1 | 0 | H | $C_6H_5$ |
| Ib-50 | COOH | H | H | H | 2 | 1 | 0 | H | 2-F—$C_6H_4$ |
| Ib-51 | COOH | H | H | H | 2 | 1 | 0 | H | 4-F—$C_6H_4$ |
| Ib-52 | COOH | H | H | H | 2 | 1 | 0 | H | 4-Cl—$C_6N_4$ |
| Ib-53 | COOH | H | H | H | 2 | 1 | 0 | H | 4-Me—$C_6H_4$ |
| Ib-54 | COOH | H | H | H | 2 | 1 | 0 | H | 4-OMe—$C_6H_4$ |
| Ib-55 | COOH | H | H | H | 2 | 1 | 0 | H | 2-thienyl |
| Ib-56 | COOH | H | H | H | 2 | 1 | 0 | H | 3-thienyl |
| Ib-57 | COOH | H | H | H | 2 | 1 | 0 | Me | $C_6H_5$ |
| Ib-58 | COOH | H | H | H | 2 | 1 | 0 | Me | 4-F—$C_6H_4$ |
| Ib-59 | COOH | H | H | H | 2 | 1 | 0 | Me | 4-Me—$C_6H_4$ |
| Ib-60 | COOH | H | H | H | 2 | 1 | 0 | Me | 2-thienyl |
| Ib-61 | COOH | H | H | H | 2 | 1 | 0 | $CH_2C_6H_5$ | 4-F—$C_6H_4$ |
| Ib-62 | COOH | H | H | H | 2 | 2 | 0 | H | $C_6H_5$ |
| Ib-63 | COOH | H | H | H | 2 | 2 | 0 | H | 4-F—$C_6H_4$ |
| Ib-64 | COOH | H | H | H | 2 | 2 | 0 | H | 4-Cl—$C_6H_4$ |
| Ib-65 | COOH | H | H | H | 2 | 2 | 0 | H | 4-Me—$C_6N_4$ |
| Ib-66 | COOH | H | H | H | 2 | 2 | 0 | H | 4-OMe—$C_6N_4$ |
| Ib-67 | COOH | H | H | H | 2 | 2 | 0 | H | 2-thienyl |
| Ib-68 | COOH | H | H | H | 2 | 2 | 0 | Me | $C_6H_5$ |
| Ib-69 | COOH | H | H | H | 2 | 2 | 0 | Me | 4-F—$C_6H_4$ |
| Ib-70 | COOH | H | H | H | 2 | 2 | 0 | Me | 4-Cl—$C_6H_4$ |
| Ib-71 | COOH | H | H | H | 2 | 2 | 0 | Me | 4-Me—$C_6H_4$ |
| Ib-72 | COOH | H | H | H | 2 | 2 | 0 | Me | 4-OMe—$C_6N_4$ |
| Ib-73 | COOH | H | H | H | 2 | 2 | 0 | Me | 2-thienyl |
| Ib-74 | COOH | H | H | H | 2 | 2 | 0 | $CH_2C_6H_5$ | $C_6H_5$ |

TABLE 9

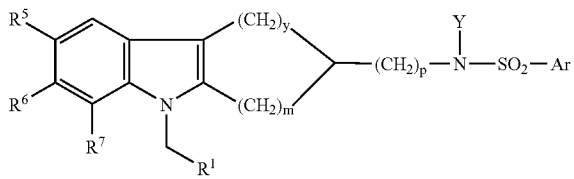

| No | R¹ | R⁵ | R⁶ | R⁷ | y | m | p | Y | Ar |
|---|---|---|---|---|---|---|---|---|---|
| Ib-75 | COOH | H | H | H | 2 | 2 | 0 | $CH_2C_6H_5$ | 4-F—$C_6H_4$ |
| Ib-76 | COOH | H | H | H | 0 | 2 | 1 | H | $C_6H_5$ |
| Ib-77 | COOH | H | H | H | 0 | 2 | 1 | H | 4-F—$C_6H_4$ |
| Ib-78 | COOH | H | H | H | 0 | 2 | 1 | H | 4-Cl—$C_6H_4$ |
| Ib-79 | COOH | H | H | H | 0 | 2 | 1 | H | 4-Me—$C_6H_4$ |
| Ib-80 | COOH | H | H | H | 0 | 2 | 1 | H | 4-OMe—$C_6H_4$ |
| Ib-81 | COOH | H | H | H | 0 | 2 | 1 | H | 2-thienyl |
| Ib-82 | COOH | H | H | H | 0 | 2 | 1 | Me | $C_6H_5$ |
| Ib-83 | COOH | H | H | H | 0 | 2 | 1 | Me | 4-F—$C_6H_4$ |
| Ib-84 | COOH | H | H | H | 0 | 2 | 1 | Me | 4-Cl—$C_6H_4$ |
| Ib-85 | COOH | H | H | H | 0 | 2 | 1 | Me | 4-Me—$C_6H_4$ |
| Ib-86 | COOH | H | H | H | 0 | 2 | 1 | Me | 4-OMe—$C_6H_4$ |
| Ib-87 | COOH | H | H | H | 0 | 2 | 1 | Me | 2-thienyl |
| Ib-88 | COOH | H | H | H | 0 | 2 | 1 | $CH_2C_6H_5$ | $C_6H_5$ |
| Ib-89 | COOH | H | H | H | 0 | 2 | 1 | $CH_2C_6H_5$ | 4-F—$C_6H_4$ |
| Ib-90 | COOH | H | H | H | 1 | 1 | 1 | H | $C_6H_5$ |
| Ib-91 | COOH | H | H | H | 1 | 1 | 1 | H | 4-F—$C_6H_4$ |
| Ib-92 | COOH | H | H | H | 1 | 1 | 1 | H | 4-Cl—$C_6H_4$ |
| Ib-93 | COOH | H | H | H | 1 | 1 | 1 | H | 4-Me—$C_6H_4$ |
| Ib-94 | COOH | H | H | H | 1 | 1 | 1 | H | 4-OMe—$C_6H_4$ |
| Ib-95 | COOH | H | H | H | 1 | 1 | 1 | H | 2-thienyl |
| Ib-96 | COOH | H | H | H | 1 | 1 | 1 | Me | $C_6H_5$ |
| Ib-97 | COOH | H | H | H | 1 | 1 | 1 | Me | 4-F—$C_6H_4$ |
| Ib-98 | COOH | H | H | H | 1 | 1 | 1 | Me | 4-Cl—$C_6H_4$ |
| Ib-99 | COOH | H | H | H | 1 | 1 | 1 | Me | 4-Me—$C_6H_4$ |
| Ib-100 | COOH | H | H | H | 1 | 1 | 1 | Me | 4-OMe—$C_6H_4$ |
| Ib-101 | COOH | H | H | H | 1 | 1 | 1 | Me | 2-thienyl |

TABLE 10

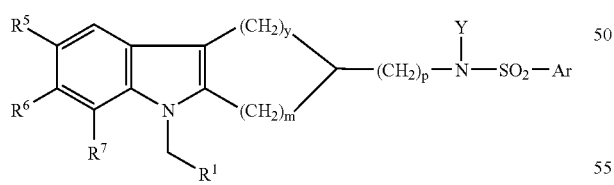

| No | R¹ | R⁵ | R⁶ | R⁷ | y | m | p | Y | Ar |
|---|---|---|---|---|---|---|---|---|---|
| Ib-102 | COOH | H | H | H | 1 | 1 | 1 | $CH_2C_6H_5$ | $C_6H_5$ |
| Ib-103 | COOH | H | H | H | 1 | 1 | 1 | $CH_2C_6H_5$ | 4-F—$C_6H_4$ |

TABLE 11
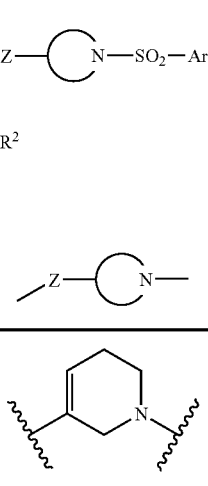
| No | R¹ | R² | R⁴ | R⁵ | R⁶ | R⁷ | Z-⟨N⟩- | Ar |
|---|---|---|---|---|---|---|---|---|
| Ic-1 | COOH | H | H | H | H | H |  | $C_6H_5$ |
| Ic-2 | COOH | H | H | H | H | H | 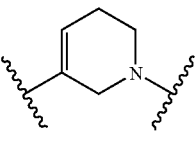 | 4-F—$C_6H_4$ |
| Ic-3 | COOH | H | H | H | H | H |  | 4-Me—$C_6H_4$ |
| Ic-4 | COOH | H | H | H | H | H | 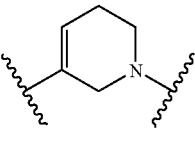 | 2-thienyl |
| Ic-5 | COOH | H | H | H | H | H |  | $C_6H_5$ |
| Ic-6 | COOH | H | H | H | H | H | 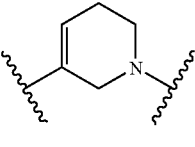 | 4-F—$C_6H_4$ |
| Ic-7 | COOH | H | H | H | H | H |  | 4-Me—$C_6H_4$ |
| Ic-8 | COOH | H | H | H | H | H | 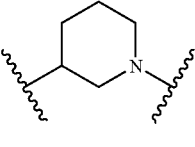 | 2-thienyl |

TABLE 11-continued
| No | R¹ | R² | R⁴ | R⁵ | R⁶ | R⁷ | Z-N- | Ar |
|---|---|---|---|---|---|---|---|---|
| Ic-9 | COOH | Me | H | H | H | H | 3-piperidinyl | 4-F—C₆H₄ |
| Ic-10 | COOH | H | H | Cl | H | H | 3-piperidinyl | 4-F—C₆H₄ |
| Ic-11 | COOH | H | H | F | H | H | 3-piperidinyl | 4-F—C₆H₄ |
TABLE 12
| No | R¹ | R² | R⁴ | R⁵ | R⁶ | R⁷ | Z-N- | Ar |
|---|---|---|---|---|---|---|---|---|
| Ic-12 | COOH | H | H | H | H | H | dihydropyrrolyl | 4-F—C₆H₄ |
| Ic-13 | COOH | H | H | H | H | H | 3-pyrrolidinyl | C₆H₅ |
| Ic-14 | COOH | H | H | H | H | H | 3-pyrrolidinyl | 4-F—C₆H₄ |

TABLE 12-continued
| No | R¹ | R² | R⁴ | R⁵ | R⁶ | R⁷ | -Z-⟨N⟩- | Ar |
|---|---|---|---|---|---|---|---|---|
| Ic-15 | COOH | H | H | H | H | H | 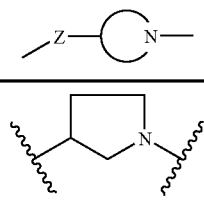 | 4-Me—C₆H₄ |
| Ic-16 | COOH | H | H | H | H | H | 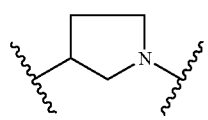 | 2-thienyl |
| Ic-17 | COOH | Me | H | H | H | H | 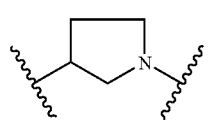 | C₆H₅ |
| Ic-18 | COOH | Me | H | H | H | H | 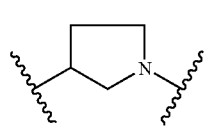 | 4-F—C₆H₄ |
| Ic-19 | COOH | H | H | Cl | H | H | 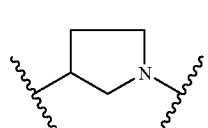 | 4-F—C₆H₄ |
| Ic-20 | COOH | H | H | F | H | H | 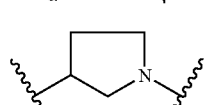 | 4-F—C₆H₄ |
| Ic-21 | COOH | H | H | H | H | H | 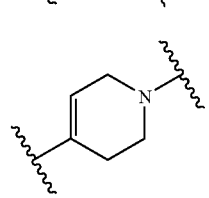 | C₆H₅ |
| Ic-22 | COOH | H | H | H | H | H | 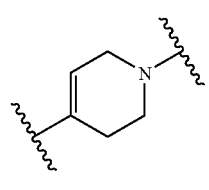 | 4-F—C₆H₄ |
| Ic-23 | COOH | H | H | H | H | H | 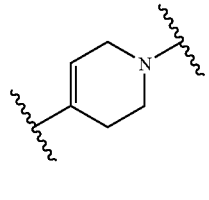 | C₆H₅ |

TABLE 12-continued
| No | R¹ | R² | R⁴ | R⁵ | R⁶ | R⁷ | Z-ring-N | Ar |
|---|---|---|---|---|---|---|---|---|
| Ic-24 | COOH | H | H | H | H | H |  | 4-F—C₆H₄ |
| Ic-25 | COOH | H | H | H | H | H |  | C₆H₅ |
| Ic-26 | COOH | H | H | H | H | H |  | 4-F—C₆H₄ |
| Ic-27 | COOH | H | H | H | H | H |  | 2-thienyl |
TABLE 13
| No | R¹ | R² | R⁴ | R⁵ | R⁶ | R⁷ | Z-ring-N | Ar |
|---|---|---|---|---|---|---|---|---|
| Ic-28 | COOH | H | H | H | H | H |  | C₆H₅ |
| Ic-29 | COOH | H | H | H | H | H |  | 4-F—C₆H₄ |

TABLE 13-continued

| No | R¹ | R² | R⁴ | R⁵ | R⁶ | R⁷ | Z-ring-N | Ar |
|---|---|---|---|---|---|---|---|---|
| Ic-30 | COOH | H | H | H | H | H | 3-piperidinyl | 4-OMe—C$_6$H$_4$ |

TABLE 14

| No | R¹ | R² | R⁴ | R⁵ | R⁶ | R⁷ | Z-ring-N | Ar |
|---|---|---|---|---|---|---|---|---|
| Ic-31 | COOH | H | H | Cl | H | H | 3-pyrrolidinyl | 2-thienyl |
| Ic-32 | COOH | H | H | Me | H | H | 3-pyrrolidinyl | 4-F—C$_6$H$_4$ |
| Ic-33 | COOH | H | H | Me | H | H | 3-pyrrolidinyl | 4-Me—C$_6$H$_4$ |
| Ic-34 | COOH | H | H | Cl | H | H | 3-pyrrolidinyl | C$_6$H$_5$ |
| Ic-35 | COOH | H | H | Cl | H | H | 3-pyrrolidinyl | CH$_2$C$_6$H$_5$ |
| Ic-36 | COOH | H | H | Cl | H | H | 3-pyrrolidinyl | 4-Cl—C$_6$H$_4$ |

TABLE 14-continued
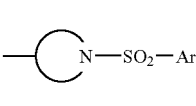
| No | R¹ | R² | R⁴ | R⁵ | R⁶ | R⁷ | Z—◯—N | Ar |
|---|---|---|---|---|---|---|---|---|
| Ic-37 | COOH | H | H | Cl | H | H | 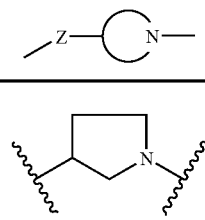 | 4-Me—$C_6H_4$ |
| Ic-38 | COOH | H | H | F | H | H | 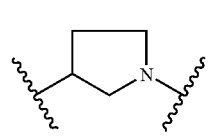 | 4-F—$C_6H_4$ |
| Ic-39 | COOH | Me | H | F | H | H | 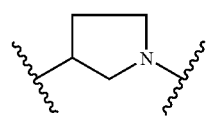 | 2-thienyl |
| Ic-40 | COOH | H | H | OMe | H | H | 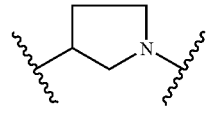 | 4-F—$C_6H_4$ |
| Ic-41 | COOH | H | H | OMe | H | H | 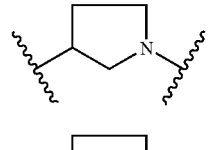 | 2-thienyl |
TABLE 15
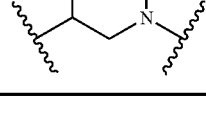
| No | R¹ | R² | R⁴ | R⁵ | R⁶ | R⁷ | Z—◯—N | Ar |
|---|---|---|---|---|---|---|---|---|
| Ic-42 | COOH | H | H | OH | H | H | 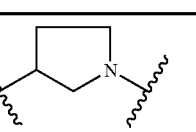 | 4-F—$C_6H_4$ |
| Ic-43 | COOH | H | H | F | H | H | 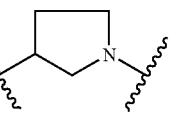 | nBu |

TABLE 15-continued
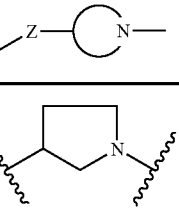
| No | R¹ | R² | R⁴ | R⁵ | R⁶ | R⁷ | -Z-◯-N- | Ar |
|---|---|---|---|---|---|---|---|---|
| Ic-44 | COOH | H | H | F | H | H | 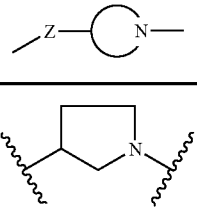 | $CH_2CH{=}CHC_6H_5$ |
| Ic-45 | COOH | H | H | F | H | H | | $4\text{-}C_6H_5\text{--}C_6H_4$ |
| Ic-46 | COOH | H | H | F | H | H | | Me |
| Ic-47 | COOH | H | H | $C_6H_5$ | H | H | | $4\text{-}F\text{--}C_6H_4$ |
| Ic-48 | COOH | H | H | $C_6H_5$ | H | H | | nBu |
| Ic-49 | COOH | H | H | $C_6H_5$ | H | H | | 2-thienyl |
| Ic-50 | COOH | H | H | F | H | H | | $CH_2CH_2C_6H_5$ |
| Ic-51 | COOH | H | H | H | Cl | H | | $4\text{-}F\text{--}C_6H_4$ |
| Ic-52 | COOH | H | H | H | Cl | H | | 2-thienyl |

TABLE 15-continued

| No | R¹ | R² | R⁴ | R⁵ | R⁶ | R⁷ | —Z—⟨N⟩— | Ar |
|---|---|---|---|---|---|---|---|---|
| Ic-53 | COOH | H | H | Cl | H | H | 3-pyrrolidinyl | 4-F—C₆H₄ |
| Ic-54 | COOH | H | H | Cl | H | H | 3-pyrrolidinyl | 3-F—C₆H₄ |
| Ic-55 | COOH | Me | H | Cl | H | H | 3-pyrrolidinyl | 4-F—C₆H₄ |
| Ic-56 | COOH | Me | H | Cl | H | H | 3-pyrrolidinyl | 2-thienyl |
| Ic-57 | COOH | H | H | Cl | H | H | 3-pyrrolidinyl | nBu |
| Ic-58 | COOH | H | H | Cl | H | H | 3-pyrrolidinyl | 4-CF₃—C₆H₄ |
| Ic-59 | COOH | H | H | Cl | H | H | 3-pyrrolidinyl | nBu |
| Ic-60 | COOH | H | H | Cl | H | H | 3-pyrrolidinyl | Octyl |

TABLE 16

| No | R¹ | R² | R⁴ | R⁵ | R⁶ | R⁷ | Z–⟨N⟩– | Ar |
|---|---|---|---|---|---|---|---|---|
| Ic-61 | COOH | H | H | Cl | H | H | pyrrolidine | 1-naphthyl |
| Ic-62 | COOH | H | H | Cl | H | H | pyrrolidine | 4-NO$_2$—C$_6$H$_4$ |
| Ic-63 | COOH | H | H | Cl | H | H | pyrrolidine | 4-CN—C$_6$H$_4$ |
| Ic-64 | COOH | H | Cl | H | H | H | pyrrolidine | 4-F—C$_6$H$_4$ |
| Ic-65 | COOH | H | Cl | H | H | H | pyrrolidine | 2-thienyl |
| Ic-66 | COOH | H | Cl | H | H | H | pyrrolidine | nBu |
| Ic-67 | COOH | H | H | Cl | H | H | pyrrolidine | 5-benzyl-thiophen-2-yl |
| Ic-68 | COOH | H | H | Cl | H | H | pyrrolidine | Quinolin-8-yl |
| Ic-69 | COOH | H | H | Cl | H | H | pyrrolidine | 3-thienyl |

TABLE 16-continued

| No | R¹ | R² | R⁴ | R⁵ | R⁶ | R⁷ | −Z−⟨N⟩− | Ar |
|---|---|---|---|---|---|---|---|---|
| Ic-70 | COOH | H | H | Cl | H | H | pyrrolidine | Benzo[b]thiophen-3-yl |
| Ic-71 | COOH | H | H | Cl | H | H | pyrrolidine | 2,4-diF-C₆H₃ |
| Ic-72 | COOH | H | H | Cl | H | H | pyrrolidine | Me |
| Ic-73 | COOH | H | H | Cl | H | H | pyrrolidine | 4-OMe—C₆H₄ |
| Ic-74 | COOH | H | H | Cl | H | H | pyrrolidine | CH₂CH=CHC₆H₅ |
| Ic-75 | COOH | H | H | Cl | H | H | pyrrolidine | Pyridin-3-yl |
| Ic-76 | COOH | Me | H | H | H | H | pyrrolidine | 2-thienyl |
| Ic-77 | COOH | Me | H | H | H | H | pyrrolidine | nBu |
| Ic-78 | COOH | H | H | Cl | H | H | pyrrolidine | 5-Cl-thiophen-2-yl |
| Ic-79 | COOH | H | H | Cl | H | H | pyrrolidine | 4-OH-C₆H₄ |

TABLE 17
| No | R¹ | R² | R⁴ | R⁵ | R⁶ | R⁷ | Z-⟨N⟩- | Ar |
|---|---|---|---|---|---|---|---|---|
| Ic-80 | COOH | H | H | H | H | H |  | 4-F—C₆H₄ |
| Ic-81 | COOH | H | H | H | H | H | 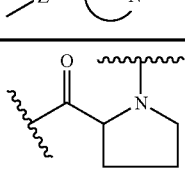 | 4-OMe—C₆H₄ |
| Ic-82 | COOH | H | H | F | H | H | 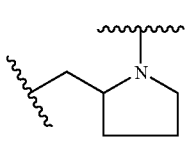 | 4-F—C₆H₄ |
| Ic-83 | COOH | H | H | F | H | H | 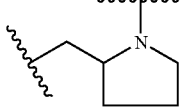 | 4-F—C₆H₄ |
| Ic-84 | COOH | H | H | F | H | H | 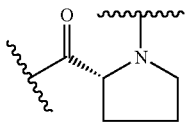 | 4-F—C₆H₄ |
| Ic-85 | COOH | H | H | F | H | H | 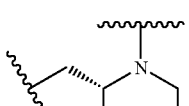 | 4-OMe—C₆H₄ |
TABLE 18
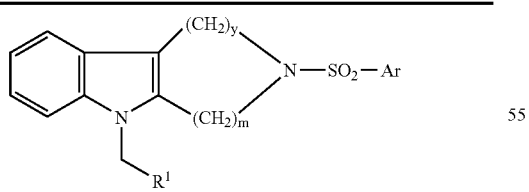
| No | y | m | R¹ | Ar |
|---|---|---|---|---|
| Id-1 | 1 | 2 | COOH | C₆H₅ |
| Id-2 | 1 | 2 | COOH | 4-F—C₆H₄ |
| Id-3 | 1 | 2 | COOH | 2-thienyl |
| Id-4 | 2 | 1 | COOH | C₆H₅ |
| Id-5 | 2 | 1 | COOH | 4-F—C₆H₄ |
| Id-6 | 2 | 1 | COOH | 2-thienyl |

TABLE 19

| No | R$^1$ | R$^4$ | R$^5$ | R$^6$ | R$^7$ | R$^{20}$ | R$^{21}$ | Y | Ar |
|---|---|---|---|---|---|---|---|---|---|
| Ie-1 | COOH | H | H | H | H | H | H | H | C$_6$H$_5$ |
| Ie-2 | COOH | H | H | H | H | H | H | H | 4-F—C$_6$H$_4$ |
| Ie-3 | COOH | H | H | H | H | H | H | H | 2-thienyl |
| Ie-4 | COOH | H | H | H | H | H | H | Me | C$_6$H$_5$ |
| Ie-5 | COOH | H | H | H | H | H | H | Me | 4-F—C$_6$H$_4$ |
| Ie-6 | COOH | H | H | H | H | H | H | Me | 2-thienyl |
| Ie-7 | COOH | H | H | H | H | H | H | CH$_2$C$_6$H$_5$ | C$_6$H$_5$ |
| Ie-8 | COOH | H | H | H | H | H | H | CH$_2$C$_6$H$_5$ | 4-F—C$_6$H$_4$ |
| Ie-9 | COOH | H | H | H | H | H | H | CH$_2$C$_6$H5 | 2-thienyl |
| Ie-10 | COOH | H | H | F | H | H | H | H | 4-F—C$_6$H$_4$ |
| Ie-11 | COOH | H | H | Me | H | H | H | H | 4-F—C$_6$H$_4$ |
| Ie-12 | COOH | H | H | F | H | H | H | Me | 4-F—C$_6$H$_4$ |
| Ie-13 | COOH | H | H | F | H | H | H | CH$_2$C$_6$H$_5$ | 4-F—C$_6$H$_4$ |
| Ie-14 | COOH | H | H | Me | H | H | H | Me | 4-F—C$_6$H$_4$ |
| Ie-15 | COOH | H | H | H | H | Me | H | CH$_2$C$_6$H$_5$ | 4-F—C$_6$H$_4$ |
| Ie-16 | COOH | H | F | H | H | H | H | H | 4-F-C$_6$H$_4$ |
| Ie-17 | COOH | H | F | H | H | H | H | Me | 4-F—C$_6$H$_4$ |
| Ie-18 | COOH | H | F | H | H | H | H | Me | 4-F—C$_6$H$_4$ |
| Ie-19 | COOH | F | H | H | H | H | H | H | 4-F—C$_6$H$_4$ |
| Ie-20 | COOH | F | H | H | H | H | H | Me | 4-F—C$_6$H$_4$ |
| Ie-21 | COOH | F | H | H | H | H | H | CH$_2$C$_6$H$_5$ | 4-F—C$_6$H$_4$ |
| Ie-22 | COOH | H | H | H | H | F | H | H | 4-F—C$_6$H$_4$ |
| Ie-23 | COOH | H | H | H | H | F | H | Me | 4-F—C$_6$H$_4$ |
| Ie-24 | COOH | H | H | H | H | F | H | CH$_2$C$_6$H$_5$ | 4-F—C$_6$H$_4$ |
| Ie-25 | COOH | H | H | H | F | H | H | Me | 4-F—C$_6$H$_4$ |
| Ie-26 | COOH | H | H | H | F | H | H | CH$_2$C$_6$H$_5$ | 4-F—C$_6$H$_4$ |
| Ie-27 | COOH | H | Br | H | H | H | H | H | 4-F—C$_6$H$_4$ |

TABLE 20

| No | R$^1$ | R$^2$ | R$^5$ | R$^{23}$ | R$^{24}$ | R$^{25}$ | R$^{26}$ | Z$^3$ | Y | Ar |
|---|---|---|---|---|---|---|---|---|---|---|
| If-1 | COOH | Me | H | Me | Me | H | H | =CH— | H | 4-F—C$_6$H$_4$ |
| If-2 | COOH | Me | H | Me | Me | H | H | =CH— | Me | 4-F—C$_6$H$_4$ |
| If-3 | COOH | Me | H | Me | Me | H | H | =CH— | CH$_2$C$_6$H$_5$ | 4-F—C$_6$H$_4$ |
| If-4 | COOH | Me | H | Me | H | H | H | =CH— | H | 4-F—C$_6$H$_4$ |
| If-5 | COOH | Me | H | Me | H | H | H | =CH— | Me | 4-F—C$_6$H$_4$ |
| If-6 | COOH | Me | H | Me | H | H | H | =CH— | CH$_2$C$_6$H$_5$ | 4-F—C$_6$H$_4$ |
| If-7 | COOH | H | H | —(CH$_2$)$_4$— | | H | H | =CH— | Me | 4-F—C$_6$H$_4$ |
| If-8 | COOH | H | H | —(CH$_2$)$_4$— | | H | H | =CH— | CH$_2$C$_6$H$_5$ | 4-F—C$_6$H$_4$ |
| If-9 | COOH | H | H | C$_6$H$_5$ | H | H | H | =CH— | H | 4-F—C$_6$H$_4$ |
| If-10 | COOH | Me | H | C$_6$H$_5$ | H | H | H | =CH— | Me | 4-F—C$_6$H$_4$ |
| If-11 | COOH | H | H | —(CH$_2$)$_3$— | | H | H | =CH— | H | 4-F—C$_6$H$_4$ |
| If-12 | COOH | H | H | —(CH$_2$)$_3$— | | H | H | =CH— | CH$_2$C$_6$H$_5$ | 4-F—C$_6$H$_4$ |
| If-13 | COOH | H | H | Me | Me | H | H | =CH— | H | 4-F—C$_6$H$_4$ |
| If-14 | COOH | H | H | Me | Me | H | H | =CH— | Me | 4-F—C$_6$H$_4$ |
| If-15 | COOH | H | H | Me | Me | H | H | =CH— | CH$_2$C$_6$H$_5$ | 4-F—C$_6$H$_4$ |
| If-16 | COOH | H | H | H | H | CH$_2$OMe | H | =CH— | H | 4-F—C$_6$H$_4$ |
| If-17 | COOH | H | Cl | Me | Me | H | H | =CH— | H | 4-F—C$_6$H$_4$ |
| If-18 | COOH | H | Cl | Me | Me | H | H | =CH— | Me | 4-F—C$_6$H$_4$ |
| If-19 | COOH | H | Cl | Me | Me | H | H | =CH— | CH$_2$C$_6$H$_5$ | 4-F—C$_6$H$_4$ |
| If-20 | COOH | H | H | H | H | H | H | =N— | CH$_2$C$_6$H$_5$ | 4-F—C$_6$H$_4$ |

TABLE 21

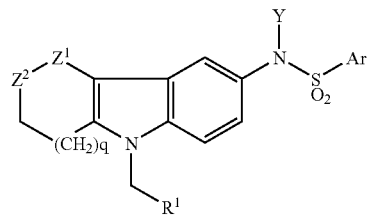

| No | R¹ | Z¹ | Z² | q | Y | Ar |
|---|---|---|---|---|---|---|
| Ig-1 | COOH | —CH$_2$— | —CH$_2$— | 0 | H | 4-F—C$_6$H$_4$ |
| Ig-2 | COOH | —CH$_2$— | —S— | 1 | H | 4-F—C$_6$H$_4$ |
| Ig-3 | COOH | —CH$_2$— | —S— | 1 | Me | 4-F—C$_6$H$_4$ |
| Ig-4 | COOH | —C(=O)— | —CH$_2$— | 1 | Me | 4-F—C$_6$H$_4$ |
| Ig-5 | COOH | —C(=O)— | —CH(Et)— | 1 | Me | 4-F—C$_6$H$_4$ |
| Ig-6 | COOH | —CH$_2$— | —N(COOEt)— | 1 | H | 4-F—C$_6$H$_4$ |
| Ig-7 | COOH | —CH$_2$— | —N(COOEt)— | 1 | Me | 4-F—C$_6$H$_4$ |
| Ig-8 | COOH | —CH$_2$— | —N(COOEt)— | 1 | H | 4-OMe—C$_6$H$_4$ |
| Ig-9 | COOH | —CH$_2$— | —N(COOEt)— | 1 | Me | 4-OMe—C$_6$H$_4$ |
| Ig-10 | COOH | —CH$_2$— | —N(COMe)— | 1 | Me | 4-OMe—C$_6$H$_4$ |
| Ig-11 | COOH | —CH$_2$— | —CH$_2$— | 2 | H | 4-F—C$_6$H$_4$ |
| Ig-12 | COOH | —CH$_2$— | —CH$_2$— | 2 | Me | 4-F—C$_6$H$_4$ |
| Ig-13 | COOH | —CH$_2$— | —CH$_2$— | 2 | CH$_2$C$_6$H$_5$ | 4-F—C$_6$H$_4$ |
| Ig-14 | COOH | —CH$_2$— | —CH$_2$— | 2 | Me | 4-OMe—C$_6$H$_4$ |
| Ig-15 | COOH | —CH$_2$— | —CH$_2$— | 2 | Et | 4-F—C$_6$H$_4$ |
| Ig-16 | COOH | —CH$_2$— | —CH$_2$— | 2 | Me | 4-OH—C$_6$H$_4$ |
| Ig-17 | COOH | —CH$_2$— | —NH— | 2 | Me | 4-F—C$_6$H$_4$ |
| Ig-18 | COOH | —CH$_2$— | —CH$_2$— | 3 | H | 4-F—C$_6$H$_4$ |
| Ig-19 | COOH | —CH$_2$— | —CH$_2$— | 3 | Me | 4-F—C$_6$H$_4$ |
| Ig-20 | COOH | —CH$_2$— | —CH$_2$— | 3 | CH$_2$C$_6$H$_5$ | 4-F—C$_6$H$_4$ |
| Ig-21 | COOH | —CH$_2$— | —CH$_2$— | 0 | Me | 4-F—C$_6$H$_4$ |
| Ig-22 | COOH | —CH$_2$— | —S(=O)— | 1 | H | 4-F—C$_6$H$_4$ |
| Ig-23 | COOH | —CH$_2$— | —S(=O)— | 1 | Me | 4-F—C$_6$H$_4$ |
| Ig-24 | COOH | —C(=O)— | —NH— | 2 | H | 4-OMe—C$_6$H$_4$ |
| Ig-25 | COOH | —C(=O)— | —NH— | 2 | Me | 4-OMe—C$_6$H$_4$ |

TABLE 22

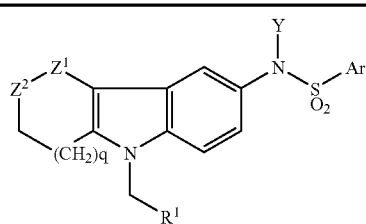

| No | R¹ | Z¹ | Z² | q | Y | Ar |
|---|---|---|---|---|---|---|
| Ig-26 | COOH | —C(=NOH)— | —CH$_2$— | 1 | Me | 4-F—C$_6$H$_4$ |
| Ig-27 | COOH | C(=NOMe)— | —CH$_2$— | 1 | Me | 4-F—C$_6$H$_4$ |

TABLE 23

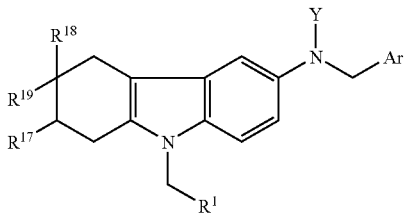

| No | R¹ | R¹⁷ | R¹⁸ | R¹⁹ | Y | Ar |
|---|---|---|---|---|---|---|
| Ih-1 | COOH | H | H | H | H | 4-F—C$_6$H$_4$ |
| Ih-2 | COOH | H | H | H | Me | 4-F—C$_6$H$_4$ |

TABLE 23-continued

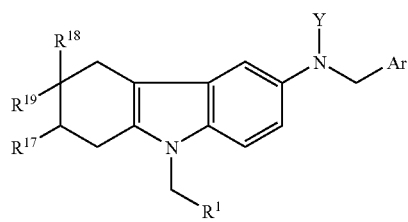

| No | R¹ | R¹⁷ | R¹⁸ | R¹⁹ | Y | Ar |
|---|---|---|---|---|---|---|
| Ih-3 | COOH | H | H | H | CH$_2$C$_6$H$_5$ | 4-F—C$_6$H$_4$ |
| Ih-4 | COOH | H | H | Me | H | 4-F—C$_6$H$_4$ |
| Ih-5 | COOH | H | H | Me | Me | 4-F—C$_6$H$_4$ |
| Ih-6 | COOH | H | H | Me | CH$_2$C$_6$H$_5$ | 4-F—C$_6$H$_4$ |
| Ih-7 | COOH | H | H | H | Me | 2-thienyl |
| Ih-8 | COOH | H | H | H | Me | nBu |
| Ih-9 | COOH | H | H | H | CH$_2$C$_6$H$_5$ | 2-thienyl |
| Ih-10 | COOH | H | H | H | CH$_2$C$_6$H$_5$ | nBu |
| Ih-11 | COOH | H | H | H | H | 2-thienyl |
| Ih-12 | COOH | H | H | H | Me | 4-OMe—C$_6$H$_4$ |
| Ih-13 | COOH | H | H | H | H | 4-OH—C$_6$H$_4$ |
| Ih-14 | COOH | H | H | H | H | 4-OMe—C$_6$H$_4$ |
| Ih-15 | COOH | H | H | H | Me | 4-OH—C$_6$H$_4$ |
| Ih-16 | COOH | H | H | Et | H | 4-F—C$_6$H$_4$ |
| Ih-17 | COOH | H | H | Et | H | 4-OMe—C$_6$H$_4$ |
| Ih-18 | COOH | H | H | Et | Me | 4-F—C$_6$H$_4$ |
| Ih-19 | COOH | H | H | Et | Me | 4-OMe—C$_6$H$_4$ |

TABLE 24

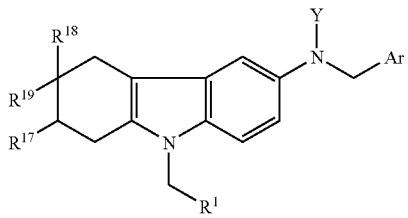

| No | R¹ | R¹⁷ | R¹⁸ | R¹⁹ | Y | Ar |
|---|---|---|---|---|---|---|
| Ih-20 | COOH | H | H | H | H | $C_6H_5$ |
| Ih-21 | COOH | H | H | H | H | 4-Me—$C_6H_4$ |
| Ih-22 | COOH | H | H | H | Me | $C_6H_5$ |
| Ih-23 | COOH | H | H | H | Me | 4-Me—$C_6H_4$ |
| Ih-24 | COOH | H | H | H | Me | $CH_2C_6H_5$ |
| Ih-25 | COOH | H | H | H | Me | $CH_2CH$=$CHC_6H_5$ |
| Ih-26 | COOH | H | Me | Me | H | 4-OMe—$C_6H_4$ |
| Ih-27 | COOH | H | Me | Me | H | 4-F—$C_6H_4$ |
| Ih-28 | COOH | H | Me | Me | H | 2-thienyl |
| Ih-29 | COOH | H | H | H | H | $CH_2C_6H_5$ |
| Ih-30 | COOH | H | H | H | H | $CH_2CH$=$CHC_6H_5$ |
| Ih-31 | COOH | H | Me | Me | Me | 4-F—$C_6H_4$ |
| Ih-32 | COOH | H | Me | Me | Me | 4-OMe—$C_6H_4$ |
| Ih-33 | COOH | H | Me | Me | Me | 2-thienyl |
| Ih-34 | COOH | H | H | $C_6H_5$ | H | 4-F—$C_6H_4$ |
| Ih-35 | COOH | H | H | $C_6H_5$ | H | 4-OMe—$C_6H_4$ |
| Ih-36 | COOH | H | H | $C_6H_5$ | Me | 4-F—$C_6H_4$ |
| Ih-37 | COOH | H | H | $C_6H_5$ | Me | 4-OMe—$C_6H_4$ |
| Ih-38 | COOH | H | Et | Et | H | 4-OMe—$C_6H_4$ |
| Ih-39 | COOH | H | H | H | H | 4-Cl—$C_6H_4$ |
| Ih-40 | COOH | H | H | H | H | 4-$CF_3$—$C_6H_4$ |
| Ih-41 | COOH | H | H | H | Me | 4-Cl—$C_6H_4$ |
| Ih-42 | COOH | H | H | H | Me | 4-$CF_3$—$C_6H$ |
| Ih-43 | COOH | H | H | H | Me | 3-thienyl |
| Ih-44 | COOH | H | H | H | Me | 4-$OCF_3$—$C_6H_4$ |
| Ih-45 | COOH | H | Et | Et | Me | 4-F—$C_6H_4$ |
| Ih-46 | COOH | H | Et | Et | Me | 4-OMe—$C_6H_4$ |
| Ih-47 | COOH | H | —$(CH_2)_5$— | | H | 4-F—$C_6H_4$ |

TABLE 25

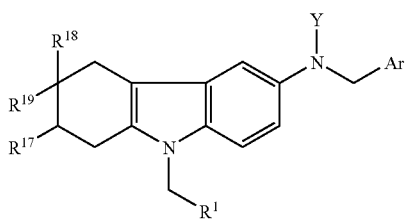

| No | R¹ | R¹⁷ | R¹⁸ | R¹⁹ | Y | Ar |
|---|---|---|---|---|---|---|
| Ih-48 | COOH | H | —$(CH_2)_5$— | | H | 4-OMe—$C_6H_4$ |
| Ih-49 | COOH | H | H | H | H | 3-thienyl |
| Ih-50 | COOH | H | H | Pr | H | 4-F—$C_6H_4$ |
| Ih-51 | COOH | H | H | tBu | H | 4-F—$C_6H_4$ |
| Ih-52 | COOH | H | H | Pr | H | 4-OMe—$C_6H_4$ |
| Ih-53 | COOH | H | H | tBu | H | 4-OMe—$C_6H_4$ |
| Ih-54 | COOH | H | H | H | H | 4-$OCF_3$—$C_6H_4$ |
| Ih-55 | COOH | H | —$(CH_2)_5$— | | Me | 4-F—$C_6H_4$ |
| Ih-56 | COOH | H | —$(CH_2)_5$— | | Me | 4-OMe—$C_6H_4$ |
| Ih-57 | COOH | H | H | Pr | Me | 4-F—$C_6H_4$ |
| Ih-58 | COOH | H | H | tBu | Me | 4-F—$C_6H_4$ |
| Ih-59 | COOH | H | H | Pr | Me | 4-OMe—$C_6H_4$ |
| Ih-60 | COOH | H | H | tBu | Me | 4-OMe—$C_6H_4$ |
| Ih-61 | COOH | H | H | pentyl | Me | 4-F—$C_6H_4$ |
| Ih-62 | COOH | H | H | pentyl | Me | 4-OMe—$C_6H_4$ |
| Ih-63 | COOH | H | H | H | Et | 4-OMe—$C_6H_4$ |
| Ih-64 | COOH | H | H | H | Pr | 4-OMe—$C_6H_4$ |
| Ih-65 | COOH | H | H | H | iBu | 4-OMe—$C_6H_4$ |

TABLE 25-continued

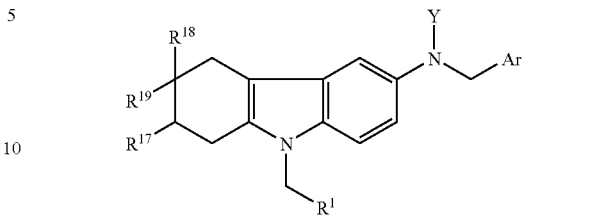

| No | R¹ | R¹⁷ | R¹⁸ | R¹⁹ | Y | Ar |
|---|---|---|---|---|---|---|
| Ih-66 | COOH | H | H | H | iPr | 4-OMe—$C_6H_4$ |
| Ih-67 | COOH | H | H | H | Et | 4-F—$C_6H_4$ |
| Ih-68 | COOH | H | H | H | Pr | 4-F—$C_6H_4$ |
| Ih-69 | COOH | H | H | H | allyl | 4-F—$C_6H_4$ |
| Ih-70 | COOH | H | H | H | propargyl | 4-F—$C_6H_4$ |
| Ih-71 | COOH | H | H | H | $CH_2CF_3$ | 4-F—$C_6H_4$ |
| Ih-72 | COOH | H | H | H | $CH_2CH_2OH$ | 4-F—$C_6H_4$ |
| Ih-73 | COOH | H | H | H | cyclo-propylmethyl | 4-F—$C_6H_4$ |
| Ih-74 | COOH | H | H | H | allyl | 4-OMe—$C_6H_4$ |

TABLE 26

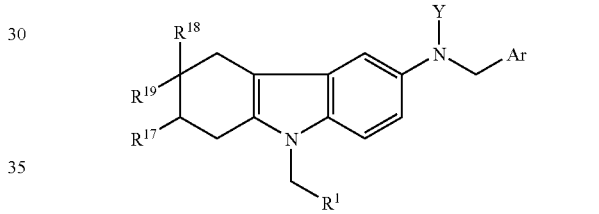

| No | R¹ | R¹⁷ | R¹⁸ | R¹⁹ | Y | Ar |
|---|---|---|---|---|---|---|
| Ih-75 | COOH | H | H | H | 2-methylpropene | 4-OMe—$C_6H_4$ |
| Ih-76 | COOH | H | H | H | propargyl | 4-OMe—$C_6H_4$ |
| Ih-77 | COOH | H | H | H | cyclopropyl-methyl | 4-OMe—$C_6H_4$ |
| Ih-78 | COOH | H | H | H | $CH_2CH_2OH$ | 4-OMe—$C_6H_4$ |
| Ih-79 | COOH | H | H | H | cyclohexylmethyl | 4-F—$C_6H_4$ |
| Ih-80 | COOH | H | H | H | cyclohexylmethyl | 4-OMe—$C_6H_4$ |
| Ih-81 | COOH | H | H | H | $CH_2OMe$ | 4-F—$C_6H_4$ |
| Ih-82 | COOH | H | H | H | $CH_2OMe$ | 4-OMe—$C_6H_4$ |
| Ih-83 | COOH | Me | H | H | Me | 4-F—$C_6H_4$ |
| Ih-84 | COOH | Me | H | H | Me | 4-OMe—$C_6H_4$ |

TABLE 27

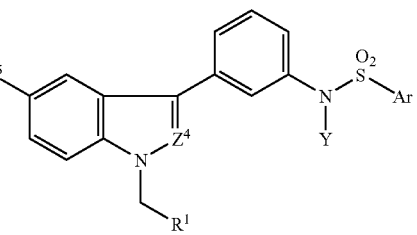

| No | R¹ | R⁵ | Z⁴ | Y | Ar |
|---|---|---|---|---|---|
| Ii-1 | COOH | Me | —N= | H | 4-F—$C_6H_4$ |
| Ii-2 | COOH | Me | —CH= | H | 4-F—$C_6H_4$ |
| Ii-3 | COOH | Me | —CH= | Me | 4-F—$C_6H_4$ |

TABLE 28

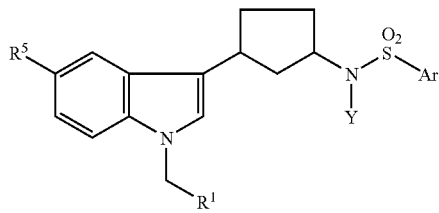

| No | R¹ | R⁵ | Y | Ar |
|---|---|---|---|---|
| Ij-1 | COOH | H | H | 4-F—$C_6H_4$ |
| Ij-2 | COOH | H | Me | 4-F—$C_6H_4$ |
| Ij-3 | COOH | H | $CH_2C_6H_5$ | 4-F—$C_6H_4$ |

TABLE 29

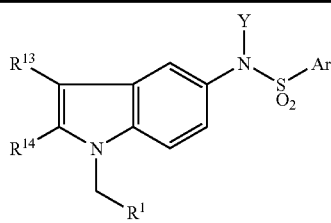

| No | R¹ | R¹³ | Z¹⁴ | Y | Ar |
|---|---|---|---|---|---|
| Ik-1 | COOH | Me | Me | Me | 4-F—$C_6H_4$ |
| Ik-2 | COOH | H | Me | Me | 4-F—$C_6H_4$ |
| Ik-3 | COOH | Et | Me | H | 4-F—$C_6H_4$ |
| Ik-4 | COOH | Pr | Me | H | 4-F—$C_6H_4$ |
| Ik-5 | COOH | Et | Me | Me | 4-F—$C_6H_4$ |
| Ik-6 | COOH | iPr | Me | Me | 4-F—$C_6H_4$ |
| Ik-7 | COOH | Me | Pr | Me | 4-F—$C_6H_4$ |
| Ik-8 | COOH | Et | H | Me | 4-F—$C_6H_4$ |
| Ik-9 | COOH | Pr | Me | H | 4-F—$C_6H_4$ |
| Ik-10 | COOH | Pr | Me | Me | 4-F—$C_6H_4$ |
| Ik-11 | COOH | Et | Pr | H | 4-F—$C_6H_4$ |
| Ik-12 | COOH | Et | Pr | H | 2-thienyl |
| Ik-13 | COOH | Et | Pr | Me | 4-F—$C_6H_4$ |
| Ik-14 | COOH | Et | Pr | Me | 2-thienyl |
| Ik-15 | COOH | Pr | Me | H | 4-OMe—$C_6H_4$ |
| Ik-16 | COOH | Pr | Me | Me | 4-OMe—$C_6H_4$ |
| Ik-17 | COOH | Et | Pr | H | 4-OMe—$C_6H_4$ |

TABLE 30

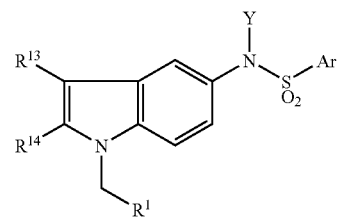

| No | R¹ | R¹³ | Z¹⁴ | Y | Ar |
|---|---|---|---|---|---|
| Ik-18 | COOH | Et | Pr | Me | 4-OMe—$C_6H_4$ |
| Ik-19 | COOH | $CH_2C_6H_5$ | Me | Me | 4-F—$C_6H_4$ |
| Ik-20 | COOH | $CH_2C_6H_5$ | Me | Me | 4-OMe—$C_6H_4$ |
| Ik-21 | COOH | iBu | Me | Me | 4-F—$C_6H_4$ |
| Ik-22 | COOH | nBu | Me | H | 4-F—$C_6H_4$ |
| Ik-23 | COOH | nBu | Me | H | 4-OMe—$C_6H_4$ |
| Ik-24 | COOH | nBu | Me | Me | 4-F—$C_6H_4$ |
| Ik-25 | COOH | nBu | Me | Me | 4-OMe—$C_6H_4$ |
| Ik-26 | COOH | iBu | Me | H | 4-OMe—$C_6H_4$ |
| Ik-27 | COOH | iBu | Me | Me | 4-OMe—$C_6H_4$ |
| Ik-28 | COOH | Pr | Me | Et | 4-OMe—$C_6H_4$ |
| Ik-29 | COOH | Pr | Me | Me | 4-OH—$C_6H_4$ |
| Ik-30 | COOH | $CH_2C_6H_5$ | Me | H | 4-F—$C_6H_4$ |
| Ik-31 | COOH | Pr | Me | Me | 4-OEt—$C_6H_4$ |
| Ik-32 | COOH | Pr | Me | proprgyl | 4-OMe—$C_6H_4$ |
| Ik-33 | COOH | $CH_2C_6H_5$ | Me | proprgyl | 4-OMe—$C_6H_4$ |
| Ik-34 | COOH | iBu | Me | Me | 4-F—$C_6H_4$ |
| Ik-35 | COOH | OMe | Me | Me | 4-F—$C_6H_4$ |
| Ik-36 | COOH | OMe | Me | Me | 4-OMe—$C_6H_4$ |
| Ik-37 | COOH | C(=O)Et | Me | Me | 4-OMe—$C_6H_4$ |
| Ik-38 | COOH | C(=O)Et | Me | Et | 4-OMe—$C_6H_4$ |
| Ik-39 | COOH | Pr | Me | Me | $C_6H_5$ |
| Ik-40 | COOH | Pr | Me | Me | 4-Me—$C_6H_4$ |
| Ik-41 | COOH | Pr | Me | Me | 2-F—$C_6H_4$ |
| Ik-42 | COOH | Pr | Me | Me | 4-Cl—$C_6H_4$ |
| Ik-43 | COOH | Pr | Me | Me | 4-Br—$C_6H_4$ |

The physical properties of the compounds are shown below

TABLE 31

| Compound No. | Physical properties |
|---|---|
| Ia-7 | ¹H-NMR(CDCl₃) δ 2.95(m, 2H), 3.28(m, 2H), 4.62(br, 1H), 4.81(s, 2H), 6.84(s, 1H), 7.06-7.22(m, 3H), 7.38-7.72(m, 4H), 7.71-7.74(m, 2H); IR (CHCl₃)3480, 2953, 1731, 1603, 1469, 1447, 1409, 1329, 1162, 1093 cm⁻¹; |
| Ia-8 | ¹H-NMR(CDCl₃) δ 2.95(t, J=6.3Hz, 2H), 3.31(dt, J=5.4 and 6.3Hz, 2H), 4.79(t, J=5.4Hz, 1H), 4.84(s, 2H), 6.90(s, 1H), 6.99-7.22(m, 5H), 7.41(d, J=7.8Hz, 1H), 7.50(m, 1H), 7.86(m, 1H); IR(CHCl₃)3482, 3374, 2929, 1732, 1601, 1475, 1453, 1411, 1384, 1335, 1266, 1169, 1156, 1126, 1077, 1015 cm⁻¹; Elemental analysis(C₁₈H₁₇FN₂O₄S•0.4H₂O)Calcd. (%): C, 56.36; H, 4.68; N, 7.30; F, 4.95; S, 8.36 Found(%): C, 56.52; H, 4.67; N, 7.10; F, 4.69; S, 8.30 |
| Ia-9 | ¹H-NMR(CDCl₃) δ 2.94(m, 2H), 3.26(m, 2H), 4.54(t, J=5.7Hz, 1H), 6.86 (s, 1H), 6.97-7.27(m, 6H), 7.37(d, J=7.8Hz, 1H), 7.65-7.69(m, 2H), 7.71-7.74(m, 2H); IR (KBr)3422, 3290, 2929, 1731, 1592, 1494, 1469, 1408, 1382, 1328, 1292, 1237, 1166, 1152, 1092, 1013 cm⁻¹; Elemental analysis |

TABLE 31-continued

| Compound No. | Physical properties |
| --- | --- |
| | ($C_{18}H_{17}FN_2O_4S$•0.5AcOEt)Calcd. (%): C, 57.13; H, 5.03; N, 6.66; F, 4.52; S, 7.63 Found(%): C, 57.36; H, 5.07; N, 6.94; F, 4.58; S, 7.35 |
| Ia-12 | $^1$H-NMR(CDCl$_3$) δ 2.92(t, J=6.6Hz, 2H), 3.21-3.25(m, 2H), 3.83(s, 3H), 4.50(br, 1H), 4.80(s, 2H), 6.80-6.82(m, 3H), 7.06(m, 1H), 7.18-7.23(m, 2H), 7.39(d, J=7.8Hz, 1H), 7.60-7.65(m, 2H); IR(CHCl$_3$)3481, 2967, 2945, 2842, 1732, 1598, 1580, 1498, 1468, 1441, 1409, 1330, 1260, 1155, 1096, 1047, 1030 cm$^{-1}$; Elemental analysis($C_{19}H_{20}N_2O_5S$•0.5AcOEt)Calcd. (%): C, 58.32; H, 5.59; N, 6.48; S, 7.41 Found(%): C, 57.95; H, 5.40; N, 6.61; S, 7.73 |
| Ia-13 | $^1$H-NMR(CDCl$_3$) δ 2.97(t, J=6.3Hz, 2H), 3.35(m, 2H), 4.62(t, J=5.7Hz, 1H), 4.82(s, 2H), 6.86(s, 1H), 7.00(m, 1H), 7.11(m, 1H), 7.19-7.26(m, 2H), 7.43-7.51(m, 3H); IR(CHCl$_3$)3360, 2930, 1732, 1469, 1407, 1382, 1334, 1158, 1092, 1069, 1048, 1016 cm$^{-1}$; Elemental analysis ($C_{16}H_{16}N_2O_4S_2$•0.4AcOEt)Calcd. (%): C, 52.89; H, 4.84; N, 7.01; S, 16.05 Found(%): C, 52.93; H, 4.88; N, 7.04; S, 16.01 |
| Ia-14 | $^1$H-NMR(CDCl$_3$) δ 2.94(t, J=6.3Hz, 2H), 3.30(dt, J=6.0 and 6.3Hz, 2H), 4.61(t, J=6.0Hz, 1H), 4.80(s, 2H), 6.85(s, 1H), 7.07-7.27(m, 5H), 7.42(d, J=7.8Hz, 1H), 7.84(dd, J=1.2 and 3.0Hz, 1H); IR(CHCl$_3$)3481, 2930, 1732, 1469, 1410, 1331, 1157, 1101, 1076, 1015 cm$^{-1}$; Elemental analysis ($C_{16}H_{16}N_2O_4S$•0.1AcOEt)Calcd. (%): C, 52.77; H, 4.54; N, 7.51; S, 17.18 Found(%): C, 52.39; H, 4.57; N, 7.40; S, 17.00 |

TABLE 32

| Compound No. | Physical properties |
| --- | --- |
| Ia-15 | $^1$H-NMR(CDCl$_3$) δ 2.96(t, J=6.3Hz, 2H), 3.29(m, 2H), 4.56(m, 1H), 4.81 (s, 2H), 6.88(s, 1H), 7.03(m, 1H), 7.13-7.21(m, 4H), 7.39(d, J=7.5Hz, 1H), 7.51-7.55(m, 4H), 7.73-7.76(m, 2H); IR(CHCl$_3$)2930, 1732, 1604, 1519, 1469, 1408, 1331, 1160, 1096, 1047 cm$^{-1}$; Elemental analysis ($C_{24}H_{21}FN_2O_4S$•0.5AcOEt)Calcd. (%): C, 62.89; H, 5.07; N, 5.83; F, 3.83; S, 6.46 Found(%): C, 62.74; H, 4.97; N, 5.90; F, 3.82; S, 6.54 |
| Ia-16 | $^1$H-NMR(CDCl$_3$) δ 2.94(t, J=6.9Hz, 2H), 3.26(m, 2H), 4.51(br, 1H), 4.81 (s, 2H), 6.86-6.94(m, 3H), 7.03-7.11(m, 3H), 7.19-7.24(m, 3H), 7.37-7.63(m, 3H), 7.64-7.70(m, 2H); IR(KBr)3279, 3059, 2930, 1730, 1583, 1488, 1469, 1410, 1382, 1327, 1298, 1245, 1152, 1094, 1013 cm$^{-1}$; Elemental analysis ($C_{24}H_{22}N_2O_3S$•0.6AcOEt)Calcd. (%): C, 62.99; H, 5.37; N, 5.57; S, 6.37 Found (%): C, 62.99; H, 5.19; N, 5.77; S, 6.47 |
| Ia-17 | $^1$H-NMR(CDCl$_3$) δ 2.92(t, J=6.3Hz, 2H), 3.31(m, 2H), 4.66(m, 1H), 4.73 (s, 2H), 6.80(s, 1H), 6.91(m, 1H), 7.06-7.11(m, 2H), 7.28(m, 1H), 7.47-7.90 (m, 5H), 8.10(dd, J=2.7 and 6.3Hz, 1H), 8.49(s, 1H); IR(CHCl$_3$)3480, 2929, 1732, 1670, 1616, 1586, 1468, 1428, 1411, 1377, 1330, 1158, 1077, 1047, 1025, 1015 cm$^{-1}$; |
| Ia-20 | $^1$H-NMR(CDCl$_3$) δ 2.31(s, 3H), 2.95(t, J=6.0Hz, 2H), 3.19(dt, J=6.0 and 6.3Hz, 2H), 4.37(t, J=6.3Hz, 1H), 4.82(s, 2H), 6.98-7.18(m, 5H), 7.30(d, J=7.5Hz, 1H), 7.63-7.68(m, 2H); IR(CHCl$_3$)2926, 1730, 1594, 1495, 1410, 1375, 1335, 1292, 1167, 1154, 1093 cm$^{-1}$ |
| Ia-25 | $^1$H-NMR(CDCl$_3$) δ 2.62(s, 3H), 2.90(t, J=6.3Hz, 2H), 3.22(t, J=6.3Hz, 2H), 4.53(br, 1H), 5.03(s, 2H), 6.74(s, 1H), 6.93-7.03(m, 4H), 7.19(m, 1H), 7.64-7.69(m, 2H); IR(CHCl$_3$)2940, 1729, 1594, 1495, 1465, 1438, 1408, 1373, 1329, 1292, 1167, 1154, 1093, 1074, 1046, 1014 cm$^{-1}$; Elemental analysis($C_{19}H_{19}FN_2O_4S$•0.5H$_2$O)Calcd. (%): C, 57.13; H, 5.05; N, 7.01; F, 4.76; S, 8.03 Found(%): C, 57.15; H, 4.99; N, 6.74; F, 4.42; S, 7.72 |
| Ia-28 | $^1$H-NMR(CDCl$_3$) δ 2.87-2.92(m, 2H), 3.19-3.24(m, 2H), 3.79(s, 3H), 4.59 (br, 1H), 4.77(s, 2H), 6.78-7.11(m, 6H), 6.63-7.68(m, 2H); IR(CHCl$_3$)2942, 2837, 1731, 1622, 1594, 1492, 1455, 1409, 1333, 1292, 1167, 1153, 1093, 1051, 1014 cm$^{-1}$; Elemental analysis($C_{19}H_{19}FN_2O_5S$•0.2H$_2$O)Calcd. (%): C, 55.66; H, 4.77; N, 6.83; F, 4.63; S, 7.82 Found(%): C, 55.52; H, 4.87; N, 6.54; F, 4.45; S, 7.55 |
| Ia-32 | $^1$H-NMR(CDCl$_3$) δ 2.87(t, J=6.3Hz, 2H), 3.20-3.22(m, 2H), 4.58(br, 1H), 4.77(s, 2H), 6.89(s, 1H), 6.98-7.18(m, 5H), 7.62-7.67(m, 2H); IR(CHCl$_3$) 3477, 2930, 1731, 1594, 1495, 1471, 1409, 1376, 1333, 1293, 1167, 1154, 1093, 1073, 1046, 1014 cm$^{-1}$ |

TABLE 33

| Compound No. | Physical properties |
| --- | --- |
| Ia-36 | $^1$H-NMR(CDCl$_3$) δ 2.90(t, J=6.6Hz, 2H), 3.23(t, J=6.6Hz, 2H), 4.44(br, 1H), 4.83(s, 2H), 6.93-7.13(m, 6H), 7.68-7.72(m, 2H); IR(KBr)3290, 2664, |

TABLE 33-continued

| Compound No. | Physical properties |
|---|---|
|  | 2573, 1721, 1629, 1591, 1493, 1460, 1440, 1410, 1346, 1323, 1292, 1252, 1090, 1049, cm$^{-1}$; Elemental analysis($C_{18}H_{16}F_2N_2O_4S$•0.2AcOEt)Calcd. (%): C, 54.80; H, 4.31; N, 6.80; F, 9.22; S, 7.78 Found(%): C, 54.70; H, 4.27; N, 6.68; F, 9.03; S, 7.81 |
| Ia-39 | $^1$H-NMR(CDCl$_3$) δ 2.79(s, 3H), 3.03(t, J=7.5Hz, 2H), 3.34(t, J=7.5Hz, 2H), 4.85(s, 2H), 6.95(s, 1H), 7.12-7.23(m, 5H), 7.55(d, J=8.1Hz, 1H), 7.74-7.79(m, 2H); IR(CHCl$_3$)3482, 2928, 2865, 1732, 1594, 1495, 1469, 1408, 1383, 1341, 1292, 1166, 1154, 1189, 1044, 1014 cm$^{-1}$; Elemental analysis($C_{19}H_{19}FN_2O_4S$•0.1AcOEt)Calcd. (%): C, 58.36; H, 5.00; N, 7.02; F, 4.76; S, 8.03 Found(%): C, 58.64; H, 5.07; N, 6.90; F, 4.46; S, 7.90 |
| Ia-41 | $^1$H-NMR(CDCl$_3$) δ 2.35(s, 3H), 2.78(s, 3H), 3.02(t, J=8.4Hz, 2H), 3.22(t, J=8.4Hz, 2H), 4.83(s, 2H), 7.09-7.17(m, 5H), 7.47(d, J=7.5Hz, 1H), 7.72-7.77(m, 2H); IR(CHCl$_3$)2928, 2866, 1906, 1731, 1594, 1496, 1469, 1416, 1376, 1341, 1292, 1166, 1154, 1090, 1046, 1013 cm$^{-1}$; Elemental analysis($C_{20}H_{21}FN_2O_4S$•0.3H$_2$O)Calcd. (%): C, 58.61; H, 5.31; N, 6.83; F, 4.64; S, 7.82 Found(%): C, 58.58; H, 5.11; N, 6.61; F, 4.32; S, 7.46 |
| Ia-42 | $^1$H-NMR(CDCl$_3$) δ 2.62(s, 3H), 2.78(s, 3H), 2.99(t, J=7.8Hz, 2H), 3.32(t, J=7.8Hz, 2H), 5.06(s, 2H), 6.83(s, 1H), 6.95-7.17(m, 4H), 7.37(d, J=7.8 Hz, 1H), 7.74-7.78(m, 2H); IR(CHCl$_3$)2933, 2869, 1731, 1594, 1495, 1463, 1439, 1406, 1375, 1342, 1292, 1166, 1154, 1089, 1044, 1014 cm$^{-1}$; Elemental analysis($C_{20}H_{21}FN_2O_4S$)Calcd. (%): C, 59.39; H, 5.23; N, 6.93; F, 4.70; S, 7.93 Found(%): C, 59.28; H, 5.26; N, 6.75; F, 4.45; S, 7.66 |
| Ia-43 | $^1$H-NMR(CDCl$_3$) δ 2.79(s, 3H), 3.00(t, J=7.8Hz, 2H), 3.33(t, J=7.8Hz, 2H), 3.86(s, 3H), 4.81(s, 2H), 6.88-7.18(m, 6H), 7.75-7.79(m, 2H); IR (CHCl$_3$)2930, 1731, 1594, 1490, 1455, 1342, 1166, 1154, 1089, 1045, 1014 cm$^{-1}$ |
| Ia-44 | $^1$H-NMR(CDCl$_3$) δ 2.78(s, 3H); 2.98(t, J=7.2Hz, 2H), 3.32(t, J=7.2Hz, 2H), 4.83(s, 2H), 7.01(s, 1H), 7.11-7.20(m, 3H), 7.47(s, 1H), 7.74-7.79(m, 2H); IR(CHCl$_3$)3481, 2928, 2864, 1732, 1594, 1496, 1471, 1342, 1293, 1241, 1166, 1154, 1089, 1072, 1041, 1014 cm$^{-1}$ |
| Ia-45 | $^1$H-NMR(CDCl$_3$) δ 2.78(s, 3H), 2.97(t, J=6.9Hz, 2H), 3.31(t, J=6.9Hz, 2H), 4.83(s, 2H), 6.97-7.19(m, 6H), 7.75-7.79(m, 2H); IR(KBr)2927, 1730, 1626, 1592, 1489, 1458, 1338, 1293, 1236, 1153, 1087, 1039, 1013 cm$^{-1}$; Elemental analysis($C_{19}H_{18}F_2N_2O_4S$•0.7MeOH)Calcd. (%): C, 54.92; H, 4.87; N, 6.50; F, 8.82; S, 7.44 Found(%): C, 55.19; H, 4.93; N, 6.33; F, 8.44; S, 7.24 |

TABLE 34

| Compound No. | Physical properties |
|---|---|
| Ia-47 | $^1$H-NMR(CDCl$_3$) δ 2.98-3.03(m, 2H), 3.38-3.43(m, 2H), 3.84(d, J=6.3Hz, 2H), 4.01(s, 2H), 5.13-5.18(m, 2H), 5.64(m, 1H), 6.81(s, 1H), 7.07-7.15(m, 3H), 7.17-7.24(m, 2H), 7.54(d, J=7.8Hz, 1H), 7.76-7.82(m, 2H); IR (CHCl$_3$) 3503, 2928, 2869, 2656, 2558, 1770, 1733, 1594, 1495, 1469, 1342, 1291, 1165, 1153 cm$^{-1}$; Elemental analysis($C_{21}H_{21}FN_2O_4S$•0.3H$_2$O)Calcd. (%): C, 59.79; H, 5.16; F, 4.50; N, 6.64; S, 7.60 Found(%): C, 59.83; H, 4.91; F, 4.42; N, 6.67; S, 7.52 |
| Ia-48 | $^1$H-NMR(CDCl$_3$) δ 1.05(s, 3H), 1.07(s, 3H), 3.12-3.18(m, 2H), 3.31-3.36(m, 2H), 4.11(m, 1H), 4.85(s, 2H), 6.92(s, 1H), 7.11-7.26(m, 5H), 7.68(d, J=7.5Hz, 1H), 7.83-7.88(m, 2H); IR(CHCl$_3$)3503, 2935, 2875, 2653, 2558, 1733, 1594, 1494, 1468, 1334, 1291, 1187, 1150 cm$^{-1}$; Elemental analysis ($C_{21}H_{23}FN_2O_4S$•0.2H$_2$O)Calcd. (%): C, 59.76; H, 5.59; F, 4.50; N, 6.64; S, 7.60 Found(%): C, 59.80; H, 5.44; F, 4.48; N, 6.65; S, 7.62 |
| Ia-51 | $^1$H-NMR(CDCl$_3$) δ 2.82(dd, J=8.1 and 5.1Hz, 2H), 3.36(dd, J=8.1 and 5.1Hz, 2H), 4.37(s, 2H), 4.77(s, 2H), 6.69(s, 1H), 7.05-7.30(m, 11H), 7.79-7.84 (m, 2H); IR(CHCl$_3$)3282, 2928, 2871, 1732, 1594, 1496, 1469, 1407, 1384, 1339, 1292, 1165, 1154, 1093, 1068, 1014 cm$^{-1}$; Elemental analysis ($C_{25}H_{23}FN_2O_4S$•0.8H$_2$O)Calcd. (%): C, 62.43; H, 5.16; N, 5.82; F, 3.95; S, 6.67 Found(%): C, 62.43; H, 5.39; N, 5.64; F, 3.70; S, 6.38 |
| Ia-52 | $^1$H-NMR(CDCl$_3$) δ 2.65(t, J=7.8Hz, 2H), 3.24-3.28(m, 2H), 3.36(s, 3H), 4.45(s, 2H), 4.49(s, 2H), 6.87-7.45(m, 12H), 7.90-7.95(m, 2H); IR(KBr) 3434, 2926, 1592, 1494, 1469, 1405, 1380, 1335, 1293, 1234, 1152, 1069, 1013 cm$^{-1}$; |
| Ia-55 | $^1$H-NMR(CDCl$_3$) δ 2.13(s, 3H), 2.78(t, J=8.1Hz, 2H), 3.19(t, J=8.1Hz, 2H), 4.36(s, 2H), 4.75(s, 2H), 7.03-7.37(m, 11H), 7.82-7.87(m, 2H); IR(CHCl$_3$)2928, 2868, 1659, 1594, 1496, 1469, 1340, 1292, 1165, 1154, 1097, 1015 cm$^{-1}$; Elemental analysis($C_{26}H_{25}FN_2O_4S$)Calcd. (%): C, 64.98; H, 5.24; N, 5.83; F, 3.95; S, 6.67 Found(%): C, 65.28; H, 5.24; N, 5.59; F, 3.64; S, 6.31 |
| Ia-56 | $^1$H-NMR(CDCl$_3$) δ 2.58(s, 3H), 2.79(t, J=7.8Hz, 2H), 3.35(t, J=7.8Hz, 2H), 4.37(s, 2H), 4.98(s, 2H), 6.57(s, 1H), 6.90-7.37(m, 10H), 7.79-7.89(m, 2H); IR(CHCl$_3$)3482, 2934, 2871, 1731, 1594, 1496, 1455, 1439, 1406, 1341, 1292, 1165, 1154, 1093, 1070, 1029, 1013 cm$^{-1}$; Elemental analysis |

TABLE 34-continued

| Compound No. | Physical properties |
| --- | --- |
| Ia-57 | ($C_{26}H_{25}FN_2O_4S$)Calcd. (%): C, 64.98; H, 5.24; N, 5.83; F, 3.95; S, 6.67 Found (%): C, 64.81; H, 5.26; N, 5.60; F, 3.75; S, 6.47 $^1$H-NMR(CDCl$_3$) δ 2.79(t, J=7.5Hz, 2H), 3.36(t, J=7.5Hz, 2H), 3.79(s, 3H), 4.37(s, 2H), 4.73(s, 2H), 6.66(s, 1H), 6.78-7.38(m, 10H), 7.80-7.84(m, 2H); IR(CHCl$_3$)2937, 1732, 1593, 1491, 1455, 1340, 1292, 1165, 1154, 1093, 1066, 1043, 1014 cm$^{-1}$; |

TABLE 35

| Compound No. | Physical properties |
| --- | --- |
| Ia-58 | $^1$H-NMR(CDCl$_3$) δ 2.77(t, J=7.8Hz, 2H), 3.31(t, J=7.8Hz, 2H), 4.36(s, 2H), 4.75(s, 2H), 6.74(s, 1H), 7.04-7.32(m, 10H), 7.81-7.86(m, 2H); IR(CHCl$_3$)3481, 2929, 2868, 1732, 1594, 1496, 1471, 1410, 1386, 1341, 1292, 1165, 1154, 1093, 1071, 1029, 1013 cm$^{-1}$; Elemental analysis ($C_{25}H_{22}ClFN_2O_4S$)Calcd. (%): C, 59.94; H, 4.43; N, 5.59; Cl, 7.08; F, 3.79; S, 6.40 Found(%): C, 59.65; H, 4.34; N, 5.48; Cl, 6.71; F, 3.62; S, 6.19 |
| Ia-59 | $^1$H-NMR(CDCl$_3$) δ 2.77(t, J=8.1Hz, 2H), 3.32(t, J=8.1Hz, 2H), 4.36(s, 2H), 4.76(s, 2H), 6.76(s, 1H), 6.80-7.37(m, 11H), 7.81-7.86(m, 2H); IR(KBr)3429, 2927, 1733, 1625, 1594, 1486, 1455, 1408, 1338, 1295, 1241, 1209, 1199, 1166, 1154, 1137, 1097, 1070, 1028, 1014 cm$^{-1}$; Elemental analysis($C_{25}H_{22}F_2N_2O_4S$•0.3AcOEt)Calcd. (%): C, 61.59; H, 4.81; N, 5.48; F, 7.44; S, 6.28 Found(%): C, 61.98; H, 4.83; N, 5.31; F, 7.12; S, 6.13 |
| Ia-61 | $^1$H-NMR(CDCl$_3$) δ 2.36(s, 3H), 2.67-2.72(m, 2H), 3.23-3.29(m, 2H), 4.34(s, 2H), 4.74(s, 2H), 5.70(br s, 1H), 6.63(s, 1H), 7.03(m, 1H), 7.11-7.27(m, 9H), 7.81-7.88(m, 2H); IR(CHCl$_3$)3502, 2929, 2868, 2656, 2558, 1732, 1594, 1495, 1468, 1340, 1240 cm$^{-1}$; Elemental analysis($C_{26}H_{25}FN_2O_4S$•0.2H$_2$O) Calcd. (%): C, 64.50; H, 5.29; F, 3.92; N, 5.79; S, 6.62 Found(%): C, 64.50; H, 5.24; F, 3.78; N, 5.82; S, 6.61 |
| Ia-62 | mp 108-110° C.; $^1$H-NMR(CDCl$_3$) δ 2.75-2.80(m, 2H), 3.28-3.34(m, 2H), 3.77 (s, 3H), 4.27(s, 2H), 4.64(s, 2H), 6.13(br s, 1H), 6.63(s, 1H), 6.80-6.82(m, 2H), 7.00-7.15(m, 7H), 7.24(m, 1H), 7.75-7.80(m, 2H); IR(Nujol)2726, 1727, 1612, 1590, 1513, 1494, 1467, 1333, 1246, 1152 cm$^{-1}$; Elemental analysis($C_{26}H_{25}FN_2O_5S$•0.3H$_2$O)Calcd. (%): C, 62.21; H, 5.14; F, 3.78; N, 5.58; S, 6.39 Found(%): C, 62.26; H, 5.16; F, 3.56; N, 5.43; S, 6.21 |
| Ia-63 | $^1$H-NMR(CDCl$_3$) δ 2.86(t, J=7.4Hz, 2H), 3.42(t, J=7.4Hz, 2H), 4.34(s, 2H), 4.80(s, 2H), 5.35(br s, 1H), 6.74(s, 1H), 7.01(m, 1H), 7.14-7.32(m, 7H), 7.83-7.87(m, 2H), 7.98-8.01(m, 2H); IR(Nujol)2725, 1725, 1591, 1520, 1493, 1465, 1377, 1345, 1235, 1153 cm$^{-1}$ |
| Ia-64 | mp 163-165° C.; $^1$H-NMR(CDCl$_3$) δ 2.50-2.56(m, 2H), 3.24-3.30(m, 2H), 4.64 (s, 2H), 4.75(s, 2H), 6.48(s, 1H), 6.95-7.07(m, 3H), 7.11-7.22(m, 3H), 7.32-7.40(m, 2H), 7.49-7.59(m, 2H), 7.81-7.93(m, 4H), 8.29-8.32(m, 2H); IR (Nujol)3105, 3061, 1736, 1592, 1492, 1465, 1343, 1333, 1239, 1221, 1170, 1152 cm$^{-1}$; Elemental analysis($C_{29}H_{25}FN_2O_4S$)Calcd. (%): C, 67.43; H, 4.88; F, 3.68; N, 5.42; S, 6.21 Found(%): C, 67.20; H, 4.71; F, 3.51; N, 5.30; S, 6.04 |

TABLE 36

| Compound No. | Physical properties |
| --- | --- |
| Ia-65 | $^1$H-NMR(CDCl$_3$) δ 2.94-2.99(m, 2H), 3.41-3.46(m, 2H), 4.57(s, 2H), 4.79(s, 2H), 6.77-6.90(m, 3H), 7.06-7.25(m, 6H), 7.41(d, J=7.8Hz, 1H), 7.75-7.79 (m, 2H); IR(CHCl$_3$)3503, 2929, 2655, 2558, 1733, 1594, 1495, 1469, 1342 cm$^{-1}$; Elemental analysis($C_{23}H_{21}FN_2O_4S_2$•0.6H$_2$O)Calcd. (%): C, 57.15; H, 4.63; F, 3.93; N, 5.80; S, 13.27 Found(%): C, 57.04; H, 4.48; F, 3.78, N, 5.63; S, 13.44 |
| Ia-66 | $^1$H-NMR(CDCl$_3$) δ 2.82(t, J=8.0Hz, 2H), 2.97-3.02(m, 2H), 3.35-3.48(m, 4H), 4.79(s, 2H), 5.99(bs, 1H), 6.83(s, 1H), 7.05-7.28(m, 10H), 7.54(d, J=7.5Hz, 1H), 7.73-7.78(m, 2H); IR(CHCl$_3$)3503, 2932, 2869, 2655, 2558, 1733, 1594, 1496, 1468, 1334 cm$^{-1}$; Elemental analysis ($C_{26}H_{25}FN_2O_4S$•0.5H$_2$O)Calcd. (%): C, 63.79; H, 5.35; F, 3.88; N, 5.72; S, 6.55 Found(%): C, 64.02; H, 5.29; F, 3.60, N, 5.75; S, 6.26 |
| Ia-69 | $^1$H-NMR(CDCl$_3$) δ 1.86(m, 2H), 2.75(t, J=6.3Hz, 2H), 3.00(m, 2H), 4.58 (t, J=5.7Hz, 2H), 4.83(s, 2H), 6.83(s, 1H), 7.06-7.24(m, 5H), 7.45(d, J=7.8Hz, 1H), 7.70-7.75(m 2H); IR(CHCl$_3$)3780, 3369, 2936, 1732, 1594, 1495, 1468, 1410, 1381, 1334, 1292, 1240, 1167, 1154, 1093, 1046, 1014 cm$^{-1}$; Elemental analysis($C_{19}H_{19}FN_2O_4S$•0.2AcOEt)Calcd. (%): C, 58.28; H, 5.09; N, 6.87; F, 4.66; S, 7.86 Found(%): C, 58.39; H, 5.14; N, 6.96; F, 4.52; S, 7.72 |

TABLE 36-continued

| Compound No. | Physical properties |
| --- | --- |
| Ia-74 | $^1$H-NMR(CDCl$_3$) δ 1.83-1.91(m, 2H), 2.75(t, J=7.2Hz, 2H), 2.97-3.04(m, 2H), 4.56(m, 1H), 4.82(s, 2H), 6.82(s, 1H), 6.95-7.12(m, 5H), 7.19-7.25(m, 3H), 7.34-7.49(m, 3H), 7.67-7.75(m, 2H); IR(CHCl$_3$)3480, 2935, 1732, 1584, 1488, 1469, 1412, 1376, 1332, 1298, 1246, 1154, 1095, 1045, 1022 cm$^{-1}$; Elemental analysis(C$_{25}$H$_{24}$N$_2$O$_5$S•0.3H$_2$O)Calcd. (%): C, 63.90; H, 5.28; N, 5.96; S, 6.82 Found(%): C, 63.95; H, 5.51; N, 5.72; S, 6.39 |
| Ia-81 | $^1$H-NMR(CDCl$_3$) δ 1.91(m, 2H), 2.73(s, 3H), 2.81(t, J=6.9Hz, 2H), 3.60(t, J=7.2Hz, 1H), 4.86(s, 2H), 6.95(s, 1H), 7.10-7.23(m, 5H), 7.54(d, J=7.8Hz, 1H), 7.73(m, 2H); IR(CHCl$_3$)3481, 2932, 2868, 1731, 1615, 1594, 1494, 1468, 1407, 1378, 1342, 1292, 1166, 1154, 1090, 1014 cm$^{-1}$ |
| Ia-85 | $^1$H-NMR(CDCl$_3$) δ 1.68-1.77(m, 2H), 2.56(t, J=6.9Hz, 2H), 3.17(t, J=7.8Hz, 2H), 4.31(s, 2H), 4.80(s, 2H), 6.67(s, 1H), 7.03-7.38(m, 11H), 7.71-7.77 (m, 2H); IR(CHCl$_3$)3481, 2931, 1732, 1594, 1495, 1468, 1339, 1292, 1165, 1154, 1095, 1013 cm$^{-1}$ |
| Ia-87 | mp 125-126° C.; $^1$H-NMR(CDCl$_3$) δ 2.39(s, 3H), 2.81(m, 1H), 2.99(m, 1H), 3.33-3.46(m, 2H), 4.82(s, 2H), 6.85(s, 1H), 7.06-7.28(m, 10H), 7.55(d, J=8.1Hz, 1H), 7.68(d, J=8.4Hz, 2H); IR(Nujol)3428, 3081, 3026, 2927, 1713, 1598, 1468, 1325, 1241, 1191, 1149 cm$^{-1}$; Elemental analysis (C$_{27}$H$_{28}$N$_2$O$_4$S)Calcd. (%): C, 68.04; H, 5.92; N, 5.88; S, 6.73 Found(%): C, 68.07; H, 5.82; N, 5.95; S, 6.60 |

TABLE 37

| Compound No. | Physical properties |
| --- | --- |
| Ia-88 | $^1$H-NMR(CDCl$_3$) δ 2.89(t, J=6.6Hz, 2H), 3.21-3.27(m, 2H), 4.53(t, J=6.6Hz, 1H), 4.81(s, 2H), 6.92-7.02(m, 3H), 7.13(m, 1H), 7.30-7.34(m, 2H), 7.59-7.62(m, 2H); IR(KBr)3290, 3087, 2571, 1721, 1627, 1586, 1490, 1409, 1346, 1323, 1251, 1225, 1163, 1092, 1048, 1013 cm$^{-1}$; Elemental analysis (C$_{18}$H$_{26}$ClFN$_2$O$_4$S)Calcd. (%): C, 52.62; H, 3.93; N, 6.82; Cl, 8.63; F, 4.62; S, 7.80 Found(%): C, 52.46; H, 3.85; N, 6.62; Cl, 8.25; F, 4.34; S, 7.64 |
| Ia-89 | $^1$H-NMR(CDCl$_3$) δ 2.85(t, J=6.6Hz, 2H), 3.19(m, 2H), 3.84(s, 3H), 4.56 (br, 1H), 4.77(s, 2H), 6.80-6.98(m, 5H), 7.10(m, 1H), 7.58-7.64(m, 2H); IR (CHCl$_3$) 2945, 2843, 1732, 1598, 1580, 1498, 1488, 1458, 1410, 1329, 1303, 1260, 1180, 1155, 1096, 1029 cm$^{-1}$; Elemental analysis (C$_{19}$H$_{19}$FN$_2$O$_5$S•0.4H$_2$O)Calcd. (%): C, 55.17; H, 4.82; N, 6.77; F, 4.59; S, 7.75 Found(%): C, 55.30; H, 4.81; N, 6.56; F, 4.33, S, 7.45 |
| Ia-90 | $^1$H-NMR(CDCl$_3$) δ 2.91(t, J=6.3Hz, 2H), 3.34-3.49(m, 2H), 4.63(t, J=6.0 Hz, 1H), 4.80(s, 2H), 6.92-7.15(m, 5H), 7.48-7.53(m, 2H); IR(KBr)3269, 2655, 2565, 1728, 1626, 1584, 1488, 1459, 1433, 1324, 1241, 1096, 1073, 1017 cm$^{-1}$; Elemental analysis(C$_{16}$H$_{15}$FN$_2$O$_4$S$_2$•0.3H$_2$O)Calcd. (%): C, 49.55; H, 4.05; N, 7.22; F, 4.90; S, 16.54 Found(%): C, 49.89; H, 3.98; N, 6.98; F, 4.54; S, 16.12 |
| Ia-91 | mp 95-97° C.; $^1$H-NMR(CDCl$_3$) δ 2.84(m, 1H), 3.02(m, 1H), 3.34-3.49(m, 2H), 4.83(s, 2H), 6.88(s, 1H), 7.04-7.29(m, 9H), 7.52-7.59(m, 3H); IR (Nujol) 3429, 3087, 3029, 2932, 1713, 1615, 1469, 1406, 1340, 1242, 1190, 1151 cm$^{-1}$; Elemental analysis(C$_{24}$H$_{24}$N$_2$O$_4$S$_2$)Calcd. (%): C, 61.52; H, 5.16; N, 5.98; S, 13.69 Found(%): C, 61.39; H, 5.06; N, 5.78; S, 13.66 |
| Ia-92 | mp 113-114.5° C.; $^1$H-NMR(CDCl$_3$) δ 2.81(m, 1H), 2.93(m, 1H), 3.35-3.42 (m, 2H), 4.79(s, 2H), 6.88(s, 1H), 7.07-7.29(m, 9H), 7.45(d, J=2.1Hz, 1H), 7.77(dd, J=5.1, 8.7Hz); IR(Nujol)3423, 3028, 1720, 1591, 1494, 1470, 1405, 1336, 1293, 1226, 1147, 1094 cm$^{-1}$; Elemental analysis (C$_{26}$H$_{24}$ClFN$_2$O$_4$S)Calcd. (%): C, 60.64; H, 4.70; N, 5.44; Cl, 6.88; F, 3.69; S, 6.23 Found(%): C, 60.54; H, 4.60; N, 5.29; Cl, 6.70; F, 3.56; S, 6.28 |
| Ia-93 | mp 103-107° C.; $^1$H-NMR(CDCl$_3$) δ 3.05(m, 2H), 3.45(m, 2H), 3.96(d, J=6.6Hz, 2H), 4.77(s, 2H), 5.94(dt, J=6.6, 15.6Hz), 6.37(d, J=15.6Hz, 1H), 6.84(s, 1H), 7.01-7.33(m, 10H), 7.49(d, J=8.1Hz, 1H), 7.82(dd, J=4.8, 8.7Hz, 2H); IR(Nujol)3456, 3058, 1725, 1591, 1493, 1469, 1405, 1334, 1292, 1235, 1165, 1153, 1091 cm$^{-1}$; Elemental analysis (C$_{27}$H$_{25}$FN$_2$O$_4$S•0.3H$_2$O•0.3MeOH)Calcd. (%): C, 64.60; H, 5.32; N, 5.52; F, 3.74; S, 6.32 Found(%): C, 64.58; H, 5.33; N, 5.47; F, 3.69; S, 6.53 |

TABLE 38

| Compound No. | Physical properties |
| --- | --- |
| Ia-94 | mp 126-129° C.; $^1$H-NMR(CDCl$_3$) δ 1.85(m, 1H), 2.58(t, J=7.8Hz, 2H), 2.99 (m, 2H), 3.19(t, J=7.8Hz, 2H), 3.39(m, 2H), 4.80(s, 2H), 6.86(s, 1H), 7.07-7.29(m, 10H), 7.50(d, J=8.1Hz, 1H), 7.75(dd, J=5.1, 9.0Hz, 2H); IR |

TABLE 38-continued

| Compound No. | Physical properties |
|---|---|
|  | (Nujol)3404, 3056, 1724, 1591, 1492, 1471, 1413, 1340, 1290, 1232, 1154, 1095 cm$^{-1}$; Elemental analysis($C_{27}H_{27}FN_2O_4S$)Calcd. (%): C, 65.57; H, 5.50; N, 5.66; F, 3.84; S, 6.48 Found(%): C, 65.48; H, 5.60; N, 5.56; F, 3.77; S, 6.35 |
| Ia-95 | $^1$H-NMR(CD$_3$OD) δ 2.39(s, 3H), 2.80(t, J=7.2Hz, 2H), 3.10-3.16(m, 2H), 6.89(m, 1H), 6.98-7.29(m, 5H), 7.63-7.66(m, 2H); IR(KBr)3293, 2575, 1721, 1628, 1598, 1491, 1459, 1440, 1407, 1321, 1252, 1224, 1187, 1092, 1048 cm$^{-1}$; Elemental analysis($C_{19}H_{19}FN_2O_4S\bullet0.2H_2O$)Calcd. (%): C, 57.91; H, 4.96; N, 7.11; F, 4.82; S, 8.14 Found(%): C, 57.87; H, 4.98; N, 6.85; F, 4.66, S, 7.93 |
| Ia-96 | $^1$H-NMR(CDCl$_3$) δ 2.86(t, J=6.3Hz, 2H), 3.25-3.32(m, 2H), 4.64(br, 1H), 4.74(s, 2H), 6.85-7.09(m, 4H), 7.57-7.66(m, 3H), 7.81-7.89(m, 3H), 8.33(s, 1H); IR(KBr)3281, 1713, 1625, 1588, 1487, 1456, 1411, 1325, 1239, 1216, 1157, 1132, 1102, 1075 cm$^{-1}$; Elemental analysis($C_{22}H_{19}FN_2O_4S\bullet0.3H_2O$) Calcd. (%): C, 61.18; H, 4.57; N, 6.49; F, 4.40; S, 7.42 Found(%): C, 61.08; H, 4.56; N, 6.22; F, 4.09, S, 7.14 |
| Ia-97 | $^1$H-NMR(CD$_3$OD) δ 2.82(t, J=6.3Hz, 2H), 3.26-3.44(m, 2H), 4.63(t, J=6.0Hz, 1H), 6.76-7.13(m, 4H), 7.76-7.81(m, 2H), 8.06-8.10(m, 2H); IR (KBr)3280, 3104, 2938, 1721, 1626, 1606, 1583, 1526, 1487, 1410, 1349, 1310, 1254, 1225, 1164, 1092, 1047 cm$^{-1}$; Elemental analysis ($C_{18}H_{16}FN_3O_6S\bullet0.2H_2O$)Calcd. (%): C, 50.87; H, 3.89; N, 9.89; F, 4.47; S, 7.54 Found(%): C, 50.99; H, 3.86; N, 9.59; F, 4.19, S, 7.31 |
| Ia-98 | $^1$H-NMR(CDCl$_3$) δ 2.73(t, J=6.3Hz, 2H), 3.18-3.22(m, 2H), 4.71(t, J=6.0Hz, 1H), 6.63(s, 1H), 6.81-7.05(m, 3H), 7.45-7.53(m, 3H), 7.89(d, J=8.1Hz, 1H), 8.03(d, J=8.1Hz, 1H), 8.22(d, J=5.4Hz, 1H), 8.40(d, J=5.4Hz, 1H); IR(CDCl$_3$) 1732, 1487, 1457, 1408, 1328, 1162, 1135, 1079, 1045 cm$^{-1}$; Elemental analysis($C_{22}H_{19}FN_2O_4S\bullet0.5H_2O$)Calcd. (%): C, 60.68; H, 4.63; N, 6.43; F, 4.36; S, 7.36 Found(%): C, 60.65; H, 4.58; N, 6.26; F, 4.10, S, 7.20 |
| Ia-99 | $^1$H-NMR(CDCl$_3$) δ 2.88(t, J=6.0Hz, 2H), 3.24-3.28(m, 2H), 4.35(br, 1H), 4.78(s, 2H), 6.92-7.13(m, 4H), 7.63(d, J=6.6Hz, 2H), 7.79(d, J=6.6Hz, 2H); IR(KBr)3269, 2655, 2565, 1728, 1626, 1584, 1488, 1459, 1433, 1324, 1241, 1096, 1073, 1017 cm$^{-1}$; Elemental analysis($C_{19}H_{16}FN_3O_4S_2\bullet0.4H_2O$) Calcd. (%): C, 55.85; H, 4.14; N, 10.28; F, 4.65; S, 7.85 Found(%): C, 55.91; H, 4.23; N, 9.89; F, 4.33, S, 7.40 |

TABLE 39

| Compound No. | Physical properties |
|---|---|
| Ia-100 | $^1$H-NMR(d$_6$-DMSO) δ 2.68(t, J=6.9Hz, 2H), 2.93-2.98(m, 2H), 4.09(br, 1H), 4.81(s, 2H), 6.59(dd, J=6.0 and 2.1Hz, 1H), 6.70(s, 1H), 7.00(s, 1H), 7.09(d, J=6.0Hz, 1H), 7.36-7.42(m, 2H), 7.78-7.87(m, 3H), 8.70(s, 1H); IR (KBr)3431, 2927, 1732, 1626, 1591, 1494, 1465, 1407, 1322, 1292, 1231, 1151, 1092, cm$^{-1}$; Elemental analysis($C_{18}H_{17}FN_2O_5S\bullet H_2O$)Calcd. (%): C, 52.68; H, 4.67; N, 6.83; F, 4.63; S, 7.81 Found(%): C, 52.41; H, 4.72; N, 6.58; F, 4.38, S, 7.76 |
| Ia-101 | $^1$H-NMR(CD$_3$OD) δ 2.91(t, J=6.9Hz, 2H), 3.21(t, J=6.9Hz, 2H), 6.63(m, 1H), 6.93(s, 1H), 7.04-7.13(m, 4H), 7.71-7.77(m, 2H); IR(KBr)3303, 1721, 1633, 1592, 1557, 1494, 1466, 1440, 1409, 1327, 1290, 1253, 1235, 1190, 1166, 1152, 1092, 1076, 1046 cm$^{-1}$; Elemental analysis($C_{18}H_{16}F_2N_2O_4S$) Calcd. (%): C, 54.82; H, 4.09; N, 7.10; F, 9.63; S, 8.13 Found(%): C, 54.63; H, 4.05; N, 6.97; F, 9.28, S, 7.87 |
| Ia-102 | $^1$H-NMR(CDCl$_3$) δ 2.79(s, 3H), 3.08(t, J=7.2Hz, 2H), 3.35(t, J=7.2Hz, 2H), 4.83(s, 2H), 6.74(m, 1H), 6.92-7.17(m, 5H), 7.74-7.79(m, 2H); IR(CHCl$_3$)2931, 1732, 1630, 1594, 1557, 1496, 1460, 1408, 1374, 1341, 1292, 1238, 1166, 1154, 1089, 1045 cm$^{-1}$; Elemental analysis ($C_{19}H_{18}F_2N_2O_4S\bullet0.4MeOH$)Calcd. (%): C, 55.32; H, 4.69; N, 6.65; F, 9.02; S, 7.61 Found(%): C, 55.52; H, 4.50; N, 6.45; F, 8.70, S, 7.31 |
| Ia-103 | $^1$H-NMR(CDCl$_3$) δ 2.87(t, J=7.8Hz, 2H), 3.43(t, J=7.8Hz, 2H), 4.40(s, 2H), 4.60(s, 2H), 6.62-7.36(m, 12H), 7.77-7.81(m, 2H); IR(CHCl$_3$) 2930, 1732, 1629, 1593, 1496, 1457, 1406, 1329, 1292, 1154, 1098 cm$^{-1}$. |
| Ia-104 | $^1$H-NMR(CDCl$_3$) δ 1.83(d, J=7.2Hz, 3H), 2.79-2.94(m, 2H), 3.19-3.49(m, 2H), 4.55(br, 1H), 5.07(q, J=7.5Hz, 1H), 6.99-7.20(m, 5H), 7.63-7.68(m, 2H); IR(CHCl$_3$)1725, 1594, 1495, 1466, 1409, 1331, 1292, 1167, 1153, 1092, 1062 cm$^{-1}$; Elemental analysis($C_{19}H_{18}ClFN_2O_4S\bullet0.5H_2O$)Calcd. (%): C, 52.60; H, 4.41; N, 6.46; Cl, 8.17; F, 4.38; S, 7.39 Found(%): C, 52.64; H, 4.36; N, 6.35; Cl, 7.95; F, 4.29, S, 7.42 |
| Ia-105 | $^1$H-NMR(CDCl$_3$) δ 1.84(d, J=7.2Hz, 3H), 2.97(t, J=8.1Hz, 2H), 3.31(t, J=8.1Hz, 2H), 5.07(q, J=7.2Hz, 1H), 7.13-7.19(m, 5H), 7.46(s, 1H), 7.75-7.80(m, 2H); IR(CHCl$_3$)1726, 1594, 1495, 1465, 1375, 1342, 1292, 1166, 1154, 1090 cm$^{-1}$; Elemental analysis($C_{20}H_{20}ClFN_2O_4S\bullet0.3H_2O$)Calcd. (%): C, 54.07; H, 4.67; N, 6.30; Cl, 7.98; F, 4.28; S, 7.22 Found(%): C, 54.09; H, 4.89; N, 5.99; Cl, 7.63; F, 4.03, S, 6.86 |

TABLE 39-continued

| Compound No. | Physical properties |
|---|---|
| Ia-106 | $^1$H-NMR(CDCl$_3$) δ 1.78(d, J=7.5Hz, 3H), 2.77(t, J=8.4Hz, 2H), 3.32(d, J=8.4Hz, 2H), 4.71(s, 1H), 5.01(q, J=7.5Hz, 1H), 6.91(s, 1H), 7.08-7.7.38 (m, 10H), 7.82-7.87(m, 2H); IR(CHCl$_3$)1725, 1594, 1496, 1465, 1341, 1292, 1165, 1154, 1092, 1066 cm$^{-1}$; Elemental analysis(C$_{26}$H$_{24}$ClFN$_2$O$_4$S•0.3H$_2$O) Calcd. (%): C, 60.01; H.4.76; N, 5.38; Cl, 6.81; F, 3.65; S, 6.16 Found(%): C, 60.24; H, 4.65; N, 5.25; Cl, 6.51; F, 3.55; S, 6.04 |

TABLE 40

| Compound No. | Physical properties |
|---|---|
| Ib-2 | $^1$H-NMR(d$_6$-DMSO) δ 2.54-2.68(m, 2H), 2.89-3.06(m, 2H), 3.35(m, 1H), 4.84(s, 2H), 6.93-7.04(m, 2H), 7.26-7.32(m, 2H), 7.45-7.52(m, 2H), 7.92-7.97(m, 2H), 8.36(d, J=7.8Hz, 1H), 12.96(br, 1H); IR(KBr)3429, 3300, 3061, 2913, 2856, 1725, 1592, 1494, 1458, 1432, 1409, 1382, 1340, 1291, 1241, 1167, 1155, 1092, 1002 cm$^{-1}$; Elemental analysis (C$_{19}$H$_{17}$FN$_2$O$_4$S•0.4H$_2$O)Calcd. (%): C, 57.68; H, 4.54; N, 7.08; F, 4.80; S, 8.11 Found(%): C, 57.89; H, 4.36; N, 6.76; F, 4.49; S, 7.77 |
| Ib-6 | $^1$H-NMR(CD$_3$OD) δ 2.56-2.65(m, 2H), 2.71(s, 3H), 2.95-3.04(m, 2H), 4.75 (d, J=18Hz, 1H), 4.80(d, J=18Hz, 1H), 5.36(m, 1H), 6.96-7.08(m, 2H), 7.19-7.41(m, 4H), 7.93-7.98(m, 2H); IR(KBr)3413, 2925, 2653, 2551, 1719, 1706, 1616, 1592, 1493, 1461, 1404, 1378, 1335, 1291, 1234, 1151, 1087, 1012 cm$^{-1}$; Elemental analysis(C$_{20}$H$_{19}$FN$_2$O$_5$S•0.4AcOEt)Calcd. (%): C, 59.27; H, 5.11; N, 6.40; F, 4.34; S, 7.33 Found(%): C, 59.03; H, 4.95; N, 6.34; F, 4.17; S, 7.29 |
| Ib-11 | $^1$H-NMR(CD$_3$OD) δ 2.46-2.55(m, 2H), 2.89-2.98(m, 2H), 4.30(d, J=7.2Hz, 1H), 4.42(d, J=7.2Hz, 1H), 4.50(d, 12.0Hz, 1H), 4.63(d, J=12.0Hz, 1H), 5.36(m, 1H), 6.95-7.39(m, 11H), 7.96-8.01(m, 2H); IR(KBr)3430, 2927, 2859, 1728, 1591, 1493, 1457, 1404, 1381, 1340, 1292, 1236, 1208, 1165, 1153, 1092, 1052, 1012 cm$^{-1}$; |
| Ib-16 | mp 162-168° C.; $^1$H-NMR(d$_6$-DMSO) δ 1.77(m, 1H), 1.92(m, 1H), 2.46-2.78 (m, 4H), 3.41(m, 1H), 4.80(d, J=18.6Hz, 1H), 4.86(d, J=18.6Hz, 1H), 6.96(m, 1H), 7.04(m, 1H), 7.25(d, J=7.2Hz, 1H), 7.29(d, J=8.1Hz, 1H), 7.40-7.48(m, 2H), 7.90-7.97(m, 3H), 12.95(br, 1H); IR(Nujol) 3261, 1734, 1590, 1493, 1469, 1444, 1329, 1188, 1168, 1153 cm$^{-1}$; [α]$_D^{24}$ + 60.4 ± 1.0° (c=1.012, MeOH); Elemental analysis(C$_{20}$H$_{19}$FN$_2$O$_4$S)Calcd. (%): C, 59.69; H, 4.76; F, 4.72; N, 6.96; S, 7.97 Found(%): C, 59.51; H, 4.68; F, 4.57; N, 6.77; S, 7.78 |
| Ib-18 | $^1$H-NMR(d$_6$-DMSO) δ 1.74(m, 1H), 1.90(m, 1H), 2.39(s, 3H), 2.45-2.75(m, 4H), 3.30(m, 1H), 4.79(d, J=19.2Hz, 1H), 4.88(d, J=19.2Hz, 1H), 6.96(m, 1H), 7.04(m, 1H), 7.24(d, J=6.9Hz, 1H), 7.29(d, J=7.8Hz, 1H), 7.40(d, J=8.1Hz, 2H), 7.76(d, J=8.1Hz, 2H), 7.82(d, J=6.6Hz, 1H), 12.93(br, 1H); IR(KBr) 3272, 2924, 1728, 1617, 1598, 1468, 1434, 1382, 1319, 1156 cm$^{-1}$; [α]$_D^{23}$ + 76.2 ± 1.2° (c=1.010, MeOH); Elemental analysis (C$_{21}$H$_{22}$N$_2$O$_4$S•0.5H$_2$O)Calcd. (%): C, 61.90; H, 5.69; N, 6.87; S, 7.87 Found (%): C, 62.01; H, 5.45; N, 6.81; S, 7.76 |

TABLE 41

| Compound No. | Physical properties |
|---|---|
| Ib-20 | $^1$H-NMR(d$_6$-DMSO) δ 1.78(m, 1H), 1.94(m, 1H), 2.48-2.80(m, 4H), 3.47(m, 1H), 4.81(d, J=18.3Hz, 1H), 4.87(d, J=18.3Hz, 1H), 6.97(m, H), 7.05(m, 1H), 7.19(dd, J=3.6, 5.1Hz, 1H), 7.26-7.32(m, 2H), 7.66(dd, J=1.5, 3.6Hz, 1H), 7.94(dd, J=1.5, 5.1Hz, 1H), 8.12(d, J=6.9Hz, 1H), 12.95(br, 1H); IR(KBr)3435, 3276, 2925, 1727, 1617, 1468, 1433, 1405, 1382, 1320, 1227, 1182, 1154 cm$^{-1}$; [α]$_D^{24}$ + 70.9 ± 1.1° (c=1.010, MeOH); Elemental analysis (C$_{18}$H$_{18}$N$_2$O$_4$S$_2$•0.5H$_2$O)Calcd. (%): C, 54.12; H, 4.79; N, 7.01; S, 16.05 Found (%): C, 54.24; H, 4.58; N, 6.90; S, 16.14 |
| Ib-21 | $^1$H-NMR(d$_6$-DMSO) δ 1.77(m, 1H), 1.95(m, 1H), 2.46-2.76(m, 4H), 3.40(m, 1H), 4.80(d, J=18.6Hz, 1H), 4.86(d, J=18.6Hz, 1H), 6.96(m, 1H), 7.04 (m, 1H), 7.26(d, J=7.5Hz, 1H), 7.29(d, J=7.8Hz, 1H), 7.41(d, J=5.1Hz, 1H), 7.78(dd, J=3.0, 5.1Hz, 1H), 7.84(d, J=6.6Hz, 1H), 8.20(m, 1H), 12.95(br, 1H); IR(KBr)3271, 1728, 1616, 1468, 1433, 1382, 1319, 1206, 1183, 1153, 1101, 1075 cm$^{-1}$; Elemental analysis(C$_{18}$H$_{18}$N$_2$O$_4$S$_2$•0.4H$_2$O)Calcd. (%): C, 54.36; H, 4.76; N, 7.04; S, 16.13 Found(%): C, 54.36; H, 4.75; N, 6.92; S, 15.96 |
| Ib-22 | $^1$H-NMR(d$_6$-DMSO) δ 1.76(m, 1H), 1.93(m, 1H), 2.45-2.76(m, 4H), 3.41(m, 1H), 4.22(s, 2H), 4.80(d, J=18.6Hz, 1H), 4.86(d, J=18.6Hz, 1H), 6.95-7.07(m, 3H), 7.20-7.37(m, 7H), 7.48(d, J=3.6Hz, 1H), 12.97(br, 1H); IR |

TABLE 41-continued

| Compound No. | Physical properties |
| --- | --- |
|  | (KBr)3431, 3271, 2923, 1726, 1486, 1453, 1382, 1320, 1153 cm$^{-1}$; Elemental analysis($C_{25}H_{24}FN_2O_4S_2 \cdot 0.3H_2O$)Calcd. (%): C, 61.78; H, 5.10; N, 5.76; S, 13.12 Found(%): C, 61.76; H, 5.01; N, 5.67; S, 13.12 |
| Ib-25 | mp 185-196° C.; $^1$H-NMR(d$_6$-DMSO) δ 1.53(m, 1H), 1.88(m, 1H), 2.48-2.85 (m, 4H), 2.83(s, 3H), 4.12(m, 1H), 4.85(s, 2H), 6.98(m, 1H), 7.06(m, 1H), 7.28-7.32(m, 2H), 7.45-7.51(m, 2H), 7.91-7.98(m, 2H), 12.95(br, 1H); IR(Nujol)2683, 1715, 1592, 1490, 1465, 1473, 1335, 1288, 1167 cm$^{-1}$; $[α]_D^{24}$ + 95.0 ± 1.3° (c=1.004, MeOH); Elemental analysis($C_{20}H_{19}FN_2O_4S$)Calcd. (%): C, 60.56; H, 5.08; F, 4.56; N, 6.73; S, 7.70 Found(%): C, 60.34; H, 5.15; F, 4.33; N, 6.47; S, 7.43 |
| Ib-27 | mp 154-160° C.; $^1$H-NMR(d$_6$-DMSO) δ 1.50(m, 1H), 1.85(m, 1H), 2.42(s, 3H), 2.52-2.78(m, 4H), 2.80(s, 3H), 4.10(m, 1H), 4.82(d, J=18.3Hz, 1H), 4.88(d, J=18.3Hz, 1H), 6.97(m, 1H), 7.05(m, 1H), 7.28-7.32(m, 2H), 7.51 (d, J=8.1Hz, 2H), 7.75(d, J=8.1Hz, 2H), 12.95(br, 1H); IR(Nujol) 2658, 1714, 1598, 1465, 1335, 1288, 1165 cm$^{-1}$; $[α]_D^{24}$ + 119.5 ± 1.6° (c=1.012, MeOH); Elemental analysis($C_{22}H_{24}N_2O_4S$)Calcd. (%): C, 64.06; H, 5.86; N, 6.79; S, 7.77 Found(%): C, 64.02; H, 5.78; N, 6.75; S, 7.68 |

TABLE 42

| Compound No. | Physical properties |
| --- | --- |
| Ib-29 | Mp 185-196° C.; $^1$H-NMR(d$_6$-DMSO) δ 1.52(m, 1H), 1.88(m, 1H), 2.53-2.82 (m, 4H), 2.86(s, 3H), 4.11(m, 1H), 4.82(d, J=18.3Hz, 1H), 4.88(d, J=18.3Hz, 1H), 6.98(m, 1H), 7.06(m, 1H), 7.26-7.33(m, 3H), 7.74(m, J=1.5, 3.6Hz, 1H), 8.03(dd, J=1.5, 5.1Hz, 1H), 12.93(br, 1H); IR(Nujol) 2683, 1715, 1592, 1490, 1465, 1473, 1335, 1288, 1167 cm$^{-1}$; $[α]_D^{24}$ + 95.0 ± 1.3° (c=1.004, MeOH); Elemental analysis($C_{20}H_{19}FN_2O_4S$)Calcd. (%): C, 60.56; H, 5.08; F, 4.56; N, 6.73; S, 7.70 Found(%): C, 60.34; H, 5.15; F, 4.33; N, 6.47; S, 7.43 |
| Ib-30 | mp 175-180° C.; $^1$H-NMR(d$_6$-DMSO) δ 1.36(m, 1H), 1.88(m, 1H), 2.52(m, 1), 2.64-2.86(m, 3H), 2.83(s, 3H), 4.11(m, 1H), 4.85(s, 2H), 6.98(m, 1H), 7.06 (m, 1H), 7.28-7.32(m, 2H), 7.45(dd, J=1.2, 5.1Hz, 1H), 7.83(dd, J=3.0, 5.1Hz, 1H), 8.31(dd, J=1.2, 3.0Hz, 1H), 12.93(br, 1H); IR(Nujol) 3100, 2662, 1721, 1468, 1336, 1323, 1253, 1201, 1163, 1138 cm$^{-1}$; Elemental analysis($C_{19}H_{20}N_2O_4S_2$)Calcd. (%): C, 56.42; H, 4.98; N, 6.93; S, 15.85 Found(%): C, 56.34; H, 4.88; N, 6.85; S, 15.80 |
| Ib-31 | mp 138-140° C.; $^1$H-NMR(d$_6$-DMSO) δ 1.49(m, 1H), 1.86(m, 1H), 2.49-2.77 (m, 4H), 2.81(s, 3H), 4.02(m, 1H), 4.25(s, 2H), 4.85(s, 2H), 6.96-7.08(m, 3H), 7.22-7.38(m, 7H), 7.56(d, J=3.9Hz, 1H), 12.97(br, 1H); IR(Nujol) 1712, 1468, 1449, 1431, 1410, 1380, 1341, 1238, 1154 cm$^{-1}$; Elemental analysis ($C_{26}H_{26}N_2O_4S_2$)Calcd. (%): C, 63.13; H, 5.30; N, 5.66; S, 12.97 Found(%): C, 62.99; H, 5.26; N, 5.56; S, 13.00 |
| Ib-77 | mp 160-172° C.; $^1$H-NMR(d$_6$-DMSO) δ 2.50(m, 1H), 2.80-3.06(m, 6H), 4.18 (d, J=18.0Hz, 1H), 4.88(d, J=18.0Hz, 1H), 6.94-7.04(m, 2H), 7.27-7.31 (m, 2H), 7.41-7.48(m, 2H), 7.85-7.91(m, 3H), 12.95(br, 1H); IR(Nujol) 3387, 3352, 2653, 1722, 1593, 1494, 1459, 1402, 1330, 1289, 1235, 1156 cm$^{-1}$; Elemental analysis($C_{20}H_{19}FN_2O_4S$)Calcd. (%): C, 59.69; H, 4.76; F, 4.72; N, 6.96; S, 7.97 Found(%): C, 59.40; H, 4.74; F, 4.60; N, 7.04; S, 7.91 |
| Ic-2 | mp 142-143° C.; $^1$H-NMR(CDCl$_3$) δ 2.42(br s, 2H), 3.31(t, J=5.7Hz, 2H), 3.97(br s, 2H), 4.87(s, 2H), 6.21(br s, 1H), 7.03(s, 1H), 7.14-7.29(m, 5H), 7.75(d, J=7.8Hz, 1H), 7.85(dd, J=4.8, 8.7Hz, 2H); IR(KBr)3348, 1770, 1590, 1491, 1466, 1347, 1331, 1167, 1156, 1095 cm$^{-1}$; Elemental analysis ($C_{21}H_{19}FN_2O_4S$)Calcd. (%): C, 60.86; H, 4.62; N, 6.76; F, 4.58; S, 7.74 Found (%): C, 60.94; H, 4.65; N, 6.65; F, 4.24; S, 7.70 |
| Ic-6 | mp 189-194° C.(dec); $^1$H-NMR(CDCl$_3$) δ 1.56(m, 1H), 1.84(m, 2H), 2.06(m, 1H), 2.40-2.54(m, 2H), 3.24(m, 1H), 3.70(m, 1H), 3.94(dd, J=2.1, 11.7Hz, 1H), 4.84(s, 2H), 6.88(s, 1H), 7.13-7.26(m, 5H), 7.63(d, J=7.8Hz, 1H), 7.76(dd, J=5.1, 9.0Hz, 2H); IR(KBr)3423, 1706, 1590, 1492, 1468, 1405, 1332, 1288, 1240, 1148 cm$^{-1}$; Elemental analysis($C_{21}H_{21}FN_2O_4S$)Calcd. (%): C, 60.56; H, 5.08; N, 6.73; F, 4.56; S, 7.70 Found(%): C, 60.51; H, 5.12; N, 6.63; F, 4.35; S, 7.56 |

TABLE 43

| Compound No. | Physical properties |
| --- | --- |
| Ic-8 | mp 152-157° C.; $^1$H-NMR(CDCl$_3$) δ 1.57(m, 1H), 1.79-1.90(m, 2H), 2.06(m, 1H), 2.53-2.65(m, 2H), 3.26(m, 1H), 3.70(m, 1H), 3.94(m, 1H), 4.84(s, 2H), |

TABLE 43-continued

| Compound No. | Physical properties |
|---|---|
| | 6.90(s, 1H), 7.10-7.28(4H, m), 7.51(m, 1H), 7.58(m, 1H), 7.64(d, J=7.8Hz, 1H); IR(Nujol)3424, 3101, 3055, 2930, 1717, 1614, 1579, 1469, 1406, 1337, 1243, 1164, 1146 cm$^{-1}$; Elemental analysis($C_{19}H_{20}N_2O_4S_2$)Calcd. (%): C, 56.42; H, 4.98; N, 6.93; S, 15.85 Found(%): C, 56.37; H, 4.93; N, 6.83; S, 15.68 |
| Ic-11 | mp 212-214° C.; $^1$H-NMR(d$_6$-DMSO) δ 1.41-1.96(m, 4H), 2.27-2.42(m, 2H), 3.06(m, 1H), 3.64-3.84(m, 2H), 4.94(s, 2H), 6.97(td, J=2.7, 9.0Hz, 1H), 7.23(s, 1H), 7.31(dd, J=2.7, 10.2Hz, 1H), 7.36(dd, J=4.5, 9.0Hz, 1H), 7.42-7.48(m, 2H), 7.80-7.86(m, 2H); IR(Nujol)2654, 2558, 1709, 1624, 1591, 1489, 1458, 1407, 1334, 1319, 1283, 1241, 1192, 1155 cm$^{-1}$; Elemental analysis($C_{21}H_{20}F_2N_2O_4S$•0.2AcOEt)Calcd. (%): C, 57.92; H, 4.82; F, 8.40; N, 6.20; S, 7.09 Found(%): C, 58.06; H, 4.67; F, 8.24; N, 6.36; S, 7.31 |
| Ic-14 | mp 155-156° C.; $^1$H-NMR(d$_6$-DMSO) δ 1.86(m, 1H), 2.21(m, 1H), 3.13(dd, J=8.4, 9.6Hz, 1H), 3.29-3.51(m, 3H), 3.73(dd, J=7.2, 9.6Hz, 1H), 4.89(s, 2H), 6.98(m, 1H), 7.06(s, 1H), 7.11(m, 1H), 7.31(m, 1H), 7.37(d, J=8.1Hz, 1H), 7.37(d, J=8.1Hz, 1H), 7.42-7.49(m, 2H), 7.88-7.95(m, 2H), 12.93(br, 1H); IR(Nujol)2662, 1732, 1712, 1587, 1490, 1469, 1341, 1333, 1241, 1198, 1162, 1095 cm$^{-1}$; Elemental analysis($C_{20}H_{19}FN_2O_4S$)Calcd. (%): C, 59.69; H, 4.76; F, 4.72; N, 6.96; S, 7.97 Found(%): C, 59.55; H, 4.66; F, 4.54; N, 6.83; S, 7.93 |
| Ic-16 | mp 126-133° C.; $^1$H-NMR(d$_6$-DMSO) δ 1.84(m, 1H), 2.22(m, 1H), 3.17(dd, J=8.7, 9.9Hz, 1H), 3.33-3.55(m, 3H), 3.76(dd, J=7.5, 9.9Hz, 1H), 4.91(s, 2H), 7.00(m, 1H), 7.07(s, 1H), 7.12(m, 1H), 7.28-7.40(m, 3H), 7.75(dd, J=1.5, 3.9Hz, 1H), 8.05(dd, J=1.5, 5.1Hz, 1H), 12.92(br, 1H); IR(Nujol) 3230, 1752, 1726, 1469, 1333, 1211, 1146, 1098, 1030 cm$^{-1}$; Elemental analysis($C_{18}H_{18}N_2O_4S_2$•0.2AcOEt)Calcd. (%): C, 55.33; H, 4.84; N, 6.86; S, 15.71 Found(%): C, 55.08; H, 4.90; N, 6.83; S, 15.56 |
| Ic-18 | mp 139-140° C.; $^1$H-NMR(d$_6$-DMSO) δ 1.84-2.16(m, 2H), 2.20(s, 3H), 3.30-3.76(m, 5H), 4.88(s, 2H), 6.77(m, 2H), 7.02(m, 1H), 7.31(d, J=8.1Hz, 1H), 7.50-7.64(m, 2H), 7.94-8.08(m, 2H); IR(Nujol)3075, 2925, 2736, 2656, 2561, 1725, 1590, 1468, 1375, 1351, 1291, 1241, 1152 cm$^{-1}$ |
| Ic-22 | mp 185-190° C. (dec); $^1$H-NMR(CDCl$_3$) δ 2.65(br t, 2H), 3.36(t, J=5.7Hz, 2H), 3.83(br s, 2H), 4.78(s, 2H), 6.10(br s, 1H), 7.06(s, 1H), 7.11-7.27(m, 5H), 7.77(d, J=8.1Hz, 1H), 7.87(dd, J=5.1, 9.0Hz, 2H); Elemental analysis($C_{21}H_{19}FN_2O_4S$)Calcd. (%): C, 60.86; H, 4.62; N, 6.76; F, 4.58; S, 7.74 Found(%): C, 60.59; H, 4.68; N, 6.57; F, 4.29; S, 7.46 |

TABLE 44

| Compound No. | Physical properties |
|---|---|
| Ic-24 | mp 119-124° C. (dec); $^1$H-NMR(CDCl$_3$) δ 1.86(m, 2H), 2.11(m, 2H), 2.45(m, 2H), 2.77(m, 1H), 3.93(m, 2H), 4.84(s, 2H), 6.81(s, 1H), 7.10(m, 1H), 7.21-7.27(m, 4H), 7.51(d, J=8.1Hz, 1H), 7.83(dd, J=5.1, 9.0Hz, 2H); IR (KBr)3422, 1715, 1593, 1493, 1467, 1349, 1333, 1240, 1168, 1154 cm$^{-1}$; Elemental analysis($C_{21}H_{21}FN_2O_4S$)Calcd. (%): C, 60.56; H, 5.08; N, 6.73; F, 4.56; S, 7.70 Found(%): C, 60.48; H, 4.98; N, 6.67; F, 4.35; S, 7.55 |
| Ic-26 | $^1$H-NMR(CDCl$_3$) δ 1.43-1.71(m, 4H), 2.89(m, 1H), 3.08(m, 1H), 3.34-3.49(m, 2H), 3.92(m, 1H), 4.86(s, 2H), 6.93(s, 1H), 7.15-7.26(m, 5H), 7.79(d, J=7.8Hz, 1H), 7.87-7.91(m, 2H); IR(KBr)2927, 1727, 1591, 1493, 1468, 1332, 1292, 1235, 1197, 1152, 1091, 1038 cm$^{-1}$; Elemental analysis ($C_{21}H_{21}FN_2O_4S$•0.6H$_2$O)Calcd. (%): C, 59.03; H, 5.24; N, 6.56; F, 4.45; S, 7.50 Found(%): C, 59.38; H, 5.21; N, 6.42; F, 4.12; S, 7.11 |
| Ic-29 | $^1$H-NMR(CDCl$_3$) δ 1.26-1.65(m, 6H), 2.97-3.21(m, 3H), 3.82(m, 1H), 4.36(m, 1H), 4.82(s, 2H), 6.86(s, 1H), 6.99-7.26(m, 5H), 7.61(d, J=4.8Hz, 1H), 7.69-7.74(m, 2H); IR(KBr)3426, 2936, 1728, 1591, 1494, 1468, 1330, 1289, 1232, 1149, 1091 cm$^{-1}$; Elemental analysis($C_{22}H_{23}FN_2O_4S$•0.4H$_2$O)Calcd. (%): C, 60.37; H, 5.48; N, 6.40; F, 4.34; S, 7.33 Found(%): C, 60.53; H, 5.49; N, 6.26; F, 3.97; S, 6.93 |
| Ic-30 | mp 205-208° C.; $^1$H-NMR(d$_6$-DMSO) δ 1.46-1.97(m, 4H), 2.16-2.37(m, 2H), 3.07(m, 1H), 3.64-3.83(m, 2H), 3.84(s, 3H), 4.93(s, 2H), 7.05(m, 1H), 7.10-7.15(m, 3H), 7.34(d, J=8.1Hz, 1H), 7.53(d, J=7.5Hz, 1H), 7.67(d, J=9.0Hz, 2H). |
| Ic-31 | mp 155-159° C.; $^1$H-NMR(d$_6$-DMSO) δ 1.80(m, 1H), 2.23(m, 1H), 3.16(dd, J=8.7, 9.3Hz, 1H), 3.34-3.56(m, 3H), 3.74(dd, J=7.5, 9.9Hz, 1H), 4.93(s, 2H), 7.12(dd, J=2.1, 8.7Hz, 1H), 7.16(s, 1H), 7.28(dd, J=3.6, 5.1Hz, 1H), 7.38(d, J=8.7Hz, 1H), 7.49(d, J=2.1Hz, 1H), 7.74(dd, J=1.5, 3.6Hz, 1H), 8.03(dd, J=1.5, 5.1Hz, 1H), 12.99(br, 1H); IR(Nujol)2669, 1745, 1669, 1469, 1388, 1347, 1226, 1156, 1040 cm$^{-1}$; Elemental analysis ($C_{18}H_{17}ClN_2O_4S_2$)Calcd. (%): C, 50.88; H, 4.03; Cl, 8.34; N, 6.59; S, 15.09 Found(%): C, 55.86; H, 3.92; Cl, 8.04; N, 6.58; S, 15.00 |

TABLE 44-continued

| Compound No. | Physical properties |
| --- | --- |
| Ic-32 | mp 169-171° C.; $^1$H-NMR(d$_6$-DMSO) δ 1.83(m, 1H), 2.19(m, 1H), 3.11(dd, J=8.7, 9.3Hz, 1H), 3.29-3.50(m, 3H), 3.71(dd, J=7.5, 9.9Hz, 1H), 4.84(s, 2H), 6.93(dd, J=1.5, 8.4Hz, 1H), 7.00(s, 1H), 7.13(d, J=1.5Hz, 1H), 7.19 (d, J=8.4Hz, 1H), 7.42-7.50(m, 2H), 7.89-7.96(m, 2H), 12.89(br, 1H); IR (Nujol)2663, 1730, 1708, 1588, 1492, 1463, 1342, 1243, 1198, 1160, 1096, 1025 cm$^{-1}$; Elemental analysis(C$_{21}$H$_{21}$FN$_2$O$_4$S)Calcd. (%): C, 60.56; H, 5.08; F, 4.56; N, 6.73; S, 7.70 Found(%): C, 60.49; H, 5.08; F, 4.27; N, 6.67; S, 7.40 |

TABLE 45

| Compound No. | Physical properties |
| --- | --- |
| Ic-33 | mp 145-149° C.; $^1$H-NMR(d$_6$-DMSO) δ 1.83(m, 1H), 2.20(m, 1H), 2.36(s, 3H), 3.16(t, J=9.0Hz, 1H), 3.34-3.54(m, 3H), 3.74(dd, J=7.5, 9.6Hz, 1H), 4.86(s, 2H), 6.94(dd, J=1.5, 8.4Hz, 1H), 7.01(s, 1H), 7.17(d, J=1.5Hz, 1H), 7.20(d, J=8.4Hz, 1H), 7.30(dd, J=3.9, 5.1Hz, 1H), 7.75(dd, J=1.5, 3.9Hz, 1H), 8.05(dd, J=1.5, 5.1Hz, 1H), 12.90(br, 1H); IR(Nujol)2662, 1705, 1484, 1463, 1348, 1246, 1156, 1034 cm$^{-1}$; Elemental analysis (C$_{19}$H$_{20}$N$_2$O$_4$S$_2$)Calcd. (%): C, 56.42; H, 4.98; N, 6.93; S, 15.85 Found(%): C, 56.33; H, 4.85; N, 6.84; S, 15.54 |
| Ic-34 | mp 145-146° C.; $^1$H-NMR(d$_6$-DMSO) δ 1.76(m, 1H), 2.20(m, 1H), 3.11(t, J=9.0Hz, 1H), 3.27-3.48(m, 3H), 3.72(dd, J=7.5, 9.6Hz, 1H), 4.90(s, 2H), 7.10(s, 1H), 7.11(dd, J=1.8, 8.7Hz, 1H), 7.37(d, J=8.7Hz, 1H), 7.46(d, J=1.8Hz, 1H), 7.61-7.66(m, 2H), 7.73(m, 1H), 7.83-7.87(m, 2H), 12.98(br, 1H); IR(Nujol)2663, 1731, 1471, 1446, 1340, 1242, 1198, 1162, 1099, 1029 cm$^{-1}$; Elemental analysis(C$_{20}$H$_{19}$ClN$_2$O$_4$S)Calcd. (%): C, 57.34; H, 4.57; Cl, 8.46; N, 6.69; S, 7.65 Found(%): C, 57.00; H, 4.48; Cl, 8.13; N, 6.71; S, 7.43 |
| Ic-35 | $^1$H-NMR(d$_6$-DMSO) δ 1.97(m, 1H), 2.30(m, 1H), 3.08(t, J=9.0Hz, 1H), 3.29-3.59(m, 3H), 3.68(d, J=8.1Hz, 1H), 4.50(d, J=13.5Hz, 1H), 4.56(d, J=13.5Hz, 1H), 4.98(s, 2H), 7.14(dd, J=1.8, 8.7Hz, 1H), 7.29(s, 1H), 7.36-7.50(m, 6H), 7.59(d, J=1.8Hz, 1H), 13.01(br, 1H); IR(KBr)3439, 2637, 1731, 1471, 1329, 1152 cm$^{-1}$; Elemental analysis (C$_{21}$H$_{21}$ClN$_2$O$_4$S.0.6H$_2$O)Calcd. (%): C, 56.84; H, 5.04; Cl, 7.99; N, 6.31; S, 7.23 Found(%): C, 56.96; H, 4.81; Cl, 7.61; N, 6.34; S, 7.17 |
| Ic-36 | mp 158-159° C.; $^1$H-NMR(d$_6$-DMSO) δ 1.82(m, 1H), 2.22(m, 1H), 3.13(t, J=9.0Hz, 1H), 3.28-3.50(m, 3H), 3.72(dd, J=7.5, 9.3Hz, 1H), 4.91(s, 2H), 7.13(dd, J=1.8, 8.7Hz, 1H), 7.16(s, 1H), 7.37(d, J=8.7Hz, 1H), 7.46(d, J=1.8Hz, 1H), 7.64-7.68(m, 2H), 7.82-7.86(m, 2H), 12.99(br, 1H); IR(Nujol) 2669, 1741, 1726, 1472, 1346, 1246, 1162, 1100, 1086, 1032 cm$^{-1}$. |
| Ic-37 | mp 195-196° C.; $^1$H-NMR(d$_6$-DMSO) δ 1.76(m, 1H), 2.19(m, 1H), 2.42(s, 3H), 3.08(t, J=9.0Hz, 1H), 3.26-3.45(m, 3H), 3.68(dd, J=7.5, 9.3Hz, 1H), 4.90(s, 2H), 7.10(s, 1H), 7.11(dd, J=1.8, 8.7Hz, 1H), 7.37(d, J=8.7Hz, 1H), 7.42-7.44(m, 4H), 7.71-7.74(m, 2H), 12.98(br, 1H); IR(Nujol)2671, 1728, 1470, 1347, 1249, 1199, 1158, 1097, 1030 cm$^{-1}$; Elemental analysis (C$_{21}$H$_{21}$ClN$_2$O$_4$S)Calcd. (%): C, 58.26; H, 4.89; Cl, 8.19; N, 6.47; S, 7.41 Found(%): C, 58.18; H, 4.87; Cl, 7.92; N, 6.40; S, 7.28 |

TABLE 46

| Compound No. | Physical properties |
| --- | --- |
| Ic-38 | mp 166-168° C.; $^1$H-NMR(d$_6$-DMSO) δ 1.81(m, 1H), 2.20(m, 1H), 3.10(t, J=9.0Hz, 1H), 3.27-3.50(m, 3H), 3.72(dd, J=7.5, 9.3Hz, 1H), 4.90(s, 2H), 6.95(m, 1H), 7.15-7.19(m, 2H), 7.34(dd, J=4.5, 9.0Hz, 1H), 7.40-7.47(m, 2H), 7.85-7.94(m, 2H), 12.96(br, 1H); IR(Nujol)2662, 1725, 1715, 1587, 1457, 1341, 1333, 1237, 1198, 1160, 1096 cm$^{-1}$; Elemental analysis (C$_{20}$H$_{18}$F$_2$N$_2$O$_4$S)Calcd. (%): C, 57.14; H, 4.32; F, 9.04; N, 6.66; S, 7.63 Found (%): C, 57.15; H, 4.25; F, 8.79; N, 6.54; S, 7.57 |
| Ic-39 | $^1$H-NMR(d$_6$-DMSO) δ 1.80(m, 1H), 2.22(m, 1H), 3.15(t, J=9.0Hz, 1H), 3.31-3.53(m, 3H), 3.75(dd, J=7.5, 9.6Hz, 1H), 4.92(s, 2H), 6.96(m, 1H), 7.15(s, 1H), 7.21(dd, J=2.4, 9.9Hz, 1H), 7.28(dd, J=3.9, 4.8Hz, 1H), 7.35 (dd, J=4.5, 9.0Hz, 1H), 7.74(dd, J=1.2, 3.9Hz, 1H), 8.03(dd, J=1.2, 4.8 Hz, 1H), 12.97(br, 1H); IR(KBr)1729, 1626, 1580, 1486, 1457, 1403, 1344, 1225, 1155 cm$^{-1}$; Elemental analysis(C$_{18}$H$_{17}$FN$_2$O$_4$S$_2$)Calcd. (%): C, 52.24; H, 4.29; F, 4.59; N, 6.77; S, 15.50 Found(%): C, 52.26; H, 4.22; F, 4.46; N, 6.33; S, 15.47 |
| Ic-40 | mp 157-160° C.; $^1$H-NMR(d$_6$-DMSO) δ 1.82(m, 1H), 2.21(m, 1H), 3.10(t, J=9.0Hz, 1H), 3.30-3.50(m, 3H), 3.71(dd, J=7.5, 9.6Hz, 1H), 3.74(s, 3H), 4.83(s, 2H), 6.75(dd, J=2.4, 8.7Hz, 1H), 6.88(d, J=2.4Hz, 1H), 7.00(s, |

TABLE 46-continued

| Compound No. | Physical properties |
|---|---|
| | 1H), 7.21(d, J=8.7Hz, 1H), 7.40-7.48(m, 2H), 7.88-7.95(m, 2H), 12.90(br, 1H); IR(Nujol)3204, 1742, 1718, 1622, 1586, 1493, 1452, 1338, 1331, 1224, 1151, 1095, 1037, 1027 cm$^{-1}$; Elemental analysis($C_{21}H_{21}FN_2O_5S$)Calcd. (%): C, 58.32; H, 4.89; F, 4.39; N, 6.48; S, 7.41 Found(%): C, 58.02; H, 5.07; F, 4.22; N, 6.30; S, 7.15 |
| Ic-41 | $^1$H-NMR(d$_6$-DMSO) δ 1.82(m, 1H), 2.23(m, 1H), 3.14(t, J=9.0Hz, 1H), 3.30-3.52(m, 3H), 3.75(m, 1H), 3.75(s, 3H), 4.85(s, 2H), 6.76(dd, J=2.4, 8.7Hz, 1H), 6.92(d, J=2.4Hz, 1H), 7.01(s, 1H), 7.22(d, J=8.7Hz, 1H), 7.29(dd, J=3.9, 5.1Hz, 1H), 7.75(dd, J=1.2, 3.6Hz, 1H), 8.04(dd, J=1.2, 5.1Hz, 1H), 12.74(br, 1H); IR(KBr)1727, 1622, 1580, 1488, 1454, 1403, 1345, 1226, 1155, 1031 cm$^{-1}$; Elemental analysis($C_{19}H_{20}N_2O_5S_2$.0.2H$_2$O) Calcd. (%): C, 53.81; H, 4.85; N, 6.61; S, 15.12 Found(%): C, 53.85; H, 4.87; N, 6.34; S, 15.01 |
| Ic-42 | $^1$H-NMR(d$_6$-DMSO) δ 1.82(m, 1H), 2.16(m, 1H), 3.09(t, J=9.0Hz, 1H), 3.25-3.47(m, 3H), 3.69(dd, J=7.5, 9.9Hz, 1H), 4.79(s, 2H), 6.63(dd, J=2.1, 9.0Hz, 1H), 6.72(d, J=2.1Hz, 1H), 6.93(s, 1H), 7.10(d, J=9.0Hz, 1H), 7.42-7.47(m, 2H), 7.88-7.93(m, 2H),(d, J=8.7Hz, 1H), 7.46(d, J=1.8Hz, 1H), 7.61-7.66(m, 2H), 7.73(m, 1H), 8.73(br, 1H), 12.87(br, 1H); IR (KBr)3436, 1730, 1625, 1590, 1492, 1466, 1332, 1293, 1226, 1153, 1096 cm$^{-1}$; Elemental analysis($C_{20}H_{19}FN_2O_5S$.0.7H$_2$O)Calcd. (%): C, 55.73; H, 4.77; F, 4.41; N, 6.50; S, 7.44 Found(%): C, 55.69; H, 4.68; F, 4.05; N, 6.28; S, 7.19 |

TABLE 47

| Compound No. | Physical properties |
|---|---|
| Ic-43 | mp 119-123° C.; $^1$H-NMR(d$_6$-DMSO) δ 0.90(t, J=7.5Hz, 3H), 1.34-1.46(m, 2H), 1.60-1.79(m, 2H), 2.03(m, 1H), 2.36(m, 1H), 3.02-3.65(m, 6H), 3.80 (dd, J=7.5, 9.0Hz, 1H), 4.96(s, 2H), 6.98(m, 1H), 7.33-7.44(m, 3H), 12.96 (br, 1H); IR(Nujol)3254, 1751, 1626, 1583, 1488, 1456, 1318, 1299, 1274, 1183, 1127, 1095, 1045 cm$^{-1}$; Elemental analysis($C_{18}H_{23}FN_2O_4S$)Calcd. (%): C, 56.53; H, 6.06; F, 4.97; N, 7.32; S, 8.38 Found(%): C, 56.46; H, 5.99; F, 4.76; N, 7.19; S, 8.20 |
| Ic-44 | mp 178-182° C.; $^1$H-NMR(d$_6$-DMSO) δ 1.99(m, 1H), 2.33(m, 1H), 3.20(t, J=9.0Hz, 1H), 3.23-3.60(m, 3H), 3.80(dd, J=7.5, 9.9Hz, 1H), 4.91(s, 2H), 6.95(m, 1H), 7.29(s, 1H), 7.31-7.47(m, 7H), 7.73-7.76(m, 2H), 12.95(br, 1H); IR(Nujol)1719, 1620, 1577, 1486, 1459, 1331, 1228, 1144, 1048, 1023 cm$^{-1}$; Elemental analysis($C_{22}H_{21}FN_2O_4S$)Calcd. (%): C, 61.67; H, 4.94; F, 4.43; N, 6.54; S, 7.48 Found(%): C, 61.45; H, 4.92; F, 4.27; N, 6.40; S, 7.40 |
| Ic-45 | mp 205-207° C.; $^1$H-NMR(d$_6$-DMSO) δ 1.82(m, 1H), 2.22(m, 1H), 3.15(t, J=9.0Hz, 1H), 3.34-3.54(m, 3H), 3.76(dd, J=7.5, 9.3Hz, 1H), 4.88(s, 2H), 6.95(m, 1H), 7.17(s, 1H), 7.20(dd, J=2.4, 9.9Hz, 1H), 7.32(dd, J=4.5, 9.0Hz, 1H), 7.43-7.56(m, 3H), 7.76-7.79(m, 2H), 9.93(s, 4H), 12.93(br, 1H); IR (Nujol)1721, 1597, 1483, 1457, 1337, 1233, 1199, 1158 cm$^{-1}$; Elemental analysis($C_{26}H_{23}FN_2O_4S$)Calcd. (%): C, 65.26; H, 4.84; F, 3.97; N, 5.85; S, 6.70 Found(%): C, 65.03; H, 4.85; F, 3.78; N, 5.72; S, 6.59 |
| Ic-46 | mp 172-174° C.; $^1$H-NMR(d$_6$-DMSO) δ 2.20(m, 1H), 2.36(m, 1H), 2.94(s, 3H), 3.16(t, J=9.0Hz, 1H), 3.33-3.64(m, 3H), 3.79(dd, J=7.2, 9.0Hz, 1H), 4.97(s, 2H), 6.98(m, 1H), 7.34(s, 1H), 7.38(dd, J=4.2, 9.0Hz, 1H), 7.44 (dd, J=2.4, 10.2Hz, 1H), 12.98(br, 1H); IR(Nujol)1722, 1487, 1456, 1318, 1233, 1196, 1141, 1042 cm$^{-1}$; Elemental analysis($C_{15}H_{17}FN_2O_4S$)Calcd. (%): C, 52.93; H, 5.03; F, 5.58; N, 8.23; S, 9.42 Found(%): C, 52.76; H, 4.96; F, 5.39; N, 8.15; S, 9.20 |
| Ic-47 | mp 171-173° C.; $^1$H-NMR(d$_6$-DMSO) δ 1.88(m, 1H), 2.26(m, 1H), 3.17(t, J=9.3Hz, 1H), 3.34-3.57(m, 3H), 3.76(dd, J=6.9, 9.3Hz, 1H), 4.93(s, 2H), 7.12(s, 1H), 7.32(m, 1H), 7.39-7.48(m, 6H), 7.63-7.68(m, 3H), 7.89-7.96(m, 2H), 12.99(br, 1H); IR(Nujol)2668, 1736, 1592, 1493, 1476, 1347, 1335, 1258, 1244, 1187, 1166, 1154 cm$^{-1}$; Elemental analysis($C_{26}H_{23}FN_2O_4S$) Calcd. (%): C, 65.26; H, 4.84; F, 3.97; N, 5.85; S, 6.70 Found(%): C, 65.29; H, 4.84; F, 3.91; N, 5.75; S, 6.78 |
| Ic-48 | mp 161-163° C.; $^1$H-NMR(d$_6$-DMSO) δ 0.89(t, J=7.5Hz, 3H), 1.34-1.46(m, 2H), 1.61-1.71(m, 2H), 2.08(m, 1H), 2.41(m, 1H), 3.04-3.20(m, 2H), 3.27-3.58(m, 3H), 3.68-3.86(m, 2H), 4.99(s, 2H), 7.29-7.33(m, 2H), 7.42-7.48(m, 4H), 7.68-7.71(m, 2H), 7.86(s, 1H), 12.97(br, 1H); IR(Nujol)2666, 1715, 1478, 1455, 1325, 1243, 1197, 1133, 1094, 1046 cm$^{-1}$; Elemental analysis ($C_{24}H_{28}N_2O_4S$)Calcd. (%): C, 65.43; H, 6.41; N, 6.36; S, 7.28 Found(%): C, 65.16; H, 6.37; N, 6.24; S, 7.29 |

TABLE 48

| Compound No. | Physical properties |
| --- | --- |
| Ic-49 | mp 174-178° C.; $^1$H-NMR($d_6$-DMSO) δ 1.86(m, 1H), 2.28(m, 1H), 3.18-3.57 (m, 4H), 3.78(dd, J=6.9, 9.3Hz, 1H), 4.94(s, 2H), 7.12(s, 1H), 7.27(dd, J=3.9, 5.1Hz, 1H), 7.32(m, 1H), 7.42-7.49(m, 4H), 7.64-7.70(m, 3H), 7.75(dd, J=1.5, 3.9Hz, 1H), 8.02(dd, J=1.5, 5.1Hz, 1H), 12.97(br, 1H); IR(Nujol) 2664, 1738, 1714, 1476, 1345, 1336, 1251, 1187, 1157, 1020 cm$^{-1}$; Elemental analysis($C_{24}H_{22}N_2O_4S$)Calcd. (%): C, 61.78; H, 4.75; N, 6.00; S, 13.74 Found (%): C, 61.73; H, 4.74; N, 5.90; S, 13.62 |
| Ic-50 | mp 160-170° C.; $^1$H-NMR($d_6$-DMSO) δ 1.99(m, 1H), 2.32(m, 1H), 3.00(t, J 8.1Hz, 1H), 3.17(t, J=9.0Hz, 1H), 3.35-3.61(m, 5H), 3.83(dd, J=7.5, 9.0Hz, 1H), 4.93(s, 2H), 6.97(m, 1H), 7.20-7.43(m, 8H), 12.94(br, 1H); IR (Nujol)3617, 3498, 2625, 1739, 1713, 1488, 1458, 1327, 1224, 1147, 1135, 1049 cm$^{-1}$; Elemental analysis($C_{22}H_{23}FN_2O_4S.H_2O$)Calcd. (%): C, 58.91; H, 5.62; F, 4.24; N, 6.25; S, 7.15 Found(%): C, 59.09; H, 5.51; F, 4.17; N, 6.12; S, 7.19 |
| Ic-51 | mp 192-194° C.; $^1$H-NMR($d_6$-DMSO) δ 1.82(m, 1H), 2.21(m, 1H), 3.11(t, J=9.0Hz, 1H), 3.27-3.50(m, 3H), 3.73(dd, J=7.5, 9.3Hz, 1H), 4.89(d, J=18.3Hz, 1H), 4.95(d, J=18.3Hz, 1H), 7.00(dd, J=1.5, 8.4Hz, 1H), 7.11(s, 1H), 7.40-7.51(m, 4H), 7.87-7.93(m, 2H), 12.97(br, 1H); IR(Nujol)2641, 1736, 1529, 1492, 1470, 1414, 1335, 1241, 1227, 1178, 1168, 1159 cm$^{-1}$; Elemental analysis($C_{20}H_{18}ClFN_2O_4S$)Calcd. (%): C, 54.98; H, 4.15; Cl, 8.11; F, 4.35; N, 6.41; S, 7.34 Found(%): C, 54.95; H, 4.07; Cl, 7.91; F, 4.33; N, 6.40; S, 7.36 |
| Ic-52 | Mp 224-226° C.; $^1$H-NMR($d_6$-DMSO) δ 1.81(m, 1H), 2.22(m, 1H), 3.15(dd, J=8.7, 9.6Hz, 1H), 3.34-3.53(m, 3H), 3.75(dd, J=7.2, 9.6Hz, 1H), 4.90(d, J=18.3Hz, 1H), 4.96(d, J=18.3Hz, 1H), 7.01(dd, J=1.8, 8.4Hz, 1H), 7.12 (s, 1H), 7.29(dd, J=3.9, 5.1Hz, 1H), 7.41(d, J=8.4Hz, 1H), 7.51(d, J=1.8Hz, 1H), 7.74(dd, J=1.5, 3.9Hz, 1H), 8.04(dd, J=1.5, 5.1Hz, 1H), 12.97 (br, 1H); IR(Nujol)1729, 1472, 1341, 1327, 1236, 1200, 1157, 1032 cm$^{-1}$; Elemental analysis($C_{18}H_{17}ClN_2O_4S_2.AcOEt$)Calcd. (%): C, 51.09; H, 4.33; Cl, 7.85; N, 6.21; S, 14.21 Found(%): C, 50.97; H, 4.22; Cl, 7.65; N, 6.31; S, 14.51 |
| Ic-53 | Mp 133-136° C.; $^1$H-NMR($d_6$-DMSO) δ 1.93(m, 1H), 2.30(m, 1H), 3.19-3.59 (m, 4H), 3.80(m, 1H), 4.89(d, J=18.9Hz, 1H), 4.95(d, J=18.9Hz, 1H), 7.12(dd, J=2.1, 8.7Hz, 1H), 7.19(s, 1H), 7.36-7.50(m, 3H), 7.53(d, J=2.1Hz, 1H), 7.69-7.88(m, 2H), 12.99(brs, 1H); IR(Nujol)3093, 2668, 2575, 1714, 1598, 1472, 1416, 1376, 1351, 1304, 1263, 1248, 1223, 1189, 1164, 1127, 1108 cm$^{-1}$; Elemental analysis($C_{20}H_{18}ClFN_2O_4S$)Calcd. (%): C, 54.98; H, 4.15; Cl, 8.11; F, 4.35; N, 6.41; S, 7.34 Found(%): C, 54.68; H, 4.01; Cl, 7.81; F, 4.17; N, 6.38; S, 7.30 |

TABLE 49

| Compound No. | Physical properties |
| --- | --- |
| Ic-54 | mp 162-165° C.; $^1$H-NMR($d_6$-DMSO) δ 1.82(m, 1H), 2.20(m, 1H), 3.11-3.52 (m, 4H), 3.75(dd, J=7.2, 9.6Hz, 1H), 4.92(d, J=18.6Hz, 1H), 4.94(d, J=18.6Hz, 1H), 7.11(dd, J=2.1, 8.4Hz, 1H), 7.16(s, 1H), 7.37(d, J=8.4Hz, 1H), 7.48(d, J=2.1Hz, 1H), 7.53-7.73(m, 4H), 12.99(brs, 1H); IR(Nujol) 3084, 2667, 2573, 1710, 1590, 1472, 1415, 1390, 1378, 1345, 1304, 1267, 1249, 1221, 1197, 1162, 1106 cm$^{-1}$; Elemental analysis ($C_{20}H_{18}ClFN_2O_4S.0.1AcOEt$)Calcd. (%): C, 54.97; H, 4.25; Cl, 7.95; F, 4.26; N, 6.29; S, 7.19 Found(%): C, 54.97; H, 4.11; Cl, 7.74; F, 4.36; N, 6.36; S, 7.25 |
| Ic-55 | mp 193-197° C.; $^1$H-NMR($d_6$-DMSO) δ 1.94-2.02(m, 2H), 2.21(s, 3H), 3.15-3.69(m, 5H), 4.92(s, 2H), 6.88(d, J=1.5Hz, 1H), 7.02(dd, J=1.5, 8.7Hz, 1H), 7.38(d, J=8.7Hz, 1H), 7.50-7.57(m, 2H), 7.96-8.01(m, 2H), 13.04(br, 1H); IR(Nujol)1734, 1592, 1494, 1469, 1338, 1169, 1159 cm$^{-1}$; Elemental analysis($C_{21}H_{20}ClFN_2O_4S$)Calcd. (%): C, 55.94; H, 4.47; Cl, 7.86; F, 4.21; N, 6.21; S, 7.11 Found(%): C, 55.78; H, 4.41; Cl, 7.59; F, 4.28; N, 6.25; S, 7.10 |
| Ic-56 | mp 196-201° C.; $^1$H-NMR($d_6$-DMSO) δ 1.98-2.07(m, 2H), 2.21(s, 3H), 3.24-3.40(m, 2H), 3.45-3.55(m, 2H), 3.65(m, 1H), 4.93(s, 2H), 7.02-7.05(m, 2H), 7.36-7.40(m, 2H), 7.81(dd, J=1.5, 3.6Hz, 1H), 8.13(dd, J=1.5, 5.1Hz, 1H), 13.06(br, 1H); IR(Nujol)3278, 1770, 1739, 1470, 1346, 1325, 1231, 1221, 1159, 1089, 1059, 1027 cm$^{-1}$; Elemental analysis($C_{19}H_{19}ClN_2O_4S_2$) Calcd. (%): C, 51.99; H, 4.36; Cl, 8.08; N, 6.38; S, 14.61 Found(%): C, 51.86; H, 4.34; Cl, 7.75; N, 6.36; S, 14.74 |
| Ic-57 | mp 153-161° C.; $^1$H-NMR($d_6$-DMSO) δ 0.94(t, J=7.8Hz, 3H), 1.39-1.52(m, 2H), 1.67-1.77(m, 2H), 2.13(m, 1H), 2.31(s, 3H), 2.31(m, 1H), 3.20(m, 1H), 3.33-3.43(m, 3H), 3.54-3.76(m, 3H), 4.96(s, 2H), 7.07(dd, J=2.1, 9.0Hz, 1H), 7.41(d, J=9.0Hz, 1H), 7.56(d, J=2.1Hz, 1H), 13.06(br, 1H); IR (Nujol)3187, 1759, 1713, 1472, 1420, 1380, 1328, 1318, 1301, 1247, 1190, 1142, 1114, 1049 cm$^{-1}$; Elemental analysis($C_{19}H_{25}ClN_2O_4S$)Calcd. (%): C, |

TABLE 49-continued

| Compound No. | Physical properties |
| --- | --- |
| | 55.26; H, 6.10; Cl, 8.59; N, 6.78; S, 7.77 Found(%): C, 55.47; H, 6.10; Cl, 8.36; N, 6.77; S, 7.54 |
| Ic-58 | mp 180-183° C.; $^1$H-NMR(d$_6$-DMSO) δ 1.85(m, 1H), 2.24(m, 1H), 3.13-3.55 (m, 4H), 3.77(dd, J=7.5, 9.6Hz, 1H), 4.90(s, 2H), 7.11(dd, J=1.8, 8.7Hz, 1H), 7.19(s, 1H), 7.37(d, J=8.7Hz, 1H), 7.48(d, J=1.8Hz, 1H), 7.98(d, J=8.4Hz, 2H), 8.06(d, J=8.4Hz, 2H), 12.95(brs, 1H); IR(Nujol)3092, 2730, 2665, 2553, 1723, 1695, 1612, 1473, 1403, 1378, 1329, 1289, 1268, 1245, 1233, 1189, 1163, 1140, 1106 cm$^{-1}$; Elemental analysis(C$_{21}$H$_{18}$ClF$_3$N$_2$O$_4$S) Calcd. (%): C, 51.80; H, 3.73; Cl, 7.28; F, 11.71; N, 5.75; S, 6.59 Found(%): C, 51.65; H, 3.66; Cl, 7.02; F, 11.55; N, 5.76; S, 6.72 |

TABLE 50

| Compound No. | Physical properties |
| --- | --- |
| Ic-59 | mp 136-142° C.; $^1$H-NMR(d$_6$-DMSO) δ 0.90(t, J=7.2Hz, 3H), 1.34-1.47(m, 2H), 1.59-1.72(m, 2H), 2.02(m, 1H), 2.36(m, 1H), 3.03-3.68(m, 6H), 3.80 (dd, J=7.5, 9.0Hz, 1H), 4.97(s, 2H), 7.13(dd, J=2.1, 8.7Hz, 1H), 7.34(s, 1H), 7.41(d, J=8.7Hz, 1H), 7.68(d, J=2.1Hz, 1H), 13.00(brs, 1H); IR (Nujol)3133, 3093, 2664, 2549, 1721, 1697, 1472, 1403, 1389, 1333, 1297, 1277, 1242, 1231, 1199, 1146, 1100 cm$^{-1}$; Elemental analysis (C$_{18}$H$_{23}$ClN$_2$O$_4$S)Calcd. (%): C, 54.20; H, 5.81; Cl, 8.89; N, 7.02; S, 8.04 Found(%): C, 54.09; H, 5.74; Cl, 8.65; N, 7.00; S, 7.93 |
| Ic-60 | mp 158-162° C.; $^1$H-NMR(d$_6$-DMSO) δ 0.81-0.91(m, 3H), 1.17-1.46(m, 10H), 1.58-1.74(m, 2H), 2.02(m, 1H), 2.35(m, 1H), 3.01-3.68(m, 6H), 3.80(dd, J=7.5, 9.0Hz, 1H), 4.97(s, 2H), 7.13(dd, J=2.1, 8.7Hz, 1H), 7.34(s, 1H), 7.41 (d, J=8.7Hz, 1H), 7.68(d, J=2.1Hz, 1H), 13.00(brs, 1H); IR(Nujol) 3135, 3094, 1720, 1695, 1471, 1403, 1391, 1378, 1333, 1285, 1230, 1199, 1146, 1119 cm$^{-1}$; Elemental analysis(C$_{22}$H$_{31}$ClN$_2$O$_4$S)Calcd. (%): C, 58.07; H, 6.87; Cl, 7.79; N, 6.16; S, 7.05 Found(%): C, 58.00; H, 6.82; Cl, 7.55; N, 6.20; S, 6.99 |
| Ic-61 | mp 220-223° C.; $^1$H-NMR(d$_6$-DMSO) δ 1.92(m, 1H), 2.29(m, 1H), 3.15-3.60 (m, 4H), 3.83(dd, J=7.5, 9.3Hz, 1H), 4.86(s, 2H), 7.09(s, 1H), 7.10(dd, J=2.1, 8.7Hz, 1H), 7.35(d, J=8.7Hz, 1H), 7.47(d, J=2.1Hz, 1H), 7.63-7.77 (m, 3H), 8.11(m, 1H), 8.16(m, 1H), 8.27(d, J=8.4Hz, 1H), 8.75(d, J=7.5Hz, 1H), 12.96(brs, 1H); IR(Nujol)3266, 3064, 3045, 1764, 1736, 1592, 1565, 1506, 1471, 1430, 1404, 1385, 1345, 1329, 1266, 1203, 1187, 1161, 1137, 1111 cm$^{-1}$; Elemental analysis(C$_{24}$H$_{21}$ClN$_2$O$_4$S.0.2H$_2$O)Calcd. (%): C, 61.00; H, 4.56; Cl, 7.50; N, 5.93; S, 6.79 Found(%): C, 61.11; H, 4.57; Cl, 7.33; N, 5.93; S, 6.63 |
| Ic-62 | mp 195-198° C.; $^1$H-NMR(d$_6$-DMSO) δ 1.88(m, 1H), 2.24(m, 1H), 3.13-3.59 (m, 4H), 3.77(dd, J=7.2, 9.3Hz, 1H), 4.89(s, 2H), 7.09(dd, J=1.8, 8.7Hz, 1H), 7.18(s, 1H), 7.34(d, J=8.7Hz, 1H), 7.43(d, J=1.8Hz, 1H), 8.06(d, J=9.0Hz, 2H), 8.35(d, J=9.0Hz, 2H), 12.97(brs, 1H); IR(Nujol)3108, 3068, 1738, 1606, 1530, 1472, 1414, 1401, 1376, 1348, 1320, 1303, 1261, 1238, 1227, 1200, 1179, 1165, 1134, 1103 cm$^{-1}$; Elemental analysis(C$_{20}$H$_{18}$ClN$_3$O$_6$S) Calcd. (%): C, 51.78; H, 3.91; Cl, 7.64; N, 9.06; S, 6.91 Found(%): C, 51.59; H, 3.81; Cl, 7.34; N, 8.87; S, 6.84 |
| Ic-63 | $^1$H-NMR(d$_6$-DMSO) δ 1.83(m, 1H), 2.22(m, 1H), 3.12-3.83(m, 5H), 4.83, 4.87(each s, total 2H), 7.06-7.19(m, 2H), 7.31-7.43(m, 2H), 7.89-8.16(m, 4H); IR(KBr)3413, 3226, 3091, 2233, 1728, 1611, 1568, 1472, 1437, 1399, 1344, 1282, 1218, 1161, 1107 cm$^{-1}$. |

TABLE 51

| Compound No. | Physical properties |
| --- | --- |
| Ic-64 | Mp 205-206° C.; $^1$H-NMR(d$_6$-DMSO) δ 1.92(m, 1H), 2.19(m, 1H), 3.10(m, 1H), 3.34-3.51(m, 2H), 3.69-3.79(m, 2H), 4.90(d, J=18.3Hz, 1H), 4.96(d, J=18.3Hz, 1H), 7.03(dd, J=1.2, 7.8Hz, 1H), 7.09(t, J=7.8Hz, 1H), 7.23(s, 1H), 7.33(dd, J=1.2, 7.8Hz, 1H), 7.39-7.45(m, 2H), 7.85-7.91(m, 2H), 13.03(br, 1H); IR(Nujol) 2662, 1723, 1589, 1491, 1476, 1447, 1350, 1332, 1248, 1236, 1182, 1162, 1098, 1029 cm$^{-1}$; Elemental analysis (C$_{20}$H$_{18}$ClFN$_2$O$_4$S)Calcd. (%): C, 54.98; H, 4.15; Cl, 8.11; F, 4.35; N, 6.41; S, 7.34 Found(%): C, 55.04; H, 4.13; Cl, 7.79; F, 4.33; N, 6.42; S, 7.32 |
| Ic-65 | mp 170-171° C.; $^1$H-NMR(d$_6$-DMSO) δ 1.93(m, 1H), 2.21(m, 1H), 3.14(m, 1H), 3.37-3.54(m, 2H), 3.72-3.83(m, 2H), 4.91(d, J=18.6Hz, 1H), 4.98(d, J=18.6Hz, 1H), 7.03(dd, J=1.2, 7.8Hz, 1H), 7.09(t, J=7.8Hz, 1H), 7.24(s, |

TABLE 51-continued

| Compound No. | Physical properties |
| --- | --- |
| | 1H), 7.26(dd, J=3.9, 5.1Hz, 1H), 7.34(dd, J=1.2, 8.1Hz, 1H), 7.70(dd, J=1.5, 3.9Hz, 1H), 8.01(dd, J=1.5, 5.1Hz, 1H), 13.02(br, 1H); IR(Nujol) 3204, 1755, 1728, 1554, 1453, 1401, 1338, 1326, 1196, 1146, 1033 cm$^{-1}$; Elemental analysis($C_{18}H_{17}ClN_2O_4S_2$)Calcd. (%): C, 50.88; H, 4.03; Cl, 8.34; N, 6.59; S, 15.09 Found(%): C, 50.87; H, 3.97; Cl, 8.10; N, 6.52; S, 14.89 |
| Ic-66 | mp 169-171° C.; $^1$H-NMR($d_6$-DMSO) δ 0.88(t, J=7.2Hz, 3H), 1.32-1.45(m, 2H), 1.59-1.69(m, 2H), 2.08(m, 1H), 2.35(m, 1H), 2.99-3.14(m, 2H), 3.21 (dd, J=8.4, 9.3Hz, 1H), 3.38-3.54(m, 2H), 3.88(dd, J=6.9, 9.6Hz, 1H), 4.04(m, 2H), 5.00(s, 2H), 7.06-7.14(m, 2H), 7.37(dd, J=1.2, 7.5Hz, 1H), 7.44(s, 1H), 13.06(br, 1H); IR(Nujol) 2660, 1715, 1555, 1480, 1451, 1404, 1327, 1246, 1182, 1140, 1096, 1041 cm$^{-1}$; Elemental analysis ($C_{18}H_{23}ClN_2O_4S$)Calcd. (%): C, 54.20; H, 5.81; Cl, 8.89; N, 7.02; S, 8.04 Found(%): C, 54.05; H, 5.76; Cl, 8.72; N, 7.00; S ,8.03 |
| Ic-67 | mp 170-173° C.; $^1$H-NMR($d_6$-DMSO) δ 1.81(m, 1H), 2.23(m, 1H), 3.11-3.49 (m, 4H), 3.70(dd, J=7.2, 9.6Hz, 1H), 4.23(s, 2H), 4.94(s, 2H), 7.06(d, J=3.9Hz, 1H), 7.13(dd, 2.1, 8.7Hz, 1H), 7.18(s, 1H), 7.21-7.36(m, 5H), 7.40 (d, J=8.7Hz, 1H), 7.50(d, J=2.1Hz, 1H), 7.57(d, J=3.9Hz, 1H), 13.00 (brs, 1H); IR(Nujol)3084, 3027, 2665, 2570, 1731, 1601, 1571, 1554, 1527, 1494, 1472, 1442, 1415, 1380, 1344, 1244, 1198, 1156, 1113 cm$^{-1}$; Elemental analysis($C_{25}H_{23}ClN_2O_4S_2$)Calcd. (%): C, 58.30; H, 4.50; Cl, 6.88; N, 5.44; S, 12.45 Found(%): C, 58.15; H, 4.39; Cl, 6.64; N, 5.39; S, 12.35 |

TABLE 52

| Compound No. | Physical properties |
| --- | --- |
| Ic-68 | mp 207-210° C.; $^1$H-NMR($d_6$-DMSO) δ 1.85(m, 1H), 2.20(m, 1H), 3.17-3.57 (m, 3H), 3.88(m, 1H), 4.13(m, 1H), 4.88(s, 2H), 7.09(dd, J=1.8, 8.7Hz, 1H), 7.14(s, 1H), 7.31(d, J=1.8Hz, 1H), 7.34(d, J=8.7Hz, 1H), 7.70(dd, J=4.2, 8.1Hz, 1H), 7.76(dd, J=7.5, 8.1Hz, 1H), 8.31(dd, J=1.5, 8.1Hz, 1H), 8.42(dd, J=1.5, 7.5Hz, 1H), 8.56(dd, J=1.5, 8.1Hz, 1H), 9.05(dd, J=1.5, 4.2Hz, 1H), 12.94(brs, 1H); IR(Nujol)3539, 3214, 3032, 2725, 2614, 1768, 1747, 1726, 1611, 1596, 1561, 1493, 1470, 1419, 1378, 1362, 1338, 1265, 1223, 1211, 1198, 1159, 1140, 1131, 1101 cm$^{-1}$; Elemental analysis($C_{23}H_{20}ClN_3O_4S$•0.5$H_2O$)Calcd. (%): C, 57.68; H, 4.42; Cl, 7.40; N, 8.77; S, 6.69 Found(%): C, 57.77; H, 4.32; Cl, 7.18; N, 8.76; S, 6.70 |
| Ic-69 | mp 166-170° C.; $^1$H-NMR($d_6$-DMSO) δ 1.80(m, 1H), 2.22(m, 1H), 3.09-3.51 (m, 4H), 3.73(dd, J=7.2, 9.3Hz, 1H), 4.93(s, 2H), 7.12(dd, J=1.8, 8.7Hz, 1H), 7.16(s, 1H), 7.38(d, J=8.7Hz, 1H), 7.46(dd, J=1.2, 5.1Hz, 1H), 7.48 (d, J=1.8Hz, 1H), 7.82(dd, J=3.0, 5.1Hz, 1H), 8.33(dd, J=1.2, 3.0Hz, 1H), 12.95(brs, 1H); IR(Nujol)3112, 3087, 2669, 1743, 1710, 1667, 1469, 1431, 1387, 1363, 1342, 1303, 1247, 1220, 1202, 1155, 1106 cm$^{-1}$; Elemental analysis ($C_{18}H_{17}ClN_2O_4S_2$)Calcd. (%): C, 50.88; H, 4.03; Cl, 8.34; N, 6.59; S, 15.09 Found(%): C, 50.76; H, 3.92; Cl, 8.14; N, 6.53; S, 15.08 |
| Ic-70 | mp 222-226° C.; $^1$H-NMR($d_6$-DMSO) δ 1.85(m, 1H), 2.22(m, 1H), 3.13-3.60(m, 4H), 3.82(dd, J=7.2, 9.3Hz, 1H), 4.85(s, 2H), 7.06(s, 1H), 7.09(dd, J=2.1, 8.7Hz, 1H), 7.33(d, J=8.7Hz, 1H), 7.39(d, J=2.1Hz, 1H), 7.47-7.58(m, 2H), 8.15(m, 1H), 8.27(m, 1H), 8.63(s, 1H), 12.86(br s, 1H); IR (Nujol)3275, 3079, 1764, 1734, 1485, 1471, 1454, 1421, 1405, 1386, 1342, 1320, 1304, 1260, 1241, 1221, 1186, 1159, 1158, 1147, 1114 cm$^{-1}$; Elemental analysis($C_{22}H_{19}ClN_2O_4S_2$)Calcd. (%): C, 55.63; H, 4.03; Cl, 7.46; N, 5.90; S, 13.50 Found(%): C, 55.46; H, 4.12; Cl, 7.17; N, 5.76; S, 13.27 |
| Ic-71 | mp 166.5-168° C.; $^1$H-NMR($d_6$-DMSO) δ 1.95(m, 1H), 2.30(m, 1H), 3.10-3.61(m, 4H), 3.78(m, 1H), 4.93(s, 2H), 7.12(dd, J=1.8, 8.7Hz, 1H), 7.19-7.32(m, 2H), 7.38(d, J=8.7Hz, 1H), 7.48-7.59(m, 2H), 7.90(m, 1H), 13.00 (brs, 1H); IR(Nujol)3092, 3056, 2731, 2658, 2550, 1722, 1696, 1604, 1473, 1426, 1403, 1384, 1340, 1272, 1233, 1206, 1196, 1163, 1120, 1103 cm$^{-1}$. |
| Ic-72 | Mp 223-225° C.; $^1$H-NMR($d_6$-DMSO) δ 1.99(m, 1H), 2.37(m, 1H), 2.94(s, 3H), 3.16(t, J=9.0Hz, 1H), 3.25-3.68(m, 3H), 3.80(dd, J=7.5, 9.0Hz, 1H), 4.98(s, 2H), 7.13(dd, J=2.1, 8.7Hz, 1H), 7.34(s, 1H), 7.40(d, J=8.7Hz, 1H), 7.70(d, J=2.1Hz, 1H), 13.00(br, 1H); IR(Nujol)3275, 1764, 1744, 1473, 1426, 1398, 1384, 1381, 1361, 1338, 1305, 1253, 1222, 1202, 1175, 1150 cm$^{-1}$; Elemental analysis($C_{15}H_{17}ClN_2O_4S$•0.2AcOEt)Calcd. (%): C, 50.68; H, 5.01; Cl, 9.47; N, 7.48; S, 8.56 Found(%): C, 50.48; H, 4.83; Cl, 9.49; N, 7.68; S, 8.52 |

TABLE 53

| Compound No. | Physical properties |
| --- | --- |
| Ic-73 | mp 196-198° C.; $^1$H-NMR($d_6$-DMSO) δ 1.76(m, 1H), 2.19(m, 1H), 3.07(m, 1H), 3.15-3.48(m, 3H), 3.67(dd, J=7.5, 9.3Hz, 1H), 3.85(s, 3H), 4.90(s, 2H), 7.08-7.16(m, 2H), 7.13(d, J=9.0Hz, 2H), 7.37(d, J=9.0Hz, 1H), 7.44 (d, J=1.8, 1H), 7.77(d, J=9.0Hz, 2H), 12.98(br, 1H); IR(Nujol)3083, 3050, 2667, 2572, 1728, 1593, 1574, 1497, 1473, 1444, 1415, 1381, 1340, 1307, 1258, 1245, 1194, 1157, 1110 cm$^{-1}$. |
| Ic-74 | mp 195-199° C.; $^1$H-NMR($d_6$-DMSO) δ 1.98(m, 1H), 2.33(m, 1H), 2.94(s, 3H), 3.16(t, J=9.0Hz, 1H), 3.25-3.68(m, 3H), 3.80(dd, J=7.5, 9.0Hz, 1H), 4.98 (s, 2H), 7.13(dd, J=2.1, 8.7Hz, 1H), 7.34(s, 1H), 7.40(d, J=8.7Hz, 1H), 7.70(d, J=2.1Hz, 1H), 13.00(brs, 1H); IR(Nujol)3054, 3028, 2645, 2541, 1716, 1616, 1576, 1494, 1470, 1448, 1408, 1381, 1336, 1301, 1261, 1228, 1192, 1146, 1111 cm$^{-1}$; Elemental analysis($C_{22}H_{22}ClN_2O_4S$•0.2AcOEt)Calcd. (%): C, 59.20; H, 4.92; Cl, 7.66; N, 6.06; S, 6.93 Found(%): C, 59.32; H, 4.76; Cl, 7.41; N, 6.19; S, 6.94 |
| Ic-75 | mp 190-193° C.; $^1$H-NMR($d_6$-DMSO) δ 1.83(m, 1H), 2.24(m, 1H), 3.16(m, 1H), 3.24-3.57(m, 3H), 3.78(dd, J=7.2, 9.6Hz, 1H), 4.88(d, J=18.2Hz, 1H), 4.94(d, J=18.2Hz, 1H), 7.11(dd, J=1.8, 8.7Hz, 1H), 7.18(s, 1H), 7.37(d, J=8.7Hz, 1H), 7.51(d, J=1.8Hz, 1H), 7.63(m, 1H), 8.24(m, 1H), 8.87(dd, J=1.8, 4.8Hz, 1H), 9.00(d, J=1.8Hz, 1H), 12.99(br s, 1H); IR (Nujol)3124, 3083, 3056, 2726, 2594, 2516, 1928, 1843, 1778, 1732, 1612, 1589, 1567, 1553, 1473, 1416, 1357, 1335, 1325, 1273, 1254, 1232, 1210, 1191, 1173, 1166, 1116 cm$^{-1}$; Elemental analysis($C_{19}H_{18}ClN_3O_4S$)Calcd. (%): C, 54.35; H, 4.32; Cl, 8.44; N, 10.01; S, 7.64 Found(%): C, 54.29; H, 4.31; Cl, 8.20; N, 9.95; S, 7.43 |
| Ic-76 | mp 105-107° C.; $^1$H-NMR($d_6$-DMSO) δ 1.94-2.20(m, 2H), 2.29(s, 3H), 3.30-3.60(m, 4H), 3.66(m, 1H), 4.88(s, 2H), 6.80-7.08(m, 3H), 7.34(d, J=7.8Hz, 1H), 7.38(dd, J=3.6, 4.8Hz, 1H), 7.80(dd, J=1.2, 3.6Hz, 1H), 8.14 (dd, J=1.2, 5.1Hz, 1H); IR(Nujol)2924, 1748, 1693, 1611, 1467, 1376, 1335, 1292, 1156 cm$^{-1}$. |
| Ic-77 | mp 125-126° C.; $^1$H-NMR($d_6$-DMSO) δ 1.07(t, J=7.2Hz, 3H), 1.38-1.52(m, 2H), 1.64(m, 2H), 2.13(m, 1H), 2.31(m, 1H), 2.31(s, 3H), 3.13-3.28(m, 2H), 3.22-3.80(m, 5H), 4.92(s, 2H), 6.94(m, 2H), 7.35(d, J=7.5Hz, 1H), 7.55(d, J=7.5Hz, 1H); IR(Nujol)3243, 3053, 2924, 1755, 1567, 1418, 1321, 1298, 1275, 1180, 1143 cm$^{-1}$; Elemental analysis($C_{19}H_{26}N_2O_4S$)Calcd. (%): C, 60.29; H, 6.92; N, 7.40; S, 8.47 Found(%): C, 59.80; H, 6.86; N, 7.29; S, 8.51 |

TABLE 54

| Compound No. | Physical properties |
| --- | --- |
| Ic-78 | mp 140-142° C.; $^1$H-NMR($d_6$-DMSO) δ 1.84(m, 1H), 2.28(m, 1H), 3.15-3.57 (m, 4H), 3.75(m, 1H), 4.93(s, 2H), 7.13(dd, J=1.8, 8.7Hz, 1H), 7.22(s, 1H), 7.33(d, J=4.2Hz, 1H), 7.39(d, J=8.7Hz, 1H), 7.53(d, J=1.8Hz, 1H), 7.62 (d, J=4.2Hz, 1H), 12.90(brs, 1H); IR(Nujol)3091, 2670, 2577, 1726, 1567, 1513, 1471, 1445, 1414, 1380, 1357, 1332, 1310, 1266, 1249, 1199, 1180, 1155, 1112 cm$^{-1}$; Elemental analysis($C_{18}H_{16}Cl_2N_2O_4S_2$•0.05AcOEt)Calcd. (%): C, 47.13; H, 3.56; Cl, 15.29; N, 6.04; S, 13.83 Found(%): C, 46.95; H, 3.47; Cl, 15.10; N, 6.11; S, 14.02 |
| Ic-79 | mp 220-221° C.; $^1$H-NMR($d_6$-DMSO) δ 1.76(m, 1H), 2.19(m, 1H), 3.06(t, J=9.3Hz, 1H), 3.22-3.46(m, 3H), 3.65(dd, J=7.5, 9.3Hz, 1H), 4.91(s, 2H), 6.92-6.96(m, 2H), 7.11(dd, J=2.1, 8.4Hz, 1H), 7.13(s, 1H), 7.37(d, J=8.4.Hz, 1H), 7.47(d, J=2.1Hz, 1H), 7.64-7.69(m, 2H), 10.48(br, 1H), 12.97(br, 1H); IR(Nujol)3409, 1741, 1712, 1603, 1586, 1500, 1472, 1440, 1319, 1245, 1151, 1094, 1028 cm$^{-1}$; Elemental analysis($C_{20}H_{19}ClN_2O_5S$)Calcd. (%): C, 55.24; H, 4.40; Cl, 8.15; N, 6.44; S, 7.37 Found(%): C, 55.21; H, 4.52; Cl, 7.62; N, 6.20; S, 7.14 |
| Ic-80 | $^1$H-NMR(CDCl$_3$) δ 1.84-1.89(m, 2H), 2.04-2.17(m, 3H), 3.49-3.54(m, 3H), 4.88(m, 1H), 5.12(m, 1H), 7.09-7.45(m, 5H), 7.85-8.08(m, 3H), 8.30(m, 1H); IR(KBr)3387, 1739, 1647, 1591, 1526, 1493, 1467, 1428, 1389, 1343, 1292, 1236, 1152, 1092, 1066, 1011 cm$^{-1}$; Elemental analysis ($C_{21}H_{19}FN_2O_5S$•1.0H$_2$O)Calcd. (%): C, 56.24; H, 4.72; N, 6.25; F, 4.24; S, 7.15 Found(%): C, 56.18; H, 4.56; N, 6.29; F, 4.11, S, 7.06 |
| Ic-81 | $^1$H-NMR(CDCl$_3$) δ 1.43-1.68(m, 4H), 2.88(m, 1H), 3.09(m, 1H), 3.34-3.44 (m, 2H), 3.85(s, 3H), 3.91(m, 1H), 4.85(s, 2H), 6.93-6.98(m, 3H), 7.20-7.26 (m, 3H), 7.80-7.83(m, 3H); IR(KBr)2945, 1728, 1596, 1497, 1468, 1331, 1260, 1153, 1092, 1024 cm$^{-1}$; Elemental analysis($C_{22}H_{24}N_2O_5S$•0.5H$_2$O) Calcd. (%): C, 60.40; H, 5.76; N, 6.40; S, 7.33 Found(%): C, 60.42; H, 5.78; N, 6.27; S, 6.97 |
| Ic-82 | $^1$H-NMR(CDCl$_3$) δ 1.86-2.20(m, 4H), 3.45-3.55(m, 2H), 4.91(s, 2H), 5.06 (m, 1H), 7.04-7.28(m, 4H), 7.74(m, 1H), 7.88(m, 1H), 8.00(dd, J=2.4, 6.9Hz, 2H), 8.10(s, 1H); IR(KBr)3433, 2929, 1738, 1626, 1590, 1528, 1493, 1394, 1344, 1293, 1233, 1153, 1092, 1062, 1010 cm$^{-1}$; |

TABLE 54-continued

| Compound No. | Physical properties |
| --- | --- |
| Ic-83 | $^1$H-NMR(CDCl$_3$) δ 1.86-2.20(m, 4H), 3.45-3.55(m, 2H), 4.91(s, 2H), 5.06 (m, 1H), 7.04-7.28(m, 4H), 7.74(m, 1H), 7.88(m, 1H), 8.00(dd, J=2.4, 6.9Hz, 2H), 8.10(s, 1H); IR(KBr)3433, 2929, 1738, 1626, 1590, 1528, 1493, 1394, 1344, 1293, 1233, 1153, 1092, 1062, 1010 cm$^{-1}$; [α]$_D^{22}$ + 29.0 ± 0.7° (c=1.001, MeOH) |
| Ic-84 | $^1$H-NMR(CDCl$_3$) δ 1.433-1.72(m, 4H), 2.89(dd, J=9.3 and 14.4Hz, 1H), 3.10(m, 1H), 3.27(dd, J=3.9 and 14.4Hz, 1H), 3.41(m, 1H), 3.87(m, 1H), 4.84(s, 2H), 6.95-7.02(m, 2H), 7.11-7.26(m, 3H), 7.40(dd, J=2.4 and 9.6Hz, 1H), 7.85-7.91(m, 2H); IR(CHCl$_3$)1729, 1593, 1493, 1456, 1348, 1292, 1164, 1154, 1092 cm$^{-1}$; [α]$_D^{22}$ + 109.6 ± 1.5(c=1.003, MeOH) |

TABLE 55

| Compound No. | Physical properties |
| --- | --- |
| Ic-85 | $^1$H-NMR(CDCl$_3$) δ 1.43-1.66(m, 4H), 2.87(dd, J=6.0 and 14.1Hz, 1H), 3.11 (m, 1H), 3.26(dd, J=3.3 and 14.1Hz, 1), 3.82(m, 1H), 3.86(s, 3H), 4.83(s, 2H), 6.95-7.01(m, 4H), 7.11(dd, J=3.9 and 8.7Hz, 1H), 7.40(dd, J=2.4 and 9.3Hz, 1H), 7.73-7.83(m, 2H); IR(CHCl$_3$)1730, 1626, 1597, 1578, 1497, 1487, 1457, 1338, 1304, 1260, 1155, 1094, 1030 cm$^{-1}$; [α]$_D^{22}$ + 124.6 ± 1.6 (c=1.002, MeOH) |
| Id-2 | mp 220-222° C.; $^1$H-NMR(CDCl$_3$) δ 2.84(t, J=5.7Hz, 2H), 3.57(t, J=5.7 Hz, 2H), 4.42(s, 2H), 4.67(s, 2H), 7.05-7.25(m, 5H), 7.35-7.43(m, 1H), 7.84-7.92(m, 2H),; IR(CHCl$_3$) 3428, 3048, 2927, 1727, 1595, 1494, 1467, 1345, 1240, 1169, 1103 cm$^{-1}$; Elemental analysis(C$_{19}$H$_{17}$FN$_2$O$_4$S)Calcd. (%): C, 58.75; H, 4.41; F, 4.89; N, 7.21; S, 8.26 Found(%): C, 58.58; H, 4.37; F, 4.69; N, 7.13; S, 8.08 |
| Ie-2 | mp 139-141° C.; $^1$H-NMR(CDCl$_3$) δ 4.95(s, 2H), 7.02-7.11(m, 3H), 7.18-7.25 (m, 2H), 7.34(m, 1H), 7.46(t, J=7.7Hz, 1H), 7.68-7.73(m, 2H), 7.80(d, J=1.8Hz, 1H), 7.99(d, J=7.5Hz, 1H); IR(Nujol)3300, 3245, 3047, 1776, 1736, 1688, 1590, 1493, 1466, 1335, 1285, 1163, 1152 cm$^{-1}$; Elemental analysis(C$_{20}$H$_{15}$FN$_2$O$_4$S•0.6CH$_3$CO$_2$C$_2$H$_5$)Calcd. (%): C, 59.62; H, 4.42; F, 4.21; N, 6.21; S, 7.11 Found(%): C, 59.45; H, 4.19; F, 4.14; N, 6.51; S, 7.02 |
| Ie-5 | mp 188-191° C.; $^1$H-NMR(CDCl$_3$) δ 3.28(d, J=1.5Hz, 3H), 5.02(s, 2H), 7.09-7.33(m, 6H), 7.49(t, J=7.8Hz, 1H), 7.57-7.61(m, 2H), 7.73(d, J=1.5Hz, 1H), 7.97(d, J=8.1Hz, 1H); IR(Nujol)3102, 3049, 2728, 1727, 1628, 1591, 1491, 1292, 1228, 1210, 1173, 1150 cm$^{-1}$; Elemental analysis (C$_{21}$H$_{17}$FN$_2$O$_4$S•0.2H$_2$O)Calcd. (%): C, 60.63; H, 4.22; F, 4.57; N, 6.73; S, 7.71 Found(%): C, 60.52; H, 4.13; F, 4.46; N, 6.82; S, 7.63 |
| Ie-8 | mp 212-213° C.; $^1$H-NMR(d$_6$-DMSO) δ 4.89(s, 2H), 5.16(s, 2H), 7.06(dd, J=8.4, 2.1Hz, 1H), 7.13-7.32(m, 6H), 7.41-7.52(m, 5H), 7.73-7.77(m, 2H), 7.84(d, J=1.8Hz, 1H), 8.04(d, J=7.8Hz, 1H), 13.05(brs, 1H); IR(Nujol) 3063, 3035, 2658, 1705, 1630, 1591, 1232, 1214, 1162 cm$^{-1}$; Elemental analysis(C$_{27}$H$_{21}$FN$_2$O$_4$S)Calcd. (%): C, 66.38; H, 4.33; F, 3.89; N, 5.73; S, 6.56 Found(%): C, 66.33; H, 4.26; F, 3.79; N, 5.80; S, 6.53 |
| Ie-10 | mp 171-175° C.; $^1$H-NMR(d$_6$-DMSO) δ 5.15(s, 2H), 6.98-7.07(m, 2H), 7.32-7.47(m, 4H), 7.74-7.81(m, 3H), 8.05-8.10(m, 2H), 10.10(s, 1H); IR(Nujol) 3621, 3313, 3107, 3070, 2727, 1737, 1702, 1636, 1603, 1592, 1490, 1330, 1164, 1146 cm$^{-1}$. |
| Ie-11 | mp 183-187° C.; $^1$H-NMR(d$_6$-DMSO) δ 2.13(s, 3H), 5.14(s, 2H), 7.00-7.95(m, 10H), 9.61(s, 1H); IR(Nujol)3517, 3236, 3105, 3068, 2732, 1735, 1635, 1607, 1591, 1494, 1408, 1335, 1270 cm$^{-1}$; Elemental analysis (C$_{21}$H$_{17}$FN$_2$O$_4$S•0.4H$_2$O)Calcd. (%): C, 60.10; H, 4.28; F, 4.53; N, 6.68; S, 7.64 Found(%): C, 60.28; H, 4.47; F, 4.42 N, 6.54; S, 7.52 |

TABLE 56

| Compound No. | Physical properties |
| --- | --- |
| Ie-12 | mp 201-203° C.; $^1$H-NMR(CDCl$_3$) δ 3.26(s, 3H), 4.95(s, 2H), 6.95-7.02(m, 2H), 7.09-7.20(m, 4H), 7.56-7.61(m, 2H), 7.72(m, 1H), 7.89(m, 1H); IR (Nujol)3106, 3067, 2744, 2657, 2558, 1734, 1635, 1605, 1592, 1495, 1483, 1340, 1236 cm$^{-1}$; Elemental analysis(C$_{21}$H$_{16}$F$_2$N$_2$O$_4$S•0.2AcOEt)Calcd. (%): C, 58.44; H, 3.96; F, 8.48; N, 6.25; S, 7.16 Found(%): C, 58.49; H, 3.72; F, 8.33; N, 6.37; S, 7.16 |
| Ie-13 | mp 215-218° C.; $^1$H-NMR(CDCl$_3$ + CD$_3$OD) δ 4.82(s, 2H), 4.86(s, 2H), 6.92-7.02(m, 3H), 7.14-7.24(m, 9H), 7.60-7.86(m, 3H); IR(Nujol)3066, 3036, 2656, 1708, 1635, 1605, 1591, 1492, 1483, 1406, 1338, 1232 cm$^{-1}$; Elemental |

TABLE 56-continued

| Compound No. | Physical properties |
| --- | --- |
| | analysis ($C_{27}H_{20}F_2N_2O_4S$•0.2AcOEt)Calcd. (%): C, 63.70; H, 4.15; F, 7.25; N, 5.34; S, 6.12 Found(%): C, 63.79; H, 4.04; F, 6.99; N, 5.31; S, 6.11 |
| Ie-14 | mp 219-225° C.; $^1$H-NMR(CDCl$_3$ + CD$_3$OD) δ 2.56(s, 3H), 3.24(s, 3H), 4.95(s, 2H), 7.09-7.23(m, 5H), 7.31(m, 1H), 7.44(m, 1H), 7.73-7.77(m, 3H); IR (Nujol)2742, 2656, 1727, 1711, 1632, 1605, 1590, 1495, 1483, 1412, 1339, 1275 cm$^{-1}$; Elemental analysis($C_{22}H_{19}FN_2O_4S$•0.2AcOEt)Calcd. (%): C, 61.67; H, 4.68; F, 4.28; N, 6.31; S, 7.22 Found(%): C, 61.82; H, 4.59; F, 4.00; N, 6.31; S, 7.14 |
| Ie-15 | mp 194-197° C.; $^1$H-NMR(CDCl$_3$ + CD$_3$OD) δ 2.13(s, 3H), 4.36(d, J=13.5Hz, 1H), 4.90(s, 2H), 5.09(d, J=13.5Hz, 1H), 7.07(s, 1H), 7.13-7.24(m, 10H), 7.31(m, 1H), 7.45(t, J=7.2Hz, 1H), 7.73-7.78(m, 2H); IR(Nujol)3060, 3032, 2739, 2644, 2557, 1715, 1633, 1604, 1593, 1494, 1478, 1414, 1342, 1240 cm$^{-1}$; Elemental analysis($C_{28}H_{23}FN_2O_4S$•0.2AcOEt)Calcd. (%): C, 66.50; H, 4.77; F, 3.65; N, 5.39; S, 6.16 Found(%): C, 66.74; H, 4.76; F, 3.39; N, 5.37; S, 6.04 |
| Ie-16 | mp 164-165° C.; $^1$H-NMR(d$_6$-DMSO) δ 5.16(s, 2H), 7.08(dd, J=1.8, 9.0Hz, 1H), 7.52-7.45(m, 4H), 7.54(dd, J=4.2, 8.7Hz, 1H), 7.75-7.79(m, 2H), 7.86 (d, J=2.1Hz, 1H), 7.95(dd, J=2.4, 9.3Hz, 1H), 10.09(s, 1H); IR(Nujol) 3301, 3191, 3108, 1778, 1691, 1590, 1496, 1474, 1337, 1286 cm$^{-1}$. |
| Ie-17 | mp 187-188° C.; $^1$H-NMR(CDCl$_3$) δ 3.26(s, 3H), 4.96(s, 2H), 7.08-7.21(m, 6H), 7.55-7.61(m, 3H), 7.66(d, J=0.9Hz, 1H); IR(Nujol)2747, 2650, 2566, 2483, 1720, 1593, 1492, 1414, 1348, 1295, 1254 cm$^{-1}$; Elemental analysis ($C_{21}H_{16}F_2N_2O_4S$•0.2AcOEt)Calcd. (%): C, 58.44; H, 3.96; F, 8.48; N, 6.25; S, 7.16 Found(%): C, 58.55; H, 3.77; F, 8.40; N, 6.23; S, 7.34 |
| Ie-18 | mp 189-191° C.; $^1$H-NMR(CDCl$_3$ + CD$_3$OD) δ 4.82(s, 2H), 4.89(s, 2H), 7.01 (dd, J=1.8, 8.7Hz, 1H), 7.14-7.27(m, 10H), 7.56(dd, J=2.4, 9.0Hz, 1H), 7.59(d, J=1.8Hz, 1H), 7.67-7.71(m, 2H); IR(Nujol)3089, 3074, 3033, 2742, 2653, 2558, 1710, 1591, 1343, 1296 cm$^{-1}$; Elemental analysis ($C_{27}H_{20}F_2N_2O_4S$•0.1AcOEt)Calcd. (%): C, 63.86; H, 4.07; F, 7.37; N, 5.44; S, 6.22 Found(%): C, 63.84; H, 3.95; F, 7.14; N, 5.31; S, 6.33 |

TABLE 57

| Compound No. | Physical properties |
| --- | --- |
| Ie-19 | Mp 189-191° C.; $^1$H-NMR(d$_6$-DMSO) δ 5.19(s, 2H), 6.99(m, 1H), 7.21(dd, J=2.1, 9.0Hz, 1H), 7.33-7.46(m, 4H), 7.51(d, J=9.0Hz, 1H), 7.75-7.79(m, 3H), 10.15(s, 1H); IR(Nujol)3262, 3103, 3061, 2661, 2558, 1715, 1640, 1611, 1590, 1484, 1406, 1331, 1294 cm$^{-1}$; Elemental analysis ($C_{20}H_{14}F_2N_2O_4S$•0.1AcOEt)Calcd. (%): C, 57.62; H, 3.51; F, 8.94; N, 6.59; S, 7.54 Found(%): C, 57.43; H, 3.26; F, 8.65; N, 6.46; S, 7.34 |
| Ie-20 | Mp 214-217° C.; $^1$H-NMR(CDCl$_3$) δ 3.27(s, 3H), 5.00(s, 2H), 6.92(dd, J=8.1, 9.9Hz, 1H), 7.06-7.17(m, 3H), 7.23(d, J=8.7Hz, 1H), 7.32(dd, J=2.1, 8.7Hz, 1H), 7.39(m, 1H), 7.56-7.63(m, 2H), 7.70(d, J=1.8Hz, 1H); IR (Nujol)3087, 2748, 2651, 2568, 2486, 1723, 1637, 1592, 1493, 1308, 1236 cm$^{-1}$; Elemental analysis($C_{21}H_{16}F_2N_2O_4S$•0.1AcOEt)Calcd. (%): C, 58.52; H, 3.86; F, 8.65; N, 6.38; S, 7.30 Found(%): C, 58.64; H, 3.61; F, 8.37; N, 6.39; S, 7.21 |
| Ie-21 | Mp 209-213° C.; $^1$H-NMR(CDCl$_3$ + CD$_3$OD) δ 4.82(s, 2H), 4.91(s, 2H), 6.90 (dd, J=8.1, 9.9Hz, 1H), 7.08-7.13(m, 2H), 7.15-7.28(m, 8H), 7.38(m, 1H), 7.65(d, J=1.8Hz, 1H), 7.68-7.73(m, 2H); IR(Nujol)3063, 3033, 2659, 1708, 1641, 1610, 1590, 1492, 1241 cm$^{-1}$; Elemental analysis ($C_{27}H_{20}F_2N_2O_4S$•0.1AcOEt)Calcd. (%): C, 63.86; H, 4.07; F, 7.37; N, 5.44; S, 6.22 Found(%): C, 63.77; H, 3.90; F, 7.21; N, 5.45; S, 6.18 |
| Ie-22 | mp 153-156° C.; $^1$H-NMR(CDCl$_3$ + CD$_3$OD) δ 5.13(s, 2H), 6.92(dd, J=1.8, 10.4Hz, 1H), 7.04-7.12(m, 2H), 7.25(td, J=0.6, 15.0Hz, 1H), 7.32(d, J=8.4Hz, 1H), 7.49(td, J=1.2, 7.7Hz, 1H), 7.55(d, J=1.8Hz, 1H), 7.72-7.77 (m, 2H), 7.96(d, J=7.5Hz, 1H); IR(Nujol)3236, 3109, 3073, ,3050, 2725, 1761, 1732, 1641, 1610, 1591, 1497, 1375, 1288 cm$^{-1}$; Elemental analysis ($C_{20}H_{14}F_2N_2O_4S$•0.2AcOEt)Calcd. (%): C, 57.56; H, 3.62; F, 8.75; N, 6.45; S, 7.39 Found(%): C, 57.27; H, 3.39; F, 8.82; N, 6.58; S, 7.49 |
| Ie-23 | $^1$H-NMR(CDCl$_3$) δ 3.25(s, 3H), 5.22(s, 2H), 6.91(dd, J=2.1, 12.9Hz, 1H), 7.09-7.16(m, 2H), 7.28-7.33(m, 2H), 7.48-7.54(m, 2H), 7.56-7.62(m, 2H), 7.94(d, J=7.8Hz, 1H); IR(Nujol)3505, 3103, 3052, 2729, 2648, 1728, 1639, 1589, 1494, 1297, 1238 cm$^{-1}$; Elemental analysis($C_{21}H_{16}F_2N_2O_4S$•0.3H$_2$O) Calcd. (%): C, 57.87; H, 3.84; F, 8.72; N, 6.43; S, 7.36 Found(%): C, 57.99; H, 3.79; F, 8.55; S, 7.07 |
| Ie-24 | mp 199-201° C.; $^1$H-NMR(CDCl$_3$ + CD$_3$OD) δ 4.80(s, 2H), 5.13(s, 2H), 6.76 (dd, J=2.1, 13.2Hz, 1H), 7.17-7.28(m, 8H), 7.32(d, J=8.4Hz, 1H), 7.44(d, J=2.1Hz, 1H), 7.49(m, 1H), 7.67-7.74(m, 2H), 7.89(d, J=7.5Hz, 1H); IR (Nujol)3087, 3062, 3032, 2644, 2560, 2470, 1714, 1638, 1585, 1493, 1300, 1249 cm$^{-1}$; Elemental analysis($C_{27}H_{20}F_2N_2O_4S$•0.1AcOEt)Calcd. (%): C, |

TABLE 57-continued

| Compound No. | Physical properties |
| --- | --- |
| | 63.86; H, 4.07; F, 7.37; N, 5.44; S, 6.22 Found(%): C, 64.07; H, 3.90; F, 7.17; N, 5.52; S, 6.10 |

TABLE 58

| Compound No. | Physical properties |
| --- | --- |
| Ie-25 | mp 204-206° C.; $^1$H-NMR(CDCl$_3$) δ 3.27(s, 3H), 5.22(s, 2H), 7.09-7.22(m, 6H), 7.56-7.61(m, 2H), 7.71-7.74(m, 2H); IR(Nujol)3327, 3085, 3046, 2680, 1774, 1637, 1592, 1578, 1339, 1242 cm$^{-1}$; Elemental analysis (C$_{21}$H$_{16}$F$_2$N$_2$O$_4$S•0.1AcOEt)Calcd. (%): C, 58.52; H, 3.86; F, 8.65; N, 6.38; S, 7.30 Found(%): C, 58.60; H, 3.70; F, 8.51; N, 6.44; S, 7.46 |
| Ie-26 | mp 194-197° C.; $^1$H-NMR(CDCl$_3$) δ 4.81(s, 2H), 5.13(s, 2H), 7.00(dd, J=2.1, 8.7Hz, 1H), 7.07-7.25(m, 11H), 7.62-7.69(m, 3H); IR(Nujol)3093, 3066, 3040, 3023, 2657, 2561, 1722, 1593, 1581, 1493, 1294, 1236 cm$^{-1}$; Elemental analysis(C$_{27}$H$_{20}$F$_2$N$_2$O$_4$S)Calcd. (%): C, 64.02; H, 3.98; F, 7.50; N, 5.53; S, 6.33 Found(%): C, 64.00; H, 3.98; F, 7.26; N, 5.49; S, 6.13 |
| Ie-27 | mp 190-191° C.; $^1$H-NMR(CDCl$_3$ + CD$_3$OD) δ 4.92(s, 2H), 7.03-7.09(m, 2H), 7.13-7.23(m, 3H), 7.54(dd, J=1.8, 8.7Hz, 1H), 7.68-7.73(m, 3H), 8.10(d, J=1.8Hz, 1H); IR(Nujol) 3263, 3102, 3060, 2657, 1715, 1591, 1487, 1406, 1335, 1286 cm$^{-1}$. |
| Ie-28 | mp 200-202° C.; $^1$H-NMR(CDCl$_3$ + CD3OD) δ 3.28(s, 3H), 4.95(s, 2H), 7.11-7.29(m, 5H), 7.54-7.61(m, 3H), 7.69(d, J=1.8Hz, 1H), 8.09(d, J=2.1Hz); IR(Nujol)3066, 2744, 2658, 2565, 1731, 1454, 1444, 1293, 1247, 1224 cm$^{-1}$; Elemental analysis (C$_{21}$H$_{16}$BrFN$_2$O$_4$S•0.4AcOEt)Calcd. (%): C, 51.55; H, 3.68; F, 3.61; N, 5.32; S, 6.09 Found(%): C, 51.74; H, 3.13; Br, 14.82; F, 3.66; N, 5.60; S, 6.28 |
| If-1 | $^1$H-NMR(CDCl$_3$) δ 1.56(s, 6H), 2.43(s, 3H), 3.20(d, J=5.7Hz, 2H), 4.21(t, J=5.7Hz, 1H), 4.82(s, 2H), 6.85-6.98(m, 3H), 7.13-7.15(m, 2H), 7.35(d, J=8.1Hz, 1H), 7.49-7.53(m, 2H); IR(KBr)3505, 1728, 1594, 1495, 1478, 1468, 1406, 1340, 1292, 1166, 1154, 1092, 1076 cm$^{-1}$; Elemental analysis (C$_{21}$H$_{23}$FN$_2$O$_4$S•0.6H$_2$O)Calcd. (%): C, 58.75; H, 5.68; N, 6.53; F, 4.43; S, 7.47 Found(%): C, 58.83; H, 5.73; N, 6.32; F, 4.29, S, 7.24 |
| If-2 | $^1$H-NMR(CDCl$_3$) δ 1.68(s, 6H), 2.28(s, 3H), 2.52(s, 3H), 3.40(s, 2H), 4.83 (s, 2H), 7.05(m, 1H), 7.13-7.18(m, 4H), 7.71-7.77(m, 3H); IR(CHCl$_3$)2976, 2930, 1729, 1594, 1495, 1479, 1467, 1393, 1342, 1293, 1166, 1155, 1089, 1015 cm$^{-1}$; Elemental analysis(C$_{22}$H$_{25}$FN$_2$O$_4$S•0.2H$_2$O)Calcd. (%): C, 60.59; H, 5.87; N, 6.42; F, 4.36; S, 7.35 Found(%): C, 60.57; H, 6.01; N, 6.31; F, 4.26, S, 7.15 |
| If-3 | $^1$H-NMR(CDCl$_3$) δ 1.58(s, 6H), 2.10(s, 3H), 3.71(s, 2H), 3.96(s, 2H), 4.56 (s, 2H), 6.47(d, J=7.2Hz, 2H), 6.95-7.15(m, 8H), 7.56(d, J=8.4Hz, 1H), 7.72-7.77(m, 2H); IR(CHCl$_3$)1729, 1594, 1495, 1479, 1467, 1342, 1292, 1239, 1165, 1154, 1091, 1056 cm$^{-1}$; Elemental analysis (C$_{28}$H$_{29}$FN$_2$O$_4$S•0.2MeOH)Calcd. (%): C, 65.77; H, 5.83; N, 5.44; F, 3.69; S, 6.23 Found(%): C, 66.15; H, 5.98; N, 5.23; F, 3.40, S, 5.87 |

TABLE 59

| Compound No. | Physical properties |
| --- | --- |
| If-4 | $^1$H-NMR(CDCl$_3$) δ 1.38(d, J=6.6Hz, 3H), 2.29(s, 3H), 3.07-3.36(m, 3H), 4.29(d, J=9.0Hz, 1H), 4.81(d, J=5.1Hz, 2H), 6.91-7.27(m, 6H), 7.54-7.59 (m, 2H); IR(CHCl$_3$)2976, 2930, 1729, 1594, 1495, 1479, 1467, 1393, 1342, 1293, 1166, 1155, 1089, 1015 cm$^{-1}$; Elemental analysis (C$_{20}$H$_{21}$FN$_2$O$_4$S•1.2MeOH)Calcd. (%): C, 57.49; H, 5.87; N, 6.32; F, 4.29; S, 7.24 Found(%): C, 57.55; H, 5.65; N, 6.14; F, 4.22, S, 7.23 |
| If-5 | $^1$H-NMR(CDCl$_3$) δ 1.48(d, J=6.9Hz, 3H), 2.35(s, 3H), 2.57(s, 3H), 3.02(m, 1H), 3.36(m, 1H), 3.65(m, 1H), 4.82(s, 2H), 7.04-7.17(m, 5H), 7.58(d, J=8.7Hz, 1H), 7.68-7.73(m, 2H); IR(CHCl$_3$)2976, 2930, 1729, 1594, 1495, 1479, 1467, 1393, 1342, 1293, 1166, 1155, 1089, 1015 cm$^{-1}$ |
| If-6 | $^1$H-NMR(CDCl$_3$) δ 1.31(d, J=6.6Hz, 3H), 2.17(s, 3H), 3.15-3.23(m, 2H), 3.70(q, J=6.6Hz, 1H), 4.17(s, 2H), 4.76(s, 2H), 6.96-7.23(m, 10H), 7.40(d, J=7.8Hz, 1H), 7.69-7.74(m, 2H); IR(CHCl$_3$)2974, 2932, 2876, 1731, 1594, 1496, 1468, 1409, 1339, 1292, 1240, 1165, 1153, 1089, 1022 cm$^{-1}$; Elemental analysis (C$_{27}$H$_{27}$FN$_2$O$_4$S•1.1MeOH)Calcd. (%): C, 63.70; H, 5.97; N, 5.29; F, 3.59; S, 6.05 Found(%): C, 64.02; H, 5.78; N, 5.20; F, 3.42, S, 5.70 |
| If-7 | $^1$H-NMR(CDCl$_3$) δ 1.73-1.85(m, 4H), 2.02-2.23(m, 4H), 3.30(s, 2H), 4.86(s, 1H), 6.91(s, 1H), 7.04-7.21(m, 5H), 7.60(d, J=8.1Hz, 1H), 7.70-7.75(m, 2H); IR(CHCl$_3$)2961, 2874, 1594, 1494, 1468, 1340, 1292, 1240, 1155, 1089 |

TABLE 59-continued

| Compound No. | Physical properties |
| --- | --- |
| | $cm^{-1}$; Elemental analysis ($C_{23}H_{25}FN_2O_4S \cdot 0.2H_2O$)Calcd. (%): C, 61.65; H, 5.71; N, 6.25; F, 4.24; S, 7.16 Found(%): C, 61.74; H, 5.93; N, 5.96; F, 3.93, S, 6.95 |
| If-8 | $^1$H-NMR(CDCl$_3$) δ 1.65-1.80(m, 4H), 2.00-2.09(m, 4H), 3.64(s, 2H), 3.80(s, 2H), 4.58(s, 2H), 6.47(s, 1H), 6.54(d, J=7.8Hz, 2H), 6.97-7.15(m, 7H), 7.37-7.45(m, 2H), 7.67-7.72(m, 2H); IR(CHCl$_3$)2960, 2874, 1731, 1592, 1495, 1468, 1339, 1292, 1239, 1165, 1154, 1092, 1022 $cm^{-1}$. |
| If-9 | mp 117-120° C.; $^1$H-NMR(CDCl$_3$) δ 3.50-3.69(m, 2H), 4.34(t, J=7.5Hz, 1H), 4.58(br t, J=6.0Hz, 1H), 4.80(d, J=18.3Hz, 1H), 4.81(d, J=18.3Hz, 1H), 6.84(s, 1H), 7.01(m, 1H), 7.08(t, J=9.0Hz, 2H), 7.17-7.30(m, 8H), 7.72(dd, J=5.1 9.0Hz, 2H); IR(Nujol) 3351, 3295, 3063, 1727, 1706, 1614, 1592, 1494, 1468, 1406, 1331, 1241, 1165, 1152 $cm^{-1}$; Elemental analysis ($C_{24}H_{21}FN_2O_4S \cdot 0.4AcOEt$)Calcd. (%): C, 63.04; H, 5.00; N, 5.74; F, 3.90; S, 6.57 Found(%): C, 62.73; H, 4.75; N, 5.77; F, 3.91; S, 6.58 |

TABLE 60

| Compound No. | Physical properties |
| --- | --- |
| If-10 | mp 167-170° C.; $^1$H-NMR(CDCl$_3$) δ 2.61(s, 3H), 3.36(dd, J=7.8, 13.5Hz, 1H), 3.93(dd, J=7.8, 13.5Hz, 1H), 4.55(t, J=7.8Hz, 1H), 4.87(s, 2H), 7.06 (m, 1H), 7.10(s, 1H), 7.13(t, J=9.0Hz, 2H), 7.20-7.31(m, 7H), 7.43(br d, J=8.1Hz, 1H), 7.70(dd, J=5.1, 9.0Hz, 2H); IR(Nujol)3429, 3030, 1722, 1704, 1592, 1493, 1469, 1406, 1332, 1237, 1150, 1087 $cm^{-1}$; Elemental analysis ($C_{25}H_{23}FN_2O_4S$)Calcd. (%): C, 64.36; H, 4.97; N, 6.00; F, 4.07; S, 6.87 Found(%): C, 64.28; H, 4.93; N, 5.91; F, 3.85, S, 6.73 |
| If-11 | $^1$H-NMR(CDCl$_3$) δ 2.00-2.41(m, 6H), 3.30(d, J=6.0Hz, 2H), 4.21(t, J=5.7 Hz, 1H), 4.84(s, 2H), 6.82-6.98(m, 4H), 7.13-7.27(m, 3H), 7.45-7.50(m, 2H); IR(CHCl$_3$)2984, 2934, 2875, 1731, 1594, 1496, 1468, 1408, 1333, 1292, 1240, 1167, 1154 $cm^{-1}$; Elemental analysis($C_{21}H_{21}FN_2O_4S \cdot 0.4H_2O$)Calcd. (%): C, 59.53; H, 5.19; N, 6.61; F, 4.48; S, 7.57 Found(%): C, 59.49; H, 5.23; N, 6.35; F, 4.20, S, 7.34 |
| If-12 | $^1$H-NMR(CDCl$_3$) δ 1.91-1.95(m, 2H), 2.25-2.42(m, 4H), 3.74(s, 2H), 3.92(s, 2H), 4.70(s, 2H), 6.53(s, 1H), 6.67(d, J=8.1Hz, 2H), 6.97-7.38(m, 9H), 7.62-7.67(m, 2H); IR(CHCl$_3$)2932, 1731, 1593, 1495, 1468, 1333, 1292, 1239, 1163, 1153, 1089 $cm^{-1}$; Elemental analysis($C_{28}H_{27}FN_2O_4S \cdot 0.8H_2O$) Calcd. (%): C, 64.55; H, 5.53; N, 5.38; F, 3.65; S, 6.15 Found(%): C, 64.61; H, 5.27; N, 5.08; F, 3.35, S, 5.87 |
| If-13 | $^1$H-NMR(CDCl$_3$) δ 1.43(s, 6H), 3.17(d, J=5.7Hz, 2H), 4.20(t, J=6.0Hz, 1H), 4.83(s, 2H), 6.85(s, 1H), 6.90-6.97(m, 3H), 7.21(d, J=3.6Hz, 2H), 7.32(d, J=8.4Hz, 1H), 7.49-7.54(m, 2H); IR(CHCl$_3$)2971, 2933, 2878, 1731, 1594, 1496, 1467, 1408, 1386, 1331, 1292, 1239, 1194, 1167, 1154, 1092, 1076 $cm^{-1}$; Elemental analysis($C_{20}H_{21}FN_2O_4S \cdot 0.5H_2O$)Calcd. (%): C, 58.10; H, 5.36; N, 6.78; F, 4.59; S, 7.76 Found(%): C, 58.05; H, 5.31; N, 6.55; F, 4.34, S, 7.58 |
| If-14 | $^1$H-NMR(CDCl$_3$) δ 1.54(s, 3H), 2.26(s, 3H), 3.37(s, 2H), 4.86(s, 2H), 6.89 (s, 1H), 7.07-7.22(m, 5H), 7.69-7.77(m, 3H); IR(CHCl$_3$)2974, 2929, 1731, 1594, 1495, 1480, 1467, 1340, 1292, 1240, 1166, 1155, 1089, 1020 $cm^{-1}$; Elemental analysis($C_{21}H_{23}FN_2O_4S \cdot 0.3H_2O$)Calcd. (%): C, 59.50; H, 5.61; N, 6.61; F, 4.48; S, 7.56 Found(%): C, 59.59; H, 5.62; N, 6.39; F, 4.26, S, 7.42 |
| If-15 | $^1$H-NMR(CDCl$_3$) δ 1.47(s, 3H), 3.67(s, 2H), 3.96(s, 2H), 4.61(s, 2H), 6.51-6.54(m, 3H), 6.95-7.15(m, 7H), 7.37(d, J=4.8Hz, 1H), 7.48(d, J=8.4Hz, 1H), 7.71-7.76(m, 2H); IR(CHCl$_3$)2972, 2931, 1731, 1594, 1495, 1468, 1339, 1292, 1239, 1165, 1154, 1091, 1056 $cm^{-1}$. |

TABLE 61

| Compound No. | Physical properties |
| --- | --- |
| If-16 | $^1$H-NMR(CDCl$_3$) δ 2.91(t, J=6.3Hz, 2H), 3.34-3.49(m, 2H), 4.63(t, J=6.0Hz, 1H), 4.80(s, 2H), 6.92-7.15(m, 5H), 7.48-7.53(m, 2H); IR(KBr)3285, 2232, 1729, 1627, 1582, 1488, 1414, 1324, 1250, 1159, 1092, 1047 $cm^{-1}$; Elemental analysis($C_{16}H_{15}FN_2O_4S_2 \cdot 0.3H_2O$)Calcd. (%): C, 49.55; H, 4.05; N, 7.22; F, 4.90; S, 16.54 Found(%): C, 49.89; H, 3.98; N, 6.98; F, 4.54, S, 16.12 |
| If-17 | $^1$H-NMR(CDCl$_3$) δ 1.42(s, 6H), 3.12(s, 3H), 3.45(br, 1H), 4.79(s, 2H), 6.90-7.24(m, 6H), 7.51-7.56(m, 2H); IR(KBr)3283, 2966, 2926, 1736, 1590, 1494, 1474, 1409, 1337, 1320, 1293, 1242, 1167, 1153 $cm^{-1}$; Elemental analysis($C_{20}H_{20}ClFN_2O_4S \cdot 0.3H_2O$)Calcd. (%): C, 54.07; H, 4.67, N, 6.30; Cl, |

TABLE 61-continued

| Compound No. | Physical properties |
| --- | --- |
| | 7.98; F, 4.28; S, 7.22 Found(%): C, 54.06; H, 4.65; N, 6.26; Cl, 7.79; F, 4.13, S, 7.12 |
| If-18 | $^1$H-NMR(CDCl$_3$) δ 1.52(s, 6H), 2.22(s, 3H), 3.32(s, 2H), 4.83(s, 2H), 6.92 (s, 1H), 7.14-7.21(m, 4H), 7.63(s, 1H), 7.74-7.78(m, 2H); IR(CHCl$_3$)2974, 2929, 1731, 1594, 1495, 1474, 1341, 1292, 1240, 1167, 1155, 1089, 1020 cm$^{-1}$; Elemental analysis(C$_{21}$H$_{22}$ClFN$_2$O$_4$S•0.3H$_2$O)Calcd. (%): C, 55.03; H, 4.97; N, 6.11; Cl, 7.74; F, 4.15; S, 7.00 Found(%): C, 55.36; H, 5.13; N, 5.90; Cl, 7.34; F, 3.93; S, 7.00 |
| If-19 | $^1$H-NMR(CDCl$_3$) δ 1.44(s, 6H), 3.63(s, 2H), 3.95(s, 2H), 4.59(s, 2H), 6.43 (d, J=7.8Hz, 2H), 6.57(s, 1H), 6.94-7.17(m, 5H), 7.33-7.38(m, 3H), 7.75-7.80(m, 2H); IR(CHCl$_3$)1732, 1594, 1495, 1475, 1341, 1292, 1165, 1154, 1091, 1056 cm$^{-1}$. |
| If-20 | $^1$H-NMR(CDCl$_3$) δ 3.05-3.10(m, 2H), 3.51-3.56(m, 2H), 4.44(s, 2H), 5.00(s, 2H), 7.07-7.13(m, 3H), 7.24-7.44(m, 8H), 7.70-7.82(m, 2H); IR(KBr)1736, 1622, 1589, 1509, 1492, 1455, 1320, 1230, 1162, 1148, 1096 cm$^{-1}$; Elemental analysis(C$_{24}$H$_{22}$FN$_3$O$_4$S)Calcd. (%): C, 61.66; H, 4.74; N, 8.99; F, 4.06; S; 6.86 Found(%): C, 61.53; H, 4.72; N, 8.91; F, 3.91, S, 6.53 |
| Ig-1 | mp 217-219° C.; $^1$H-NMR(d$_6$-DMSO) δ 2.36-2.79(m, 6H), 4.80(s, 2H), 6.71 (dd, J=2.1, 8.4Hz, 1H), 7.00(d, J=2.1Hz, 1H), 7.17(d, J=8.7Hz, 1H), 7.31-7.37(m, 2H), 7.69-7.74(m, 2H), 9.83(s, 1H), 13.00(br, 1H); IR(Nujol) 2926, 1725, 1592, 1492, 1476, 1347, 1237, 1149 cm$^{-1}$; IR(Nujol)3207, 2925, 2853, 1738, 1587, 1464, 1150 cm$^{-1}$; Elemental analysis(C$_{19}$H$_{17}$FN$_2$O$_4$S) Calcd. (%): C, 58.75; H, 4.41; F, 4.89; N, 7.21; S, 8.26 Found: C, 58.71; H, 4.39; F, 4.65; N, 7.07; S, 8.03 |
| Ig-2 | mp 223-226° C.; $^1$H-NMR(d$_6$-DMSO) δ 2.80-2.88(m, 2H), 2.94-3.00(m, 2H), 3.69(s, 2H), 4.85(s, 2H), 6.75(dd, J=1.8, 8.4Hz, 1H), 7.12(d, J=1.8Hz, 1H), 7.23(d, J=8.4Hz, 1H), 7.29-7.39(m, 2H), 7.68-7.77(m, 2H), 9.96(br s, 1H); IR(Nujol)3228, 3105, 3070, 3047, 2924, 2854, 1734, 1590, 1467, 1332, 1226, 1182, 1167, 1151 cm$^{-1}$; Elemental analysis(C$_{19}$H$_{17}$FN$_2$O$_4$S$_2$.0.3AcOEt) Calcd. (%): C, 54.28; H, 4.18; F, 4.43; N, 6.53; S, 14.94 Found(%): C, 54.05; H, 3.98; N, 4.29; N, 6.55; S, 14.92 |

TABLE 62

| Compound No. | Physical properties |
| --- | --- |
| Ig-3 | mp 214-217° C.; $^1$H-NMR(d$_6$-DMSO) δ 2.81-2.92(m, 2H), 2.93-3.03(m, 2H), 3.17(s, 3H), 3.70(s, 2H), 4.92(s, 2H), 6.72(dd, J=2.1, 8.7Hz, 1H), 7.12(d, J=2.1Hz, 1H), 7.33(d, J=8.7Hz, 1H), 7.38-7.48(m, 2H), 7.56-7.64(m, 2H), 13.08(br, 1H); IR(Nujol)3103, 2923, 2742, 2656, 2554, 1724, 1591, 1478, 1342, 1239, 1169, 1147 cm$^{-1}$ |
| Ig-4 | mp 218-220° C.; $^1$H-NMR(d$_6$-DMSO) δ 2.05-2.18(m, 2H), 2.43(t, J=6.3Hz, 2H), 2.90(t, J=6.0Hz, 2H), 3.18(s, 3H), 5.09(s, 2H), 6.91(dd, J=2.1, 8.7Hz, 1H), 7.38-7.45(m, 2H), 7.49(d, J=8.7Hz, 1H), 7.57-7.62(m, 2H), 7.66 (d, J=2.1Hz, 1H); IR(Nujol)3501, 3335, 2925, 2854, 1714, 1631, 1592, 1473, 1454, 1343, 1265, 1239, 1172, 1152 cm$^{-1}$; Elemental analysis (C$_{21}$H$_{19}$FN$_2$O$_5$S•H$_2$O)Calcd. (%): C, 56.24; H, 4.72; F, 4.24; N, 6.25; S, 7.15 Found(%): C, 56.18; H, 4.72; F, 4.14; N, 6.15; S, 7.07 |
| Ig-5 | mp 220-222° C.; $^1$H-NMR(d$_6$-DMSO) δ 0.94(t, J=7.5Hz, 2H), 1.40-1.57(m, 1H), 1.72-2.00(m, 2H), 2.19-2.40(m, 2H), 2.80-3.06(m, 2H), 3.18(s, 3H), 5.08(s, 2H), 6.90(dd, J=2.1, 8.7Hz, 1H), 7.38-7.45(m, 2H), 7.48(d, J=8.7 Hz, 1H), 7.57-7.62(m, 2H), 7.68(d, J=2.1Hz, 1H), 13.30(br, 1H); IR(Nujol) 2924, 2854, 1733, 1593, 1534, 1477, 1464, 1353, 1206, 1172 cm$^{-1}$; Elemental analysis(C$_{23}$H$_{23}$FN$_2$O$_5$S)Calcd. (%): C, 60.25; H, 5.06; F, 4.14; N, 6.11; S, 6.99 Found(%): C, 60.04; H, 5.15; F, 3.90; N, 6.07; S, 6.78 |
| Ig-6 | mp 128-130° C.; $^1$H-NMR(d$_6$-DMSO) δ 1.22(t, J=6.0Hz, 3H), 2.67(br t, 2H), 3.72(t, J=6.0Hz, 2H), 4.09(q, J=7.2Hz, 2H), 4.47(s, 2H), 4.84(s, 2H), 6.77(dd, J=1.8, 8.4Hz, 1H), 7.07(s, 1H), 7.26(d, J=9.0Hz, 1H), 7.31-7.37 (m, 2H), 7.70-7.75(m, 2H), 9.88(s, 1H), 13.00(br 1H); IR(Nujol)3187, 2925, 2854, 1764, 1678, 1585, 1468, 1448, 1269, 1235, 1171, 1158 cm$^{-1}$. |
| Ig-7 | mp 200-202° C.; $^1$H-NMR(d$_6$-DMSO) δ 1.22(t, J=7.2Hz, 3H), 2.71(br t, 2H), 3.18(s, 3H), 3.74(br t, 2H), 4.09(q, J=7.2Hz, 2H), 4.49(s, 2H), 4.92(s, 2H), 6.79(dd, J=1.8, 9.0Hz, 1H), 7.10(br, 1H), 7.35(d, J=8.4Hz, 1H), 7.39-7.45(m, 2H), 7.56-7.62(m, 2H), 13.00(br 1H); IR(Nujol) 2925, 2854, 1697, 1677, 1476, 1340, 1238, 1147 cm$^{-1}$; Elemental analysis (C$_{23}$H$_{24}$FN$_3$O$_6$S•0.4H$_2$O)Calcd. (%): C, 55.61; H, 5.03; F, 3.82; N, 8.46; S, 6.46 Found(%): C, 55.58; H, 5.10; F, 3.71; N, 8.39; S, 6.41 |
| Ig-8 | mp 229-232° C.; $^1$H-NMR(d$_6$-DMSO) δ 1.22(t, J=6.9Hz, 3H), 2.67(br t, 2H), 3.72(t, J=6.0Hz, 2H), 3.77(s, 3H), 4.06(q, J=7.2Hz, 2H), 4.47(s, 2H), 4.85(s, 2H), 6.69(dd, J=2.1, 8.7Hz, 1H), 7.07(d, J=2.1Hz, 1H), 6.99-7.03 (m, 2H), 7.23(d, J=8.7Hz, 1H), 7.59-7.63(m, 2H); IR(Nujol)3309, 3218, 2925, 2853, 1741, 1644, 1598, 1491, 1259, 1247, 1155 cm$^{-1}$. |

TABLE 63

| Compound No. | Physical properties |
| --- | --- |
| Ig-9 | mp 232-234° C.; $^1$H-NMR($d_6$-DMSO) δ 1.22(t, J=6.9Hz, 3H), 2.71(br t, 2H), 3.13(s, 3H), 3.74(t, J=5.7Hz, 2H), 3.85(s, 3H), 4.09(q, J=6.9Hz, 2H), 4.49(s, 2H), 4.92(s, 2H), 6.79(dd, J=1.8, 8.7Hz, 1H), 7.08-7.11(m, 3H), 7.34(d, J=8.7Hz, 1H), 7.43-7.47(m, 2H); IR(Nujol)3143, 2925, 2854, 1722, 1690, 1598, 1497, 1472, 1229, 1163 cm$^{-1}$; Elemental analysis ($C_{24}H_{27}N_3O_7S$)Calcd. (%): C, 57.47; H, 5.43; N, 8.38; S, 6.39 Found(%): C, 57.48; H, 5.41; N, 8.28; S, 6.23 |
| Ig-10 | mp 245-250° C.; $^1$H-NMR($d_6$-DMSO at 80° C.) δ 2.11(s, 3H), 2.78(br, 2H), 3.14 (s, 3H), 3.80(br, 2H), 3.85(s, 3H), 4.55(s, 2H), 4.85(s, 2H), 6.80(br d, J=8.7Hz, 1H), 7.05-7.08(m, 3H), 7.28(d, J=8.7Hz, 1H), 7.47-7.51(m, 2H); IR (Nujol)2923, 2853, 1737, 1596, 1474, 1340, 1259, 1162 cm$^{-1}$. |
| Ig-11 | mp 209-211° C.; $^1$H-NMR($d_6$-DMSO) δ 1.60-1.90(m, 6H), 2.60-2.76(m, 4H), 4.87(s, 2H), 6.69(dd, J=1.8, 8.7Hz, 1H), 7.05(d, J=1.8Hz, 1H), 7.17(d, J=8.7Hz, 1H), 7.31-7.38(m, 2H), 7.70-7.75(m, 2H), 9.80(s, 1H), 12.90(br, 1H); IR(Nujol)3220, 2922, 2854, 1733, 1593, 1482, 1323, 1194, 1149 cm$^{-1}$; Elemental analysis($C_{21}H_{21}FN_2O_4S$)Calcd. (%): C, 60.56; H, 5.08; F, 4.56; N, 6.73; S, 7.70 Found(%): C, 60.48; H, 4.92; F, 4.32; N, 6.68; S, 7.56 |
| Ig-12 | mp 157-160° C.; $^1$H-NMR(CDCl$_3$) δ 1.70-1.93(m, 6H), 2.66-2.79(m, 4H), 3.22 (s, 3H), 4.83(s, 2H), 6.80(dd, J=1.8, 8.7Hz, 1H), 7.03(d, J=8.7Hz, 1H), 7.08-7.16(m, 3H), 7.57-7.63(m, 2H); IR(Nujol)2923, 2853, 1725, 1592, 1480, 1346, 1235, 1148 cm$^{-1}$; Elemental analysis($C_{22}H_{23}FN_2O_4S$)Calcd. (%): C, 61.38; H, 5.39; F, 4.41; N, 6.51; S, 7.45 Found(%): C, 60.98; H, 5.42; F, 4.10; N, 6.41; S, 7.43 |
| Ig-13 | mp 155-157° C.; $^1$H-NMR(CDCl$_3$) δ 1.60-1.92(m, 6H), 2.60-2.74(m, 4H), 4.76 (s, 4H), 6.66(dd, J=1.8, 8.7Hz, 1H), 6.93(d, J=8.4Hz, 1H), 7.04(d, J=1.8Hz, 1H), 7.09-7.28(m, 7H), 7.65-7.70(m, 2H); IR(Nujol)2923, 2854, 1726, 1593, 1479, 1346, 1241, 1167, 1153 cm$^{-1}$; Elemental analysis($C_{28}H_{27}FN_2O_4S$) Calcd. (%): C, 66.39; H, 5.37; F, 3.75; N, 5.53; S, 6.33 Found(%): C, 66.39; H, 5.40; F, 3.53; N, 5.51; S, 6.09 |
| Ig-14 | mp 144-150° C.; $^1$H-NMR($d_6$-DMSO) δ 1.61-1.76(m, 4H), 1.78-1.90(m, 2H), 2.60-2.76(m, 4H), 3.13(s, 3H), 3.84(s, 3H), 4.93(s, 2H), 6.64(dd, J=1.8, 8.4Hz, 1H), 7.02(d, J=1.8Hz, 1H), 7.07-7.10(m, 2H), 7.35(d, J=8.4Hz, 1H), 7.45-7.49(m, 2H); IR(Nujol)2926, 2853, 1727, 1596, 1496, 1477, 1353, 1256, 1243, 1162, 1151 cm$^{-1}$; Elemental analysis($C_{23}H_{26}N_2O_5S$)Calcd. (%): C, 62.42; H, 5.92; N, 6.33; S, 7.25 Found(%): C, 62.72; H, 5.83; N, 6.18; S, 7.08 |

TABLE 64

| Compound No. | Physical properties |
| --- | --- |
| Ig-15 | mp 151-155° C.; $^1$H-NMR($d_6$-DMSO) δ 0.97(t, J=6.9Hz, 3H), 1.61-1.76(m, 4H), 1.78-1.90(m, 2H), 2.62-2.76(m, 4H), 3.60(q, J=6.9Hz, 2H), 4.94(s, 2H), 6.58(dd, J=1.8, 8.4Hz, 1H), 7.01(d, J=1.8Hz, 1H), 7.28(d, J=8.4 Hz, 1H), 7.38-7.45(m, 2H), 7.63-7.68(m, 2H); IR(Nujol)2924, 2854, 1728, 1592, 1478, 1345, 1233, 1170, 1143 cm$^{-1}$; Elemental analysis($C_{23}H_{26}N_2O_5S$) Calcd. (%): C, 62.14; H, 5.67; F, 4.27; N, 6.30; S, 7.21 Found(%): C, 61.99; H, 5.39; F, 4.08; N, 6.31; S, 7.04 |
| Ig-16 | mp 186-189° C.; $^1$H-NMR($d_6$-DMSO) δ 1.60-1.76(m, 4H), 1.78-1.90(m, 2H), 2.60-2.80(m, 4H), 3.10(s, 3H), 4.94(s, 2H), 6.64(dd, J=1.8, 8.7Hz, 1H), 6.85-6.89(m, 2H), 7.03(d, J=1.8Hz, 1H), 7.25(d, J=8.7Hz, 1H), 7.33-7.37 (m, 2H), 10.47(br s, 1H), 12.96(br s, 1H); IR(Nujol)3400, 2924, 2853, 1722, 1600, 1586, 1498, 1476, 1444, 1321, 1251, 1144 cm$^{-1}$; Elemental analysis ($C_{22}H_{24}N_2O_5S$•0.3H$_2$O)Calcd. (%): C, 60.90; H, 5.71; N, 6.46; S, 7.39 Found (%): C, 60.85; H, 5.38; N, 6.25; S, 7.18 |
| Ig-17 | mp 264-266° C.; $^1$H-NMR($d_6$-DMSO) δ 1.96-2.07(m, 2H), 2.97(t, J=6.3Hz, 2H), 3.13-3.20(m, 2H), 3.17(s, 3H), 5.02(s, 2H), 6.82(dd, J=2.1, 8.7Hz, 1H), 7.37-7.45(m, 3H), 7.55-7.64(m, 3H), 7.96(d, J=2.1Hz, 1H); IR(Nujol) 3521, 3381, 2924, 2854, 1713, 1614, 1592, 1528, 1476, 1445, 1339, 1254 cm$^{-1}$; Elemental analysis($C_{21}H_{20}FN_3O_5S$•H$_2$O)Calcd. (%): C, 54.42; H, 4.78; F, 4.10; N, 9.07; S, 6.92 Found(%): C, 54.43; H, 4.82; F, 3.96; N, 8.83; S, 6.67 |
| Ig-18 | mp 193-197° C.; $^1$H-NMR($d_6$-DMSO) δ 1.32-1.68(m, 8H), 2.63-2.79(m, 4H), 4.85(s, 2H), 6.73(dd, J=1.8, 8.7Hz, 1H), 7.00(d, J=1.8Hz, 1H), 7.17(d, J=8.7Hz, 1H), 7.31-7.37(m, 2H), 7.70-7.75(m, 2H), 9.79(s, 1H); IR(Nujol) 3280, 2924, 2853, 1703, 1594, 1475, 1331, 1291, 1244, 1167, 1153 cm$^{-1}$; Elemental analysis($C_{22}H_{23}FN_2O_4S$)Calcd. (%): C, 61.38; H, 5.39; F, 4.41; N, 6.51; S, 7.47 Found(%): C, 61.21; H, 5.31; F, 4.29; N, 6.42; S, 7.47 |
| Ig-19 | mp 175-177° C.; $^1$H-NMR($d_6$-DMSO) δ 1.35-1.71(m, 8H), 2.66-2.82(m, 4H), 3.18(s, 3H), 4.92(s, 2H), 6.71(dd, J=2.1, 8.7Hz, 1H), 6.98(d, J=2.1Hz, 1H), 7.26(d, J=8.7Hz, 1H), 7.37-7.43(m, 3H), 7.57-7.62(m, 2H); IR(Nujol) 2925, 2851, 1729, 1590, 1478, 1347, 1243, 1162, 1150 cm$^{-1}$; Elemental |

TABLE 64-continued

| Compound No. | Physical properties |
| --- | --- |
|  | analysis($C_{23}H_{25}FN_2O_4S$)Calcd. (%): C, 62.14; H, 5.67; F, 4.27; N, 6.30; S, 7.21 Found(%): C, 62.01; H, 5.72; F, 4.01; N, 6.15; S, 7.08 |
| Ig-20 | mp 188-192° C.; $^1$H-NMR($d_6$-DMSO)) δ 1.32-1.70(m, 8H), 2.60-2.78(m, 4H), 4.81(s, 2H), 4.86(s, 2H), 6.66(dd, J=1.8, 8.7Hz, 1H), 6.90(d, J=2.1Hz, 1H), 7.15-7.29(m, 6H), 7.43-7.46(m, 2H), 7.70-7.75(m, 2H); IR(Nujol)2924, 2853, 1713, 1596, 1474, 1343, 1164, 1153 cm$^{-1}$; Elemental analysis ($C_{29}H_{29}FN_2O_4S$)Calcd. (%): C, 66.90; H, 5.61; F, 3.65; N, 5.38; S, 6.16 Found (%): C, 66.87; H, 5.59; F, 3.52; N, 5.37; S, 6.01 |

TABLE 65

| Compound No. | Physical properties |
| --- | --- |
| Ig-21 | mp 165-175° C.; $^1$H-NMR($d_6$-DMSO) δ 2.38-2.79(m, 6H), 3.16(s, 3H), 4.88(s, 2H), 6.67(dd, J=2.1, 8.4Hz, 1H), 6.99(d, J=2.1Hz, 1H), 7.27(d, J=8.7 Hz, 1H), 7.38-7.45(m, 2H), 7.56-7.61(m, 2H); IR(Nujol)2924, 2855, 1730, 1592, 1469, 1343, 1242, 1234, 1150 cm$^{-1}$; Elemental analysis($C_{20}H_{19}FN_2O_4S$) Calcd. (%): C, 59.69; H, 4.76; F, 4.72; N, 6.96; S, 7.97 Found(%): C, 59.73; H, 4.72; F, 4.69; N, 6.90; S, 7.90 |
| Ig-22 | mp 261-265° C.; $^1$H-NMR($d_6$-DMSO) δ 2.80-3.15(m, 4H), 3.88(d, J=15.3Hz, 1H), 4.09(d, J=15.3Hz, 1H), 4.90(s, 2H), 6.75(dd, J=1.8, 8.7Hz, 1H), 7.15(d, J=1.8Hz, 1H), 7.28(d, J=8.7Hz, 1H), 7.29-7.39(m, 2H), 7.67-7.76 (m, 2H), 9.89(br s, 1H), 13.04(br, 1H); IR(Nujol)3560, 3316, 3166, 3102, 3069, 2924, 2724, 2599, 2506, 1896, 1717, 1590, 1466, 1242, 1227, 1166, 1155 cm$^{-1}$ |
| Ig-23 | mp 239-244° C.; $^1$H-NMR($d_6$-DMSO) δ 2.90-3.15(m, 4H), 3.17(s, 3H), 3.90(d, J=15.3Hz, 1H), 4.10(d, J=15.3Hz, 1H), 4.97(s, 2H), 6.75(dd, J=1.8, 8.7Hz, 1H), 7.20(d, J=1.8Hz, 1H), 7.35(d, J=8.7Hz, 1H), 7.40-7.47(m, 2H), 7.55-7.64(m, 2H), 13.13(br, 1H); IR(Nujol) 1718, 1590, 1479, 1348, 1234, 1152 cm$^{-1}$; Elemental analysis($C_{20}H_{19}FN_2O_5S_2$)Calcd. (%): C, 53.32; H, 4.25; F, 4.22; N, 6.22; S, 14.24 Found(%): C, 53.15; H, 4.47; F, 4.20; N, 6.19; S, 14.23 |
| Ig-24 | mp 251-254° C.; $^1$H-NMR($d_6$-DMSO) δ 1.96-2.05(m, 2H), 2.93(t, J=6.3Hz, 2H), 3.11-3.20(m, 2H), 3.76(s, 3H), 4.94(s, 2H), 6.92(dd, J=2.1, 8.7Hz, 1H), 6.98-7.03(m, 2H), 7.27(d, J=8.7Hz, 1H), 7.50(t, J=5.1Hz, 1H), 7.58-7.63(m, 2H), 8.00(d, J=2.1Hz, 1H), 9.73(s, 1H); IR(Nujol)3429, 3171, 2924, 2853, 1745, 1595, 1577, 1481, 1450, 1269, 1154 cm$^{-1}$; Elemental analysis($C_{21}H_{21}N_3O_6S \cdot H_2O$)Calcd. (%): C, 54.65; H, 5.02; N, 9.11; S, 6.95 Found(%): C, 54.58; H, 4.58; N, 9.05; S, 7.00 |
| Ig-25 | mp 251-254° C.; $^1$H-NMR($d_6$-DMSO) δ 1.96-2.05(m, 2H), 2.97(t, J=6.3Hz, 2H), 3.12(s, 3H), 3.12-3.21(m, 2H), 3.84(s, 3H), 5.01(s, 2H), 6.81(dd, J=2.1, 9.0Hz, 1H), 7.05-7.11(m, 2H), 7.37(d, J=9.0Hz, 1H), 7.44-7.49(m, 2H), 7.57(t, J=4.8Hz, 1H), 7.99(d, J=2.1Hz, 1H), 13.2(br, 1H); IR(Nujol) 3451, 3316, 2925, 2854, 1747, 1721, 1612, 1596, 1534, 1475, 1444, 1339, 1258 cm$^{-1}$; Elemental analysis($C_{22}H_{23}N_3O_6S \cdot 1.1H_2O$)Calcd. (%): C, 55.36; H, 5.32; N, 8.80; S, 6.72 Found(%): C, 55.21; H, 5.10; N, 8.85; S, 6.84 |
| Ig-26 | dp 217-219° C.; $^1$H-NMR($d_6$-DMSO) δ 1.84-2.00(m, 2H), 2.64-2.81(m, 4H), 3.16(s, 3H), 4.98(s, 2H), 6.75(dd, J=2.1, 8.7Hz, 1H), 7.35-7.61(m, 5H), 7.74(d, J=2.1Hz, 1H), 10.39(s, 1H), 13.0.(br, 1H); IR(Nujol)3400, 2925, 2854, 1705, 1605, 1590, 1476, 1459, 1418, 1377, 1316, 1231, 1170, 1157 cm$^{-1}$; Elemental analysis($C_{21}H_{20}FN_3O_5S$)Calcd. (%): C, 56.62; H, 4.53; F, 4.26; N, 9.43; S, 7.20 Found(%): C, 56.59; H, 4.39; F, 4.37; N, 9.26; S, 7.12 |

TABLE 66

| Compound No. | Physical properties |
| --- | --- |
| Ig-27 | dp 203-208° C.; $^1$H-NMR($d_6$-DMSO) δ 1.84-1.97(m, 2H), 2.60-2.78(m, 4H), 3.18(s, 3H), 3.76(s, 3H), 4.99(s, 2H), 6.85(dd, J=2.1, 8.7Hz, 1H), 7.38-7.66(m, 6H), 7.74(d, J=2.1Hz, 1H), 13.0(br, 1H); IR(Nujol)3179, 2925, 2854, 1736, 1592, 1471, 1376, 1345, 1172, 1149 cm$^{-1}$; Elemental analysis ($C_{22}H_{22}FN_3O_5S$)Calcd. (%): C, 57.51; H, 4.83; F, 4.13; N, 9.14; S, 6.98 Found (%): C, 57.40; H, 4.65; F, 4.18; N, 8.95; S, 7.03 |
| Ih-1 | mp 218-222° C.; $^1$H-NMR($d_6$-DMSO) δ 1.65-1.88(m, 4H), 2.50-2.60(m, 4H), 4.79(s, 2H), 6.72(dd, J=1.2, 9.0Hz, 1H), 7.03(d, J=1.2Hz, 1H), 7.18(d, J=8.4Hz, 1H), 7.31-7.37(m, 2H), 7.69-7.75(m, 2H), 9.80(s, 1H), 12.90(br, 1H); IR(Nujol)3221, 2925, 2854, 1737, 1587, 1478, 1403, 1231 cm$^{-1}$. |
| Ih-2 | mp 179-182° C.; $^1$H-NMR($d_6$-DMSO) δ 1.70-1.90(m, 4H), 2.50-2.64(m, 4H), 3.17(s, 3H), 4.86(s, 2H), 6.69(dd, J=2.1, 8.4Hz, 1H), 7.00(d, J=2.1Hz, |

TABLE 66-continued

| Compound No. | Physical properties |
| --- | --- |
|  | 1H), 7.27(d, J=8.7Hz, 1H), 7.39-7.49(m, 2H), 7.58-7.63(m, 2H); IR(Nujol) 2926, 1725, 1592, 1492, 1476, 1347, 1237, 1149 cm$^{-1}$; Elemental analysis ($C_{21}H_{21}FN_2O_4S$)Calcd. (%): C, 60.56; H, 5.08; F, 4.56; N, 6.73; S, 7.70 Found (%): C, 60.38; H, 5.07; F, 4.44; N, 6.73; S, 7.71 |
| Ih-3 | mp 198-202° C.; $^1$H-NMR(d$_6$-DMSO) δ 1.64-1.86(m, 4H), 2.44-2.60(m, 4H), 4.80(s, 4H), 6.64(dd, J=1.8, 8.7Hz, 1H), 6.93(d, J=1.8Hz, 1H), 7.16-7.30 (m, 6H), 7.40-7.49(m, 2H), 7.68-7.78(m, 2H); IR(Nujol)2924, 2854, 1727, 1594, 1494, 1475, 1346, 1243 cm$^{-1}$; Elemental analysis($C_{27}H_{25}FN_2O_4S$) Calcd. (%): C, 65.84; H, 5.12; F, 3.86; N, 5.69; S, 6.51 Found(%): C, 65.53; H, 5.11; F, 3.73; N, 5.63; S, 6.30 |
| Ih-4 | mp 180-183° C.; $^1$H-NMR(d$_6$-DMSO) δ 1.07(d, J=6.9Hz, 3H), 1.44(m, 1H), 1.74-1.98(m, 2H), 2.10(m, 1H), 2.52-2.70(m, 3H), 4.78(s, 2H), 6.72(dd, J=2.1, 8.7Hz, 1H), 7.02(d, J=1.5Hz, 1H), 7.17(d, J=8.4Hz, 1H), 7.30-7.40 (m, 2H), 7.68-7.78(m, 2H), 9.80(br s, 1H), 12.91(br, 1H); IR(Nujol)3217, 2953, 2853, 2721, 1733, 1567, 1418, 1321, 1298, 1180, 1143 cm$^{-1}$; Elemental analysis($C_{21}H_{21}FN_2O_4S$)Calcd. (%): C, 60.56; H, 5.08; F, 4.56; N, 6.73; S, 7.70 Found(%): C, 60.35; H, 5.09; F, 4.41; N, 6.66; S, 7.67 |
| Ih-5 | mp 100-101° C.; $^1$H-NMR(d$_6$-DMSO) δ 1.07(d, J=6.9Hz, 3H), 1.46(m, 1H), 1.74-1.94(m, 2H), 2.10(m, 1H), 2.40-2.75(m, 3H), 3.17(s, 3H), 4.83(s, 2H), 6.67(dd, J=2.1, 8.4Hz, 1H), 7.00(d, J=2.1Hz, 1H), 7.17(d, J=9.0Hz, 1H), 7.38-7.48(m, 2H), 7.55-7.63(m, 2H), 12.90(br, 1H); IR(Nujol)3103, 3068, 2854, 2726, 1726, 1619, 1475, 1346, 1293, 1235, 1171 cm$^{-1}$; Elemental analysis($C_{22}H_{23}FN_2O_4S$•0.2AcOEt)Calcd. (%): C, 61.11; H, 5.53; F, 4.24; N, 6.25; S, 7.16 Found(%): C, 60.90; H, 5.44; F, 4.01; N, 6.43; S, 7.38 |

TABLE 67

| Compound No. | Physical properties |
| --- | --- |
| Ih-6 | mp 176-178° C.; $^1$H-NMR(d$_6$-DMSO) δ 1.06(d, J=6.9Hz, 3H), 1.41(m, 1H), 1.70-1.84(m, 2H), 2.08(m, 1H), 2.42-2.70(m, 3H), 4.79(s, 4H), 6.64(dd, J=2.1, 8.4Hz, 1H), 7.00(d, J=2.1Hz, 1H), 7.17(d, J=8.4Hz, 1H), 7.14-7.30 (m, 5H), 7.40-7.50(m, 2H), 7.66-7.76(m, 2H), 12.99(br, 1H); IR(Nujol) 3106, 2854, 1717, 1594, 1494, 1291, 1251, 1235, 1188, 1165, 1154 cm$^{-1}$; Elemental analysis($C_{28}H_{27}FN_2O_4S$)Calcd. (%): C, 66.39; H, 5.37; F, 3.75; N, 5.53; S, 6.33 Found(%): C, 66.19; H, 5.36; F, 3.52; N, 5.43; S, 6.33 |
| Ih-7 | mp 205-210° C.; $^1$H-NMR(d$_6$-DMSO) δ 1.85-1.91(m, 4H), 2.40-2.75(m, 4H), 3.20(s, 3H), 4.86(s, 2H), 6.61(dd, J=2.1, 8.7Hz, 1H), 7.02(d, J=2.1Hz, 1H), 7.22(dd, J=3.6, 5.1Hz, 1H), 7.28(d, J=8.7Hz, 1H), 7.45(dd, J=1.5, 3.6Hz, 1H), 8.00(dd, J=1.5, 5.1Hz, 1H), 12.85(br, 1H); IR(Nujol)3099, 3085, 2924, 2741, 2653, 2552, 1722, 1578, 1476, 1348, 1310, 1240, cm$^{-1}$; Elemental analysis($C_{19}H_{20}N_2O_4S_2$•0.2AcOEt)Calcd. (%): C, 56.42; H, 4.98; N, 6.93; S, 15.85 Found(%): C, 56.30; H, 5.24; N, 6.50; S, 14.88 |
| Ih-8 | mp 134-136° C.; $^1$H-NMR(d$_6$-DMSO) δ 0.86(t, J=7.2Hz, 3H), 1.30-1.46(m, 2H), 1.58-1.70(m, 2H), 1.72-1.90(m, 4H), 2.54-2.66(m, 4H), 3.03-3.12(m, 2H), 3.26(s, 3H), 4.87(s, 2H), 7.07(dd, J=2.1, 8.7Hz, 1H), 7.32(d, J=8.7Hz, 1H), 7.38(d, J=2.1Hz, 1H), 12.98(br, 1H); IR(Nujol)3042, 2923, 2739, 2650, 2549, 1723, 1583, 1411, 1385, 1323, 1234, 1213, 1136 cm$^{-1}$; Elemental analysis($C_{19}H_{26}N_2O_4S$)Calcd. (%): C, 60.29; H, 6.92; N, 7.40; S, 8.46 Found (%): C, 60.41; H, 6.77; N, 7.37; S, 8.16 |
| Ih-9 | mp 222-225° C.; $^1$H-NMR(d$_6$-DMSO) δ 1.66-1.88(m, 4H), 2.40-2.64(m, 4H), 4.81(s, 4H), 6.68(dd, J=2.1, 8.7Hz, 1H), 6.97(d, J=2.1Hz, 1H), 7.12(m, 7H), 7.57(dd, J=1.2, 3.6Hz, 1H), 8.02(dd, J=1.2, 5.1Hz, 1H), 12.97(br, 1H); IR(Nujol)3122, 2923, 2737, 2652, 2558, 1722, 1584, 1403, 1349, 1155 cm$^{-1}$. |
| Ih-10 | mp 143-145° C.; $^1$H-NMR(d$_6$-DMSO) δ 0.90(t, J=7.5Hz, 3H), 1.34-1.50(m, 2H), 1.66-1.89(m, 6H), 2.50-2.60(m, 4H), 3.11-3.22(m, 2H), 4.81(s, 2H), 4.88(s, 2H), 6.99(dd, J=2.1, 8.7Hz, 1H), 7.14-7.23(m, 6H), 7.30(d, J=2.1Hz, 1H), 12.99(br, 1H); IR(Nujol)3030, 2853, 2728, 2647, 1725, 1582, 1408, 1385, 1296, 1134 cm$^{-1}$; Elemental analysis($C_{25}H_{30}N_2O_4S$)Calcd. (%): C, 66.05; H, 6.65; N, 6.16; S, 7.00 Found(%): C, 65.67; H, 6.40; N, 6.21; S, 6.95 |
| Ih-11 | mp 218-220° C.; $^1$H-NMR(d$_6$-DMSO) δ 1.70-1.90(m, 4H), 2.46-2.66(m, 4H), 4.80(s, 2H), 6.77(dd, J=1.8, 8.7Hz, 1H), 7.06-7.10(m, 2H), 7.20(d, J=8.7Hz, 1H), 7.38(dd, J=2.1, 4.2Hz, 1H), 7.82(dd, J=2.1, 5.4Hz, 1H), 9.90(br s, 1H), 12.96(br, 1H); IR(Nujol)3099, 2854, 2741, 2653, 2552, 1722, 1578, 1508, 1439, 1385, 1348, 1310, 1240, 1151 cm$^{-1}$; Elemental analysis ($C_{18}H_{18}N_2O_4S_2$•0.2AcOEt)Calcd. (%): C, 55.33; H, 4.84; N, 6.86; S, 15.71 Found(%): C, 55.14; H, 4.61; N, 7.05; S, 15.77 |

TABLE 68

| Compound No. | Physical properties |
|---|---|
| Ih-12 | mp 174-176° C.; $^1$H-NMR(d$_6$-DMSO) δ 1.70-1.90(m, 4H), 2.40-2.64(m, 4H), 3.12(s, 3H), 3.84(s, 3H), 4.85(s, 2H), 6.68(dd, J=2.1, 8.7Hz, 1H), 6.99(d, J=1.8Hz, 1H), 7.08(d, J=9.0Hz, 2H), 7.25(d, J=8.7Hz, 1H), 7.45(d, J=9.0Hz, 2H), 12.97(br, 1H); IR(Nujol) 2925, 2746, 2662, 2563, 1727, 1709, 1595, 1474, 1380, 1350, 1246, 1149 cm$^{-1}$; Elemental analysis(C$_{22}$H$_{23}$FN$_2$O$_4$S) Calcd. (%): C, 61.67; H, 5.65; N, 6.54; S, 7.48 Found(%): C, 61.40; H, 5.69; N, 6.44; S, 7.22 |
| Ih-13 | mp 225-228° C.; $^1$H-NMR(d$_6$-DMSO) δ 1.66-1.96(m, 4H), 2.44-2.60(m, 4H), 4.77(s, 2H), 6.72(dd, J=2.1, 8.7Hz, 1H), 6.99(d, J=9.0Hz, 2H), 7.00(d, J=2.1Hz, 1H), 7.14(d, J=8.7Hz, 1H), 7.47(d, J=9.0Hz, 2H), 9.51(br s, 1H), 12.99(br, 1H); IR(Nujol)3456, 3289, 2924, 1720, 1590, 1284, 1260, 1145 cm$^{-1}$. |
| Ih-14 | mp 189-194° C.; $^1$H-NMR(d$_6$-DMSO) δ 1.68-1.86(m, 4H), 2.44-2.60(m, 4H), 3.76(s, 3H), 4.78(s, 2H), 6.73(dd, J=1.8, 8.7Hz, 1H), 6.97(m, 3H), 7.08(d, J=9.0Hz, 2H), 7.60(d, J=8.7Hz, 1H), 9.52(br s, 1H), 12.92(br, 1H); IR (Nujol)3296, 3203, 2924, 1723, 1403, 1295, 1145 cm$^{-1}$; Elemental analysis (C$_{21}$H$_{22}$N$_2$O$_5$S•0.3AcOEt)Calcd. (%): C, 60.85; H, 5.35; N, 6.76; S, 7.74 Found (%): C, 60.47; H, 5.58; N, 6.35; S, 7.27 |
| Ih-15 | mp 114-118° C.; $^1$H-NMR(d$_6$-DMSO) δ 1.70-1.90(m, 4H), 2.44-2.66(m, 4H), 3.10(s, 3H), 4.84(s, 2H), 6.68(dd, J=2.1, 8.7Hz, 1H), 6.87(d, J=9.0Hz, 2H), 6.97(d, J=2.1Hz, 1H), 7.24(d, J=8.7Hz, 1H), 7.34(d, J=9.0Hz, 2H), 12.99(br, 1H); IR(Nujol)3376, 2924, 1728, 1586, 1499, 1376, 1329, 1283, 1226, 1147 cm$^{-1}$. |
| Ih-16 | mp 182-185° C.; $^1$H-NMR(d$_6$-DMSO) δ 0.98(t, J=9.9Hz, 3H), 1.35-1.64(m, 4H), 1.90-2.18(m, 2H), 2.50-2.70(m, 3H), 4.80(s, 2H), 6.72(dd, J=2:1, 8.7Hz, 1H), 7.04(d, J=1.8Hz, 1H), 7.18(d, J=8.7Hz, 1H), 7.32-7.38(m, 2H), 7.70-7.75(m, 2H), 9.83(s, 1H); IR(Nujol)3287, 2956, 2922, 2853, 1722, 1590, 1492, 1469, 1404, 1254, 1163, 1148 cm$^{-1}$; Elemental analysis (C$_{22}$H$_{23}$FN$_2$O$_4$S)Calcd. (%): C, 61.38; H, 5.39; F, 4.41; N, 6.51; S, 7.45 Found (%): C, 61.25; H, 5.36; F, 4.30; N,6.43; S, 7.19 |
| Ih-17 | mp 186-188° C.; $^1$H-NMR(d$_6$-DMSO) δ 0.98(t, J=6.9Hz, 3H), 1.37-1.64(m, 4H), 1.92-2.18(m, 2H), 2.50-2.70(m, 3H), 3.77(s, 3H), 4.79(s, 2H), 6.74(dd, J=1.8, 8.7Hz, 1H), 7.00-7.17(m, 4H), 7.59-7.63(m, 2H), 9.65(s, 1H); IR (Nujol)3223, 2924, 2853, 1727, 1594, 1260, 1143 cm$^{-1}$; Elemental analysis (C$_{23}$H$_{26}$N$_2$O$_5$S)Calcd. (%): C, 62.42; H, 5.93; N, 6.33; S, 7.11 Found(%): C, 62.21; H, 5.88; N, 6.27; S, 7.11 |
| Ih-18 | mp 153-155° C.; $^1$H-NMR(d$_6$-DMSO) δ 0.97(t, J=7.2Hz, 3H), 1.35-1.68(m, 4H), 1.90-2.18(m, 2H), 2.54-2.72(m, 3H), 3.17(s, 3H), 4.85(s, 2H), 6.69(dd, J=2.1, 8.4Hz, 1H), 7.01(d, J=2.1Hz, 1H), 7.26(d, J=8.4Hz, 1H), 7.38-7.45(m, 2H), 7.57-7.62(m, 2H); IR(Nujol)2924, 1719, 1592, 1476, 1345, 1237, 1146 cm$^{-1}$; Elemental analysis(C$_{23}$H$_{25}$FN$_2$O$_4$S)Calcd. (%): C, 62.14; H, 5.67; F, 4.27; N, 6.30; S, 7.21 Found(%): C, 62.38; H, 5.84; F, 4.00; N.6.10; S, 6.83 |

TABLE 69

| Compound No. | Physical properties |
|---|---|
| Ih-19 | mp 119-122° C.; $^1$H-NMR(d$_6$-DMSO) δ 0.97(t, J=6.9Hz, 3H), 1.37-1.70(m, 4H), 1.92-2.18(m, 2H), 2.50-2.74(m, 3H), 3.13(s, 3H), 3.84(s, 3H), 4.85(s, 2H), 6.69(dd, J=2.1, 8.4Hz, 1H), 6.99(d, J=2.1Hz, 1H), 7.07-7.10(m, 2H), 7.24(d, J=8.4Hz, 1H), 7.44-7.48(m, 2H); IR(Nujol)2925, 1719, 1597, 1579, 1476, 1342, 1245, 1150 cm$^{-1}$; Elemental analysis(C$_{24}$H$_{28}$N$_2$O$_5$S)Calcd. (%): C, 63.14; H, 6.18; N, 6.14; S, 7.02 Found(%): C, 63.30; H, 6.38; N, 5.94; S, 6.61 |
| Ih-20 | mp 193-200° C.; $^1$H-NMR(d$_6$-DMSO) δ 1.65-1.86(m, 4H), 2.46-2.60(m, 4H), 4.78(s, 2H), 6.73(dd, J=2.1, 8.7Hz, 1H), 7.02(d, J=2.1Hz, 1H), 7.16(d, J=8.7Hz, 1H), 7.45- 7.60(m, 3H), 7.65-7.72(m, 2H), 9.78(s, 1H), 12.93(brs, 1H); IR(Nujol)3206, 1765, 1735, 1584, 1478, 1459, 1448, 1435, 1398, 1366, 1349, 1334, 1309, 1282, 1265, 1236, 1204, 1147 cm$^{-1}$; Elemental analysis (C$_{20}$H$_{20}$N$_2$O$_4$S)Calcd. (%): C, 62.48; H, 5.24; N, 7.29; S, 8.34 Found(%): C, 62.29; H, 5.23; N, 7.18; S, 8.24 |
| Ih-21 | mp 182-190° C.; $^1$H-NMR(d$_6$-DMSO) δ 1.67-1.87(m, 4H), 2.30(s, 3H), 2.46-2.60(m, 4H), 4.78(s, 2H), 6.73(dd, J=2.1, 8.7Hz, 1H), 7.04(d, J=2.1Hz, 1H), 7.15(d, J=8.7Hz, 1H), 7.28(d, J=8.4Hz, 2H), 7.56(d, J=8.4Hz, 2H), 9.71(s, 1H), 12.93(br s, 1H); IR(Nujol)3222, 3114, 3062, 1756, 1738, 1596, 1478, 1456, 1417, 1404, 1381, 1365, 1346, 1322, 1303, 1291, 1260, 1194, 1146 cm$^{-1}$; Elemental analysis(C$_{21}$H$_{22}$N$_2$O$_4$S)Calcd. (%): C, 63.30; H, 5.56; N, 7.03; S, 8.05 Found(%): C, 63.21; H, 5.53; N, 6.99; S, 7.98 |
| Ih-22 | mp 199-205° C.; $^1$H-NMR(d$_6$-DMSO) δ 1.68-1.88(m, 4H), 2.44-2.64(m, 4H), 3.16(s, 3H), 4.86(s, 2H), 6.67(dd, J=2.1, 8.7Hz, 1H), 6.97(d, J=2.1Hz, 1H), 7.26(d, J=8.7Hz, 1H), 7.51-7.62(m, 4H), 7.70(m, 1H), 12.99(br s, |

TABLE 69-continued

| Compound No. | Physical properties |
| --- | --- |
|  | 1H); IR(Nujol)3063, 2743, 2653, 2552, 2454, 1721, 1738, 1615, 1579, 1476, 1440, 1425, 1411, 1387, 1364, 1345, 1332, 1309 1290, 1266, 1240, 1213, 1190, 1173 1157 cm$^{-1}$; Elemental analysis(C$_{21}$H$_{22}$N$_2$O$_4$S)Calcd. (%): C, 63.30; H, 5.56; N, 7.03; S, 8.05 Found(%): C, 63.16; H, 5.48; N, 6.95 S, 7.83 |
| Ih-23 | mp 182-188° C.; $^1$H-NMR(d$_6$-DMSO) δ 1.68-1.89(m, 4H), 2.40(s, 3H), 2.45-2.64(m, 4H), 3.14(s, 3H), 4.86(s, 2H), 6.66(dd, J=2.1, 8.7Hz, 1H), 7.01(d, J=2.1Hz, 1H), 7.25(d, J=8.7Hz, 1H), 7.38(d, J=8.4Hz, 2H), 7.43(d, J=8.4Hz, 2H), 12.97(br s, 1H); IR(Nujol)2655, 2553, 1712, 1619, 1597, 1477, 1407, 1383, 1365, 1343, 1306, 1290, 1267, 1243, 1213, 1185, 1168, 1148, 1121, 1110 cm$^{-1}$; Elemental analysis(C$_{22}$H$_{24}$N$_2$O$_4$S)Calcd. (%): C, 64.06; H, 5.86; N, 6.79; S, 7.77 Found(%): C, 64.14; H, 5.84; N, 6.73; S, 7.61 |

TABLE 70

| Compound No. | Physical properties |
| --- | --- |
| Ih-24 | Mp 240-250° C.; $^1$H-NMR(d$_6$-DMSO) δ 1.71-1.90(m, 4H), 2.54-2.66(m, 4H), 3.25(s, 3H), 4.47(s, 2H), 4.88(s, 2H), 6.99(dd, J=1.8, 8.4Hz, 1H), 7.18(d, J=1.8Hz, 1H), 7.31(d, J=8.4Hz, 1H), 7.34-7.42(m, 5H), 12.99(br s, 1H); IR (Nujol)2657, 2557, 1710, 1620, 1603, 1582, 1496, 1479, 1456, 1440, 1412, 1383, 1340, 1311, 1289, 1269, 1250, 1217, 1190, 1173, 1160, 1140 cm$^{-1}$; Elemental analysis(C$_{22}$H$_{24}$N$_2$O$_4$S•0.2AcOEt)Calcd. (%): C, 63.67; H, 6.00; N, 6.51; S, 7.45 Found(%): C, 63.75; H, 5.96; N, 6.51; S, 7.38 |
| Ih-25 | mp 218-226° C.; $^1$H-NMR(d$_6$-DMSO) δ 1.68-1.90(m, 4H), 2.50-2.65(m, 4H), 3.25(s, 3H), 4.86(s, 2H), 7.02(dd, J=1.8, 8.4Hz, 1H), 7.24(d, J=15.3Hz, 1H), 7.29-7.47(m, 5H), 7.37(d, J=15.3Hz, 1H), 7.69-7.77(m, 2H), 12.95(br s, 1H); IR(Nujol)3057, 2662, 2568, 1721, 1616, 1578, 1478, 1451, 1410, 1385, 1338, 1307, 1290, 1253, 1212, 1179, 1166, 1154, 1133 cm$^{-1}$; Elemental analysis(C$_{23}$H$_{24}$N$_2$O$_4$S•0.2AcOEt)Calcd. (%): C, 64.65; H, 5.84; N, 6.34; S, 7.25 Found(%): C, 6.45; H, 5.80; N, 6.36; S, 7.26 |
| Ih-26 | mp 114-118° C.; $^1$H-NMR(d$_6$-DMSO) δ 1.70-1.90(m, 4H), 2.44-2.66(m, 4H), 3.10(s, 3H), 4.84(s, 2H), 6.68(dd, J=2.1, 8.7Hz, 1H), 6.87(d, J=9.0Hz, 2H), 6.97(d, J=2.1Hz, 1H), 7.24(d, J=8.7Hz, 1H), 7.34(d, J=9.0Hz, 2H), 12.99(br, 1H); IR(Nujol)3376, 2924, 1728, 1586, 1499, 1376, 1329, 1283, 1226, 1147 cm$^{-1}$ |
| Ih-27 | mp 165-168° C.; $^1$H-NMR(d$_6$-DMSO) δ 0.97(s, 6H), 1.52-1.62(m, 2H), 2.31(s, 2H), 2.50-2.60(m, 2H), 4.80(s, 2H), 6.71(dd, J=1.8, 8.7Hz, 1H), 7.00(d, J=1.8Hz, 1H), 7.25(d, J=8.7Hz, 1H), 7.30-7.39(m, 2H), 7.68-7.76(m, 2H), 9.82(br s, 1H), 12.91(br, 1H); IR(Nujol)3252, 2925, 1752, 1590, 1467, 1291, 1233, 1146 cm$^{-1}$; Elemental analysis(C$_{22}$H$_{23}$N$_2$FO$_4$S)Calcd. (%): C, 61.38; H, 5.39; F, 4.41; N, 6.51; S, 7.49 Found(%): C, 61.42; H, 5.57; F, 4.20; N, 6.70; S, 7.17 |
| Ih-28 | mp 122-125° C.; $^1$H-NMR(d$_6$-DMSO) δ 0.98(s, 6H), 1.54-1.64(m, 2H), 2.33(s, 2H), 2.52-2.60(m, 2H), 4.82(s, 2H), 6.77(dd, J=1.8, 8.7Hz, 1H), 7.04-7.10 (m, 2H), 7.21(d, J=8.7Hz, 1H), 7.40(dd, J=1.5, 3.6Hz, 1H), 7.82(dd, J=1.5, 4.8Hz, 1H), 9.93(br s, 1H), 12.90(br, 1H); IR(Nujol)3250, 3112, 2923, 2666, 1709, 1474, 1411, 1251, 1159 cm$^{-1}$ |
| Ih-29 | mp 155-160° C.; $^1$H-NMR(d$_6$-DMSO) δ 1.72-1.93(m, 4H), 2.54-2.66(m, 4H), 4.30(s, 2H), 4.86(s, 2H), 6.96(dd, J=2.1, 9.0Hz, 1H), 7.22(d, J=2.1Hz, 1H), 7.25-7.40(m, 6H), 9.40(s, 1H), 12.95(br s, 1H); IR(Nujol)3568, 3438, 3349, 3195, 3060, 2728, 2537, 1728, 1713, 1625, 1583, 1469, 1456, 1438, 1427, 1411, 1378, 1350, 1318, 1279, 1257, 1243, 1217, 1192, 1172, 1146, 1130 cm$^{-1}$; Elemental analysis(C$_{21}$H$_{22}$N$_2$O$_4$S)Calcd. (%): C, 63.30; H, 5.56; N, 7.03; S, 8.05 Found(%): C, 63.00; H, 5.75; N, 6.91; S, 7.88 |

TABLE 71

| Compound No. | Physical properties |
| --- | --- |
| Ih-30 | Mp 208-213° C.; $^1$H-NMR(d$_6$-DMSO) δ 1.68-1.88(m, 4H), 2.50-2.62(m, 4H), 4.80(s, 2H), 6.92(dd, J=1.8, 8.7Hz, 1H), 7.15(d, J=15.3Hz, 1H), 7.20(d, J=1.8Hz, 1H), 7.23(d, J=8.7Hz, 1H), 7.27(d, J=15.3Hz, 1H), 7.33-7.42 (m, 3H), 7.58-7.66(m, 2H), 9.53(s, 1H), 12.92(brs, 1H); IR(Nujol)3279, 3259, 3241, 3044, 3023, 2652, 2550, 2362, 1729, 1713, 1618, 1589, 1576, 1490, 1469, 1449, 1430, 1412, 1403, 1384, 1351, 1318, 1308, 1275, 1260, 1237, 1214, 1198, 1175, 1136 cm$^{-1}$; Elemental analysis(C$_{22}$H$_{22}$N$_2$O$_4$S)Calcd. (%): C, 64.37; H, 5.40; N, 6.82; S, 7.81 Found(%): C, 64.28; H; 5.50; N; 6.78; S, 7.56 |

TABLE 71-continued

| Compound No. | Physical properties |
| --- | --- |
| Ih-31 | mp 112-115° C.; $^1$H-NMR(d$_6$-DMSO) δ 0.99(s, 6H), 1.54-1.66(m, 2H), 2.34(s, 2H), 2.56-2.66(m, 2H), 3.16(s, 3H), 4.87(s, 2H), 6.67(dd, J=2.1, 8.7Hz, 1H), 7.00(d, J=2.1Hz, 1H), 7.26(d, J=8.7Hz, 1H), 7.36-7.46(m, 2H), 7.57-7.66(m, 2H), 12.95(br, 1H); IR(Nujol)2915, 1725, 1709, 1475, 1345,1308, 1291, 1239, 1166 cm$^{-1}$. |
| Ih-32 | mp 180-184° C.; $^1$H-NMR(d$_6$-DMSO) δ 0.99(s, 6H), 1.56-1.64(m, 2H), 2.33(s, 2H), 2.54-2.66(m, 2H), 3.21(s, 3H), 3.84(s, 3H), 4.87(s, 2H), 6.67(dd, J=2.1, 8.7Hz, 1H), 6.97(d, J=1.5Hz, 1H), 7.08(d, J=9.0Hz, 2H), 7.26(d, J=9.0Hz, 1H), 7.46(d, J=9.0Hz, 2H), 12.97(br, 1H); IR(Nujol)3084, 2923, 2675, 2563, 1734, 1712, 1584, 1474, 1347, 1253, 1159 cm$^{-1}$; Elemental analysis(C$_{24}$H$_{28}$N$_2$O$_5$S)Calcd. (%): C, 63.14; H, 6.18; N, 6.14; S, 7.05 Found (%): C, 62.92; H, 5.98; N, 6.09; S, 6.76 |
| Ih-33 | mp 174-180° C.; $^1$H-NMR(d$_6$-DMSO) δ 0.99(s, 6H), 1.57-1.65(m, 2H), 2.35(s, 2H), 2.54-2.65(m, 2H), 3.20(s, 3H), 4.87(s, 2H), 6.71(dd, J=2.1, 9.0Hz, 1H), 7.03(d, J=2.1Hz, 1H), 7.21-7.32(m, 2H), 7.45(dd, J=1.5, 3.6Hz, 1H), 8.00(dd, J=1.2, 2.1Hz, 1H), 12.98(br, 1H); IR(Nujol)2923, 2745, 2657, 2560, 1731, 1597, 1579, 1474, 1335, 1308, 1265, 1240, 1147 cm$^{-1}$; Elemental analysis(C$_{21}$H$_{24}$N$_2$O$_4$S$_2$•0.2AcOEt)Calcd. (%): C, 58.31; H, 5.59; N, 6.22; S, 14.83 Found(%): C, 58.16; H, 5.73; N, 6.22; S, 14.25 |
| Ih-34 | mp 146-149° C.; $^1$H-NMR(d$_6$-DMSO) δ 1.90-2.18(m, 2H), 2.57-3.02(m, 5H), 4.84(s, 2H), 6.75(dd, J=2.1, 8.7Hz, 1H), 7.22-7.39(m, 8H), 7.69-7.73(m, 2H), 9.84(s, 1H), 13.00(br, 1H); IR(Nujol)3208, 2925, 2854, 1729, 1592, 1495, 1286, 1240, 1197, 1156, 1146 cm$^{-1}$; Elemental analysis (C$_{26}$H$_{23}$FN$_2$O$_4$S.0.3H$_2$O)Calcd. (%): C, 64.53; H, 4.92; F, 3.93; N, 5.79; S, 6.63 Found(%): C, 64.52; H, 4.55; F, 3.82; N, 5.75; S, 6.48 |
| Ih-35 | mp 152-155° C.; $^1$H-NMR(d$_6$-DMSO) δ 1.90-2.19(m, 2H), 2.53-3.02(m, 5H), 3.76(s, 3H), 4.83(s, 2H), 6.76(dd, J=2.1, 8.7Hz, 1H), 6.98-7.38(m, 9H), 7.59-7.62(m, 2H), 9.66(s, 1H), 13.00(br, 1H); IR(Nujol)3305, 2924, 2853, 1716, 1594, 1474, 1258, 1152 cm$^{-1}$; Elemental analysis (C$_{27}$H$_{26}$N$_2$O$_5$S.0.3H$_2$O)Calcd. (%): C, 65.53; H, 5.41; N, 5.65; S, 6.47 Found (%): C, 65.53; H, 5.28; N, 5.38; S, 6.12 |

TABLE 72

| Compound No. | Physical properties |
| --- | --- |
| Ih-36 | mp 204-206° C.; $^1$H-NMR(d$_6$-DMSO) δ 1.95-2.18(m, 2H), 2.54-3.02(m, 5H), 3.16(s, 3H), 4.90(s, 2H), 6.72(dd, J=2.1, 9.0Hz, 1H), 7.04(d, J=2.1Hz, 1H), 7.20-7.61(m, 10H); IR(Nujol)2925, 2854, 1726, 1589, 1476, 1346, 1336, 1254, 1224, 1148 cm$^{-1}$; Elemental analysis(C$_{27}$H$_{25}$FN$_2$O$_4$S)Calcd. (%): C, 65.84; H, 5.12; F, 3.86; N, 5.69; S, 6.513 Found(%): C, 65.542; H, 4.94; F, 3.87; N, 5.61; S, 6.48 |
| Ih-37 | mp 121-124° C.; $^1$H-NMR(d$_6$-DMSO) δ 1.94-2.19(m, 2H), 2.52-3.03(m, 5H), 3.12(s, 3H), 3.81(s, 3H), 4.89(s, 2H), 6.72(d, J=8.7Hz, 1H), 6.99(s, 1H), 7.06-7.09(m, 2H), 7.20-7.47(m, 8H); IR(Nujol)2924, 2853, 1741, 1689, 1596, 1480, 1458, 1340, 1259, 1197, 1180, 1162, 1150 cm$^{-1}$ |
| Ih-38 | mp 168-172° C.; $^1$H-NMR(d$_6$-DMSO) δ 0.81(t, J=7.8Hz, 6H), 1.21-1.40(m, 4H), 1.60(t, J=6.0Hz, 2H), 2.28(s, 2H), 2.50(m, 2H), 3.76(s, 3H), 4.78(s, 2H), 6.73(dd, J=2.1, 8.7Hz, 1H), 6.97-7.03(m, 3H), 7.15(d, J=8.7Hz, 1H), 7.57-7.62(m, 2H), 9.62(s, 1H), 12.95(br, 1H); IR(Nujol)3303, 2924, 2853, 1719, 1598, 1498, 1486, 1469, 1404, 1254, 1155 cm$^{-1}$; Elemental analysis (C$_{25}$H$_{30}$N$_2$O$_5$S)Calcd. (%): C, 63.81; H, 6.43; N, 5.95; S, 6.65 Found(%): C, 63.54; H, 6.31; N, 5.90; S, 6.65 |
| Ih-39 | mp 188-197° C.; $^1$H-NMR(d$_6$-DMSO) δ 1.68-1.88(m, 4H), 2.46-2.62(m, 4H), 4.79(s, 2H), 6.71(dd, J=1.8, 8.7Hz, 1H), 7.03(d, J=1.8Hz, 1H), 7.18(d, J=8.7Hz, 1H), 7.58(d, J=8.7Hz, 2H), 7.66(d, J=8.7Hz, 2H), 9.87(s, 1H), 12.90(brs, 1H); IR(Nujol)3208, 3084, 1755, 1736, 1581, 1474, 1419, 1404, 1381, 1365, 1348, 1333, 1384, 1322, 1304, 1279, 1261, 1198, 1154 cm$^{-1}$; Elemental analysis(C$_{20}$H$_{19}$ClN$_2$O$_4$S)Calcd. (%): C, 57.34; H, 4.57; Cl, 8.46; N, 6.69; S, 7.65 Found(%): C, 57.28; H, 4.75; Cl, 7.94; N, 6.86; S, 7.39 |
| Ih-40 | mp 170-175° C.; $^1$H-NMR(d$_6$-DMSO) δ 1.68-1.87(m, 4H), 2.43-2.60(m, 4H), 4.79(s, 2H), 6.73(dd, J=1.8, 8.7Hz, 1H), 7.02(d, J=1.8Hz, 1H), 7.14(d, J=8.7Hz, 1H), 7.87(d, J=8.7Hz, 2H), 7.92(d, J=8.7Hz, 2H), 10.03(s, 1H), 12.91(brs, 1H); IR(Nujol)3216, 3046, 1754, 1738, 1605, 1593, 1472, 1423, 1405, 1380, 1366, 1340, 1325, 1306, 1294, 1282, 1265, 1216, 1194, 1173, 1154, 1110 cm$^{-1}$; Elemental analysis(C$_{21}$H$_{19}$F$_3$N$_2$O$_4$S)Calcd. (%): C, 55.75; H, 4.23; F, 12.60; N, 6.19; S, 7.09 Found(%): C, 55.94; H, 4.46; F, 12.31; N, 6.46; S, 6.94 |
| Ih-41 | mp 162-165° C.; $^1$H-NMR(d$_6$-DMSO) δ 1.68-1.89(m, 4H), 2.46-2.65(m, 4H), 3.17(s, 3H), 4.86(s, 2H), 6.68(dd, J=2.1, 8.7Hz, 1H), 7.02(d, J=2.1Hz, 1H), 7.27(d, J=8.7Hz, 1H), 7.53(d, J=8.7Hz, 2H), 7.66(d, J=8.7Hz, 2H), 12.90(brs, 1H); IR(Nujol)3095, 2743, 2656, 2556, 1729, 1711, 1584, |

TABLE 72-continued

| Compound No. | Physical properties |
| --- | --- |
| | 1476, 1444, 1427, 1411, 1385, 1346, 1310, 1280, 1267, 1242, 1213, 1189, 1173, 1156 cm$^{-1}$; Elemental analysis($C_{21}H_{21}ClN_2O_4S\cdot 0.05$AcOEt)Calcd. (%): C, 58.22; H, 4.93; Cl, 8.11; N, 6.41; S, 7.33 Found(%): C, 58.32; H, 4.94; Cl, 7.85; N, 6.68; S, 7.30 |

TABLE 73

| Compound No. | Physical properties |
| --- | --- |
| Ih-42 | mp 181-188° C.; $^1$H-NMR(d$_6$-DMSO) δ 1.68-1.88(m, 4H), 2.44-2.64(m, 4H), 3.21(s, 3H), 4.87(s, 2H), 6.70(dd, J=1.8, 8.7Hz, 1H), 6.99(d, J=1.8Hz, 1H), 7.29(d, J=8.7Hz, 1H), 7.56(d, J=8.4Hz, 2H), 7.97(d, J=8.4Hz, 2H), 12.99(brs, 1H); IR(Nujol)3111, 3085, 3053, 2739, 2653, 2552, 1733, 1712, 1609, 1582, 1477, 1447, 1426, 1408, 1386, 1366, 1348, 1327, 1311, 1281, 1267, 1239, 1214, 1191, 1174, 1158, 1128, 1110 cm$^{-1}$; Elemental analysis($C_{22}H_{21}F_3N_2O_4S$)Calcd. (%): C, 56.65; H, 4.54; F, 12.22; N, 6.01; S, 6.87 Found(%): C, 56.77; H, 4.62; F, 11.93; N, 6.30; S, 6.88 |
| Ih-43 | mp 227-232° C.; $^1$H-NMR(d$_6$-DMSO) δ 1.68-1.88(m, 4H), 2.46-2.64(m, 4H), 3.18(s, 3H), 4.86(s, 2H), 6.71(dd, J=2.1, 8.7Hz, 1H), 6.98(d, J=2.1Hz, 1H), 7.11(dd, J=1.5, 5.1Hz, 1H), 7.27(d, J=8.7Hz, 1H), 7.77(dd, J=3.0, 5.1Hz, 1H), 8.03(dd, J=1.5, 3.0Hz, 1H), 12.99(brs, 1H); IR(Nujol)3120, 3086, 2742, 2651, 2552, 2455, 1721, 1615, 1577, 1499, 1475, 1439, 1425, 1410, 1386, 1362, 1342, 1309, 1267, 1240, 1209, 1190, 1174, 1152, 1101 cm$^{-1}$; Elemental analysis($C_{19}H_{20}N_2O_4S_2$)Calcd. (%): C, 56.42 H, 4.98; N, 6.93; S, 15.85 Found(%): C, 56.15; H, 4.93; N, 6.87; S, 15.71 |
| Ih-44 | mp 164-168° C.; $^1$H-NMR(d$_6$-DMSO) δ 1.68-1.88(m, 4H), 2.44-2.64(m, 4H), 3.21(s, 3H), 4.87(s, 2H), 6.70(dd, J=1.8, 8.7Hz, 1H), 6.99(d, J=1.8Hz, 1H), 7.29(d, J=8.7Hz, 1H), 7.56(d, J=8.4Hz, 2H), 7.97(d, J=8.4Hz, 2H), 12.99(brs, 1H); IR(Nujol)3016, 2745, 2658, 2560, 1721, 1591, 1581, 1477, 1446, 1427, 1414, 1389, 1351, 1334, 1310, 1293, 1264, 1246, 1212, 1190, 1162, 1102 cm$^{-1}$; Elemental analysis($C_{22}H_{21}F_3N_2O_5S$)Calcd. (%): C, 54.77; H, 4.39; F, 11.81; N, 5.81; S, 6.65 Found(%): C, 54.69; H, 4.28; F, 11.56; N, 5.82; S, 6.59 |
| Ih-45 | mp 97-100° C.; $^1$H-NMR(d$_6$-DMSO) δ 0.82(t, J=7.5Hz, 6H), 1.21-1.40(m, 4H), 1.63(t, J=6.0Hz, 2H), 2.31(s, 2H), 2.55(br t, 2H), 3.17(s, 3H), 4.85(s, 2H), 6.68(dd, J=2.1, 8.7Hz, 1H), 6.98(d, J=2.1Hz, 1H), 7.26(d, J=8.7Hz, 1H), 7.38-7.62(m, 4H); IR(Nujol)2956, 2854, 1738, 1699, 1591, 1495, 1475, 1331, 1236, 1196, 1151 cm$^{-1}$. |
| Ih-46 | mp 103-105° C.; $^1$H-NMR(d$_6$-DMSO) δ 0.82(t, J=7.2Hz, 6H), 1.20-1.40(m, 4H), 1.63(br t, 2H), 2.30(s, 2H), 2.55(br t, 2H), 3.13(s, 3H), 3.84(s, 3H), 4.85(s, 2H), 6.68(dd, J=2.1, 8.7Hz, 1H), 6.95(d, J=2.1Hz, 1H), 7.07-7.10 (m, 2H), 7.24(d, J=8.7Hz, 1H), 7.44-7.48(m, 2H); IR(Nujol)2925, 2854, 1758, 1739, 1683, 1599, 1474, 1338, 1264, 1182, 1164, 1153 cm$^{-1}$. |
| Ih-47 | Mp 160-163° C.; $^1$H-NMR(d$_6$-DMSO) δ 1.24-1.57(m, 10H), 1.66(t, J=6.0Hz, 2H), 2.36(s, 2H), 2.53(br t, 2H), 4.78(s, 2H), 6.71(dd, J=2.1, 8.7Hz, 1H), 7.01(d, J=2.1Hz, 1H), 7.16(d, J=8.7Hz, 1H), 7.31-7.37(m, 2H), 7.70-7.75 (m, 2H), 9.79(s, 1H); 12.9(br, 1H); IR(Nujol)3297, 3278, 2919, 2854, 1746, 1720, 1590, 1468, 1251, 1162, 1151 cm$^{-1}$. |

TABLE 74

| Compound No. | Physical properties |
| --- | --- |
| Ih-48 | mp 201-204° C.; $^1$H-NMR(d$_6$-DMSO) δ 1.24-1.59(m, 10H), 1.66(t, J=6.0Hz, 2H), 2.36(s, 2H), 2.53(br t, 2H), 3.77(s, 3H), 4.78(s, 2H), 6.73(dd, J=1.8, 8.7Hz, 1H), 6.99-7.16(m, 3H), 7.15(d, J=8.7Hz, 1H), 7.59-7.63(m, 2H), 9.62(s, 1H); 12.5(br, 1H); IR(Nujol)3249, 2924, 2853, 1737, 1595, 1470, 1329, 1262, 1154 cm$^{-1}$. |
| Ih-49 | mp 198-205° C.; $^1$H-NMR(d$_6$-DMSO) δ 1.68-1.86(m, 4H), 2.46-2.60(m, 4H), 4.80(s, 2H), 6.76(dd, J=1.8, 8.7Hz, 1H), 7.03(d, J=1.8Hz, 1H), 7.18(d, J=8.7Hz, 1H), 7.22(dd, J=1.5, 5.1Hz, 1H), 7.66(dd, J=3.0, 5.1Hz, 1H), 7.96(dd, J=1.5, 3.0Hz, 1H), 9.71(s, 1H); 12.93(brs, 1H); IR(Nujol)3205, 3103, 1735, 1478, 1459, 1435, 1401, 1365, 1349, 1333, 1312, 1281, 1264, 1206, 1146 cm$^{-1}$; Elemental analysis($C_{18}H_{18}N_2O_4S_2$)Calcd. (%): C, 55.37; H, 4.65; N, 7.17; S, 16.42 Found(%): C, 55.22; H, 4.56; N, 7.04; S, 16.15 |
| Ih-50 | mp 177-181° C.; $^1$H-NMR(d$_6$-DMSO) δ 0.91(t, J=6.9Hz, 3H), 1.30-1.50(m, 6H), 1.90-2.16(m, 2H), 2.46-2.70(m, 3H), 4.77(s, 2H), 6.71(dd, J=2.1, 8.7Hz, 1H), 7.01(d, J=2.1Hz, 1H), 7.15(d, J=8.7Hz, 1H), 7.30-7.38(m, 2H), |

TABLE 74-continued

| Compound No. | Physical properties |
| --- | --- |
|  | 7.67-7.75(m, 2H), 9.81(br s, 1H); IR(Nujol)3294, 3102, 3069, 3032, 2919, 2667, 2573, 1722, 1590, 1470, 1403, 1341, 1293, 1254 cm;$^{-1}$ |
| Ih-51 | mp 112-115° C.; $^1$H-NMR(d$_6$-DMSO) δ 0.96(s, 9H), 1.21-1.48(m, 2H), 2.02-2.30(m, 2H), 2.42-2.78(m, 3H), 4.77(s, 2H), 6.70(dd, J=1.8, 8.7Hz, 1H), 7.05(d, J=1.8Hz, 1H), 7.15(d, J=8.7Hz, 1H), 7.30-7.40(m, 2H), 7.68-7.77 (m, 2H), 9.80(br s, 1H); IR(Nujol)3249, 2923, 2662, 1711, 1591, 1495, 1477, 1414, 1339, 1295, 1241, 1194, 1156 cm$^{-1}$. |
| Ih-52 | mp 168-171° C.; $^1$H-NMR(d$_6$-DMSO) δ 0.92(t, J=6.6Hz, 3H), 1.32-1.52(m, 6H), 1.90-2.16(m, 2H), 2.46-2.76(m, 3H), 3.76(s, 3H), 4.74(s, 2H), 6.72(dd, J=2.1, 8.7Hz, 1H), 6.96-7.06(m, 3H), 7.13(d, J=8.7Hz, 1H), 7.60(d, J=9.0Hz, 2H), 9.61(s, 1H); IR(Nujol)3302, 3017, 2923, 2669, 2563, 1720, 1594, 1471, 1402, 1336, 1253, 1193 cm$^{-1}$ |
| Ih-53 | mp 179-181° C.; $^1$H-NMR(d$_6$-DMSO) δ 0.96(s, 9H), 1.21-1.50(m, 2H), 2.00-2.30(m, 2H), 2.40-2.78(m, 3H), 3.76(s, 3H), 4.77(s, 2H), 6.72(dd, J=1.8, 8.7Hz, 1H), 6.96-7.08(m, 3H), 7.12(d, J=8.7Hz, 1H), 7.59(d, J=8.7Hz, 2H), 9.61(br s, 1H); IR(Nujol)3665, 3297, 2923, 2666, 2570, 1718, 1594, 1470, 1403, 1254, 1194 cm$^{-1}$. |
| Ih-54 | mp 151-158° C.; $^1$H-NMR(d$_6$-DMSO) δ 1.67-1.86(m, 4H), 2.44-2.61(m, 4H), 4.79(s, 2H), 6.73(dd, J=2.1, 8.7Hz, 1H), 6.98(d, J=2.1Hz, 1H), 7.19(d, J=8.7Hz, 1H), 7.51(d, J=8.7Hz, 2H), 7.78(d, J=8.7Hz, 2H), 9.89(s, 1H), 12.93(brs, 1H); IR(Nujol)3287, 3104, 3038, 1720, 1592, 1487, 1473, 1411, 1399, 1376, 1366, 1355, 1336, 1292, 1247, 1209, 1170, 1152 cm$^{-1}$. |

TABLE 75

| Compound No. | Physical properties |
| --- | --- |
| Ih-55 | mp 155-158° C.; $^1$H-NMR(d$_6$-DMSO) δ 1.23-1.53(m, 10H), 1.68(t, J=6.0Hz, 2H), 2.39(s, 2H), 2.56(br t, 2H), 3.17(s, 3H), 4.86(s, 2H), 6.68(dd, J=2.1, 9.0Hz, 1H), 7.00(d, J=2.1Hz, 1H), 7.26(d, J=9.0Hz, 1H), 7.38-7.63(m, 4H); IR(Nujol)2917, 2854, 1725, 1590, 1478, 1342, 1233, 1146 cm$^{-1}$; Elemental analysis(C$_{26}$H$_{29}$FN$_2$O$_4$S)Calcd. (%): C, 64.44; H, 6.03; F, 3.92; N, 5.78; S, 6.62 Found(%): C, 64.12; H, 6.16; F, 3.59; N, 5.52; S, 6.18 |
| Ih-56 | mp 132-135° C.; $^1$H-NMR(d$_6$-DMSO) δ 1.22-1.54(m, 10H), 1.66(t, J=6.0Hz, 2H), 2.38(s, 2H), 2.56(br t, 2H), 3.13(s, 3H), 3.84(s, 3H), 4.85(s, 2H), 6.68 (dd, J=2.1, 8.7Hz, 1H), 6.98(d, J=2.1Hz, 1H), 7.07-7.11(m, 2H), 7.25(d, J=8.7Hz, 1H), 7.45-7.49(m, 2H); IR(Nujol)2917, 2854, 1725, 1597, 1496, 1477, 1338, 1255, 1236, 1148 cm$^{-1}$ |
| Ih-57 | mp 161-163° C.; $^1$H-NMR(d$_6$-DMSO) δ 0.92(t, J=6.9Hz, 3H), 1.22-1.50(m, 5H), 1.62-1.78(m, 1H), 1.90-2.18(m, 2H), 2.46-2.74(m, 3H), 3.17(s, 3H), 4.84(s, 2H), 6.69(dd, J=2.1, 8.7Hz, 1H), 7.00(d, J=2.1Hz, 1H), 7.26(d, J=8.7Hz, 1H), 7.38-7.48(m, 2H), 7.56-7.64(m, 2H); IR(Nujol)2924, 2746, 2657, 2561, 1716, 1591, 1476, 1347, 1307, 1289, 1242, 1148 cm$^{-1}$; Elemental analysis(C$_{24}$H$_{27}$N$_2$FO$_4$S)Calcd. (%): C, 62.86; H, 5.93; F, 4.14; N, 6.11; S, 6.99 Found(%): C, 62.92; H, 6.09; F, 3.93; N, 6.20; S, 6.69 |
| Ih-58 | mp 162-164° C.; $^1$H-NMR(d$_6$-DMSO) δ 0.97(s, 9H), 1.28-1.58(m, 2H), 2.02-2.30(m, 2H), 2.42-2.80(m, 3H), 3.17(s, 3H), 4.84(s, 2H), 6.67(dd, J=2.1, 8.7Hz, 1H), 7.02(d, J=2.1Hz, 1H), 7.25(d, J=8.7Hz, 1H), 7.36-7.46(m, 2H), 7.56-7.64(m, 2H), 12.98(br, 1H); IR(Nujol)3100, 3080, 3049, 2924, 2743, 2633, 1590, 1437, 1412, 1344, 1235, 1169, 1145 cm$^{-1}$ |
| Ih-59 | mp 152-155° C.; $^1$H-NMR(d$_6$-DMSO) δ 0.92(t, J=6.9Hz, 3H), 1.30-1.54(m, 6H), 1.90-2.16(m, 2H), 2.46-2.76(m, 3H), 3.12(s, 3H), 3.84(s, 3H), 4.85(s, 2H), 6.68(dd, J=2.1, 8.7Hz, 1H), 6.97(d, J=2.1Hz, 1H), 7.09(d, J=7.5Hz, 1H), 7.24(d, J=8.7Hz, 2H), 7.45(d, J=8.7Hz, 2H), 13.00(br s, 1H); IR (Nujol)2952, 2752, 2665, 2569, 1729, 1598, 1576, 1499, 1476, 1345, 1308, 1246, 1153 cm$^{-1}$; Elemental analysis(C$_{25}$H$_{30}$N$_2$O$_5$S)Calcd. (%): C, 63.81; H, 6.43; N, 5.95; S, 6.81 Found(%): C, 63.72; H, 6.38; N, 6.00; S, 6.68 |
| Ih-60 | mp 140-144° C.; $^1$H-NMR(d$_6$-DMSO) δ 0.97(s, 9H), 1.24-1.50(m, 2H), 2.00-2.30(m, 2H), 2.40-2.78(m, 3H), 3.13(s, 3H), 3.84(s, 3H), 4.84(s, 2H), 6.68 (dd, J=2.1, 8.4Hz, 1H), 6.99(d, J=2.1Hz, 1H), 7.09(d, J=9.0Hz, 2H), 7.22(d, J=8.4Hz, 1H), 7.46(d, J=8.7Hz, 2H), 13.00(br, 1H); IR(Nujol) 2924, 2746, 2641, 2559, 1717, 1596, 1578, 1476, 1341, 1241, cm$^{-1}$; Elemental analysis(C$_{26}$H$_{32}$N$_2$O$_5$S)Calcd. (%): C, 64.44; H, 6.66; N, 5.78; S, 6.66 Found (%): C, 64.23; H, 6.78; N, 5.90; S, 6.36 |

TABLE 76

| Compound No. | Physical properties |
| --- | --- |
| Ih-61 | mp 169-171° C.; $^1$H-NMR(d$_6$-DMSO) δ 0.89(t, J=6.9Hz, 3H), 1.20-2.19(m, 12H), 2.57-2.76(m, 3H), 3.17(s, 3H), 4.85(s, 2H), 6.70(dd, J=2.1, 8.4Hz, 1H), 7.00(d, J=2.1Hz, 1H), 7.26(d, J=8.4Hz, 1H), 7.38-7.46(m, 2H), 7.57-7.62(m, 2H), 13.00(br s, 1H); IR(Nujol) 2920, 2854, 1720, 1591, 1476, 1346, 1240, 1146 cm$^{-1}$; Elemental analysis(C$_{26}$H$_{31}$FN$_2$O$_4$S)Calcd. (%): C, 64.18; H, 6.42; F, 3.90; N, 5.76; S, 6.59 Found(%): C, 64.20; H, 6.46; F, 3.66; N, 5.80; S, 6.52 |
| Ih-62 | mp 157-160° C.; $^1$H-NMR(d$_6$-DMSO) δ 0.89(t, J=6.9Hz, 3H), 1.26-2.19(m, 12H), 2.54-2.76(m, 3H), 3.13(s, 3H), 3.84(s, 3H), 4.85(s, 2H), 6.69(dd, J=2.1, 8.7Hz, 1H), 6.98(d, J=2.1Hz, 1H), 7.06-7.12(m, 2H), 7.25(d, J=8.7Hz, 1H), 7.43-7.48(m, 2H), 13.00(br s, 1H); IR(Nujol)2924, 2854, 1721, 1597, 1496, 1476, 1338, 1256, 1242, 1149 cm$^{-1}$; Elemental analysis (C$_{27}$H$_{34}$N$_2$O$_5$S)Calcd. (%): C, 65.04; H, 6.87; N, 5.62; S, 6.43 Found(%): C, 64.92; H, 6.88; N, 5.62; S, 6.42 |
| Ih-63 | mp 183-189° C.; $^1$H-NMR(d$_6$-DMSO) δ 0.95(t, J=7.2Hz, 3H), 1.74-1.84(m, 4H), 2.51-2.60(m, 4H), 3.55(q, J=7.2Hz, 2H), 3.84(s, 3H), 4.86(s, 2H), 6.62(dd, J=2.1, 8.7Hz, 1H), 6.95(d, J=2.1Hz, 1H), 7.06-7.11(m, 2H), 7.27(d, J=8.7Hz, 1H), 7.49-7.54(m, 2H), 13.04(br, 1H); IR(Nujol)3201, 3114, 1767, 1748, 1593, 1579, 1493, 1477, 1458, 1427, 1377, 1324, 1308, 1257, 1189, 1154, 1084, 1065, 1057 cm$^{-1}$; Elemental analysis(C$_{23}$H$_{26}$N$_2$O$_5$S) Calcd. (%): C, 62.42; H, 5.92; N, 6.33; S, 7.25 Found(%): C, 62.36; H, 5.91; N, 6.32; S, 7.07 |
| Ih-64 | mp 146-150° C.; $^1$H-NMR(d$_6$-DMSO) δ 0.84(t, J=7.2Hz, 3H), 1.25-1.36(m, 2H), 1.70-1.88(m, 4H), 2.50-2.61(m, 4H), 3.44(t, J=6.9Hz, 2H), 3.84(s, 3H), 4.85(s, 2H), 6.62(dd, J=2.1, 8.7Hz, 1H), 6.94(d, J=2.1Hz, 1H), 7.06-7.11(m, 2H), 7.26(d, J=8.7Hz, 1H), 7.47-7.52(m, 2H), 12.92(br, 1H); IR(Nujol)2744, 2654, 2557, 1741, 1720, 1596, 1580, 1494, 1475, 1440, 1414, 1375, 1342, 1306, 1255, 1240, 1176, 1166, 1148, 1107, 1092, 1072, 1058, 1033 cm$^{-1}$; Elemental analysis(C$_{24}$H$_{28}$N$_2$O$_5$S.0.4AcOEt)Calcd. (%): C, 62.52; H, 6.39; N, 5.70; S, 6.52 Found(%): C, 62.58; H, 6.44; N, 5.76; S, 6.30 |
| Ih-65 | mp 200-210° C.; $^1$H-NMR(d$_6$-DMSO) δ 0.86(d, J=6.6Hz, 6H), 1.41(m, 1H), 1.70-1.88(m, 4H), 2.50-2.64(m, 4H), 3.32(d, J=6.6Hz, 2H), 3.84(s, 3H), 4.85(s, 2H), 6.64(dd, J=2.1, 8.7Hz, 1H), 6.95(d, J=2.1Hz, 1H), 7.05-7.10 (m, 2H), 7.26(d, J=8.7Hz, 1H), 7.45-7.50(m, 2H); IR(Nujol)3150, 2575, 2421, 1738, 1715, 1621, 1596, 1579, 1497, 1476, 1467, 1426, 1376, 1366, 1320, 1307, 1265, 1211, 1180, 1146, 1090, 1069, 1055 cm$^{-1}$; Elemental analysis(C$_{25}$H$_{30}$N$_2$O$_5$S)Calcd. (%): C, 63.81; H, 6.43; N, 5.95; S, 6.81 Found (%): C, 63.72; H, 6.32; N, 5.89; S, 6.55 |

TABLE 77

| Compound No. | Physical properties |
| --- | --- |
| Ih-66 | mp 184-193° C.; $^1$H-NMR(d$_6$-DMSO) δ 0.97(d, J=6.9Hz, 6H), 1.72-1.89(m, 4H), 2.51-2.65(m, 4H), 3.85(s, 3H), 4.47(m, 1H), 4.87(s, 2H), 6.63(dd, J=2.1, 8.7Hz, 1H), 6.95(d, J=2.1Hz, 1H), 7.08-7.13(m, 2H), 7.29(d, J=8.7Hz, 1H), 7.62-7.67(m, 2H); IR(Nujol)3261, 1750, 1713, 1596, 1577, 1498, 1476, 1378, 1364, 1338, 1318, 1303, 1265, 1217, 1183, 1146, 1112, 1086 cm$^{-1}$. |
| Ih-67 | mp 183-186° C.; $^1$H-NMR(d$_6$-DMSO) δ 0.97(t, J=7.2Hz, 3H), 1.70-1.90(m, 4H), 2.53-2.64(m, 4H), 3.60(q, J=7.2Hz, 2H), 4.86(s, 2H), 6.63(dd J=1.8, 8.7Hz, 1H), 6.95(d, J=1.8Hz, 1H), 7.28(d, J=8.7Hz, 1H), 7.38-7.45(m, 2H), 7.62-7.68(m, 2H); IR(Nujol)2925, 2854, 1725, 1711, 1592, 1476, 1341, 1243, 1182, 1172, 1148 cm$^{-1}$; Elemental analysis(C$_{22}$H$_{23}$N$_2$O$_4$S)Calcd. (%): C, 61.38; H, 5.39; F, 4.41; N, 6.51; S, 7.45 Found(%): C, 61.12; H, 5.55; F, 4.14; N, 6.33; S, 7.08 |
| Ih-68 | mp 182-184° C.; $^1$H-NMR(d$_6$-DMSO) δ 0.85(t, J=7.5Hz, 3H), 1.24-1.41(m, 2H), 1.70-1.90(m, 4H), 2.52-2.64(m, 4H), 3.51(t, J=6.3Hz, 2H), 4.86(s, 2H), 6.64(dd, J=1.8, 8.7Hz, 1H), 6.95(d, J=1.8Hz, 1H), 7.27(d, J=8.7 Hz, 1H), 7.38-7.45(m, 2H), 7.62-7.66(m, 2H); IR(Nujol)2925, 2854, 1727, 1709, 1592, 1492, 1475, 1341, 1291, 1241, 1172, 1146 cm$^{-1}$; Elemental analysis(C$_{23}$H$_{25}$N$_2$O$_4$S)Calcd. (%): C, 62.14; H, 5.67, F, 4.27; N, 6.30; S, 7.21 Found(%): C, 61.94; H, 5.70; F, 4.07; N, 6.32; S, 6.96 |
| Ih-69 | mp 165-168° C.; $^1$H-NMR(d$_6$-DMSO) δ 1.70-1.90(m, 4H), 2.52-2.64(m, 4H), 4.22(d, J=5.7Hz, 2H), 4.85(s, 2H), 4.99-5.13(m, 2H), 5.62-5.80(m, 1H), 6.66(dd, J=2.1, 8.7Hz, 1H), 6.97(d, J=2.1Hz, 1H), 7.24(d, J=8.7Hz, 1H), 7.39-7.46(m, 2H), 7.64-7.69(m, 2H); IR(Nujol)2925, 2853, 1727, 1709, 1592, 1493, 1477, 1344, 1243, 1166, 1154 cm$^{-1}$; Elemental analysis (C$_{23}$H$_{23}$FN$_2$O$_4$S)Calcd. (%): C, 62.43; H, 5.24; F, 4.29; N, 6.30; S, 7.25 Found (%): C, 62.22; H, 5.27; F, 4.12; N, 6.32; S, 6.99 |
| Ih-70 | mp 199-204° C.; $^1$H-NMR(d$_6$-DMSO) δ 1.70-1.90(m, 4H), 2.52-2.64(m, 4H), 3.20(br t, 1H), 4.49(d, J=2.4Hz, 2H), 4.87(s, 2H), 6.77(dd, J=1.8, 8.4Hz, 1H), 7.08(d, J=1.8Hz, 1H), 7.29(d, J=8.4Hz, 1H), 7.39-7.46(m, 2H), |

TABLE 77-continued

| Compound No. | Physical properties |
| --- | --- |
| | 7.68-7.73(m, 2H); IR(Nujol)3292, 2925, 2854, 1724, 1592, 1477, 1337, 1238, 1155 cm$^{-1}$; Elemental analysis($C_{23}H_{21}FN_2O_4S$)Calcd. (%): C, 62.71; H, 4.81; F, 4.31; N, 6.36; S, 7.28 Found(%): C, 62.55; H, 4.91; F, 4.10; N, 6.32; S, 7.21 |
| Ih-71 | mp 164-167° C.; $^1$H-NMR($d_6$-DMSO) δ 1.70-1.90(m, 4H), 2.52-2.64(m, 4H), 4.55(d, J=9.0Hz, 2H), 4.86(s, 2H), 6.70(dd, J=2.1, 8.7Hz, 1H), 7.00(d, J=2.1Hz, 1H), 7.29(d, J=8.7Hz, 1H), 7.38-7.45(m, 2H), 7.67-7.73(m, 2H); IR(Nujol)2920, 2854, 1724, 1710, 1593, 1495, 1478, 1344, 1240, 1167, 1155 cm$^{-1}$. |

TABLE 78

| Compound No. | Physical properties |
| --- | --- |
| Ih-72 | mp 143-147° C.; $^1$H-NMR($d_6$-DMSO) δ 1.70-1.90(m, 4H), 2.52-2.64(m, 4H), 3.33-3.50(m, 2H), 3.61(t, J=6.3Hz, 2H), 4.73(br s, 1H), 4.86(s, 2H), 6.65 (dd, J=2.1, 8.7Hz, 1H), 6.99(d, J=2.1Hz, 1H), 7.27(d, J=8.7Hz, 1H), 7.38-7.45(m, 2H), 7.63-7.69(m, 2H); IR(Nujol)3610, 3439, 2925, 2854, 1724, 1710, 1591, 1493, 1476, 1341, 1238, 1166, 1153 cm$^{-1}$ |
| Ih-73 | mp 184-189° C.; $^1$H-NMR($d_6$-DMSO) δ 0.05-0.10(m, 2H), 0.31-0.37(m, 2H), 1.70-1.91(m, 4H), 2.52-2.60(m, 4H), 3.45(d, J=6.9Hz, 2H), 4.86(s, 2H), 6.68(dd, J=2.1, 8.7Hz, 1H), 6.99(d, J=2.1Hz, 1H), 7.28(d, J=8.7Hz, 1H), 7.37-7.44(m, 2H), 7.62-7.68(m, 2H); IR(Nujol)2923, 2854, 1725, 1712, 1592, 1492, 1470, 1343, 1241, 1164, 1151 cm$^{-1}$; Elemental analysis ($C_{24}H_{25}FN_2O_4S$)Calcd. (%): C, 63.14; H, 5.52; F, 4.16; N, 6.14; S, 7.02 Found (%): C, 63.05; H, 5.54; F, 3.95; N, 6.13; S, 6.88 |
| Ih-74 | mp 139-144° C.; $^1$H-NMR($d_6$-DMSO) δ 1.70-1.88(m, 4H), 2.49-2.63(m, 4H), 3.84(s, 3H), 4.18(d, 6.3Hz, 2H), 4.84(s, 2H), 4.98(dd, J=1.5, 10.2Hz, 2H), 5.08(dd, J=1.5, 17.1Hz, 1H), 5.70(m, 1H), 6.63(dd, J=2.1, 8.7Hz, 1H), 6.96(d, J=2.1Hz, 1H), 7.06-7.11(m, 2H), 7.23(d, J=8.7Hz, 1H), 7.50-7.55 (m, 2H), 13.00(br, 1H); IR(Nujol)2753, 2651, 2570, 1719, 1597, 1578, 1496, 1477, 1464, 1444, 1417, 1377, 1341, 1308, 1252, 1179, 1155, 1092, 1060, 1022 cm$^{-1}$; Elemental analysis($C_{24}H_{26}N_2O_5S$)Calcd. (%): C, 63.42; H, 5.77; N, 6.16; S, 7.05 Found(%): C, 63.26; H, 5.54; N, 6.19; S, 6.82 |
| Ih-75 | mp 134-138° C.; $^1$H-NMR($d_6$-DMSO) δ 1.44(s, 3H), 1.54(s, 3H), 1.70-1.86(m, 4H), 2.49-2.63(m, 4H), 3.84(s, 3H), 4.31(d, J=6.9Hz, 2H), 4.85(s, 2H), 5.04 (m, 1H), 6.64(dd, J=2.1, 8.7Hz, 1H), 6.94(d, J=2.1Hz, 1H), 7.06-7.11(m, 2H), 7.23(d, J=8.7Hz, 1H), 7.49-7.54(m, 2H), 13.00(br, 1H); IR(Nujol) 2742, 2655, 2558, 1721, 1596, 1580, 1496, 1476, 1465, 1441, 1413, 1388, 1376, 1364, 1338, 1306, 1256, 1242, 1213, 1177, 1155, 1112, 1094, 1080, 1036 cm$^{-1}$; Elemental analysis($C_{26}H_{30}N_2O_5S$)Calcd. (%): C, 64.71; H, 6.27; N, 5.80; S, 6.64 Found(%): C, 64.68; H, 6.04; N, 5.82; S, 6.36 |
| Ih-76 | mp 193-202° C.; $^1$H-NMR($d_6$-DMSO) δ 1.72-1.88(m, 4H), 2.49-2.64(m, 4H), 3.16(t, J=2.4Hz, 1H), 3.84(s, 3H), 4.44(d, 2.4Hz, 2H), 4.86(s, 2H), 6.74 (dd, J=2.1, 8.7Hz, 1H), 7.07(d, J=2.1Hz, 1H), 7.05-7.10(m, 2H), 7.27(d, J=8.7Hz, 1H), 7.53-7.58(m, 2H), 13.02(br, 1H); IR(Nujol)3281, 3030, 2746, 2657, 2562, 1721, 1597, 1580, 1499, 1477, 1462, 1438, 1426, 1413, 1388, 1329, 1306, 1265, 1245, 1154, 1098, 1034 cm$^{-1}$; Elemental analysis ($C_{24}H_{24}N_2O_5S$)Calcd. (%): C, 63.70; H, 5.35; N, 6.19; S, 7.09 Found(%): C, 63.61; H, 5.36; N, 6.29; S, 6.89 |

TABLE 79

| Compound No. | Physical properties |
| --- | --- |
| Ih-77 | mp 176-189° C.; $^1$H-NMR($d_6$-DMSO) δ 0.02-0.08(m, 2H), 0.30-0.36(m, 2H), 0.77(m, 1H), 1.70-1.88(m, 4H), 2.49-2.64(m, 4H), 3.41(d, J=6.9Hz, 2H), 3.84(s, 3H), 4.86(s, 2H), 6.67(dd, J=2.1, 8.7Hz, 1H), 6.99(d, J=2.1Hz, 1H), 7.05-7.10(m, 2H), 7.26(d, J=8.7Hz, 1H), 7.49-7.54(m, 2H), 12.96(br, 1H); IR(Nujol)3146, 1739, 1594, 1579, 1496, 1477, 1442, 1426, 1397, 1377, 1339, 1319, 1303, 1263, 1216, 1187, 1146, 1089, 1065, 1047 cm$^{-1}$; Elemental analysis($C_{25}H_{28}N_2O_5S$)Calcd. (%): C, 64.08; H, 6.02; N, 5.98; S, 6.84 Found (%): C, 63.97; H, 6.09; N, 6.05; S, 6.63 |
| Ih-78 | mp 167-177° C.; $^1$H-NMR($d_6$-DMSO) δ 1.72-1.89(m, 4H), 2.49-2.65(m, 4H), 3.34(t, J=6.6Hz, 2H), 3.56(t, J=6.6Hz, 2H), 3.84(s, 3H), 4.68(br, 1H), 4.85(s, 2H), 6.64(dd, J=2.1, 8.7Hz, 1H), 6.98(d, J=2.1Hz, 1H), 7.06-7.11 (m, 2H), 7.25(d, J=8.7Hz, 1H), 7.50-7.54(m, 2H), 12.96(br, 1H); IR(Nujol) 3554, 3230, 1770, 1747, 1593, 1578, 1495, 1478, 1458, 1396, 1377, 1325, 1301, 1261, 1221, 1185, 1156, 1088, 1060 cm$^{-1}$; Elemental analysis |

TABLE 79-continued

| Compound No. | Physical properties |
| --- | --- |
|  | ($C_{23}H_{26}N_2O_6S$)Calcd. (%): C, 60.25; H, 5.72; N, 6.11; S, 6.99 Found(%): C, 60.09; H, 5.60; N, 6.07; S, 6.87 |
| Ih-79 | mp 185-197° C.; $^1$H-NMR(d$_6$-DMSO) δ 0.85-1.25(m, 6H), 1.52-1.90(m, 9H), 2.49-2.63(m, 4H), 3.38(d, J=7.2Hz, 2H), 4.86(s, 2H), 6.66(dd, J=2.1, 8.7Hz, 1H), 6.93(d, J=2.1Hz, 1H), 7.27(d, J=8.7Hz, 1H), 7.36-7.43(m, 2H), 7.57-7.63(m, 2H), 12.99(br, 1H); IR(Nujol)3110, 3052, 2735, 2656, 2548, 1734, 1710, 1593, 1492, 1472, 1423, 1407, 1384, 1343, 1289, 1234, 1169, 1153, 1099, 1091, 1063 cm$^{-1}$; Elemental analysis($C_{27}H_{31}FN_2O_4S$)Calcd. (%): C, 65.04; H, 6.27; F, 3.81; N, 5.62; S, 6.43 Found(%): C, 64.81; H, 6.26; F, 3.69; N, 5.58; S, 6.32 |
| Ih-80 | mp 197-207° C.; $^1$H-NMR(d$_6$-DMSO) δ 0.84-1.20(m, 6H), 1.52-1.88(m, 9H), 2.49-2.63(m, 4H), 3.34(d, J=6.9Hz, 2H), 3.83(s, 3H), 4.85(s, 2H), 6.65(dd, J=1.8, 8.7Hz, 1H), 6.93(d, J=1.8Hz, 1H), 7.04-7.09(m, 2H), 7.26(d, J=8.7Hz, 1H), 7.44-7.50(m, 2H), 13.03(br, 1H); IR(Nujol)3159, 1740, 1580, 1499, 1475, 1445, 1387, 1376, 1365, 1349, 1321, 1306, 1265, 1198, 1161, 1142, 1091 cm$^{-1}$; Elemental analysis($C_{28}H_{34}N_2O_5S$)Calcd. (%): C, 65.86; H, 6.71; N, 5.49; S, 6.28 Found(%): C, 65.79; H, 6.74; N, 5.52; S, 6.24 |
| Ih-81 | mp 177-180° C.; $^1$H-NMR(d$_6$-DMSO) δ 1.70-1.88(m, 4H), 2.49-2.63(m, 4H), 3.82(s, 3H), 4.85(s, 2H), 5.02(s, 2H), 6.70(dd, J=2.1, 8.7Hz, 1H), 7.02(d, J=2.1Hz, 1H), 7.26(d, J=8.7Hz, 1H), 7.35-7.43(m, 2H), 7.68-7.75(m, 2H), 12.99(br, 1H); IR(Nujol)3059, 3012, 2741, 2654, 2550, 1726, 1707, 1593, 1496, 1478, 1444, 1426, 1410, 1387, 1338, 1296, 1235, 1213, 1179, 1156, 1110, 1099, 1082, 1033 cm$^{-1}$; Elemental analysis($C_{22}H_{23}FN_2O_5S$)Calcd. (%): C, 59.18; H, 5.19; F, 4.26; N, 6.27; S, 7.18 Found(%): C, 59.08; H, 5.29; F, 4.05; N, 6.19; S, 6.96 |

TABLE 80

| Compound No. | Physical properties |
| --- | --- |
| Ih-82 | mp 153-157° C.; $^1$H-NMR(d$_6$-DMSO) δ 1.70-1.88(m, 4H), 2.49-2.63(m, 4H), 3.31(s, 3H), 3.83(s, 3H), 4.84(s, 2H), 4.99(s, 2H), 6.69(dd, J=2.1, 8.7Hz, 1H), 7.02(d, J=2.1Hz, 1H), 7.03-7.08(m, 2H), 7.25(d, J=8.7Hz, 1H), 7.55-7.60(m, 2H), 12.99(br, 1H); IR(Nujol)2747, 2656, 2561, 1726, 1597, 1579, 1498, 1476, 1442, 1414, 1386, 1338, 1307, 1260, 1242, 1178, 1157, 1140, 1113, 1097, 1066, 1037 cm$^{-1}$; Elemental analysis($C_{23}H_{26}N_2O_6S$)Calcd. (%): C, 60.25; H, 5.72; N, 6.11; S, 6.99 Found(%): C, 60.14; H, 5.82; N, 6.09; S, 6.97 |
| Ih-83 | mp 189-193° C.; $^1$H-NMR(d$_6$-DMSO) δ 1.09(d, J=6.3Hz, 3H), 1.30-1.45(m, 1H), 1.80-2.00(m, 2H), 2.07-2.80(m, 4H), 3.16(s, 3H), 4.85(s, 2H), 6.67(dd, J=2.1, 8.7Hz, 1H), 7.01(d, J=2.1Hz, 1H), 7.27(d, J=8.7Hz, 1H), 7.39-7.62(m, 4H), 12.91(br, 1H); IR(Nujol) 2923, 2854, 1730, 1592, 1476, 1346, 1237, 1150 cm$^{-1}$; Elemental analysis($C_{22}H_{23}FN_2O_4S$)Calcd. (%): C, 61.38; H, 5.39; F, 4.41; N, 6.51; S, 7.45 Found(%): C, 61.34; H, 5.42; F, 4.21; N, 6.62; S, 7.30 |
| Ih-84 | mp 157-161° C.; $^1$H-NMR(d$_6$-DMSO) δ 1.09(d, J=6.6Hz, 3H), 1.30-1.45(m, 1H), 1.80-2.00(m, 2H), 2.10-2.80(m, 4H), 3.12(s, 3H), 3.84(s, 3H), 4.85(s, 2H), 6.67(dd, J=2.1, 9.0Hz, 1H), 7.00(d, J=2.1Hz, 1H), 7.07-7.27(m, 2H), 7.45(d, J=9.0Hz, 1H), 7.44-7.48(m, 2H), 13.00(br, 1H); IR(Nujol)2924, 2853, 1724, 1595, 1475, 1341, 1248, 1151 cm$^{-1}$; Elemental analysis ($C_{22}H_{23}FN_2O_4S$)Calcd. (%): C, 62.42; H, 5.92; N, 6.33; S, 7.25 Found(%): C, 62.41; H, 5.93; N, 6.48; S, 7.19 |
| Ii-1 | $^1$H-NMR(CDCl$_3$) δ 5.17(s, 2H), 7.07-7.45(m, 7H), 7.58(t, J=2.1Hz, 1H), 7.70(m, 1H), 7.81-7.91(m, 3H); IR(KBr)3249, 1730, 1610, 1591, 1495, 1495, 1475, 1390, 1324, 1235, 1168, 1153, 1090, 1011 cm$^{-1}$; Elemental analysis($C_{21}H_{16}FN_3O_4S$•MeOH)Calcd. (%): C, 57.76; H, 4.41; N, 9.19; F, 4.15; S, 7.01 Found(%): C, 57.72; H, 4.07; N, 8.80; F, 4.10, S, 7.06 |
| Ii-2 | $^1$H-NMR(CDCl$_3$ + CD$_3$OD) δ 4.87(s, 2H), 6.99(m, 1H), 7.08-7.42(m, 9H), 7.73(d, J=7.8Hz, 1H), 7.82(m, 2H); IR(KBr)3254, 1726, 1607, 1590, 1550, 1494, 1468, 1406, 1378, 1335, 1293, 1238, 1166, 1153, 1089 cm$^{-1}$; Elemental analysis($C_{22}H_{17}FN_2O_4S$•0.8MeOH)Calcd. (%): C, 60.84; H, 4.52; N, 6.22; F, 4.22; S, 7.12 Found(%): C, 60.52; H, 4.13; N, 6.19; F, 3.85; S, 6.99 |
| Ii-3 | $^1$H-NMR(CD$_3$OD) δ 3.33(s, 3H), 5.08(s, 2H), 7.02(m, 1H), 7.17-7.51(m, 8H), 7.64-7.76(m, 4H); IR(CHCl$_3$)3066, 2928, 1727, 1591, 1550, 1493, 1469, 1380, 1349, 1293, 1234, 1175, 1151, 1087 cm$^{-1}$. |
| Ij-1 | $^1$H-NMR(CDCl$_3$) δ 1.55-2.30(m, 6H), 3.34(m, 1H), 3.82(m, 1H), 4.77(br, 1H), 4.82(s, 2H), 6.75-7.25(m, 6H), 7.45-7.91(m, 3H); IR(KBr)3275, 2955, 1731, 1592, 1494, 1469, 1328, 1292, 1237, 1152, 1092, 1014 cm$^{-1}$; Elemental analysis($C_{21}H_{21}FN_2O_4S$•1.1H$_2$O)Calcd. (%): C, 57.57; H, 5.38; N, 6.39; F, 4.34; S, 7.32 Found(%): C, 57.73; H, 5.08; N, 6.11; F, 4.04, S, 6.87 |

TABLE 81

| Compound No. | Physical properties |
| --- | --- |
| Ij-2 | $^1$H-NMR(CDCl$_3$) δ 1.59-2.18(m, 6H), 2.70(s, 3H), 3.25(m, 1H), 4.56(m, 1H), 4.83(s, 2H), 6.80(s, 1H), 7.07-7.22(m, 6H), 7.51(m, 1H), 7.75-7.87(m, 2H); IR(KBr)2952, 1729, 1591, 1493, 1469, 1335, 1292, 1233, 1152, 1087, 1013 cm$^{-1}$. |
| Ij-3 | $^1$H-NMR(CDCl$_3$) δ 1.43-2.18(s, 6H), 3.17(s, 1H), 4.26-4.82(m, 5H), 6.59-7.44(m, 12H), 7.75-7.87(m, 2H); IR(KBr)3433, 2951, 1731, 1591, 1494, 1469, 1337, 1292, 1235, 1152, 1092 cm$^{-1}$. |
| Ik-1 | mp 165-179° C.; $^1$H-NMR(d$_6$-DMSO) δ 2.09(s, 3H), 2.23(s, 3H), 3.17(d, J=0.6Hz, 3H), 4.90(s, 2H), 6.68(dd, J=2.1, 8.7Hz, 1H), 7.02(d, J=2.1Hz, 1H), 7.26(d, J=8.7Hz, 1H), 7.39-7.44(m, 2H), 7.57-7.62(m, 2H), 12.97(br, 1H); IR(Nujol)3211, 1766, 1739, 1590, 1492, 1481, 1461, 1418, 1377, 1326, 1291, 1264, 1238, 1177, 1137, 1095, 1082, 1063 cm$^{-1}$; Elemental analysis (C$_{19}$H$_{19}$FN$_2$O$_4$S)Calcd. (%): C, 58.45; H, 4.91; F, 4.87; N, 7.18; S, 8.21 Found(%): C, 58.46; H, 4.76; F, 4.57; N, 7.12; S, 8.18 |
| Ik-2 | mp 206-208° C.(dec); $^1$H-NMR(d$_6$-DMSO) δ 2.31(s, 3H), 3.16(s, 3H), 4.93(s, 2H), 6.72(dd, J=2.1, 8.4Hz, 1H), 7.09(d, J=2.1Hz, 1H), 7.29(d, J=8.4Hz, 1H), 7.38-7.44(m, 2H), 7.55-7.60(m, 2H); IR(Nujol)3105, 3055, 2657, 2566, 1721, 1591, 1556, 1494, 1480, 1453, 1399, 1349, 1338, 1294, 1241, 1230, 1167, 1151, 1089, 1065 cm$^{-1}$; Elemental analysis(C$_{18}$H$_{17}$FN$_2$O$_4$S) Calcd. (%): C, 57.44; H, 4.55; F, 5.05; N, 7.44; S, 8.52 Found(%): C, 57.50; H, 4.44; F, 4.99; N, 7.39; S, 8.47 |
| Ik-3 | mp 172-178° C.; $^1$H-NMR(d$_6$-DMSO) δ 1.02(t, J=7.5Hz, 3H), 2.20(s, 3H), 2.53(q, J=7.5Hz, 2H), 4.83(s, 2H), 6.74(dd, J=2.1, 8.7Hz, 1H), 7.01(d, J=2.1Hz, 1H), 7.18(d, J=8.7Hz, 1H), 7.30-7.38(m, 2H), 7.67-7.74(m, 2H), 9.77(s, 1H), 12.98(br, 1H); IR(Nujol)3254, 1726, 1589, 1487, 1410, 1377, 1333, 1289, 1246, 1233, 1167, 1088 cm$^{-1}$; Elemental analysis(C$_{19}$H$_{19}$FN$_2$O$_4$S) Calcd. (%): C, 58.45; H, 4.91; F, 4.87; N, 7.18; S, 8.21 Found(%): C, 58.39; H, 4.88; F, 4.75; N, 7.21; S, 8.18 |
| Ik-4 | mp 165-171° C.; $^1$H-NMR(d$_6$-DMSO) δ 1.19(d, J=6.9Hz, 6H), 2.20(s, 3H), 3.05(septet, J=6.9Hz, 1H), 4.80(s, 2H), 6.75(dd, J=1.8, 8.4Hz, 1H), 7.01 (d, J=1.8Hz, 1H), 7.28(d, J=8.4Hz, 1H), 7.31-7.39(m, 2H), 7.67-7.73(m, 2H), 9.72(s, 1H), 13.00(br, 1H); IR(Nujol)3250, 3124, 1741, 1591, 1483, 1377, 1318, 1293, 1200, 1146, 1088 cm$^{-1}$; Elemental analysis(C$_{20}$H$_{21}$FN$_2$O$_4$S) Calcd. (%): C, 59.39; H, 5.23; F, 4.70; N, 6.93; S, 7.93 Found(%): C, 59.28; H, 5.19; F, 4.58; N, 6.93; S, 7.86 |
| Ik-5 | mp 161-167° C.; $^1$H-NMR(d$_6$-DMSO) δ 1.02(t, J=7.5Hz, 3H), 2.23(s, 3H), 2.55(q, J=7.5Hz, 2H), 3.18(s, 3H), 4.91(s, 2H), 6.75(dd, J=2.1, 8.7Hz, 1H), 6.96(d, J=2.1Hz, 1H), 7.28(d, J=8.7Hz, 1H), 7.38-7.45(m, 2H), 7.55-7.62(m, 2H), 12.99(br, 1H); IR(Nujol)3185, 1766, 1478, 1328, 1180, 1143, 1087 cm$^{-1}$; Elemental analysis(C$_{20}$H$_{21}$FN$_2$O$_4$S)Calcd. (%): C, 59.39; H, 5.23; F, 4.70; N, 6.93; S, 7.93 Found(%): C, 59.33; H, 5.16; F, 4.58; N, 6.93; S, 7.82 |

TABLE 82

| Compound No. | Physical properties |
| --- | --- |
| Ik-6 | Mp 210-217° C.; $^1$H-NMR(d$_6$-DMSO) δ 1.18(d, J=7.2Hz, 6H), 2.24(s, 3H), 3.07(septet, J=7.2Hz, 1H), 3.19(s, 3H), 4.89(s, 2H), 6.77(dd, J=2.1, 9.0 Hz, 1H), 7.01(d, J=2.1Hz, 1H), 7.28(d, J=9.0Hz, 1H), 7.36-7.44(m, 2H), 7.56-7.62(m, 2H), 12.99(br, 1H); IR(Nujol)3241, 1771, 1750, 1587, 1482, 1324, 1178, 1086 cm$^{-1}$; Elemental analysis(C$_{21}$H$_{23}$FN$_2$O$_4$S)Calcd. (%): C, 60.27; H, 5.54; F, 4.54; N, 6.69; S, 7.66 Found(%): C, 60.04; H, 5.61; F, 4.30; N, 6.49; S, 7.30 |
| Ik-7 | Mp 121-124° C.; $^1$H-NMR(d$_6$-DMSO) δ 0.90(t, J=7.5Hz, 3H), 1.43-1.55(m, 2H), 2.10(s, 3H), 2.64(t, J=7.5Hz, 2H), 3.18(s, 3H), 4.89(s, 2H), 6.69(dd, J=2.1, 8.7Hz, 1H), 7.05(d, J=2.1Hz, 1H), 7.22(d, J=8.7Hz, 1H), 7.40-7.47(m, 2H), 7.60-7.66(m, 2H), 12.97(br, 1H); IR(Nujol)3232, 1766, 1747, 1480, 1327, 1183, 1143, 1088 cm$^{-1}$; Elemental analysis(C$_{21}$H$_{23}$FN$_2$O$_4$S) Calcd. (%): C, 60.27; H, 5.54; F, 4.54; N, 6.69; S, 7.66 Found(%): C, 60.17; H, 5.51; F, 4.45; N, 6.73; S, 7.53 |
| Ik-8 | Mp 175-177° C.; $^1$H-NMR(d$_6$-DMSO) δ 1.16(t, J=7.2Hz, 3H), 2.58(q, J=7.2Hz, 2H), 3.18(s, 3H), 4.92(s, 2H), 6.80(dd, J=2.1, 9.0Hz, 1H), 7.08(d, J=2.1Hz, 1H), 7.14(s, 1H), 7.29(d, J=9.0Hz, 1H), 7.39-7.45(m, 2H), 7.57-7.63(m, 2H), 12.95(br, 1H); IR(Nujol)2655, 1730, 1711, 1591, 1481, 1389, 1345, 1251, 1177, 1156 cm$^{-1}$; Elemental analysis(C$_{19}$H$_{19}$FN$_2$O$_4$S)Calcd. (%): C, 58.45; H, 4.91; F, 4.87; N, 7.18; S, 8.21 Found(%): C, 58.41; H, 4.94; F, 4.77; N, 7.03; S, 7.99 |
| Ik-9 | Mp 225-240° C.; $^1$H-NMR(d$_6$-DMSO) δ 0.79(t, J=7.2Hz, 3H), 1.34-1.46(m, 2H), 2.18(s, 3H), 2.48(t, J=7.2Hz, 2H), 4.74(s, 2H), 6.73(dd, J=2.1, 8.7Hz, 1H), 6.94(d, J=2.1Hz, 1H), 7.15(d, J=8.7Hz, 1H), 7.29-7.37(m, 2H), 7.66-7.72(m, 2H), 9.73(brs, 1H); IR(Nujol)3265, 1754, 1712, 1590, 1484, |

TABLE 82-continued

| Compound No. | Physical properties |
| --- | --- |
|  | 1462, 1377, 1332, 1290, 1236, 1200, 1158, 1087 cm$^{-1}$; Elemental analysis (C$_{20}$H$_{21}$FN$_2$O$_4$S•0.2H$_2$O)Calcd. (%): C, 58.87; H, 5.29; F, 4.66; N, 6.87; S, 7.86 Found(%): C, 58.75; H, 5.12; F, 4.46; N, 6.82; S, 7.82 |
| Ik-10 | Mp 160-174° C.; $^1$H-NMR(d$_6$-DMSO) δ 0.81(t, J=7.2Hz, 3H), 1.34-1.46(m, 2H), 2.23(s, 3H), 2.50(t, J=7.2Hz, 2H), 3.19(s, 3H), 4.91(s, 2H), 6.76(dd, J=2.1, 8.7Hz, 1H), 6.90(d, J=2.1Hz, 1H), 7.28(d, J=8.7Hz, 1H), 7.36-7.43(m, 2H), 7.55-7.60(m, 2H), 12.98(br, 1H); IR(Nujol)3243, 1767, 1587, 1482, 1325, 1178, 1140, 1085 cm$^{-1}$; Elemental analysis(C$_{21}$H$_{23}$FN$_2$O$_4$S) Calcd. (%): C, 60.27; H, 5.54; F, 4.54; N, 6.69; S, 7.66 Found(%): C, 60.22; H, 5.57; F, 4.32; N, 6.62; S, 7.59 |

TABLE 83

| Compound No. | Physical properties |
| --- | --- |
| Ik-11 | Mp 165-173° C.; $^1$H-NMR(d$_6$-DMSO) δ 0.90(t, J=7.5Hz, 3H), 1.05(t, J=7.5Hz, 3H), 1.39-1.49(m, 2H), 2.53-2.62(m, 4H), 4.81(s, 2H), 6.75(dd, J=1.8, 8.7Hz, 1H), 7.02(d, J=1.8Hz, 1H), 7.13(d, J=8.7Hz, 1H), 7.32-7.36(m, 2H), 7.70-7.75(m, 2H), 9.79(s, 1H); IR(Nujol)3270, 2666, 1709, 1594, 1494, 1479, 1466, 1427, 1408, 1379, 1361, 1329, 1290, 1239, 1195, 1163, 1091 cm$^{-1}$; Elemental analysis(C$_{21}$H$_{23}$FN$_2$O$_4$S)Calcd. (%): C, 60.27; H, 5.54; F, 4.54; N, 6.69; S, 7.66 Found(%): C, 60.10; H, 5.49; F, 4.43; N, 6.63; S, 7.63 |
| Ik-12 | mp 182-190° C.; $^1$H-NMR(d$_6$-DMSO) δ 0.91(t, J=7.5Hz, 3H), 1.09(t, J=7.5Hz, 3H), 1.40-1.53(m, 2H), 2.53-2.63(m, 4H), 4.83(s, 2H), 6.79(dd, J=2.1, 8.7Hz, 1H), 7.05-7.08(m, 1H), 7.12(d, J=2.1Hz, 1H), 7.16(d, J=8.7Hz, 1H), 7.39-7.41(m, 1H), 7.82-7.84(m, 1H), 9.90(s, 1H); IR(Nujol)3249, 3103, 3081, 2660, 1708, 1480, 1468, 1429, 1404, 1378, 1362, 1334, 1235, 1198, 1158, 1091, 1017 cm$^{-1}$; Elemental analysis(C$_{19}$H$_{22}$N$_2$O$_4$S$_2$)Calcd. (%): C, 56.14; H, 5.45; N, 6.89; S, 15.78 Found(%): C, 56.05; H, 5.45; N, 6.74; S, 15.56 |
| Ik-13 | mp 134-137° C.; $^1$H-NMR(d$_6$-DMSO) δ 0.91(t, J=7.5Hz, 3H), 1.04(t, J=7.5Hz, 3H), 1.41-1.54(m, 2H), 2.54-2.65(m, 4H), 3.18(s, 3H), 4.88(s, 2H), 6.76(dd, J=2.1, 8.7Hz, 1H), 6.96(d, J=2.1Hz, 1H), 7.23(d, J=8.7Hz, 1H), 7.38-7.44(m, 2H), 7.57-7.63(m, 2H), 13.09(br, 1H); IR(Nujol)3063, 2659, 2558, 2464, 1706, 1592, 1493, 1476, 1430, 1418, 1378, 1343, 1322, 1291, 1234, 1194, 1168, 1149, 1085, 1064 cm$^{-1}$; Elemental analysis(C$_{22}$H$_{25}$FN$_2$O$_4$S) Calcd. (%): C, 61.09; H, 5.83; F, 4.39; N, 6.48; S, 7.41 Found(%): C, 61.05; H, 5.79; F, 4.25; N, 6.40; S, 7.45 |
| Ik-14 | mp 130-132° C.; $^1$H-NMR(d$_6$-DMSO) δ 0.92(t, J=7.5Hz, 3H), 1.07(t, J=7.5Hz, 3H), 1.42-1.54(m, 2H), 2.54-2.66(m, 4H), 3.21(s, 3H), 4.89(s, 2H), 6.77(dd, J=2.1, 8.7Hz, 1H), 7.04(d, J=2.1Hz, 1H), 7.22(d, J=2.1Hz, 1H), 7.22-7.25(m, 2H), 7.47(dd, J=1.2, 3.6Hz, 1H), 8.00(dd, J=1.2, 5.1Hz, 1H), 12.99(br, 1H); IR(Nujol)3102, 3075, 2654, 2554, 1723, 1477, 1422, 1405, 1379, 1350, 1236, 1227, 1194, 1149, 1085, 1061, 1015 cm$^{-1}$; Elemental analysis(C$_{20}$H$_{24}$N$_2$O$_4$S$_2$)Calcd. (%): C, 57.12; H, 5.75; N, 6.66; S, 15.25 Found(%): C, 56.90; H, 5.74; N, 6.60; S, 15.17 |
| Ik-15 | mp 235-250° C.; $^1$H-NMR(d$_6$-DMSO) δ 0.80(t, J=7.2Hz, 3H), 1.34-1.47(m, 2H), 2.18(s, 3H), 2.48(t, J=7.2Hz, 2H), 3.75(s, 3H), 4.69(s, 2H), 6.72(dd, J=2.1, 8.7Hz, 1H), 6.95(d, J=2.1Hz, 1H), 6.96-7.01(m, 2H), 7.11(d, J=8.7Hz, 1H), 7.52-7.57(m, 1H), 9.52(brs, 1H); IR(Nujol)3254, 1744, 1596, 1485, 1460, 1375, 1260, 1170, 1092, 1028 cm$^{-1}$; Elemental analysis (C$_{21}$H$_{24}$N$_2$O$_5$S•0.4H$_2$O)Calcd. (%): C, 59.53; H, 5.90; N, 6.61; S, 7.57 Found (%): C, 59.61; H, 5.69; N, 6.61; S, 7.57 |

TABLE 84

| Compound No. | Physical properties |
| --- | --- |
| Ik-16 | mp 152-162° C.; $^1$H-NMR(d$_6$-DMSO) δ 0.82(t, J=7.2Hz, 3H), 1.34-1.46(m, 2H), 2.23(s, 3H), 2.49(t, J=7.2Hz, 2H), 3.14(s, 3H), 3.83(s, 3H), 4.91(s, 2H), 6.76(dd, J=2.1, 8.7Hz, 1H), 6.88(d, J=2.1Hz, 1H), 7.04-7.09(m, 2H), 7.26(d, J=8.7Hz, 1H), 7.42-7.47(m, 2H), 12.97(br, 1H); IR(Nujol)3222, 1765, 1741, 1593, 1482, 1379, 1327, 1306, 1265, 1177, 1142, 1088, 1017 cm$^{-1}$; Elemental analysis(C$_{22}$H$_{26}$N$_2$O$_5$S)Calcd. (%): C, 61.38; H, 6.09; N, 6.51; S, 7.45 Found(%): C, 61.26; H, 6.12; N, 6.52; S, 7.51 |
| Ik-17 | mp 173-183° C.; $^1$H-NMR(d$_6$-DMSO) δ 0.90(t, J=7.5Hz, 3H), 1.05(t, J=7.5Hz, 3H), 1.38-1.51(m, 2H), 2.53-2.61(m, 4H), 3.76(s, 3H), 4.80(s, 2H), 6.75(dd, J=1.8, 8.7Hz, 1H), 6.99-7.02(m, 2H), 7.04(d, J=1.8Hz, 1H), 7.11(d, J=8.7Hz, 1H), 7.59-7.62(m, 2H), 9.61(s, 1H); IR(Nujol)3241, 3170, 3013, |

TABLE 84-continued

| Compound No. | Physical properties |
| --- | --- |
| | 1759, 1732, 1597, 1577, 1498, 1478, 1466, 1383, 1355, 1321, 1263, 1190, 1146, 1090, 1028 cm$^{-1}$; Elemental analysis($C_{22}H_{26}N_2O_5S$)Calcd. (%): C, 61.38; H, 6.09; N, 6.51; S, 7.45 Found(%): C, 61.05; H, 6.05; N, 6.51; S, 7.32 |
| Ik-18 | mp 114-116° C.; $^1$H-NMR(d$_6$-DMSO) δ 0.92(t, J=7.2Hz, 3H), 1.04(t, J=7.2Hz, 3H), 1.41-1.54(m, 2H), 2.54-2.65(m, 4H), 3.14(s, 3H), 3.83(s, 3H), 4.88 (s, 2H), 6.76(dd, J=2.1, 8.7Hz, 1H), 6.94(d, J=2.1Hz, 1H), 7.07-7.09(m, 2H), 7.21(d, J=8.7Hz, 1H), 7.45-7.48(m, 2H); IR(Nujol)3314, 3100, 3067, 1767, 1742, 1596, 1579, 1497, 1480, 1465, 1377, 1342, 1318, 1302, 1263, 1168, 1138, 1088, 1060 cm$^{-1}$; Elemental analysis($C_{21}H_{20}F_2N_2O_4S.0.2AcOEt$) Calcd. (%): C, 61.85; H, 6.46; N, 6.06; S, 6.94 Found(%): C, 61.66; H, 6.47; N, 6.08; S, 6.88 |
| Ik-19 | mp 162-169° C.; $^1$H-NMR(d$_6$-DMSO) δ 2.29(s, 3H), 3.13(s, 3H), 3.91(s, 2H), 4.95(s, 2H), 6.78(dd, J=2.1, 8.7Hz, 1H), 6.94(d, J=2.1Hz, 1H), 7.06-7.36 (m, 8H), 7.49-7.56(m, 2H), 13.02(br, 1H); IR(Nujol)3149, 1739, 1590, 1476, 1415, 1376, 1346, 1165, 1151 cm$^{-1}$; Elemental analysis($C_{25}H_{23}FN_2O_4S$) Calcd. (%): C, 64.36; H, 4.97; F, 4.07; N, 6.00; S, 6.87 Found(%): C, 64.31; H, 4.88; F, 3.95; N, 5.97; S, 6.73 |
| Ik-20 | mp 192-197° C.; $^1$H-NMR(d$_6$-DMSO) δ 2.29(s, 3H), 3.08(s, 3H), 3.83(s, 3H), 3.92(s, 2H), 4.94(s, 2H), 6.75(dd, J=2.1, 8.7Hz, 1H), 6.96-7.24(m, 8H), 7.29(d, J=8.7Hz, 1H), 7.40-7.44(m, 2H), 13.02(br, 1H); IR(Nujol) 1703, 1598, 1496, 1479, 1338, 1256, 1146, 1090, 1027 cm$^{-1}$; Elemental analysis ($C_{26}H_{26}N_9O_5S$)Calcd. (%): C, 65.25; H, 5.48; N, 5.85; S, 6.70 Found(%): C, 64.95; H, 5.49; N, 5.70; S, 6.35 |

TABLE 85

| Compound No. | Physical properties |
| --- | --- |
| Ik-21 | mp 140-147° C.; $^1$H-NMR(d$_6$-DMSO) δ 0.80(d, J=6.6Hz, 6H), 1.60(septet, J=6.6Hz, 1H), 2.22(s, 3H), 2.38(d, J=6.6Hz, 2H), 3.19(s, 3H), 4.92(s, 2H), 6.78(dd, J=2.1, 8.7Hz, 1H), 6.85(d, J=2.1Hz, 1H), 7.28(d, J=8.7 1H), 7.35-7.43(m, 2H), 7.55-7.62(m, 2H), 12.98(br, 1H); IR(Nujol)3253, 1766, 1587, 1481, 1324, 1177, 1139, 1085 cm$^{-1}$; Elemental analysis($C_{22}H_{25}FN_2O_4S$) Calcd. (%): C, 61.09; H, 5.83; F, 4.39; N, 6.48; S, 7.41 Found(%): C, 60.97; H, 5.75; F, 4.23; N, 6.37; S, 7.32 |
| Ik-22 | mp 137-142° C.; $^1$H-NMR(d$_6$-DMSO) δ 0.85(t, J=7.2Hz, 3H), 1.14-1.40(m, 4H), 2.19(s, 3H), 2.50(t-like, 2H), 4.84(s, 2H), 6.76(dd, J=1.8, 8.7Hz, 1H), 6.93(d, J=1.8Hz, 1H), 7.19(d, J=8.7Hz, 1H), 7.30-7.36(m, 2H), 7.67-7.72 (m, 2H), 12.98(br, 1H); IR(Nujol)3255, 3106, 3041, 2652, 2550, 1714, 1592, 1484, 1466, 1407, 1378, 1351, 1332, 1290, 1233, 1199, 1169, 1159, 1091 cm$^{-1}$; Elemental analysis($C_{21}H_{23}FN_2O_4S$)Calcd. (%): C, 60.27; H, 5.54; F, 4.54; N, 6.69; S, 7.66 Found(%): C, 60.22; H, 5.52; F, 4.39; N, 6.78; S, 7.56 |
| Ik-23 | mp 130-140° C.; $^1$H-NMR(d$_6$-DMSO) δ 0.86(t, J=6.9Hz, 3H), 1.15-1.42(m, 4H), 2.18(s, 3H), 2.50(t-like, 2H), 3.76(s, 3H), 4.82(s, 2H), 6.75(dd, J=2.1, 9.0Hz, 1H), 6.97(d, J=2.1Hz, 1H), 6.97-7.02(m, 2H), 7.16(d, J=9.0Hz, 1H), 7.56-7.61(m, 2H), 9.57(s, 1H), 12.95(br, 1H); IR(Nujol)3248, 3076, 2651, 2553, 1714, 1598, 1578, 1499, 1484, 1465, 1410, 1379, 1328, 1301, 1261, 1232, 1181, 1157, 1093, 1029 cm$^{-1}$; Elemental analysis($C_{22}H_{26}N_2O_5S$) Calcd. (%): C, 61.38; H, 6.09; N, 6.51; S, 7.45 Found(%): C, 61.21; H, 6.04; N, 6.48; S, 7.27 |
| Ik-24 | mp 125-129° C.; $^1$H-NMR(d$_6$-DMSO) δ 0.86(t, J=6.9Hz, 3H), 1.17-1.40(m, 4H), 2.22(s, 3H), 2.50(t-like, 2H), 3.19(s, 3H), 4.90(s, 2H), 6.78(dd, J=2.1, 8.7Hz, 1H), 6.87(d, J=2.1Hz, 1H), 7.28(d, J=8.7Hz, 1H), 7.36-7.43(m, 2H), 7.55-7.61(m, 2H), 13.03(br, 1H); IR(Nujol)3253, 3121, 3091, 3074, 1768, 1591, 1479, 1416, 1377, 1327, 1292, 1229, 1186, 1166, 1137, 1099, 1087, 1072, 1055 cm$^{-1}$; Elemental analysis($C_{22}H_{25}FN_2O_4S$)Calcd. (%): C, 61.09; H, 5.83; F, 4.39; N, 6.48; S, 7.41 Found(%): C, 61.10; H, 5.72; F, 4.31; N, 6.46; S, 7.39 |
| Ik-25 | mp 140-145° C.; $^1$H-NMR(d$_6$-DMSO) δ 0.86(t, J=7.2Hz, 3H), 1.18-1.41(m, 4H), 2.22(s, 3H), 2.50(t-like, 2H), 3.14(s, 3H), 3.83(s, 3H), 4.90(s, 2H), 6.76(dd, J=2.1, 8.7Hz, 1H), 6.88(d, J=2.1Hz, 1H), 7.04-7.09(m, 2H), 7.26 (d, J=8.7Hz, 1H), 7.42-7.47(m, 2H), 12.98(br, 1H); IR(Nujol)3241, 3090, 3066, 3016, 1764, 1737, 1702, 1593, 1576, 1495, 1481, 1467, 1457, 1415, 1378, 1328, 1305, 1264, 1172, 1141, 1087, 1017 cm$^{-1}$; Elemental analysis ($C_{23}H_{28}N_2O_5S$)Calcd. (%): C, 62.14; H, 6.35; N, 6.30; S, 7.21 Found(%): C, 62.04; H, 6.23; N, 6.29; S, 7.09 |

TABLE 86

| Compound No. | Physical properties |
| --- | --- |
| Ik-26 | mp 139-147° C.; $^1$H-NMR($d_6$-DMSO) δ 0.79(d, J=6.6Hz, 6H), 1.63(m, 1H), 2.18(s, 3H), 2.37(d, J=6.6Hz, 2H), 3.76(s, 3H), 4.84(s, 2H), 6.75(dd, J=1.8, 8.7Hz, 1H), 6.93(d, J=1.8Hz, 1H), 6.96-7.01(m, 2H), 7.16(d, J=8.7 Hz, 1H), 7.55-7.60(m, 2H), 9.54(s, 1H), 12.90(br, 1H); IR(Nujol)3325, 3254, 3098, 3077, 1748, 1595, 1578, 1484, 1464, 1436, 1418, 1378, 1333, 1317, 1304, 1291, 1260, 1203, 1166, 1141, 1112, 1091 cm$^{-1}$; Elemental analysis($C_{22}H_{26}N_2O_5S$)Calcd. (%): C, 61.38; H, 6.09; N, 6.51; S, 7.45 Found (%): C, 61.13; H, 6.13; N, 6.55; S, 7.24 |
| Ik-27 | mp 148-160° C.; $^1$H-NMR($d_6$-DMSO) δ 0.80(d, J=6.6Hz, 6H), 1.61(m, 1H), 2.22(s, 3H), 2.37(d, J=6.6Hz, 2H), 3.15(s, 3H), 3.83(s, 3H), 4.91(s, 2H), 6.77(dd, J=2.1, 8.4Hz, 1H), 6.84(d, J=2.1Hz, 1H), 7.03-7.08(m, 2H), 7.26 (d, J=8.4Hz, 1H), 7.42-7.47(m, 2H), 12.96(br, 1H); IR(Nujol)3252, 3097, 3077, 3058, 3025, 1750, 1724, 1595, 1577, 1482, 1465, 1415, 1373, 1320, 1305, 1270, 1212, 1188, 1163, 1144, 1091, 1053, cm$^{-1}$; Elemental analysis ($C_{23}H_{28}N_2O_5S$)Calcd. (%): C, 62.14; H, 6.35; N, 6.30; S, 7.21 Found(%): C, 62.16; H, 6.39; N, 6.32; S, 7.22 |
| Ik-28 | mp 150-175° C.; $^1$H-NMR($d_6$-DMSO) δ 0.82(t, J=7.5Hz, 3H), 0.96(t, J=7.2Hz, 3H), 1.33-1.45(m, 2H), 2.23(s, 3H), 2.48(t, J=7.5Hz, 2H), 3.58(q, J=7.2Hz, 2H), 3.83(s, 3H), 4.91(s, 2H), 6.71(dd, J=1.8, 8.7Hz, 1H), 6.83(d, J=1.8Hz, 1H), 7.04-7.09(m, 2H), 7.27(d, J=8.7Hz, 1H), 7.48-7.53(m, 2H), 12.97(br, 1H); IR(Nujol)3178, 1762, 1742, 1728, 1594, 1577, 1476, 1379, 1328, 1306, 1261, 1181, 1139 cm$^{-1}$; Elemental analysis($C_{23}H_{28}N_2O_5S$)Calcd. (%): C, 62.14; H, 6.35; N, 6.30; S, 7.21 Found(%): C, 61.87; H, 6.31; N, 6.33; S, 6.94 |
| Ik-29 | mp 153-165° C.; $^1$H-NMR($d_6$-DMSO) δ 0.83(t, J=7.5Hz, 3H), 1.36-1.48(m, 2H), 2.23(s, 3H), 2.50(t, J=7.5Hz, 2H), 3.12(s, 3H), 4.89(s, 2H), 6.74(dd, J=2.1, 8.7Hz, 1H), 6.83-6.88(m, 2H), 6.91(d, J=2.1Hz, 1H), 7.25(d, J=8.7Hz, 1H), 7.31-7.36(m, 2H), 10.48(br, 1H), 13.03(br, 1H); IR(Nujol) 3177, 1719, 1586, 1479, 1442, 1377, 1335, 1241, 1222, 1152 cm$^{-1}$; Elemental analysis($C_{21}H_{24}N_2O_5S$)Calcd. (%): C, 60.56; H, 5.81; N, 6.73; S, 7.70 Found (%): C, 60.38; H, 5.94; N, 6.52; S, 7.32 |
| Ik-30 | mp 202-210° C.; $^1$H-NMR($d_6$-DMSO) δ 2.27(s, 3H), 3.89(s, 2H), 4.88(s, 2H), 6.75(dd, J=2.1, 8.4Hz, 1H), 7.01(d, J=2.1Hz, 1H), 7.07-7.33(m, 8H), 7.62-7.68(m, 2H), 7.97(s, 1H), 12.98(br, 1H); IR(Nujol)3263, 1709, 1594, 1481, 1411, 1379, 1334, 1292, 1234, 1169 cm$^{-1}$; Elemental analysis ($C_{24}H_{21}FN_2O_4S$)Calcd. (%): C, 63.70; H, 4.68; F, 4.20; N, 6.19; S, 7.09 Found (%): C, 63.47; H, 4.75; F, 3.93; N, 6.17; S, 6.74 |

TABLE 87

| Compound No. | Physical properties |
| --- | --- |
| Ik-31 | mp 130-155° C.; $^1$H-NMR($d_6$-DMSO) δ 0.82(t, J=7.5Hz, 3H), 1.33-1.45(m, 5H), 2.23(s, 3H), 2.49(t, J=7.5Hz, 2H), 3.14(s, 3H), 4.10(q, J=7.2Hz, 2H), 4.90(s, 2H), 6.76(dd, J=2.1, 8.7Hz, 1H), 6.87(d, J=2.1Hz, 1H), 7.02-7.07(m, 2H), 7.26(d, J=8.7Hz, 1H), 7.40-7.45(m, 2H), 12.93(br, 1H); IR(Nujol)3247, 1739, 1594, 1480, 1415, 1377, 1304, 1256, 1153 cm$^{-1}$. |
| Ik-32 | mp 90-96° C.; $^1$H-NMR($d_6$-DMSO) δ 0.81(t, J=7.5Hz, 3H), 1.33-1.45(m, 2H), 2.23(s, 3H), 2.48(t, J=7.5Hz, 2H), 3.19(t, J=2.4Hz, 1H), 3.83(s, 3H), 4.46(q, J=2.4Hz, 2H), 4.90(s, 2H), 6.82(dd, J=2.1, 8.4Hz, 1H), 6.98 (d, J=2.1Hz, 1H), 7.04-7.09(m, 2H), 7.28(d, J=8.4Hz, 1H), 7.53-7.58(m, 2H), 13.03(br, 1H); IR(Nujol)3588, 3310, 2642, 1733, 1707, 1687, 1599, 1580, 1499, 1479, 1465, 1414, 1379, 1345, 1257, 1159, 1029 cm$^{-1}$; Elemental analysis($C_{24}H_{26}N_2O_5S$•0.8$H_2O$)Calcd. (%): C, 61.47; H, 5.93; N, 5.97; S, 6.84 Found(%): C, 61.56; H, 5.69; N, 5.87; S, 6.58 |
| Ik-33 | mp 144-157° C.; $^1$H-NMR($d_6$-DMSO) δ 2.29(s, 3H), 3.10(t, J=2.1Hz, 1H), 3.82(s, 2H), 3.89(s, 2H), 4.41(d, J=2.1Hz, 2H), 4.94(s, 2H), 6.82(dd, J=2.1, 8.7Hz, 1H), 7.00-7.24(m, 8H), 7.31(d, J=8.7Hz, 1H), 7.52-7.55(m, 2H), 13.06(br, 1H); IR(Nujol)3291, 2644, 1933, 1716, 1598, 1579, 1498, 1475, 1346, 1335, 1262, 1240, 1158, 1095 cm$^{-1}$; Elemental analysis ($C_{28}H_{26}N_2O_5S$)Calcd. (%): C, 66.91; H, 5.21; N, 5.57; S, 6.38 Found (%): C, 66.65; H, 5.26; N, 5.56; S, 6.14 |
| Ik-34 | mp 123-130° C.; $^1$H-NMR($d_6$-DMSO) δ 0.80(d, J=6.9Hz, 6H), 1.59(septet, J=6.9Hz, 1H), 2.22(s, 3H), 2.37(d, J=6.9Hz, 2H), 3.22(t, J=2.4Hz, 1H), 4.52(d, J=2.4Hz, 2H), 4.92(s, 2H), 6.84(dd, J=1.8, 8.7Hz, 1H), 6.96(d, J=1.8Hz, 1H), 7.30(d, J=8.7 1H), 7.35-7.42(m, 2H), 7.67-7.72(m, 2H), 13.03(br, 1H); IR(Nujol)3307, 2654, 1732, 1592, 1493, 1475, 1379, 1350, 1246, 1168, 1096 cm$^{-1}$; Elemental analysis($C_{24}H_{25}FN_2O_4S$)Calcd. (%): C, 63.14; H, 5.52; F, 4.16; N, 6.14; S, 7.02 Found(%): C, 62.99; H, 5.36; F, 4.25; N, 6.13; S, 7.44 |
| Ik-35 | mp 157-160° C.; $^1$H-NMR($d_6$-DMSO) δ 2.21(s, 3H), 3.18(s, 3H), 3.70(s, 3H), 4.90(s, 2H), 6.77(dd, J=2.1, 8.7Hz, 1H), 7.01(d, J=2.1Hz, 1H), 7.33(d, |

TABLE 87-continued

| Compound No. | Physical properties |
| --- | --- |
| | J=8.7 1H), 7.38-7.55(m, 2H), 7.56-7.62(m, 2H), 13.05(br, 1H); IR(Nujol) 1741, 1592, 1485, 1469, 1385, 1343, 1298, 1292, 1267, 1240, 1204, 1171, 1090, 1059 cm$^{-1}$; Elemental analysis($C_{19}H_{19}FN_2O_5S$)Calcd. (%): C, 56.15; H, 4.71; F, 4.67; N, 6.89; S, 7.89 Found(%): C, 56.28; H, 4.62; F, 4.37; N, 6.90; S, 7.70 |

TABLE 88

| Compound No. | Physical properties |
| --- | --- |
| Ik-36 | mp 170-180° C.; $^1$H-NMR(d$_6$-DMSO) δ 2.21(s, 3H), 3.14(s, 3H), 3.69(s, 3H), 3.83(s, 3H), 4.90(s, 2H), 6.77(dd, J=2.1, 8.7Hz, 1H), 6.98(d, J=2.1Hz, 1H), 7.06-7.11(m, 2H), 7.32(d, J=8.7Hz, 1H), 7.43-7.48(m, 2H), 13.03(br, 1H); IR(Nujol)1726, 1597, 1498, 1479, 1415, 1383, 1338, 1305, 1266, 1254, 1150, 1091, 1026, 1011 cm$^{-1}$; Elemental analysis($C_{20}H_{22}N_2O_6S$)Calcd. (%): C, 57.40; H, 5.30; N, 6.69; S, 7.66 Found(%): C, 56.78; H, 5.33; N, 6.64; S, 7.30 |
| Ik-37 | mp 142-152° C.; $^1$H-NMR(d$_6$-DMSO) δ 1.04(t, J=7.2Hz, 3H), 2.63(s, 3H), 2.72(q, J=7.2Hz, 2H), 3.17(s, 3H), 3.84(s, 3H), 5.11(s, 2H), 6.93(dd, J=2.1, 8.7Hz, 1H), 7.08-7.13(m, 2H), 7.46-7.51(m, 4H), 13.30(br, 1H); IR (Nujol)3544, 3355, 1734, 1693, 1598, 1577, 1513, 1498, 1477, 1459, 1412, 1378, 1341, 1262, 1208, 1161, 1149, 1107, 1092, 1066, 1034 cm$^{-1}$; Elemental analysis($C_{22}H_{24}N_2O_6S$•0.4$H_2O$)Calcd. (%): C, 58.50; H, 5.53; N, 6.20; S, 7.10 Found(%): C, 58.43; H, 5.67; N, 6.23; S, 6.88 |
| Ik-38 | mp 105-115° C.; $^1$H-NMR(d$_6$-DMSO) δ 0.97(t, J=7.2Hz, 3H), 1.03(t, J=7.2Hz, 3H), 2.63(s, 3H), 2.69(q, J=7.2Hz, 2H), 3.61(q, J=7.2Hz, 2H), 3.84 (s, 3H), 5.12(s, 2H), 6.89(dd, J=1.8, 8.7Hz, 1H), 7.08-7.13(m, 2H), 7.41(d, J=1.8Hz, 1H), 7.49-7.57(m, 3H), 13.32(br, 1H); IR(Nujol)3313, 1729, 1631, 1596, 1576, 1509, 1496, 1479, 1461, 1446, 1412, 1378, 1337, 1260, 1221, 1188, 1147, 1107, 1092, 1065, 1028 cm$^{-1}$; Elemental analysis ($C_{23}H_{26}N_2O_6S$•0.5$H_2O$)Calcd. (%): C, 59.09; H, 5.82; N, 5.99; S, 6.86 Found (%): C, 59.18; H, 5.72; N, 6.11; S, 6.99 |
| Ik-39 | mp 169-176° C.; $^1$H-NMR(d$_6$-DMSO) δ 0.81(t, J=7.5Hz, 3H), 1.33-1.45(m, 2H), 2.23(s, 3H), 2.49(t, J=7.5Hz, 2H), 3.18(s, 3H), 4.90(s, 2H), 6.73(dd, J=2.1, 8.7Hz, 1H), 6.89(d, J=2.1Hz, 1H), 7.26(d, J=8.7Hz, 1H), 7.51-7.59(m, 4H), 7.70(m, 1H), 13.00(br, 1H); IR(Nujol)3060, 2756, 2658, 2564, 1729, 1708, 1584, 1480, 1447, 1415, 1380, 1335, 1307, 1246, 1170, 1146, 1085, 1069, 1053 cm$^{-1}$; Elemental analysis($C_{21}H_{24}N_2O_4S$)Calcd. (%): C, 62.98; H, 6.04; N, 6.99; S, 8.01 Found(%): C, 62.88; H, 5.76; N, 6.93; S, 7.95 |
| Ik-40 | mp 130-136° C.; $^1$H-NMR(d$_6$-DMSO) δ 0.82(t, J=7.2Hz, 3H), 1.33-1.45(m, 2H), 2.23(s, 3H), 2.39(s, 3H), 2.50(t, J=7.2Hz, 2H), 3.18(s, 3H), 4.90(s, 2H), 6.74(dd, J=2.1, 8.7Hz, 1H), 6.87(d, J=2.1Hz, 1H), 7.26(d, J=8.7 Hz, 1H), 7.34-7.42(m, 4H), 13.00(br, 1H); IR(Nujol)3284, 3048, 1750, 1722, 1597, 1580, 1481, 1456, 1416, 1375, 1338, 1321, 1308, 1290, 1205, 1193, 1166, 1146, 1087, 1055 cm$^{-1}$; Elemental analysis($C_{22}H_{26}N_2O_4S$)Calcd. (%): C, 63.75; H, 6.32; N, 6.76; S, 7.74 Found(%): C, 63.58; H, 6.05; N, 6.73; S, 7.94 |

TABLE 89

| Compound No. | Physical properties |
| --- | --- |
| Ik-41 | mp 152-159° C.; $^1$H-NMR(d$_6$-DMSO) δ 0.79(t, J=7.2Hz, 3H), 1.31-1.43(m, 2H), 2.22(s, 3H), 2.48(t, J=7.2Hz, 2H), 3.32(s, 3H), 4.89(s, 2H), 6.80(dd, J=2.1, 8.7Hz, 1H), 7.00(d, J=2.1Hz, 1H), 7.25-7.31(m, 2H), 7.46-7.53(m, 2H), 7.73(m, 1H), 13.01(br, 1H); IR(Nujol)3081, 3026, 2756, 2656, 2596, 2562, 1730, 1709, 1596, 1475, 1448, 1416, 1380, 1350, 1269, 1244, 1211, 1182, 1172, 1142, 1124, 1072, 1051 cm$^{-1}$; Elemental analysis($C_{21}H_{23}FN_2O_4S$) Calcd. (%): C, 60.27; H, 5.54; F, 4.54; N, 6.69; S, 7.66 Found(%): C, 60.29; H, 5.36; F, 4.57; N, 6.63; S, 7.62 |
| Ik-42 | mp 147-154° C.; $^1$H-NMR(d$_6$-DMSO) δ 0.82(t, J=7.2Hz, 3H), 1.33-1.45(m, 2H), 2.23(s, 3H), 2.49(t, J=7.2Hz, 2H), 3.19(s, 3H), 4.91(s, 2H), 6.77(dd, J=2.1, 8.7Hz, 1H), 6.89(d, J=2.1Hz, 1H), 7.28(d, J=8.7Hz, 1H), 7.49-7.53(m, 2H), 7.61-7.65(m, 2H), 12.99(br, 1H); IR(Nujol)3276, 3097, 1770, 1581, 1479, 1417, 1396, 1378, 1324, 1185, 1174, 1162, 1143, 1092, 1055, 1011 cm$^{-1}$; Elemental analysis($C_{21}H_{23}ClN_2O_4S$)Calcd. (%): C, 57.99; H, 5.33; Cl, 8.15; N, 6.44; S, 7.37 Found(%): C, 58.05; H, 5.01; Cl, 7.79; N, 6.46; S, 7.36 |

TABLE 89-continued

| Compound No. | Physical properties |
| --- | --- |
| Ik-43 | mp 143-150° C.; $^1$H-NMR($d_6$-DMSO) δ 0.83(t, J=7.2Hz, 3H), 1.33-1.45(m, 2H), 2.23(s, 3H), 2.49(t, J=7.2Hz, 2H), 3.19(s, 3H), 4.91(s, 2H), 6.78(dd, J=2.1, 8.7Hz, 1H), 6.88(d, J=2.1Hz, 1H), 7.28(d, J=8.7Hz, 1H), 7.41-7.45(m, 2H), 7.75-7.79(m, 2H), 12.98(br, 1H); IR(Nujol)3021, 2655, 1717, 1574, 1478, 1467, 1415, 1387, 1377, 1357, 1251, 1190, 1170, 1156, 1069 cm$^{-1}$; Elemental analysis($C_{21}H_{23}BrN_2O_4S$)Calcd. (%): C, 52.61; H, 4.84; Br, 16.67; N, 5.84; S, 6.69 Found(%): C, 52.70; H, 4.56; Br, 16.11; N, 5.82; S, 6.67 |

Experiment 1 Binding Activity to CRTH2

The membrane fraction prepared with CRTH2-transfected K562 cells was used for a binding assay. To a binding-reaction solution (50 mM Tris/HCl, pH 7.4, 10 mM $MgCl_2$) the membrane fraction (0.06 mg) and 3 nM [$^3$H]$PGD_2$ (172 Ci/mmol) were added, and the mixture was reacted at room temperature for 60 min. After the reaction, the mixture was filtered through a glass fiber filter paper and washed several times with cooled physiological saline, then the radioactivity retained on the filter paper was measured. The specific-binding ratio was calculated by subtracting the non-specific binding ratio which is the radioactivity similarly measured in the presence of 10 μM $PGD_2$ from the total binding. The inhibitory activity of each compound was expressed as the concentration required for 50% inhibition ($IC_{50}$), which was determined by depicting a substitution curve by plotting the binding ratio (%) in the presence of each compound, where the binding ratio in the absence of a test compound is 100%. The results are shown below.

TABLE 90

| Compound No. | CRTH2 inhibitory activity $IC_{50}$ (μM) |
| --- | --- |
| Ia-15 | 0.037 |
| Ia-20 | 0.022 |
| Ia-32 | 0.018 |
| Ia-36 | 0.015 |
| Ia-39 | 0.045 |
| Ia-41 | 0.034 |
| Ia-44 | 0.023 |
| Ia-45 | 0.019 |
| Ia-47 | 0.051 |
| Ia-48 | 0.057 |
| Ia-51 | 0.02 |
| Ia-52 | 0.024 |
| Ia-55 | 0.042 |
| Ia-57 | 0.057 |
| Ia-58 | 0.033 |
| Ia-59 | 0.023 |
| Ia-61 | 0.045 |
| Ia-62 | 0.049 |
| Ia-63 | 0.054 |
| Ia-65 | 0.027 |
| Ia-66 | 0.037 |
| Ia-85 | 0.08 |
| Ib-6 | 0.055 |
| (+)-Ib-16 | 0.0059 |
| (+)-Ib-18 | 0.013 |
| (+)-Ib-20 | 0.0079 |
| Ib-21 | 0.012 |
| (+)-Ib-25 | 0.0036 |

TABLE 91

| Compound No. | CRTH2 inhibitory activity $IC_{50}$ (μM) |
| --- | --- |
| (+)-Ib-27 | 0.0062 |
| (+)-Ib-29 | 0.0049 |
| Ib-30 | 0.0053 |
| Ib-31 | 0.059 |
| Ic-2 | 0.021 |
| Ic-6 | 0.0045 |
| Ic-14 | 0.0055 |
| Ic-24 | 0.068 |
| Ie-2 | 0.039 |
| Ie-5 | 0.018 |
| Ie-8 | 0.026 |
| If-1 | 0.019 |
| If-4 | 0.016 |
| If-9 | 0.012 |
| Ig-3 | 0.0097 |
| Ig-4 | 0.0078 |
| Ig-11 | 0.01 |
| Ig-14 | 0.0083 |
| Ig-15 | 0.0075 |
| Ig-16 | 0.0036 |
| Ig-18 | 0.019 |
| Ih-2 | 0.0099 |
| Ih-3 | 0.033 |
| Ih-4 | 0.024 |
| Ih-5 | 0.023 |
| Ih-6 | 0.034 |
| Ii-1 | 0.035 |
| Ii-2 | 0.035 |
| Ii-3 | 0.064 |
| Ij-1 | 0.026 |
| Ij-2 | 0.053 |
| Ij-3 | 0.053 |

TABLE 92

| Compound No. | CRTH2 inhibitory activity $IC_{50}$ (μM) |
| --- | --- |
| Ik-1 | 0.048 |
| Ik-2 | 0.086 |
| Ik-3 | 0.051 |
| Ik-4 | 0.047 |
| Ik-5 | 0.019 |

Experiment 2 Evaluation of Antagonistic Activity to CRTH2

To evaluate the antagonistic activity of compounds against CRTH2, calcium mobilization assay induced by $PGD_2$ was performed using CRTH2 transfectants.

The human CRTH2-transfected K562 cells were suspended at $2 \times 10^6$ cells/ml in assay buffer (10 mM HEPES buffer, pH 7.4, 0.1% Bovine serum albumin), and were incubated with Fura-2 AM (2 μM) for 60 min at room temperature. After washing cells were resuspended again with assay buffer, incubated at 37° C., and then treated with various concentrations of compounds for 2 min. The emitted fluorescence was measured on a calcium analyzer (CAF-110) after addition of PGD$_2$. The antagonistic activity of each compound at 1 µM was expressed as percent inhibition of the calcium mobilization in drug-untreated cells. The results are shown below.

TABLE 93

| Compound No. | antagonistic activity to CRTH2 (% INH) |
|---|---|
| Ia-9 | 94 |
| Ia-51 | 91 |
| Ib-31 | 96 |
| Ib-16 | 100 |
| Ib-25 | 100 |
| Ic-6 | 100 |
| Ib-29 | 100 |
| Ia-36 | 89 |
| Ic-19 | 91 |
| Ic-31 | 98 |
| Ic-34 | 94 |
| Ic-53 | 60 |
| Ic-54 | 85 |
| Ic-55 | 100 |
| Ic-56 | 100 |
| Ic-57 | 100 |
| Ih-2 | 91 |

FORMULATION EXAMPLE

Formulation Example 1

Granules are prepared using the following ingredients.

| Ingredients | The compound represented by the formula (I) | 10 mg |
|---|---|---|
| | Lactose | 700 mg |
| | Corn starch | 274 mg |
| | HPC-L | 16 mg |
| | | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2
Powders for filling capsules are prepared using the following ingredients.

| Ingredients | The compound represented by the formula (I) | 10 mg |
|---|---|---|
| | Lactose | 79 mg |
| | Corn starch | 10 mg |
| | Magnesium stearate | 1 mg |
| | | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3
Granules for filling capsules are prepared using the following ingredients.

| Ingredients | The compound represented by the formula (I) | 15 mg |
|---|---|---|
| | Lactose | 90 mg |
| | Corn starch | 42 mg |
| | HPC-L | 3 mg |
| | | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation 4
Tablets are prepared using the following ingredients.

| Ingredients | The compound represented by the formula (I) | 10 mg |
|---|---|---|
| | Lactose | 90 mg |
| | Microcrystal cellulose | 30 mg |
| | CMC-Na | 15 mg |
| | Magnesium stearate | 5 mg |
| | | 150 mg |

The compound represented by the formula (I), lactose, microcrystal cellulose, and CMC-Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

INDUSTRIAL APPLICABILITY

The pharmaceutical composition and the compound of the present invention show superior CRTH2 receptor antagonistic activity and are useful for an agent for treating or preventing allergic diseases.

The invention claimed is:

1. A compound of the formula (I):

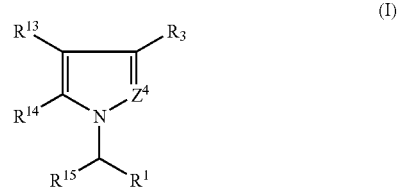

wherein
a group represented by the formula:

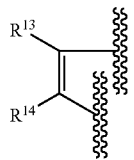

is a group represented by the formula:

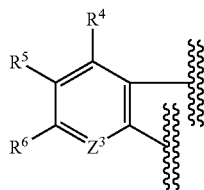

wherein
$Z^3$ is $=C(-R^7)-$;
$R^4$, $R^5$, $R^6$ and $R^7$ are each independently hydrogen, halogen, alkyl, or phenyl; $R^1$ is —COOH, or alkyloxycarbonyl;
$Z^4$ is —C($-R^2$)=; $R^2$ is hydrogen or alkyl;
$R^{15}$ is hydrogen;

$R^3$ is a group represented by the formula:

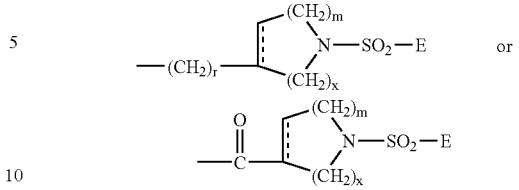

wherein r is an integer from 0 to 1; x is an integer from 0 to 1; m is an integer from 1 to 2, provided that x=m=2; a broken line represents the presence or absence of a bond;

E is phenyl unsubstituted or substituted with halogen, alkyl, alkoxy, nitro, cyano, hydroxy, haloalkyl, or phenyl; naphthyl; thienyl unsubstituted or substituted with benzyl or halogen; benzothiophene; quinolinyl; pyridyl; alkyl; phenylalkyl; or phenylalkenyl; or a pharmaceutically acceptable salt thereof.

2. A compound as described in claim 1, wherein $R^1$ is —COOH, a pharmaceutically acceptable salt thereof.

3. A pharmaceutical composition containing a compound, a pharmaceutically acceptable salt thereof as described in claim 1.

* * * * *